US012559800B2

(12) United States Patent
Williams

(10) Patent No.: US 12,559,800 B2
(45) Date of Patent: Feb. 24, 2026

(54) KMT2A-MAML2 FUSION MOLECULES AND USES THEREOF

(71) Applicant: Foundation Medicine, Inc., Cambridge, MA (US)

(72) Inventor: Erik Williams, Boston, MA (US)

(73) Assignee: Foundation Medicine, Inc., Boston, MA (US)

( * ) Notice: Subject to any disclaimer, the term of this patent is extended or adjusted under 35 U.S.C. 154(b) by 1034 days.

(21) Appl. No.: 17/638,740

(22) PCT Filed: Aug. 31, 2020

(86) PCT No.: PCT/US2020/048834
§ 371 (c)(1),
(2) Date: Feb. 25, 2022

(87) PCT Pub. No.: WO2021/042066
PCT Pub. Date: Mar. 4, 2021

(65) Prior Publication Data
US 2022/0290253 A1     Sep. 15, 2022

Related U.S. Application Data

(60) Provisional application No. 62/894,539, filed on Aug. 30, 2019.

(51) Int. Cl.
*C12Q 1/6886* (2018.01)
*G01N 33/574* (2006.01)

(52) U.S. Cl.
CPC ......... *C12Q 1/6886* (2013.01); *G01N 33/574* (2013.01); *C12Q 2600/156* (2013.01); *C12Y 201/01* (2013.01); *G01N 2333/4706* (2013.01); *G01N 2333/91017* (2013.01)

(58) Field of Classification Search
CPC .................................................... C12Q 1/6886
USPC ....................................................... 424/133.1
See application file for complete search history.

(56) References Cited

U.S. PATENT DOCUMENTS

| | | | |
|---|---|---|---|
| 4,816,567 | A | 3/1989 | Cabilly et al. |
| 5,223,409 | A | 6/1993 | Ladner et al. |
| 5,225,539 | A | 7/1993 | Winter |
| 5,545,806 | A | 8/1996 | Lonberg et al. |
| 5,569,825 | A | 10/1996 | Lonberg et al. |
| 5,624,821 | A | 4/1997 | Winter et al. |
| 5,625,126 | A | 4/1997 | Lonberg et al. |
| 5,633,425 | A | 5/1997 | Lonberg et al. |
| 5,648,260 | A | 7/1997 | Winter et al. |
| 5,661,016 | A | 8/1997 | Lonberg et al. |
| 5,776,688 | A | 7/1998 | Bittner et al. |
| 9,340,830 | B2 | 5/2016 | Lipson et al. |
| 2011/0104680 | A1 | 5/2011 | Chinnaiyan et al. |
| 2013/0034559 | A1 | 2/2013 | Queva et al. |
| 2016/0376663 | A1 | 12/2016 | Brown |

FOREIGN PATENT DOCUMENTS

| | | | |
|---|---|---|---|
| EP | | 171496 A2 | 2/1986 |
| EP | | 173494 A2 | 3/1986 |
| EP | | 184187 A2 | 6/1986 |
| EP | | 125023 B1 | 6/1991 |
| WO | WO-1986001533 A1 | | 3/1986 |
| WO | WO-1987002671 A1 | | 5/1987 |
| WO | WO-1990002809 A1 | | 3/1990 |
| WO | WO-1991017271 A1 | | 11/1991 |
| WO | WO-1992001047 A1 | | 1/1992 |
| WO | WO-1992009690 A2 | | 6/1992 |
| WO | WO-1992015679 A1 | | 9/1992 |
| WO | WO-1992018619 A1 | | 10/1992 |
| WO | WO-1992020791 A1 | | 11/1992 |
| WO | WO-1993001288 A1 | | 1/1993 |
| WO | WO-1994029351 A2 | | 12/1994 |
| WO | WO-2001014424 A2 | | 3/2001 |
| WO | WO-2006121168 A1 | | 11/2006 |
| WO | WO-2007005874 A2 | | 1/2007 |
| WO | WO-2009101611 A1 | | 8/2009 |
| WO | WO-2009114335 A2 | | 9/2009 |
| WO | WO-2010027827 A1 | | 3/2010 |
| WO | WO-2010077634 A1 | | 7/2010 |
| WO | WO-2011066342 A2 | | 6/2011 |
| WO | WO-2011066359 A1 | | 6/2011 |
| WO | WO-2012092426 A1 | | 7/2012 |
| WO | WO-2018175501 A1 | | 9/2018 |
| WO | WO-2019067092 A1 | | 4/2019 |
| WO | WO-2020127487 A1 | | 6/2020 |
| WO | WO-2021042066 A1 | | 3/2021 |

OTHER PUBLICATIONS

Chen et al (International Journal of Oncology, 2015, 46: 2629-2638).*
Waks et al (JAMA, 2019, 321(3): 288-300).*
Ried et al (Euro Journ of Cardio-Thoracic Surg, 2016, 49: 1545-1552).*
Beidler et al., (1988). "Cloning and High Level Expression of a Chimeric Antibody With Specificity for Human Carcinoembryonic Antigen," Journal of Immunology, 141:4053-4060.
Better et al., (1988). "*Escherichia coli* secretion of an active chimeric antibody fragment," Science 240:1041-1043.
Cao et al., (2014). "Targeting MLL1 H3K4 Methyltransferase Activity in Mixed-Lineage Leukemia," Mol Cell, 53(2):247-261.
Chalmers et al., (2017). "Analysis of 100,000 human cancer genomes reveals the landscape of tumor mutational burden," Genome Med, 9(1):34, 14 pages.

(Continued)

*Primary Examiner* — Sean E Aeder
(74) *Attorney, Agent, or Firm* — MORRISON & FOERSTER LLP

(57)     ABSTRACT

The present disclosure provides KMT2A-MAML2 fusion nucleic acid molecules, and KMT2A-MAML2 fusion polypeptides, as well as methods, kits and reagents for detecting such KMT2A-MAML2 fusion nucleic acid molecules and KMT2A-MAML2 fusion polypeptides. The disclosure also provides methods for evaluating, identifying, assessing, and/or treating an individual having a cancer, such an epithelial neoplasm or a thymoma.

36 Claims, 5 Drawing Sheets

Specification includes a Sequence Listing.

(56)     References Cited

OTHER PUBLICATIONS

Chen et al., (2014). "Aberrantly activated AREG-EGFR signaling is required for the growth and survival of CRTC1-MAML2 fusion-positive mucoepidermoid carcinoma cells," Oncogene, 33:3869-3877.

Chen et al., (2014). "Novel Biologic Therapies for 'Thymic Epithelial Tumors," Front Oncol., 4:103, 3 pages.

Detterbeck et al., (2011). "The Masaoka-Koga Stage Classification for Thymic Malignancies: Clarification and Definition of Terms," J Thoracic Oncology, 6(7 Suppl 3):S1710-6.

Duncan et al., (1988). "The binding site for C1q on IgG," Nature, 322:738-740.

Engels, (2010). "Epidemiology of thymoma and associated malignancies," J Thorac Oncol, 5(10):S260-S265.

Espinoza et al., (2013). "Notch inhibitors for cancer treatment," Pharmacol Ther., 139(2):95-110, 36 pages.

Forbes et al., (2015). "Cosmic: exploring the world's knowledge of somatic mutations in human cancer," Nucleic Acids Res, 43:D805-D811.

Frampton et al., (2013). "Development and validation of a clinical cancer genomic profiling test based on massively parallel DNA sequencing," Nature Biotechnology, and Online Methods Supplementary Information, 31(11):1023-1033.

Fuchs et al., (1991). "Targeting recombinant antibodies to the surface of Escherichia coli: fusion to a peptidoglycan associated lipoprotein," Biotechnology, 9:1370-1372.

Griffiths et al., (1993). "Human anti-self antibodies with high specificity from phage display libraries," Embo J., 12(2):725-734.

Hay et al., (1992). "Bacteriophage cloning and Escherichia coli expression of a human IgM fab," Hum Antibod Hybridomas, 3:81-85.

Huse et al., (1989). "Generation of a Large Combinatorial Library of the Immunoglobulin Repertoire in Phage Lambda," Science, 246:1275-1281, 7 pages.

International Search Report and Written Opinion received for International Patent Application No. PCT/US2020/048834 mailed on Dec. 15, 2020, 11 pages.

Jones et al., (1986). "Replacing the complementarity-determining regions in a human antibody with those from a mouse," Nature, 321:522-525.

Klossowski et al., (2020)."Menin inhibitor MI-3454 induces remission in MLL1-rearranged and NPM1-mutated models of leukemia," J Clin Inv., 130(2):981-997.

Kochert et al., (2011). "High-level expression of Mastermind-like 2 contributes to aberrant activation of the Notch signaling pathway in human lymphomas," Oneogene, 30(15):1831-1840.

Kohler et al., (1975). "Continuous cultures of fused cells secreting antibody of predefined specificity," Nature, 256:495-497.

Kozbor et al., (1983). "The production of monoclonal antibodies from human lymphocytes," Immunol Today, 4:72-9.

Krivtsov et al., (2019). "A Menin-MLL Inhibitor Induces Specific Chromatin Changes and Eradicates Disease in Models of MLL-Rearranged Leukemia," Cancer Cell, 36(6):660-673,e11.

Li et al., (2017). "Pathological complete response to ge fitinib in a 10-year-old boy with EGER-negative pulmonary mucoepidermoid carcinoma: a case report and literature review," Clin Respir J, 11(3):346-351.

Liu et al., (1987). "Chimeric mouse-human IgG1 antibody that can mediate lysis of cancer cells," Pnas USA, 84:3439-3443.

Liu et al., (1987). "Production of a mouse-human chimeric monoclonal antibody to CD20 with potent Fc-dependent biologic activity," J. Immunol., 139:3521-3526.

Lonberg et al., (1995). "Human antibodies from transgenic mice," Int Rev Immunol., 13:65-93.

Mariani et al., (2020). "Inv(11)(q21q23); KMT2A-MAML2, a Recurrent Genetic Abnormality in T-Cell Therapy-related Acute Lymphoblastic Leukemia, "J Pediatr Hematol Oncol., 42(4):e258-e261.

Menu et al., (2017). "First case of B All with KMT2A-MAML2 rearrangement: a case report," BMC Cancer, 17:363, 5 pages.

Metzker, (2010). "Sequencing Technologies—the Next Generation," Nature Reviews, 11:31-46.

Metzler et al., (2008). "inv(11)(q21q23) fuses MLL to the Notch co-activator mastermind-like 2 in secondary T-cell acute lymphoblastic leukemia," Leukemia, 22(9):1807-11.

Milne et al., (2002). "MLL Targets Set Domain Methyltransferase Activity to Hox Gene Promoters," Mol Cell, 10(5):1107-1117.

Morrison, (1985). "Transfectomas Provide Novel Chimeric Antibodies," Science, 229:1202-1207.

Nemoto et al., (2007). "Identification of a novel fusion gene MLL-MAML2 in secondary acute myelogenous leukemia and myelodysplastic syndrome with inv(11)(q21q23)," Genes Chromosom Cancer, 46(9):813-9.

Nishimura et al., (1987). "Recombinant Human-Mouse Chimeric Monoclonal Antibody Specific for Common Acute Lymphocytic Leukemia Antigen," Cancer Res, 47:999-1005.

Oi et al., (1986). "Chimeric Antibodies," BioTechniques, 4:214-221.

O'Neill, (2009). "Gefitinib as targeted therapy for mucoepidermoid carcinoma of the lung: Possible significance of CRTC1-MAML2 oncogene," Lung Cancer, 64(1):129-130.

Palande et al., (2020). "A liquid biopsy platform for detecting gene-gene fusions as glioma diagnostic biomarkers and drug targets," bioRxiv, 31 pages.

Petrini et al., (2013). "Whole Genorne and Transcriptome Sequencing of a R3 Thymoma," PLoS One, 8(4):e60572, 9 pages.

Petrini et al., (2014). "A specific missense mutation in GTF21 occurs at high frequency in thymic epithelial tumors," Nat Genet, 46(8):844-849, 23 pages.

Radovich et al., (2018). "The Integrated Genomic Landscape of Thymic Epithelial Tumors," Cancer Cell, 33(2):244-258.e10.

Scorsetti et al., (2016). "Thymoma and thymic carcinomas," Crit Rev Oncol Hematol, 99:332-50.

Shaw et al., (1988). "Mouse/Human Chimeric Antibodies to a Tumor-Associated Antigen: Biologic Activity of the Four Human IgG Subclasses," J. Natl. Cancer Inst., 80:1553-1559.

Sun et al., (1987). "Chimeric antibody with human constant regions and mouse variable regions directed against carcinoma-associated antigen 17-1A," PNAS USA, 84:214-218.

Sun et al., (2018). "A computational approach to distinguish somatic vs. germline origin of genomic alterations from deep sequencing of cancer specimens without a matched normal," PLoS Comput Biol, 14(2):e1005965, 13 pages.

Tang et al., (2014). "Homozygous inv(11)(q21q23) and MLL gene rearrangement in two patients with myeloid neoplasms," Int J Clin Exp Pathol., 7(6):3196-201.

Thomas et al., (2015). "Sunitinih in patients with chemotherapy-refractory thymoma and thymic carcinoma: An open-label phase 2 trial," Lancet Oncol, 16(2):177-186, 13 pages.

Tonon et al., (2013). "t1(11;19)(q21;p13) translocation in mucoepidermoid carcinoma creates a novel fusion product that disrupts a Notch signaling pathway," Nat Genet, 33(2):208-13.

Travis et al., (2015). Introduction to the 2015 World Health Organization Classification of Tumors of the Lung, Pleura, Thymus, and Heart, J Thorac Oncol, 10(9):1240-1242.

Verhoey et al., (1988). "Reshaping human antibodies: grafting an antilysozyme activity," Science, 239(4847):1534-6.

Wachter et al., (2014). "Functional characterisation of different MLL fusion proteins by using inducible Sleeping Beauty vectors," Cancer Lett, 352(2):196-202.

Walker et al., (2018). "Entospletinib in Combination with Induction Chemotherapy in Previously Untreated Acute Myeloid Leukemia: Response and Predictive Significance of HOXA9 and MEIS1 Expression," Cancer Res, 26(22):5852-5859.

Winters et al., (2017). "MLL-Rearranged Leukemias—An Update on Science and Clinical Approaches," Front Pediatr., 5:4, 21 pages.

Wood et al., (1985). "The synthesis and in vivo assembly of functional antibodies in yeast," Nature, 314:446-449.

(56)         References Cited

OTHER PUBLICATIONS

Xu et al., (2020). "Discovery of M-808 as a Highly Potent, Covalent, Small-Molecule Inhibitor of the Menin—MLL Interaction with Strong in Vivo Antitumor Activity," J Med Chem, 63(9):4997-5010, 33 pages.

Ziemin-van der Poel et al., (1991). "Identification of a gene, MLL, that spans the breakpoint in 11q23 translocations associated with human leukemias," PNAS USA, 88(23):10735-10739.

Obama et al., (1998). "Secondary monocytic leukemia with rearrangement of the MLL gene occurring during the course of adult T-cell leukemia," Int J Hematol., 68(3):323-6.

Massoth et al., (2020). "Pan-Cancer Landscape Analysis Reveals Recurrent KMT2A-MAML2 Gene Fusion in Aggressive Histologic Subtypes of Thymoma," JCO Precis Oncol, 4:109-115.

* cited by examiner

KMT2A-MAML2 FUSION MOLECULES AND USES THEREOF

CROSS-REFERENCE TO RELATED APPLICATION

This application is a national stage application under 35 U.S.C. § 371 of International Application No. PCT/US2020/048834, filed internationally on Aug. 31, 2020, which claims the benefit of U.S. Provisional Application 62/894,539, filed Aug. 30, 2019, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 197102003000SEQLIST.TXT, date recorded: Feb. 25, 2022, size: 126,838 bytes ).

FIELD OF THE INVENTION

The present disclosure relates to KMT2A-MAML2 fusion nucleic acid molecules and polypeptides, methods of detecting KMT2A-MAML2 fusions, as well as methods of diagnosis and treatment of diseases such as cancer.

BACKGROUND OF THE INVENTION

Thymoma, a neoplasm that arises from or exhibits thymic epithelial differentiation, is the most common tumor of the adult thymus (Engels E A, *Epidemiology of thymoma and associated malignancies*, J Thorac Oncol, vol. 10, pp. S260-5 (2010)). Thymoma has an unusually strong association with autoimmune diseases, particularly myasthenia gravis, which typically resolve with successful tumor resection. Nevertheless, the etiology and pathogenesis of thymoma remain largely unknown.

The most significant prognostic factors in thymoma are World Health Organization (WHO) histologic type, tumor stage, and completeness of surgical resection. WHO histologic types A (oval or fusiform-shaped cells) and AB (mixed histology) thymomas are associated with a favorable clinical course, with a 100% 5-year overall survival (Scorsetti M et al., *Critical Reviews in Oncology/Hematology Thymoma and thymic carcinomas*, Crit Rev Oncol/Hematol, vol. 99, pp. 332-350 (2016)). Types B1, B2, and B3 (epithelioid shape, with progressively decreased lymphoid infiltrate) show progressively worse survival, with type B3 demonstrating a 5-year survival ranging from 43% to 70% (Scorsetti M et al., *Critical Reviews in Oncology, Hematology Thymoma and thymic carcinomas*, Crit Rev Oncol/Hematol, vol. 99, pp. 332-350 (2016)). Surgery is the standard of care for localized tumors, with radiation and chemotherapy reserved for advanced stages (Scorsetti M et al., *Critical Reviews in Oncology/Hematology Thymoma and thymic carcinomas*, Crit Rev Oncol/Hematol, vol. 99, pp. 332-350 (2016)).

Recent genomic studies of thymic epithelial tumors have demonstrated a high prevalence of a thymoma-specific codon mutation (L424H) in the GTF2I gene of 100% of type A and 70% of AB thymomas, while whole- and arm-level copy number alterations, but no specific recurrently mutated genes, are common in types B2 and B3 thymomas (Radovich M et al., *The Integrated Genomic Landscape of*

*Thymic Epithelial Tumors*, Cancer Cell, vol. 33, no. 2, pp. 244-258.e10 (2018); Petrini I et al., *A specific missense mutation in GTF2I occurs at high frequency in thymic epithelial tumors*, Nat Genet, vol. 46, no. 8, pp. 844-849 (2014)). Thymomas have demonstrated a relatively low overall mutational burden, and reports of effective targeted therapies are sparse (Radovich M et al., *The Integrated Genomic Landscape of Thymic Epithelial Tumors*, Cancer Cell, vol. 33, no. 2, pp. 244-258.e10 (2018); Chen Y and Thomas A, *Novel Biologic Therapies for Thymic Epithelial Tumors*, Front Oncol, vol. 4, pp. 1-3 (2014); Thomas A et al., *Sunitinib in patients with chemotherapy-refractory thymoma and thymic carcinoma: An open-label phase 2 trial*, Lancet Oncol, vol. 16, no. 2, 177-186 (2015)). Only rare reports of gene fusions in thymoma are present in the literature, and, to our knowledge, no recurrent fusion has been reported to date (Petrini I et al., *A specific missense mutation in GTF2I occurs at high frequency in thymic epithelial tumors*, Nat Genet, vol. 46, no. 8, pp. 844-849 (2014); Petrini I et al., *Whole Genome and Transcriptome Sequencing of a B3 Thymoma*, PLoS One, vol. 8, no. 4, (2013)).

Accordingly, there is a need in the art for identifying novel genetic lesions associated with cancers, such as epithelial neoplasms, e.g., thymomas, and for developing methods of identifying, evaluating, and treating cancer patients with such genetic lesions.

All references cited herein, including patents, patent applications and publications, are hereby incorporated by reference in their entirety. To the extent that any reference incorporated by reference conflicts with the instant disclosure, the instant disclosure shall control.

BRIEF SUMMARY OF THE INVENTION

In some aspects, provided herein are KMT2A-MAML2 fusion nucleic acid molecules comprising exon 10 or a portion thereof, intron 10 or a portion thereof, exon 11 or a portion thereof, or intron 11 or a portion thereof of KMT2A and intron 1 or a portion thereof, exon 2 or a portion thereof, intron 2 or a portion thereof, exon 3 or a portion thereof, intron 3 or a portion thereof, or exon 4, of MAML2, and a KMT2A-MAML2 breakpoint that fuses exon 10 or the portion thereof, intron 10 or the portion thereof, exon 11 or the portion thereof, or intron 11 or the portion thereof, of KMT2A to intron 1 or the portion thereof, exon 2 or the portion thereof, intron 2 or the portion thereof, exon 3 or the portion thereof, intron 3 or the portion thereof, or exon 4, of MAML2. In some embodiments, the nucleic acid molecule comprises 5 or more nucleotides from exon 10, intron 10, exon 11, or intron 11 of KMT2A on the 5' end of the KMT2A-MAML2 breakpoint, and 5 or more nucleotides from intron 1, exon 2, intron 2, exon 3, intron 3, or exon 4, of MAML2 on the 3' end of the KMT2A-MAML2 breakpoint. In some embodiments, wherein the nucleic acid molecule comprises a nucleotide sequence comprising, in the 5' to 3' direction: (a) exon 10 or the portion thereof, or exon 11 or the portion thereof, of KMT2A fused to exon 2 or the portion thereof, exon 3 or the portion thereof, or exon 4, of MAML2; (b) intron 10 or the portion thereof, or intron 11 or the portion thereof, of KMT2A fused to intron 1 or the portion thereof, intron 2 or the portion thereof, or intron 3 or the portion thereof, of MAML2; (c) exon 10 or the portion thereof, or exon 11 or the portion thereof, of KMT2A fused to intron 1 or the portion thereof, intron 2 or the portion thereof, or intron 3 or the portion thereof, of MAML2; or (d) intron 10 or the portion thereof, or intron 11 or the portion thereof, of KMT2A fused to exon 2 or the portion thereof, exon 3 or the portion thereof, or exon 4, of MAML2. In some embodiments, the nucleic acid molecule comprises a nucleotide sequence comprising, in the 5' to 3' direction: (a) exons 1-9 and exon 10, or a portion of exon 10, of KMT2A and exon 2 or a portion thereof and exons 3-5, exon 3 or a portion thereof and exons 4-5, or exons 4-5, of MAML2; or (b) exons 1-10 and exon 11, or a portion of exon 11, of KMT2A and exon 2 or a portion thereof and exons 3-5, exon 3 or a portion thereof and exons 4-5, or exons 4-5, of MAML2. In some embodiments, the nucleic acid molecule is an isolated nucleic acid molecule. In some embodiments, the nucleic acid molecule is an RNA molecule. In some embodiments, the nucleic acid molecule is a DNA molecule. In some embodiments, the nucleic acid molecule is a cfDNA or a cfRNA molecule.

In some embodiments, the KMT2A-MAML2 fusion nucleic acid molecule comprises a KMT2A-MAML2 breakpoint comprising: (a) the nucleic acid sequence of SEQ ID NO: 21 or an nucleic acid sequence at least about 85% (e.g., any of about 85%, 86%, 87%0, 88%, 89%, 90%, 91%, 92%, 93%, 94%, 95%, 96, 97%, 98%, 99%, or 100%) identical to SEQ ID NO: 21 fused to the nucleic acid sequence of SEQ ID NO: 22 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 22; (b) the nucleic acid sequence of SEQ ID NO: 23 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 23 fused to the nucleic acid sequence of SEQ ID NO: 24 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 24; (c) the nucleic acid sequence of SEQ ID NO: 25 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 25 fused to the nucleic acid sequence of SEQ ID NO: 26 or an nucleic acid sequence at least about 85% (e.g., any of about 85%, 860, 87%, 88%, 89%, 90%, 910, 92%, 93%, 94%, 95%, 96%, 97%, 98%, 990, or 100%) identical to SEQ ID NO: 26; or (d) the nucleic acid sequence of SEQ ID NO: 27 or an nucleic acid sequence at least about 85% (e.g., any of about 850, 86%, 87%, 88%, 89%, 90%, 91%, 92%, 930, 94%, 95%, 96%, 97%, 98%, 99%, or 100%) identical to SEQ ID NO: 27 fused to the nucleic acid sequence of SEQ ID NO: 28 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 28.

In some embodiments, the KMT2A-MAML2 breakpoint comprises a nucleotide sequence comprising a fusion of the nucleotide sequence of SEQ ID NO: 7, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 8, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 9, or a nucleotide sequence at least about 85% (e.g., any of about 85%, 86%, 87%, 88%, 899%, 90%, 91%, 92%, 93%, 94%, 95%, 96%, 97%, 98%, 99%, or 100%) identical thereto, fused to the nucleotide sequence of SEQ ID NO: 10, or a nucleotide sequence at least about 85% (e.g., any of about 85%, 86%, 87%, 88%, 89%, 90%, 91% 92%, 93%, 94%, 95%, 96%, 97%, 98%, 990, or 100%) identical thereto. In some embodiments, the KMT2A-MAML2 breakpoint comprises a nucleotide sequence comprising a fusion of the nucleotide sequence of SEQ ID NO: 11, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 12, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 13, or a nucleotide sequence at least about 8596 (e.g., any of about 8596, 86%, 87%, 88%, 89%, 90%, 91%, 9296, 93%, 94%, 95%, 96%, 97%, 98%, 99%, or 100%) identical thereto, fused to the nucleotide sequence of SEQ ID NO: 14, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 15, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 16, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 17, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 18, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 19, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 20, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 21, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 22, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 23, or a nucleotide sequence at least about 85% (e.g., any of about 85%, 86%, 87%, 88%, 89%, 90%, 91%, 92%, 93%, 94%, 95%, 96%, 97%, 98%, 99%, or 100%)

identical thereto, fused to the nucleotide sequence of SEQ ID NO: 24, or a nucleotide sequence at least about 85% (e.g., any of about 85%, 86%, 87%, 88%, 89%, 90%, 91%, 92%, 93%, 94%, 95%, 96%, 97%, 98%, 990%, or 100%) identical thereto. In some embodiments, the KMT2A-MAML2 break- point comprises a nucleotide sequence comprising a fusion of the nucleotide sequence of SEQ ID NO: 25, or a nucleo- tide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 26, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 27, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 28, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto.

In another aspect, provided herein are probes or baits for the detection of a KMT2A-MAML2 fusion nucleic acid molecule, comprising a capture nucleic acid molecule con- figured to hybridize to a target nucleic acid molecule com- prising a KMT2A-MAML2 fusion nucleic acid molecule provided herein, or its complement. In some embodiments, the capture nucleic acid molecule is configured to hybridize to the KMT2A-MAML2 fusion nucleic acid molecule of the target nucleic acid molecule, or its complement. In some embodiments, the capture nucleic acid molecule is config- ured to hybridize to the KMT2A-MAML2 breakpoint. In some embodiments, the probe or bait is a bait, and the capture nucleic acid molecule comprises between about 50 and about 1000 nucleotides, between about 100 and about 500 nucleotides, between about 100 and about 300 nucleo- tides, or between about 100 and 200 nucleotides. In some embodiments, the probe or bait is a probe, and the capture nucleic acid molecule comprises between about 10 and about 30 nucleotides. In some embodiments, the probe or bait is conjugated to a detection reagent. In some embodi- ments, the detection reagent is a fluorescent marker. In some embodiments, the probe or bait is conjugated to an affinity tag. In some embodiments, the affinity tag is an antibody, an antibody fragment, or biotin. In some embodiments, the capture nucleic acid molecule comprises a DNA, RNA, or mixed DNA/RNA molecule.

In another aspect, provided herein are kits comprising a probe or bait provided herein and instructions for use of the probe or bait to detect a KMT2A-MAML2 fusion nucleic acid molecule provided herein.

In another aspect, provided herein are vectors comprising a KMT2A-MAML2 fusion nucleic acid molecule provided herein.

In another aspect, provided herein are host cells compris- ing a vector provided herein.

In another aspect, provided herein are KMT2A-MAML2 fusion polypeptides comprising: (a) an amino acid sequence encoded by a nucleic acid molecule comprising exon 10 or a portion thereof, or exon 11 or a portion thereof, of KMT2A and exon 2 or a portion thereof, exon 3 or a portion thereof, or exon 4, of MAML2, and a KMT2A-MAML2 breakpoint that fuses exon 10 or a portion thereof, or exon 11 or a portion thereof, of KMT2A to exon 2 or a portion thereof, exon 3 or a portion thereof, or exon 4, of MAML2; or (b) an amino acid sequence at least about 85% (e.g., any of about 85%, 86%, 87%, 88%, 89%, 90%, 91%, 92%, 93%, 94%, 95%, 96%, 97%, 98%, 99%, or 100%) identical to the KMT2A-MAML2 fusion polypeptide of (a). In some embodiments, the fusion polypeptide comprises 5 or more amino acids encoded by the 3' end of exon 10 or the portion thereof, or the 3' end of exon 11 or the portion thereof, of KMT2A fused to 5 or more amino acids encoded by the 5' end of exon 2 or the portion thereof, exon 3 or the portion thereof, or exon 4, of MAML2. In some embodiments, the fusion polypeptide comprises: (a) an amino acid sequence encoded by a nucleic acid molecule comprising, in the 5' to 3' direction, exons 1-9 and exon 10, or a portion of exon 10, of KMT2A and exon 2 or a portion thereof and exons 3-5, exon 3 or a portion thereof and exons 4-5, or exons 4-5, of MAML2; (b) an amino acid sequence encoded by a nucleic acid molecule comprising, in the 5' to 3' direction, exons 1-10 and exon 11, or a portion of exon 11, of KMT2A and exon 2 or a portion thereof and exons 3-5, exon 3 or a portion thereof and exons 4-5, or exons 4-5, of MAML2; or (c) an amino acid sequence at least about 85% (e.g., any of about 85%, 86%, 87%, 88%, 89%, 90%, 91%, 92%, 93%, 94%, 95%, 96%, 97%, 98%, 99%, or 100%) identical to the KMT2A-MAML2 fusion polypeptide of (a)-(b). In some embodiments, in vivo expression of the fusion polypeptide results in modulation in the expression of one or more genes in the NOTCH pathway. In some embodiments, the fusion polypeptide comprises a histone methyltransferase activity. In some embodiments, the fusion polypeptide comprises a constitutive histone methyltransferase activity. In some embodiments, the fusion polypeptide is an isolated polypep- tide.

In another aspect, provided herein are antibodies or anti- body fragments that specifically bind to a KMT2A-MAML2 fusion polypeptide provided herein. In some embodiments, the antibody or antibody fragment comprises a label or a tag. In some embodiments, the label or tag is a radiolabel, a fluorescent label, an enzymatic label, a nucleotide sequence tag, or biotin.

In another aspect, provided herein are kits comprising an antibody or antibody fragment provided herein and instruc- tions for use of the antibody or antibody fragment to detect the KMT2A-MAML2 fusion polypeptide provided herein. In another aspect, provided herein are kits comprising a KMT2A-MAML2 fusion polypeptide provided herein. In another aspect, provided herein are kits comprising an antibody or antibody fragment provided herein, a KMT2A- MAML2 fusion polypeptide provided herein, and instruc- tions for use of the antibody or antibody fragment to detect the KMT2A-MAML2 fusion polypeptide provided herein.

In another aspect, provided herein is a method of detect- ing the presence of a KMT2A-MAML2 fusion, the method comprising detecting a KMT2A-MAML2 fusion nucleic acid molecule provided herein, or a KMT2A-MAML2 fusion polypeptide provided herein, in a sample. In some embodiments, the sample is obtained from an individual. In some embodiments, the individual has a cancer, is suspected of having cancer, is being tested for cancer, or is being tested for a susceptibility to cancer. In some embodiments, the method further comprises selectively enriching for one or more nucleic acids comprising KMT2A or MAML2 nucleo- tide sequences to produce an enriched sample. In some embodiments, the method further comprises selectively enriching for one or more nucleic acids comprising the KMT2A-MAML2 breakpoint to produce an enriched sample. In some embodiments, selectively enriching comprises using a bait provided herein. In some embodiments, the method comprises detecting the KMT2A-MAML2 fusion nucleic acid molecule, the method comprising: combining a bait set comprising a bait provided herein with the sample, thereby hybridizing baits in the bait set to one or more nucleic acid molecules in the sample and producing nucleic acid hybrids; isolating the nucleic acid hybrids to produce an enriched sample; and sequencing the one or more nucleic acid molecules in the enriched sample. In some embodiments, the method comprises detecting the KMT2A-MAML2 fusion nucleic acid molecule, the method comprising: combining or staining the sample with a probe provided herein; and confirming that the probe has hybridized to the KMT2A-MAML2 fusion nucleic acid molecule. In some embodiments, the method comprises detecting the KMT2A-MAML2 fusion nucleic acid molecule, the method comprising: combining or staining the sample with a first probe configured to hybridize to a nucleic acid molecule encoding KMT2A and a second probe configured to hybridize to a nucleic acid molecule encoding MAML2; and confirming that the first probe and the second probe have both hybridized to the same nucleic acid molecule, thereby detecting the KMT2A-MAML2 fusion nucleic acid molecule. In some embodiments, confirming that the first probe and the second probe have both hybridized to the same nucleic acid molecule comprises detecting co-localization of the first probe and the second probe. In some embodiments, the cancer is an epithelial neoplasm.

In another aspect, provided herein is a method of assessing an individual, wherein the individual has cancer, is suspected of having cancer, is being tested for cancer, or is being tested for a susceptibility to cancer, the method comprising: (a) detecting a KMT2A-MAML2 fusion nucleic acid molecule provided herein, or a KMT2A-MAML2 fusion polypeptide provided herein, in a sample from the individual; and (b) providing an assessment of the presence of the KMT2A-MAML2 fusion nucleic acid molecule or polypeptide in the sample. In some embodiments, the cancer is an epithelial neoplasm.

In another aspect, provided herein is a method of assessing a cancer in an individual, the method comprising detecting a KMT2A-MAML2 fusion nucleic acid molecule provided herein, or a KMT2A-MAML2 fusion polypeptide provided herein, in a sample obtained from the individual, wherein the presence of the KMT2A-MAML2 fusion nucleic acid molecule or polypeptide in the sample identifies the cancer as likely to respond to an anti-cancer therapy. In some embodiments, the cancer is an epithelial neoplasm.

In another aspect, provided herein is a method of identifying an individual having cancer who may benefit from a treatment comprising an anti-cancer therapy, the method comprising detecting a KMT2A-MAML2 fusion nucleic acid molecule provided herein, or a KMT2A-MAML2 fusion polypeptide provided herein, in a sample obtained from the individual, wherein the presence of the KMT2A-MAML2 fusion nucleic acid molecule or polypeptide in the sample identifies the individual as one who may benefit from the treatment comprising an anti-cancer therapy. In some embodiments, the cancer is an epithelial neoplasm.

In another aspect, provided herein is a method of selecting a therapy for an individual having cancer, the method comprising acquiring knowledge of a KMT2A-MAML2 fusion nucleic acid molecule provided herein, or a KMT2A-MAML2 fusion polypeptide provided herein, in a sample obtained from the individual, wherein: (a) the presence of the KMT2A-MAML2 fusion nucleic acid molecule or polypeptide in the sample identifies the individual as one who may benefit from treatment comprising an anti-cancer therapy; or (b) responsive to the acquisition of said knowledge: (i) the individual is classified as a candidate to receive treatment with an anti-cancer therapy; and/or (ii) the individual is identified as likely to respond to a treatment that comprises an anti-cancer therapy. In some embodiments, acquiring knowledge comprises detecting a KMT2A-MAML2 fusion nucleic acid molecule provided herein, or a KMT2A-MAML2 fusion polypeptide provided herein, in a sample from the individual. In some embodiments, the cancer is an epithelial neoplasm.

In another aspect, provided herein is a method of identifying one or more treatment options for an individual having cancer, the method comprising: (a) acquiring knowledge of a KMT2A-MAML2 fusion nucleic acid molecule provided herein, or a KMT2A-MAML2 fusion polypeptide provided herein, in a sample from the individual; and (b) generating a report comprising one or more treatment options identified for the individual based at least in part on said knowledge, wherein the one or more treatment options comprise an anti-cancer therapy. In some embodiments, acquiring knowledge comprises detecting a KMT2A-MAML2 fusion nucleic acid molecule provided herein, or a KMT2A-MAML2 fusion polypeptide provided herein, in a sample from the individual. In some embodiments, the cancer is an epithelial neoplasm.

In another aspect, provided herein is a method of treating cancer, comprising administering to an individual an effective amount of an anti-cancer therapy, wherein the cancer comprises a KMT2A-MAML2 fusion nucleic acid molecule provided herein, or a KMT2A-MAML2 fusion polypeptide provided herein. In some embodiments, the cancer is an epithelial neoplasm.

In another aspect, provided herein is a method of treating cancer, comprising, responsive to knowledge of a KMT2A-MAML2 fusion nucleic acid molecule provided herein, or a KMT2A-MAML2 fusion polypeptide provided herein, in a sample from an individual, administering to the individual an effective amount of an anti-cancer therapy. In some embodiments, the cancer is an epithelial neoplasm.

In another aspect, provided herein is a method of treating cancer, comprising: (a) acquiring knowledge of a KMT2A-MAML2 fusion nucleic acid molecule provided herein, or a KMT2A-MAML2 fusion polypeptide provided herein, in a sample from an individual; and (b) administering to the individual an effective amount of an anti-cancer therapy. In some embodiments, acquiring knowledge comprises detecting a KMT2A-MAML2 fusion nucleic acid molecule provided herein, or a KMT2A-MAML2 fusion polypeptide provided herein, in a sample from the individual. In some embodiments, the cancer is an epithelial neoplasm.

In another aspect, provided herein is a method of assessing an individual, wherein the individual has an epithelial neoplasm, is suspected of having an epithelial neoplasm, is being tested for an epithelial neoplasm, or is being tested for a susceptibility to an epithelial neoplasm, the method comprising: (a) detecting a KMT2A-MAML2 fusion nucleic acid molecule or a KMT2A-MAML2 fusion polypeptide in a sample from the individual; and (b) providing an assessment of the presence of the KMT2A-MAML2 fusion nucleic acid or polypeptide in the sample.

In another aspect, provided herein is a method of assessing an epithelial neoplasm in an individual, the method comprising detecting a KMT2A-MAML2 fusion nucleic acid molecule or a KMT2A-MAML2 fusion polypeptide in a sample obtained from the individual, wherein the presence of the KMT2A-MAML2 fusion nucleic acid molecule or polypeptide in the sample identifies the epithelial neoplasm as likely to respond to an anti-cancer therapy.

In another aspect, provided herein is a method of identifying an individual having an epithelial neoplasm who may benefit from a treatment comprising an anti-cancer therapy, the method comprising detecting a KMT2A-MAML2 fusion nucleic acid molecule or a KMT2A-MAML2 fusion polypeptide in a sample obtained from the individual, wherein the presence of the KMT2A-MAML2 fusion nucleic acid molecule or polypeptide in the sample identifies the individual as one who may benefit from the treatment comprising an anti-cancer therapy.

In another aspect, provided herein is a method of selecting a therapy for an individual having an epithelial neoplasm, the method comprising acquiring knowledge of a KMT2A-MAML2 fusion nucleic acid molecule or a KMT2A-MAML2 fusion polypeptide in a sample obtained from the individual, wherein: (a) presence of the KMT2A-MAML2 fusion nucleic acid molecule or polypeptide in the sample identifies the individual as one who may benefit from treatment comprising an anti-cancer therapy; or (b) responsive to the acquisition of said knowledge: (i) the individual is classified as a candidate to receive treatment with an anti-cancer therapy; and/or (ii) the individual is identified as likely to respond to a treatment that comprises an anti-cancer therapy. In some embodiments, acquiring knowledge comprises detecting the KMT2A-MAML2 fusion nucleic acid molecule or the KMT2A-MAML2 fusion polypeptide in a sample from the individual.

In another aspect, provided herein is a method of identifying one or more treatment options for an individual having an epithelial neoplasm, the method comprising: (a) acquiring knowledge of a KMT2A-MAML2 fusion nucleic acid molecule or a KMT2A-MAML2 fusion polypeptide in a sample from the individual; and (b) generating a report comprising one or more treatment options identified for the individual based at least in part on the presence of the KMT2A-MAML2 fusion nucleic acid molecule or polypeptide in the sample, wherein the one or more treatment options comprise an anti-cancer therapy. In some embodiments, acquiring knowledge comprises detecting the KMT2A-MAML2 fusion nucleic acid molecule or the KMT2A-MAML2 fusion polypeptide in a sample from the individual.

In another aspect, provided herein is a method of treating an epithelial neoplasm, comprising administering to an individual an effective amount of an anti-cancer therapy, wherein the epithelial neoplasm comprises a KMT2A-MAML2 fusion nucleic acid molecule or a KMT2A-MAML2 fusion polypeptide.

In another aspect, provided herein is a method of treating an epithelial neoplasm, comprising, responsive to knowledge of a KMT2A-MAML2 fusion nucleic acid molecule or of a KMT2A-MAML2 fusion polypeptide in a sample from an individual, administering to the individual an effective amount of an anti-cancer therapy.

In another aspect, provided herein is a method of treating an epithelial neoplasm, comprising: (a) acquiring knowledge of a KMT2A-MAML2 fusion nucleic acid molecule or a KMT2A-MAML2 fusion polypeptide in a sample from an individual; and (b) administering to the individual an effective amount of an anti-cancer therapy. In some embodiments, acquiring knowledge comprises detecting the KMT2A-MAML2 fusion nucleic acid molecule or the KMT2A-MAML2 fusion polypeptide in a sample from the individual.

In some embodiments of any of the preceding aspects, the KMT2A-MAML2 fusion nucleic acid molecule comprises: exon 7 or a portion thereof, intron 7 or a portion thereof, exon 8 or a portion thereof, intron 8 or a portion thereof, exon 9 or a portion thereof, intron 9 or a portion thereof, exon 10 or a portion thereof, intron 10 or a portion thereof, exon 11 or a portion thereof, or intron 11 or a portion thereof, of KMT2A and intron 1 or a portion thereof, exon 2 or a portion thereof, intron 2 or a portion thereof, exon 3 or a portion thereof, intron 3 or a portion thereof, or exon 4, of MAML2; and a KMT2A-MAML2 breakpoint that fuses exon 7 or the portion thereof, intron 7 or the portion thereof, exon 8 or the portion thereof, intron 8 or the portion thereof, exon 9 or the portion thereof, intron 9 or the portion thereof, exon 10 or the portion thereof, intron 10 or the portion thereof, exon 11 or the portion thereof, or intron 11 or the portion thereof, of KMT2A to intron 1 or the portion thereof, exon 2 or the portion thereof, intron 3 or the portion thereof, exon 3 or the portion thereof, or exon 4, of MAML2. In some embodiments, the KMT2A-MAML2 fusion nucleic acid molecule comprises 5 or more nucleotides from exon 7, intron 7, exon 8, intron 8, exon 9, intron 9, exon 10, intron 10, exon 11, or intron 11 of KMT2A on the 5' end of the KMT2A-MAML2 breakpoint, and 5 or more nucleotides from intron 1, exon 2, intron 2, exon 3, intron 3, or exon 4, of MAML2 on the 3' end of the KMT2A-MAML2 breakpoint. In some embodiments, the KMT2A-MAML2 fusion nucleic acid molecule comprises: (a) exon 7 or the portion thereof, exon 8 or the portion thereof, exon 9 or the portion thereof, exon 10 or the portion thereof, or exon 11 or the portion thereof, of KMT2A fused to exon 2 or the portion thereof, exon 3 or the portion thereof, or exon 4 or the portion thereof, of MAML2; (b) intron 7, 8, 9, 10, or 11, or the portion thereof, of KMT2A fused to intron 1, 2, or 3, or the portion thereof, of MAML2; (c) exon 7 or the portion thereof, exon 8 or the portion thereof, exon 9 or the portion thereof, exon 10 or the portion thereof, or exon 11 or the portion thereof, of KMT2A fused to intron 1, 2, or 3, or the portion thereof, of MAML2; or (d) intron 7, 8, 9, 10, or 11, or the portion thereof, of KMT2A fused to exon 2 or the portion thereof, exon 3 or the portion thereof, or exon 4 or the portion thereof, of MAML2. In some embodiments, the KMT2A-MAML2 fusion nucleic acid molecule comprises a nucleotide sequence comprising, in the 5' to 3' direction: (a) exons 1-6 and exon 7, or a portion of exon 7, of KMT2A and exon 2 or a portion thereof and exons 3-5, exon 3 or a portion thereof and exons 4-5, or exons 4-5, of MAML2; (b) exons 1-7 and exon 8, or a portion of exon 8, of KMT2A and exon 2 or a portion thereof and exons 3-5, exon 3 or a portion thereof and exons 4-5, or exons 4-5, of MAML2; (c) exons 1-8 and exon 9, or a portion of exon 9, of KMT2A and exon 2 or a portion thereof and exons 3-5, exon 3 or a portion thereof and exons 4-5, or exons 4-5, of MAML2; (d) exons 1-9 and exon 10, or a portion of exon 10, of KMT2A and exon 2 or a portion thereof and exons 3-5, exon 3 or a portion thereof and exons 4-5, or exons 4-5, MAML2; or (e) exons 1-10 and exon 11, or a portion of exon 11, of KMT2A and exon 2 or a portion thereof and exons 3-5, exon 3 or a portion thereof and exons 4-5, or exons 4-5, of MAML2.

In some embodiments, the KMT2A-MAML2 breakpoint comprises a nucleotide sequence comprising a fusion of the nucleotide sequence of SEQ ID NO: 7, or a nucleotide sequence at least about 85% (e.g., any of about 85%, 86%, 87%, 88%, 89%, 90%, 91%, 92%, 93%, 94%, 95%, 96%, 97%, 98%, 990%, or 100%) identical thereto, fused to the nucleotide sequence of SEQ ID NO: 8, or a nucleotide sequence at least about 85% (e.g., any of about 85%, 86%, 87%, 88%, 89%, 90%, 91%, 92%, 93%, 94%, 95%, 96%, 97%, 98%, 99%/0, or 100%) identical thereto. In some embodiments, the KMT2A-MAML2 breakpoint comprises a nucleotide sequence comprising a fusion of the nucleotide sequence of SEQ ID NO: 9, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 10, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 11, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 12, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 13, or a nucleotide sequence at least about 8596 (e.g., any of about 8596, 86%, 87%, 88%, 89%, 90%, 91%, 9296, 93%, 94%, 95%, 96%, 97%, 98%, 99%, or 100%) identical thereto, fused to the nucleotide sequence of SEQ ID NO: 14, or a nucleotide sequence at least about 85% (e.g., any of about 85%, 8696, 87%, 88%, 89%, 90%, 91%, 92%, 93%, 94%, 95%, 96%, 97%, 98%, 9996, or 100%) identical thereto. In some embodiments, the KMT2A-MAML2 breakpoint comprises a nucleotide sequence comprising a fusion of the nucleotide sequence of SEQ ID NO: 15, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 16, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 17, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 18, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 19, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 20, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 21, or a nucleotide sequence at least about 85% (e.g., any of about 85%, 86%, 87%, 88%, 89%, 90%, 91%, 92%, 93%, 94%, 95%, 96%, 97%/0, 98%, 99%, or 100%) identical thereto, fused to the nucleotide sequence of SEQ ID NO: 22, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 23, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 24, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 25, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 26, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 27, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 28, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto.

In some embodiments of any of the preceding aspects, the KMT2A-MAML2 fusion polypeptide comprises: (a) an amino acid sequence encoded by a nucleic acid molecule comprising: exon 7 or a portion thereof, exon 8 or a portion thereof, exon 9 or a portion thereof, exon 10 or a portion thereof, or exon 11 or a portion thereof, of KMT2A and exon 2 or a portion thereof, exon 3 or a portion thereof, or exon 4, of MAML2; and a KMT2A-MAML2 breakpoint that fuses exon 7 or the portion thereof, exon 8 or the portion thereof, exon 9 or the portion thereof, exon 10 or the portion thereof, or exon 11 or the portion thereof, of KMT2A to exon 2 or the portion thereof, exon 3 or the portion thereof, or exon 4, of MAML2; or (b) an amino acid sequence at least about 85% (e.g., any of about 85%, 86%, 87%, 88%, 89%, 90%, 91%, 92%, 93%, 94%, 95%, 96%, 97%, 98%, 99%, or 100%) identical to the KMT2A-MAML2 fusion polypeptide of (a). In some embodiments, the KMT2A-MAML2 fusion polypeptide comprises 5 or more amino acids encoded by the 3' end of exon 7 or the portion thereof, the 3' end of exon 8 or the portion thereof, the 3' end of exon 9 or the portion thereof, the 3' end of exon 10 or the portion thereof, or the 3' end of exon 11 or the portion thereof, of KMT2A fused to 5 or more amino acids encoded by the 5' end of exon 2 or the portion thereof, exon 3 or the portion thereof, or exon 4, of MAML2. In some embodiments, the fusion polypeptide comprises: (a) an amino acid sequence encoded by a KMT2A-MAML2 fusion nucleic acid molecule comprising, in the 5' to 3' direction: (i) exons 1-6 and exon 7, or a portion of exon 7, of KMT2A and exon 2 or a portion thereof and exons 3-5, exon 3 or a portion thereof and exons 4-5, or exons 4-5, of MAML2, (ii) exons 1-7 and exon 8, or a portion of exon 8, of KMT2A and exon 2 or a portion thereof and exons 3-5, exon 3 or a portion thereof and exons 4-5, or exons 4-5, of MAML2, (iii) exons 1-8 and exon 9, or a portion of exon 9, of KMT2A and exon 2 or a portion thereof and exons 3-5, exon 3 or a portion thereof and exons 4-5, or exons 4-5, of MAML2, (iv) exons 1-9 and exon 10, or a portion of exon 10, of KMT2A and exon 2 or a portion thereof and exons 3-5, exon 3 or a portion thereof and exons 4-5, or exons 4-5, of MAML2, or (v) exons 1-10 and exon 11, or a portion of exon 11, of KMT2A and exon 2 or a portion thereof and exons 3-5, exon 3 or a portion thereof and exons 4-5, or exons 4-5, of MAML2; or (b) an amino acid sequence at least about 85% (e.g., any of about 85%, 86%, 87%, 88%, 89%, 90%, 91%, 92%, 93%, 94%, 95%, 96%, 97%, 98%, 99%, or 100%) identical to the KMT2A-MAML2 fusion polypeptide of (a). In some embodiments, in vivo expression of the fusion polypeptide results in modulation in the expression of one or more genes in the NOTCH pathway. In some embodiments, the KMT2A-MAML2 fusion polypeptide comprises a histone methyltransferase activity. In some embodiments, the KMT2A-MAML2 fusion polypeptide comprises a constitutive histone methyltransferase activity.

In some embodiments of any of the preceding aspects, the epithelial neoplasm is a thymoma. In some embodiments, the thymoma has a B2 histology, a B3 histology, or a B2-B3 histology. In some embodiments, the thymoma is a stage 2b, 4a, or 4b thymoma. In some embodiments, the thymoma is recurrent. In some embodiments, the thymoma is metastatic. In some embodiments, the thymoma comprises a mutation in a gene selected from the group consisting of TP53, ARID1A, TERT, and SF3B1. In some embodiments, the thymoma comprises a mutation in one or more genes provided in Tables 3-6.

In some embodiments, the individual has received a prior anti-cancer treatment. In some embodiments, the individual has received a prior anti-cancer treatment comprising one or more of a chemotherapy, surgical resection, radiation, MGCD516, BBI608, paclitaxel, or sunitinib. In some embodiments, the anti-cancer therapy is a small molecule, an antibody, or a nucleic acid. In some embodiments, the anti-cancer therapy is an agent that inhibits activity or expression of the KMT2A-MAML2 polypeptide, or a NOTCH pathway inhibitor. In some embodiments, the NOTCH pathway inhibitor inhibits Notch1.

In some embodiments, the anti-cancer therapy is an agent that inhibits activity or expression of epidermal growth factor receptor (EGFR). In some embodiments, the agent is a small molecule, an antibody, or a nucleic acid. In some embodiments, the agent is selected from lapatinib, gefitinib, erlotinib, cetuximab, canertinib, panitumumab, nimotuzumab, OSI-632, vandetanib, afatinib, MP-412, AEE-788, neratinib, XL-647, dacomitinib, AZD-8931, CUDC-101, and CO-1686.

In some embodiments of any of the preceding aspects, the sample comprises fluid, cells, or tissue. In some embodiments, the sample comprises a tumor biopsy or a circulating tumor cell. In some embodiments, the sample is a nucleic acid sample. In some embodiments, the nucleic acid sample comprises mRNA, genomic DNA, circulating tumor DNA, cell-free RNA, or cell-free DNA. In some embodiments, the KMT2A-MAML2 fusion nucleic acid molecule is detected in the sample by one or more methods selected from the group consisting of a nucleic acid hybridization assay, an amplification-based assay, a PCR-RFLP assay, real-time PCR, sequencing, a screening analysis, FISH, spectral karyotyping or MFISH, comparative genomic hybridization, in situ hybridization, sequence-specific priming (SSP) PCR, HPLC, and mass-spectrometric genotyping. In some embodiments, the sample is a protein sample. In some embodiments, the KMT2A-MAML2 fusion polypeptide is detected in the sample by one or more methods selected from the group consisting of immunoblotting. ELISA, immunohistochemistry, and mass spectrometry.

In some embodiments, the KMT2A-MAML2 fusion nucleic acid molecule comprises a KMT2A-MAML2 breakpoint comprising: (a) the nucleic acid sequence of SEQ ID NO: 7 or an nucleic acid sequence at least about 85% (e.g., any of about 85%, 86%, 87%, 88%, 89/c, 90%, 91%, 92%, 93%, 94%, 95%, 96%, 97%, 98%, 99%, or 100%) identical to SEQ ID NO: 7 fused to the nucleic acid sequence of SEQ ID NO: 8 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 8; (b) the nucleic acid sequence of SEQ ID NO: 9 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 9 fused to the nucleic acid sequence of SEQ ID NO: 10 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 10; (c) the nucleic acid sequence of SEQ ID NO: 11 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 11 fused to the nucleic acid sequence of SEQ ID NO: 12 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 12; (d) the nucleic acid sequence of SEQ ID NO: 13 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 13 fused to the nucleic acid sequence of SEQ ID NO: 14 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 14; (e) the nucleic acid sequence of SEQ ID NO: 15 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 15 fused to the nucleic acid sequence of SEQ ID NO: 16 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 16; (f) the nucleic acid sequence of SEQ ID NO: 17 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 17 fused to the nucleic acid sequence of SEQ ID NO: 18 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 18; (g) the nucleic acid sequence of SEQ ID NO: 19 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 19 fused to the nucleic acid sequence of SEQ ID NO: 20 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 20; (h) the nucleic acid sequence of SEQ ID NO: 21 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 21 fused to the nucleic acid sequence of SEQ ID NO: 22 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 22; (i) the nucleic acid sequence of SEQ ID NO: 23 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 23 fused to the nucleic acid sequence of SEQ ID NO: 24 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 24; (j) the nucleic acid sequence of SEQ ID NO: 25 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 25 fused to the nucleic acid sequence of SEQ ID NO: 26 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 26; or (k) the nucleic acid sequence of SEQ ID NO: 27 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 27 fused to the nucleic acid sequence of SEQ ID NO: 28 or an nucleic acid sequence at least about 85% (e.g., any of about 85%, 86%, 87%, 88%, 89%, 90%, 91%, 92%, 93%, 94%, 95%, 96%, 97%, 98%, 99%, or 100%) identical to SEQ ID NO: 28.

BRIEF DESCRIPTION OF THE DRAWINGS

FIG. 1A shows computed tomography (CT) of the chest from the patient's first recurrence, demonstrates a 7.8 cm anterior mediastinal mass (arrow) in contact with the pericardium aorta, portions of the main and left pulmonary artery. FIG. 1B shows histopathologic examination of the tumor showing sheets of large, epithelioid cells lacking significant lymphocytic infiltration, consistent with type B3 thymoma (×400). FIG. 1C provides immunohistochemistry (IHC) for a wide spectrum keratin (MNF116), showing diffusely positive, staining neoplastic cell membranes (×400). FIG. 1D shows IHC for terminal deoxynucleotidyl transferase, highlighting the nuclei of scattered T-cell lineage thymocytes associated with the tumor (×400).

FIG. 2 is a schematic of an exemplary KMT2A-MAML2 fusion identified in the index case, featuring KMT2A exons 1-10 and MAML2 exons 2-5 Exon numbers are shown above their respective boxes for reference sequence KMT2A transcript variant 2 (NM_005933; SEQ ID NO: 1) and MAML2 (NM_032427; SEQ ID NO: 2). The corresponding amino acid sequences for reference sequence KMT2A transcript variant 2 (NM 005933) and for MAML2 (NM_032427) are provided in Table 9 as SEQ ID NO: 3 and SEQ ID NO: 4, respectively. The fusion breakpoint is shown as a dotted line. The fusion protein contains the CXXC-type DNA binding domain of KMT2A, as well as the central and C-terminal acidic domains of MAML2. These domains were preserved across all 11 cases.

DETAILED DESCRIPTION OF THE INVENTION

Figure 1A:
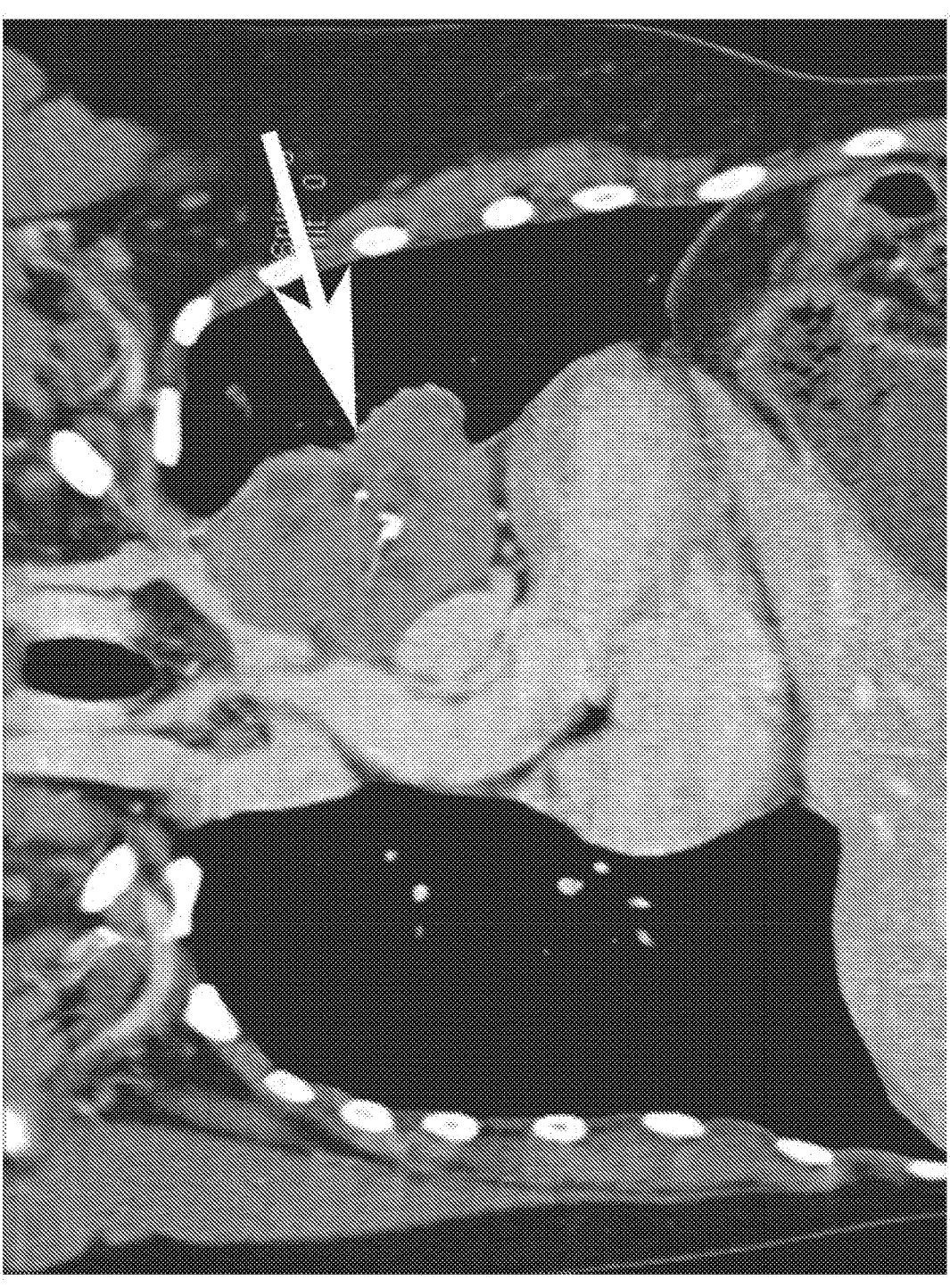
FIGS. 1A-1D provide radiology and pathology results from the index patient described in Example 1.

Described herein are KMT2A-MAML2 fusions, including KMT2A-MAML2 nucleic acid fusion molecules and KMT2A-MAML2 polypeptide fusion molecules. In certain fusions, exon 7, exon 8, exon 9, exon 10, or exon 11, or a portion of any such exon, or any intron following any one of exon 7, exon 8, exon 9, exon 10, or exon 11 (i.e., intron 7, 8, 9, 10, or 11, or any portion of such intron), of KMTA2 is directly fused to exon 2 or a portion of exon 2, an intron preceding exon 2 (i.e., intron 1), exon 3 or a portion of exon 3, an intron preceding exon 3 (i.e., intron 2) or any portion of such intron, exon 4, or an intron preceding exon 4 (i.e., intron 3) or any portion of such intron, of MAML2, thereby establishing a KMT2A-MAML2 breakpoint between the KMT2A sequence and the MAML2 sequence. Also described are methods of selecting a cancer treatment in a patient having a KMT2A-MAML2 fusion, a method of treating cancer (e.g., an epithelial cancer, such as a thymoma) having a KMT2A-MAML2 fusion, and methods of diagnosing a patient with a cancer having a KMT2A-MAML2 fusion. Detection of the KMT2A-MAML2 fusion may be through, for example, detection of the KMT2A-MAML2 polypeptide, or a nucleic acid molecule having a KMT2A-MAML2 breakpoint.

The present disclosure is based, at least in part, on the discovery of KMT2A-MAML2 gene fusions in epithelial neoplasms such as thymomas. The KMT2A-MAML2 gene fusions described herein represent the first recurrent gene fusions identified in thymomas.

In some aspects, provided herein are KMT2A-MAML2 fusion nucleic acid molecules. In some embodiments, a KMT2A-MAML2 fusion nucleic acid molecule provided herein comprises exon 7 or a portion thereof, intron 7 or a portion thereof, exon 8 or a portion thereof, intron 8 or a portion thereof, exon 9 or a portion thereof, intron 9 or a portion thereof, exon 10 or a portion thereof, intron 10 or a portion thereof, exon 11 or a portion thereof, or intron 11 or a portion thereof of KMT2A and intron 1 or a portion thereof, exon 2 or a portion thereof, intron 2 or a portion thereof, exon 3 or a portion thereof, intron 3 or a portion thereof, or exon 4, of MAML2, and a KMT2A-MAML2 breakpoint that fuses exon 7 or the portion thereof, intron 7 or the portion thereof, exon 8 or the portion thereof, intron 8 or the portion thereof, exon 9 or the portion thereof, intron 9 or the portion thereof, exon 10 or the portion thereof, intron 10 or the portion thereof, exon 11 or the portion thereof, or intron 11 or the portion thereof, of KMT2A to intron 1 or the portion thereof, exon 2 or the portion thereof, intron 2 or the portion thereof, exon 3 or the portion thereof, intron 3 or the portion thereof, or exon 4, of MAML2. In some embodiments, the exon-exon fusions or exon-intron fusions are in-frame fusions.

The fusion breakpoint may occur anywhere within the exon (e.g., exon 7, 8, 9, 10, or 11) or the intron (e.g., intron 7, 8, 9, 10, or 11) of KMT2A. and anywhere within exon 2, exon 3, intron 1, intron 2, or intron 3 of MAML2. When the fusion junction occurs between an intron of KMT2A and an intron of MAML2, the resulting mRNA sequences has a fusion junction between the preceding exon of KMT2A and the following exon of MAML2. For example, a fusion of intron 10 of KMT2A and intron 1 of MAML2 in the DNA sequence would result in an mRNA sequence having a breakpoint between exon 10 of KMT2A and exon 2 of MAML2. One skilled in the art could readily determine the exon and intron sequences within the KMT2A and MAML2 genes, for example using an NCBI database (e.g., Gen-Bank).

In certain aspects, provided herein are KMT2A-MAML2 fusion polypeptides comprising an amino acid sequence encoded by a KMT2A-MAML2 fusion nucleic acid molecule described herein, or an amino acid sequence at least about 85% identical to the amino acid sequence encoded by a KMT2A-MAML2 fusion nucleic acid molecule described herein.

In some aspects, provided herein are methods of detecting the presence of a KMT2A-MAML2 fusion, comprising: detecting a KMT2A-MAML2 fusion nucleic acid molecule of the disclosure in a sample; or detecting a KMT2A-MAML2 fusion polypeptide of the disclosure in a sample.

In some aspects, provided herein are methods of assessing cancer in an individual. In some embodiments, the methods comprise: detecting a KMT2A-MAML2 fusion nucleic acid molecule of the disclosure in a sample obtained from the individual; or detecting a KMT2A-MAML2 fusion polypeptide of the disclosure in a sample obtained from the individual.

In some aspects, provided herein are methods of assessing an individual having cancer, comprising detecting a KMT2A-MAML2 fusion nucleic acid molecule of the disclosure in a sample obtained from the individual, or detecting a KMT2A-MAML2 fusion polypeptide of the disclosure in a sample obtained from the individual. In some embodiments, the methods comprise providing an assessment of the presence of a KMT2A-MAML2 fusion in the sample.

In some aspects, provided herein are methods of assessing a cancer in an individual, comprising detecting a KMT2A-MAML2 fusion nucleic acid molecule of the disclosure in a sample obtained from the individual, or detecting a KMT2A-MAML2 fusion polypeptide of the disclosure in a sample obtained from the individual. In some embodiments, the presence of the KMT2A-MAML2 fusion nucleic acid molecule or polypeptide in the sample identifies the cancer as likely to respond to an anti-cancer therapy described herein.

In some aspects, provided herein are methods of identifying an individual having cancer who may benefit from a treatment comprising an anti-cancer therapy, comprising detecting a KMT2A-MAML2 fusion nucleic acid molecule of the disclosure in a sample obtained from the individual, or detecting a KMT2A-MAML2 fusion polypeptide of the disclosure in a sample obtained from the individual. In some embodiments, the presence of the KMT2A-MAML2 fusion nucleic acid molecule or polypeptide in the sample identifies the individual as one who may benefit from the treatment comprising an anti-cancer therapy described herein.

In some aspects, provided herein are methods of selecting a therapy for an individual having cancer, comprising acquiring knowledge of a KMT2A-MAML2 fusion nucleic acid molecule of the disclosure in a sample obtained from the individual or of a KMT2A-MAML2 fusion polypeptide of the disclosure in a sample obtained from the individual. In some embodiments, the presence of the KMT2A-MAML2 fusion nucleic acid molecule or polypeptide in the sample identifies the individual as one who may benefit from treatment comprising an anti-cancer therapy. In some embodiments, responsive to the acquisition of said knowledge: (i) the individual is classified as a candidate to receive treatment with an anti-cancer therapy described herein; and/or (ii) the individual is identified as likely to respond to a treatment that comprises an anti-cancer therapy described herein.

In some aspects, provided herein are methods of identifying one or more treatment options for an individual having cancer, comprising acquiring knowledge of a KMT2A-MAML2 fusion nucleic acid molecule of the disclosure in a sample obtained from the individual or of a KMT2A-MAML2 fusion polypeptide of the disclosure in a sample obtained from the individual; and generating a report comprising one or more treatment options identified for the individual based at least in part on said knowledge, wherein the one or more treatment options comprise an anti-cancer therapy described herein.

In other aspects, provided herein are methods of treating cancer.

In certain aspects, provided herein are methods of treating cancer, comprising administering to an individual an effective amount of an anti-cancer therapy described herein, wherein the cancer comprises a KMT2A-MAML2 fusion nucleic acid molecule of the disclosure or a KMT2A-MAML2 fusion polypeptide of the disclosure.

In certain aspects, provided herein are methods of treating cancer, comprising, responsive to knowledge of a KMT2A-MAML2 fusion nucleic acid molecule of the disclosure or a KMT2A-MAML2 fusion polypeptide of the disclosure in a sample from an individual, administering to the individual an effective amount of an anti-cancer therapy described herein.

In some embodiments, the cancer is an epithelial neoplasm. In some embodiments, the epithelial neoplasm is a thymoma.

In certain aspects, provided herein are probes or baits for the detection of a KMT2A-MAML2 fusion nucleic acid molecule provided herein. In some embodiments, the probes or baits provided herein comprise a capture nucleic acid molecule configured to hybridize to a target nucleic acid molecule comprising a KMT2A-MAML2 fusion nucleic acid molecule described herein, or a fragment thereof.

In some aspects, provided herein are antibodies or antibody fragments that specifically bind to a KMT2A-MAML2 fusion polypeptide of the disclosure, or a fragment thereof.

Definitions

Before describing the invention in detail, it is to be understood that this invention is not limited to particular compositions or biological systems. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "or" is used herein to mean, and is used interchangeably with, the term "and/or", unless context clearly indicates otherwise.

The terms "about" or "approximately" as used herein refer to the usual error range for the respective value readily known to the skilled person in this technical field, for example, an acceptable degree of error or deviation for the quantity measured given the nature or precision of the measurements. Reference to "about" or "approximately" a value or parameter herein includes (and describes) embodiments that are directed to that value or parameter per se.

The term "fusion" or "fusion molecule" is used generically herein, and includes any fusion molecule (e.g., a gene (e.g., in genomic DNA), a gene product (e.g., cDNA, mRNA, polypeptide, protein), and variants thereof) that includes a fragment of a first gene or gene product and a fragment of a second gene or gene product described herein. A fusion molecule includes a "breakpoint" or "fusion junction," which is the transition (i.e., direct fusion) point between the first gene or gene product, or fragment thereof, and the second gene or gene product, or fragment thereof.

The term "isolated" in the context of a nucleic acid molecule or a polypeptide refers the that nucleic acid molecule or polypeptide being separated from other nucleic acid molecules or polypeptides that are present in the natural source of the nucleic acid molecule or polypeptide. In some certain embodiments, the isolated nucleic acid molecule or polypeptide is free of or substantially free of other cellular material or culture medium when produced by recombinant techniques, or free of or substantially free of chemical precursors or other chemicals when chemically synthesized.

As used herein, the term "configured to hybridize to" indicates that a nucleic acid molecule has a nucleotide sequence with sufficient length and sequence complementarity to the nucleotide sequence of a target nucleic acid to allow the nucleic acid molecule to hybridize to the target nucleic acid with a $T_m$ of at least 65° C. in an aqueous solution of 1×SCC (150 mM sodium chloride and 15 mM trisodium citrate) and 0.1% SDS. Other hybridization conditions may be used when hybridizing a nucleic acid molecule to a target nucleic acid molecule, for example in the context of a described method.

"Percent (%) sequence identity" with respect to a reference polypeptide or polynucleotide sequence is defined as the percentage of amino acid residues or nucleotides in a sequence that are identical to the amino acid residues or nucleotides in the reference polypeptide or polynucleotide sequence, after aligning the sequences and introducing gaps, if necessary, to achieve the maximum percent sequence identity, and not considering any conservative substitutions as part of the sequence identity.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human. In some embodiments, the individual is human patient, e.g., a human patient having a cancer described herein, and/or a fusion nucleic acid molecule or polypeptide described herein.

An "effective amount" or a "therapeutically effective amount" of an agent, e.g., an anti-cancer agent, or a pharmaceutical formulation, refers to an amount effective, at dosages and for periods of time necessary, to achieve the desired therapeutic or prophylactic result, e.g., in the treatment or management of a cancer, for example, delaying or minimizing one or more symptoms associated with the cancer. In some embodiments, an effective amount or a therapeutically effective amount of an agent refers to an amount of the agent at dosages and for periods of time necessary, alone or in combination with other therapeutic agents, which provides a therapeutic or prophylactic benefit in the treatment or management of a disease such as a cancer. In some embodiments, an effective amount or a therapeutically effective amount of an agent enhances the therapeutic or prophylactic efficacy of another therapeutic agent or another therapeutic modality.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, delaying progression of disease, alleviation of symptoms, diminishment of any direct or indirect pathological consequences of the disease, decreasing the rate of disease progression, amelioration or palliation of the disease state, and remission or improved prognosis. In some embodiments, the terms "treatment," "treat," or "treating" include preventing a disease, such as cancer, e.g., before an individual begins to suffer from a cancer or from re-growth or recurrence of the cancer. In some embodiments, the terms "treatment," "treat," or "treating" include inhibiting or reducing the severity of a disease such as a cancer.

"Likely to" or "increased likelihood." as used herein, refer to an increased probability that an event, item, object, thing or person will occur. Thus, in one example, an individual that is likely to respond to treatment with an anti-cancer therapy, e.g., an anti-cancer therapy provided herein, alone or in combination, has an increased probability of responding to treatment with the anti-cancer therapy alone or in combination, relative to a reference individual or group of individuals. "Unlikely to" refers to a decreased probability that an event, item, object, thing or person will occur with respect to a reference. Thus, an individual that is unlikely to respond to treatment with an anti-cancer therapy, e.g., an anti-cancer therapy provided herein, alone or in combination, has a decreased probability of responding to treatment with the anti-cancer therapy, alone or in combination, relative to a reference individual or group of individuals.

"Sample," as used herein, refers to a biological sample obtained or derived from a source of interest, as described herein.

KMT2A-MAML2 Fusion Nucleic Acid Molecules

Provided herein are KMT2A-MAML2 fusion nucleic acid molecules.

In some embodiments, a KMT2A-MAML2 fusion nucleic acid molecule provided herein comprises an exon or a portion thereof of KMT2A and an exon or a portion thereof of MAML2, and a KMT2A-MAML2 breakpoint that fuses the exon or a portion thereof of KMT2A to the exon or a portion thereof of MAML2.

In some embodiments, the KMT2A-MAML2 fusion nucleic acid molecule comprises exon 7 or a portion thereof of KMT2A and exon 2 or a portion thereof of MAML2, and a KMT2A-MAML2 breakpoint that fuses exon 7 or the portion thereof of KMT2A to exon 2 or the portion thereof of MAML2. In some embodiments, the KMT2A-MAML2 breakpoint fuses the 3' end of exon 7 of KMT2A to the 5' end of exon 2 of MAML2. In some embodiments, the KMT2A-MAML2 breakpoint fuses the 3' end of a portion of exon 7 of KMT2A to the 5' end of exon 2 of MAML2. In some embodiments, the KMT2A-MAML2 breakpoint fuses the 3' end of exon 7 of KMT2A to the 5' end of a portion of exon 2 of MAML2. In some embodiments, the KMT2A-MAML2 breakpoint fuses the 3' end of a portion of exon 7 of KMT2A to the 5' end of a portion of exon 2 of MAML2. In some embodiments, the KMT2A-MAML2 fusion nucleic acid molecule comprises 5 or more, 10 or more, or 20 or more nucleotides on the 5' end of the KMT2A-MAML2 breakpoint, and 5 or more, 10 or more, or 20 or more nucleotides on the 3' end of the KMT2A-MAML2 breakpoint.

In some embodiments, the KMT2A-MAML2 fusion nucleic acid molecule comprises exon 7 or a portion thereof of KMT2A fused to exon 2 of MAML2. In some embodiments, the 3' end of exon 7 of KMT2A is fused to the 5' end of exon 2 of MAML2. In some embodiments, the 3' end of a portion of exon 7 of KMT2A is fused to the 5' end of exon 2 of MAML2.

In some embodiments, the KMT2A-MAML2 fusion nucleic acid molecule comprises an intron, or a portion thereof, between exon 7 and exon 8 of KMT2A fused to an intron, or a portion thereof between exon 1 and exon 2 of MAML2. In some embodiments, an intron between exon 7 and exon 8 of KMT2A is fused to an intron between exon 1 and exon 2 of MAML2. In some embodiments, a portion of an intron between exon 7 and exon 8 of KMT2A is fused to a portion of an intron between exon 1 and exon 2 of MAML2. In some embodiments, an intron between exon 7 and exon 8 of KMT2A is fused to a portion of an intron between exon 1 and exon 2 of MAML2. In some embodiments, a portion of an intron between exon 7 and exon 8 of KMT2A is fused to an intron between exon 1 and exon 2 of MAML2. In some embodiments, a portion of intron 7 of KMT2A is fused to intron 1 of MAML2. In some embodiments, intron 7 of KMT2A is fused to a portion of intron 1 of MAML2. In some embodiments, intron 7 of KMT2A is fused to intron 1 of MAML2.

In some embodiments, the KMT2A-MAML2 fusion nucleic acid molecule comprises exon 7 or a portion thereof of KMT2A fused to an intron, or a portion thereof, between exon 1 and exon 2 of MAML2. In some embodiments, the 3' end of exon 7 of KMT2A is fused to an intron between exon 1 and exon 2 of MAML2. In some embodiments, the 3' end of a portion of exon 7 of KMT2A is fused to an intron between exon 1 and exon 2 of MAML2. In some embodiments, the 3' end of exon 7 of KMT2A is fused to a portion of an intron between exon 1 and exon 2 of MAML2. In some embodiments, the 3' end of exon 7 of KMT2A is fused to intron 1 of MAML2. In some embodiments, the 3' end of a portion of exon 7 of KMT2A is fused to intron 1 of MAML2. In some embodiments, the 3' end of exon 7 of KMT2A is fused to a portion of intron 1 of MAML2.

In some embodiments, the KMT2A-MAML2 fusion nucleic acid molecule comprises an intron, or a portion thereof, between exon 7 and exon 8 of KMT2A fused to exon 2 of MAML2. In some embodiments, an intron between exon 7 and exon 8 of KMT2A is fused to the 5' end of exon 2 of MAML2. In some embodiments, an intron between exon 7 and exon 8 of KMT2A is fused to the 5' end of a portion of exon 2 of MAML2. In some embodiments, a portion of an intron between exon 7 and exon 8 of KMT2A is fused to the 5' end of exon 2 of MAML2. In some embodiments, intron 7 of KMT2A is fused to the 5' end of exon 2 of MAML2. In some embodiments, intron 7 of KMT2A is fused to the 5' end of a portion of exon 2 of MAML2. In some embodiments, a portion of intron 7 of KMT2A is fused to the 5' end of exon 2 of MAML2.

In some embodiments, the KMT2A-MAML2 fusion nucleic acid molecule comprises exons 1-6 and exon 7, or a portion thereof, of KMT2A and exons 2-5 of MAML2. In some embodiments, the KMT2A-MAML2 fusion nucleic acid molecule comprises exons 1-6 and exon 7 of KMT2A and exons 2-5 of MAML2. In some embodiments, the KMT2A-MAML2 fusion nucleic acid molecule comprises exons 1-6 and a portion of exon 7 of KMT2A and exons 2-5 of MAML2.

In some embodiments, the KMT2A-MAML2 fusion nucleic acid molecule comprises exon 8 or a portion thereof of KMT2A and exon 2 or a portion thereof of MAML2, and a KMT2A-MAML2 breakpoint that fuses exon 8 or the portion thereof of KMT2A to exon 2 or the portion thereof of MAML2. In some embodiments, the KMT2A-MAML2 breakpoint fuses the 3' end of exon 8 of KMT2A to the 5' end of exon 2 of MAML2. In some embodiments, the KMT2A-MAML2 breakpoint fuses the 3' end of a portion of exon 8 of KMT2A to the 5' end of exon 2 of MAML2. In some embodiments, the KMT2A-MAML2 breakpoint fuses the 3' end of exon 8 of KMT2A to the 5' end of a portion of exon 2 of MAML2. In some embodiments, the KMT2A-MAML2 breakpoint fuses the 3' end of a portion of exon 8 of KMT2A to the 5' end of a portion of exon 2 of MAML2. In some embodiments, the KMT2A-MAML2 fusion nucleic acid molecule comprises 5 or more, 10 or more, or 20 or more nucleotides on the 5' end of the KMT2A-MAML2 breakpoint, and 5 or more, 10 or more, or 20 or more nucleotides on the 3' end of the KMT2A-MAML2 breakpoint.

In some embodiments, the KMT2A-MAML2 fusion nucleic acid molecule comprises exon 8 or a portion thereof of KMT2A fused to exon 2 of MAML2. In some embodiments, the 3' end of exon 8 of KMT2A is fused to the 5' end of exon 2 of MAML2. In some embodiments, the 3' end of a portion of exon 8 of KMT2A is fused to the 5' end of exon 2 of MAML2.

In some embodiments, the KMT2A-MAML2 fusion nucleic acid molecule comprises an intron, or a portion thereof, between exon 8 and exon 9 of KMT2A fused to an intron, or a portion thereof between exon 1 and exon 2 of MAML2. In some embodiments, an intron between exon 8 and exon 9 of KMT2A is fused to an intron between exon 1 and exon 2 of MAML2. In some embodiments, a portion of an intron between exon 8 and exon 9 of KMT2A is fused to a portion of an intron between exon 1 and exon 2 of MAML2. In some embodiments, an intron between exon 8 and exon 9 of KMT2A is fused to a portion of an intron between exon 1 and exon 2 of MAML2. In some embodiments, a portion of an intron between exon 8 and exon 9 of KMT2A is fused to an intron between exon 1 and exon 2 of MAML2. In some embodiments, a portion of intron 8 of KMT2A is fused to intron 1 of MAML2. In some embodiments, intron 8 of KMT2A is fused to a portion of intron 1 of MAML2. In some embodiments, intron 8 of KMT2A is fused to intron 1 of MAML2.

In some embodiments, the KMT2A-MAML2 fusion nucleic acid molecule comprises exon 8 or a portion thereof of KMT2A fused to an intron, or a portion thereof, between exon 1 and exon 2 of MAML2. In some embodiments, the 3' end of exon 8 of KMT2A is fused to an intron between exon 1 and exon 2 of MAML2. In some embodiments, the 3' end of a portion of exon 8 of KMT2A is fused to an intron between exon 1 and exon 2 of MAML2. In some embodiments, the 3' end of exon 8 of KMT2A is fused to a portion of an intron between exon 1 and exon 2 of MAML2. In some embodiments, the 3' end of exon 8 of KMT2A is fused to intron 1 of MAML2. In some embodiments, the 3' end of a portion of exon 8 of KMT2A is fused to intron 1 of MAML2. In some embodiments, the 3' end of exon 8 of KMT2A is fused to a portion of intron 1 of MAML2.

In some embodiments, the KMT2A-MAML2 fusion nucleic acid molecule comprises an intron, or a portion thereof, between exon 8 and exon 9 of KMT2A fused to exon 2 of MAML2. In some embodiments, an intron between exon 8 and exon 9 of KMT2A is fused to the 5' end of exon 2 of MAML2. In some embodiments, an intron between exon 8 and exon 9 of KMT2A is fused to the 5' end of a portion of exon 2 of MAML2. In some embodiments, a portion of an intron between exon 8 and exon 9 of KMT2A is fused to the 5' end of exon 2 of MAML2. In some embodiments, intron 8 of KMT2A is fused to the 5' end of exon 2 of MAML2. In some embodiments, intron 8 of KMT2A is fused to the 5' end of a portion of exon 2 of MAML2. In some embodiments, a portion of intron 8 of KMT2A is fused to the 5' end of exon 2 of MAML2.

In some embodiments, the KMT2A-MAML2 fusion nucleic acid molecule comprises exons 1-7 and exon 8, or a portion thereof, of KMT2A and exons 2-5 of MAML2. In some embodiments, the KMT2A-MAML2 fusion nucleic acid molecule comprises exons 1-7 and exon 8 of KMT2A and exons 2-5 of MAML2. In some embodiments, the KMT2A-MAML2 fusion nucleic acid molecule comprises exons 1-7 and a portion of exon 8 of KMT2A and exons 2-5 of MAML2.

In some embodiments, the KMT2A-MAML2 fusion nucleic acid molecule comprises exon 9 or a portion thereof of KMT2A and exon 2 or a portion thereof of MAML2, and a KMT2A-MAML2 breakpoint that fuses exon 9 or the portion thereof of KMT2A to exon 2 or the portion thereof of MAML2. In some embodiments, the KMT2A-MAML2 breakpoint fuses the 3' end of exon 9 of KMT2A to the 5' end of exon 2 of MAML2. In some embodiments, the KMT2A-MAML2 breakpoint fuses the 3' end of a portion of exon 9 of KMT2A to the 5' end of exon 2 of MAML2. In some embodiments, the KMT2A-MAML2 breakpoint fuses the 3' end of exon 9 of KMT2A to the 5' end of a portion of exon 2 of MAML2. In some embodiments, the KMT2A-MAML2 breakpoint fuses the 3' end of a portion of exon 9 of KMT2A to the 5' end of a portion of exon 2 of MAML2. In some embodiments, the KMT2A-MAML2 fusion nucleic acid molecule comprises 5 or more, 10 or more, or 20 or more nucleotides on the 5' end of the KMT2A-MAML2 breakpoint, and 5 or more, 10 or more, or 20 or more nucleotides on the 3' end of the KMT2A-MAML2 breakpoint.

In some embodiments, the KMT2A-MAML2 fusion nucleic acid molecule comprises exon 9 or a portion thereof of KMT2A fused to exon 2 of MAML2. In some embodiments, the 3' end of exon 9 of KMT2A is fused to the 5' end of exon 2 of MAML2. In some embodiments, the 3' end of a portion of exon 9 of KMT2A is fused to the 5' end of exon 2 of MAML2.

In some embodiments, the KMT2A-MAML2 fusion nucleic acid molecule comprises an intron, or a portion thereof, between exon 9 and exon 10 of KMT2A fused to an intron, or a portion thereof between exon 1 and exon 2 of MAML2. In some embodiments, an intron between exon 9 and exon 10 of KMT2A is fused to an intron between exon 1 and exon 2 of MAML2. In some embodiments, a portion of an intron between exon 9 and exon 10 of KMT2A is fused to a portion of an intron between exon 1 and exon 2 of MAML2. In some embodiments, an intron between exon 9 and exon 10 of KMT2A is fused to a portion of an intron between exon 1 and exon 2 of MAML2. In some embodiments, a portion of an intron between exon 9 and exon 10 of KMT2A is fused to an intron between exon 1 and exon 2 of MAML2. In some embodiments, a portion of intron 9 of KMT2A is fused to intron 1 of MAML2. In some embodiments, intron 9 of KMT2A is fused to a portion of intron 1 of MAML2. In some embodiments, intron 9 of KMT2A is fused to intron 1 of MAML2.

In some embodiments, the KMT2A-MAML2 fusion nucleic acid molecule comprises exon 9 or a portion thereof of KMT2A fused to an intron, or a portion thereof, between exon 1 and exon 2 of MAML2. In some embodiments, the 3' end of exon 9 of KMT2A is fused to an intron between exon 1 and exon 2 of MAML2. In some embodiments, the 3' end of a portion of exon 9 of KMT2A is fused to an intron between exon 1 and exon 2 of MAML2. In some embodiments, the 3' end of exon 9 of KMT2A is fused to a portion of an intron between exon 1 and exon 2 of MAML2. In some embodiments, the 3' end of exon 9 of KMT2A is fused to intron 1 of MAML2. In some embodiments, the 3' end of a portion of exon 9 of KMT2A is fused to intron 1 of MAML2. In some embodiments, the 3' end of exon 9 of KMT2A is fused to a portion of intron 1 of MAML2.

In some embodiments, the KMT2A-MAML2 fusion nucleic acid molecule comprises an intron, or a portion thereof, between exon 9 and exon 10 of KMT2A fused to exon 2 of MAML2. In some embodiments, an intron between exon 9 and exon 10 of KMT2A is fused to the 5' end of exon 2 of MAML2. In some embodiments, an intron between exon 9 and exon 10 of KMT2A is fused to the 5' end of a portion of exon 2 of MAML2. In some embodiments, a portion of an intron between exon 9 and exon 10 of KMT2A is fused to the 5' end of exon 2 of MAML2. In some embodiments, intron 9 of KMT2A is fused to the 5' end of exon 2 of MAML2. In some embodiments, intron 9 of KMT2A is fused to the 5' end of a portion of exon 2 of MAML2. In some embodiments, a portion of intron 9 of KMT2A is fused to the 5' end of exon 2 of MAML2.

In some embodiments, the KMT2A-MAML2 fusion nucleic acid molecule comprises exons 1-8 and exon 9, or a portion thereof, of KMT2A and exons 2-5 of MAML2. In some embodiments, the KMT2A-MAML2 fusion nucleic acid molecule comprises exons 1-8 and exon 9 of KMT2A and exons 2-5 of MAML2. In some embodiments, the KMT2A-MAML2 fusion nucleic acid molecule comprises exons 1-8 and a portion of exon 9 of KMT2A and exons 2-5 of MAML2.

In some embodiments, the KMT2A-MAML2 fusion nucleic acid molecule comprises exon 10 or a portion thereof of KMT2A and exon 2 or a portion thereof of MAML2, and a KMT2A-MAML2 breakpoint that fuses exon 10 or the portion thereof of KMT2A to exon 2 or the portion thereof of MAML2. In some embodiments, the KMT2A-MAML2 breakpoint fuses the 3' end of exon 10 of KMT2A to the 5' end of exon 2 of MAML2. In some embodiments, the KMT2A-MAML2 breakpoint fuses the 3' end of a portion of exon 10 of KMT2A to the 5' end of exon 2 of MAML2. In some embodiments, the KMT2A-MAML2 breakpoint fuses the 3' end of exon 10 of KMT2A to the 5' end of a portion of exon 2 of MAML2. In some embodiments, the KMT2A-MAML2 breakpoint fuses the 3' end of a portion of exon 10 of KMT2A to the 5' end of a portion of exon 2 of MAML2. In some embodiments, the KMT2A-MAML2 fusion nucleic acid molecule comprises 5 or more, 10 or more, or 20 or more nucleotides on the 5' end of the KMT2A-MAML2 breakpoint, and 5 or more, 10 or more, or 20 or more nucleotides on the 3' end of the KMT2A-MAML2 breakpoint.

In some embodiments, the KMT2A-MAML2 fusion nucleic acid molecule comprises exon 10 or a portion thereof of KMT2A fused to exon 2 of MAML2. In some embodiments, the 3' end of exon 10 of KMT2A is fused to the 5' end of exon 2 of MAML2. In some embodiments, the 3' end of a portion of exon 10 of KMT2A is fused to the 5' end of exon 2 of MAML2.

In some embodiments, the KMT2A-MAML2 fusion nucleic acid molecule comprises an intron, or a portion thereof, between exon 10 and exon 11 of KMT2A fused to an intron, or a portion thereof between exon 1 and exon 2 of MAML2. In some embodiments, an intron between exon 10 and exon 11 of KMT2A is fused to an intron between exon 1 and exon 2 of MAML2. In some embodiments, a portion of an intron between exon 10 and exon 11 of KMT2A is fused to a portion of an intron between exon 1 and exon 2 of MAML2. In some embodiments, an intron between exon 10 and exon 11 of KMT2A is fused to a portion of an intron between exon 1 and exon 2 of MAML2. In some embodiments, a portion of an intron between exon 10 and exon 11 of KMT2A is fused to an intron between exon 1 and exon 2 of MAML2. In some embodiments, a portion of intron 10 of KMT2A is fused to intron 1 of MAML2. In some embodiments, intron 10 of KMT2A is fused to a portion of intron 1 of MAML2. In some embodiments, intron 10 of KMT2A is fused to intron 1 of MAML2.

In some embodiments, the KMT2A-MAML2 fusion nucleic acid molecule comprises exon 10 or a portion thereof of KMT2A fused to an intron, or a portion thereof, between exon 1 and exon 2 of MAML2. In some embodiments, the 3' end of exon 10 of KMT2A is fused to an intron between exon 1 and exon 2 of MAML2. In some embodiments, the 3' end of a portion of exon 10 of KMT2A is fused to an intron between exon 1 and exon 2 of MAML2. In some embodiments, the 3' end of exon 10 of KMT2A is fused to a portion of an intron between exon 1 and exon 2 of MAML2. In some embodiments, the 3' end of exon 10 of KMT2A is fused to intron 1 of MAML2. In some embodiments, the 3' end of a portion of exon 10 of KMT2A is fused to intron 1 of MAML2. In some embodiments, the 3' end of exon 10 of KMT2A is fused to a portion of intron 1 of MAML2.

In some embodiments, the KMT2A-MAML2 fusion nucleic acid molecule comprises an intron, or a portion thereof, between exon 10 and exon 11 of KMT2A fused to exon 2 of MAML2. In some embodiments, an intron between exon 10 and exon 11 of KMT2A is fused to the 5' end of exon 2 of MAML2. In some embodiments, an intron between exon 10 and exon 11 of KMT2A is fused to the 5' end of a portion of exon 2 of MAML2. In some embodiments, a portion of an intron between exon 10 and exon 11 of KMT2A is fused to the 5' end of exon 2 of MAML2. In some embodiments, intron 10 of KMT2A is fused to the 5' end of exon 2 of MAML2. In some embodiments, intron 10 of KMT2A is fused to the 5' end of a portion of exon 2 of MAML2. In some embodiments, a portion of intron 10 of KMT2A is fused to the 5' end of exon 2 of MAML2.

In some embodiments, the KMT2A-MAML2 fusion nucleic acid molecule comprises exons 1-9 and exon 10, or a portion thereof, of KMT2A and exons 2-5 of MAML2. In some embodiments, the KMT2A-MAML2 fusion nucleic acid molecule comprises exons 1-9 and exon 10 of KMT2A and exons 2-5 of MAML2. In some embodiments, the KMT2A-MAML2 fusion nucleic acid molecule comprises exons 1-9 and a portion of exon 10 of KMT2A and exons 2-5 of MAML2.

In some embodiments, the KMT2A-MAML2 fusion nucleic acid molecule comprises exon 11 or a portion thereof of KMT2A and exon 2 or a portion thereof of MAML2, and a KMT2A-MAML2 breakpoint that fuses exon 11 or the portion thereof of KMT2A to exon 2 or the portion thereof of MAML2. In some embodiments, the KMT2A-MAML2 breakpoint fuses the 3' end of exon 11 of KMT2A to the 5' end of exon 2 of MAML2. In some embodiments, the KMT2A-MAML2 breakpoint fuses the 3' end of a portion of exon 11 of KMT2A to the 5' end of exon 2 of MAML2. In some embodiments, the KMT2A-MAML2 breakpoint fuses the 3' end of exon 11 of KMT2A to the 5' end of a portion of exon 2 of MAML2. In some embodiments, the KMT2A-MAML2 breakpoint fuses the 3' end of a portion of exon 11 of KMT2A to the 5' end of a portion of exon 2 of MAML2. In some embodiments, the KMT2A-MAML2 fusion nucleic acid molecule comprises 5 or more, 10 or more, or 20 or more nucleotides on the 5' end of the KMT2A-MAML2 breakpoint, and 5 or more, 10 or more, or 20 or more nucleotides on the 3' end of the KMT2A-MAML2 breakpoint.

In some embodiments, the KMT2A-MAML2 fusion nucleic acid molecule comprises exon 11 or a portion thereof of KMT2A fused to exon 2 of MAML2. In some embodiments, the 3' end of exon 11 of KMT2A is fused to the 5' end of exon 2 of MAML2. In some embodiments, the 3' end of a portion of exon 11 of KMT2A is fused to the 5' end of exon 2 of MAML2.

In some embodiments, the KMT2A-MAML2 fusion nucleic acid molecule comprises an intron, or a portion thereof, between exon 11 and exon 12 of KMT2A fused to an intron, or a portion thereof between exon 1 and exon 2 of MAML2. In some embodiments, an intron between exon 11 and exon 12 of KMT2A is fused to an intron between exon 1 and exon 2 of MAML2. In some embodiments, a portion of an intron between exon 11 and exon 12 of KMT2A is fused to a portion of an intron between exon 1 and exon 2 of MAML2. In some embodiments, an intron between exon 11 and exon 12 of KMT2A is fused to a portion of an intron between exon 1 and exon 2 of MAML2. In some embodiments, a portion of an intron between exon 11 and exon 12 of KMT2A is fused to an intron between exon 1 and exon 2 of MAML2. In some embodiments, a portion of intron 11 of KMT2A is fused to intron 1 of MAML2. In some embodiments, intron 11 of KMT2A is fused to a portion of intron 1 of MAML2. In some embodiments, intron 11 of KMT2A is fused to intron 1 of MAML2.

In some embodiments, the KMT2A-MAML2 fusion nucleic acid molecule comprises exon 11 or a portion thereof of KMT2A fused to an intron, or a portion thereof, between exon 1 and exon 2 of MAML2. In some embodiments, the 3' end of exon 11 of KMT2A is fused to an intron between exon 1 and exon 2 of MAML2. In some embodiments, the 3' end of a portion of exon 11 of KMT2A is fused to an intron between exon 1 and exon 2 of MAML2. In some embodiments, the 3' end of exon 11 of KMT2A is fused to a portion of an intron between exon 1 and exon 2 of MAML2. In some embodiments, the 3' end of exon 11 of KMT2A is fused to intron 1 of MAML2. In some embodiments, the 3' end of a portion of exon 11 of KMT2A is fused to intron 1 of MAML2. In some embodiments, the 3' end of exon 11 of KMT2A is fused to a portion of intron 1 of MAML2.

In some embodiments, the KMT2A-MAML2 fusion nucleic acid molecule comprises an intron, or a portion thereof, between exon 11 and exon 12 of KMT2A fused to exon 2 of MAML2. In some embodiments, an intron between exon 11 and exon 12 of KMT2A is fused to the 5' end of exon 2 of MAML2. In some embodiments, an intron between exon 11 and exon 12 of KMT2A is fused to the 5' end of a portion of exon 2 of MAML2. In some embodiments, a portion of an intron between exon 11 and exon 12 of KMT2A is fused to the 5' end of exon 2 of MAML2. In some embodiments, intron 11 of KMT2A is fused to the 5' end of exon 2 of MAML2. In some embodiments, intron 11 of KMT2A is fused to the 5' end of a portion of exon 2 of MAML2. In some embodiments, a portion of intron 11 of KMT2A is fused to the 5' end of exon 2 of MAML2.

In some embodiments, the KMT2A-MAML2 fusion nucleic acid molecule comprises exons 1-10 and exon 11, or a portion thereof, of KMT2A and exons 2-5 of MAML2. In some embodiments, the KMT2A-MAML2 fusion nucleic acid molecule comprises exons 1-10 and exon 11 of KMT2A and exons 2-5 of MAML2. In some embodiments, the KMT2A-MAML2 fusion nucleic acid molecule comprises exons 1-10 and a portion of exon 11 of KMT2A and exons 2-5 of MAML2.

In some embodiments, a KMT2A-MAML2 fusion nucleic acid molecule provided herein, e.g., a DNA molecule, results in an mRNA molecule comprising a fusion, e.g., an in-frame fusion, of exon 7 or a portion thereof, exon 8 or a portion thereof, exon 9 or a portion thereof, exon 10 or a portion thereof, or exon 11 or a portion thereof, of KMT2A fused to exon 2 or a portion thereof of MAML2.

In some embodiments, a KMT2A-MAML2 fusion nucleic acid molecule provided herein comprises a KMT2A-MAML2 breakpoint resulting in an in-frame fusion of an exon described herein or a portion thereof of KMT2A with an exon described herein or a portion thereof of MAML2, e.g., resulting in an RNA molecule, such as an mRNA molecule comprising an in-frame fusion of an exon described herein or a portion thereof of KMT2A to an exon described herein or a portion thereof of MAML2. In some embodiments, a KMT2A-MAML2 fusion nucleic acid molecule provided herein is an mRNA molecule comprising a fusion, e.g., an in-frame fusion, of exon 7 or a portion thereof, exon 8 or a portion thereof, exon 9 or a portion thereof, exon 10 or a portion thereof, or exon 11 or a portion thereof, of KMT2A fused to exon 2 or a portion thereof of MAML2.

In some embodiments, the KMT2A breakpoint occurs within an intron or within an exon of KMT2A, e.g., within intron 7 or within exon 7, within intron 8 or within exon 8, within intron 9 or within exon 9, within intron 10 or within exon 10, or within intron 11 or within exon 11, of KMT2A. In some embodiments, the KMT2A breakpoint occurs at the 3' end or at the 5' end of an intron, or at the 3' end or at the 5' end of an exon, of KMT2A, e.g., at the 3' end or at the 5' end of intron 7, at the 3' end or at the 5' end of exon 7, at the 3' end or at the 5' end of intron 8, at the 3' end or at the 5' end of exon 8, at the 3' end or at the 5' end of intron 9, at the 3' end or at the 5' end of exon 9, at the 3' end or at the 5' end of intron 10, at the 3' end or at the 5' end of exon 10, at the 3' end or at the 5' end of intron 11, or at the 3' end or at the 5' end of exon 11, of KMT2A. In some embodiments, the MAML2 breakpoint occurs within an intron or within an exon of MAML2, e.g., within intron 1 or within exon 2 of MAML2. In some embodiments, the MAML2 breakpoint occurs at the 3' end or at the 5' end of an intron, or at the 3' end or at the 5' end of an exon, of MAML2, e.g., at the 3' end or at the 5' end of intron 1, or at the 3' end or at the 5' end of exon 2, of MAML2.

In some embodiments, a KMT2A-MAML2 fusion nucleic acid molecule provided herein comprises at least one exon of KMT2A or a portion thereof and at least one exon of MAML2 or a portion thereof. In some embodiments, a KMT2A-MAML2 fusion nucleic acid molecule provided herein comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, or 36 exons of KMT2A and at least 1, at least 2, at least 3, at least 4, or 5 exons of MAML2.

In some embodiments, a KMT2A-MAML2 fusion nucleic acid molecule provided herein comprises, in the 5' to 3' direction, a fusion of exon 7 of KMT2A with exon 2 of MAML2 In some embodiments, a KMT2A-MAML2 fusion nucleic acid molecule provided herein comprises, in the 5' to 3' direction, exons 1-7 of KMT2A and exons 2-5 MAML2.

In some embodiments, a KMT2A-MAML2 fusion nucleic acid molecule provided herein comprises, in the 5' to 3' direction, a fusion of exon 8 of KMT2A with exon 2 of MAML2. In some embodiments, a KMT2A-MAML2 fusion nucleic acid molecule provided herein comprises, in the 5' to 3' direction, exons 1-8 of KMT2A and exons 2-5 MAML2.

In some embodiments, a KMT2A-MAML2 fusion nucleic acid molecule provided herein comprises, in the 5' to 3' direction, a fusion of exon 9 of KMT2A with exon 2 of MAML2. In some embodiments, a KMT2A-MAML2 fusion nucleic acid molecule provided herein comprises, in the 5' to 3' direction, exons 1-9 of KMT2A and exons 2-5 MAML2.

In some embodiments, a KMT2A-MAML2 fusion nucleic acid molecule provided herein comprises, in the 5' to 3' direction, a fusion of exon 10 of KMT2A with exon 2 of MAML2. In some embodiments, a KMT2A-MAML2 fusion nucleic acid molecule provided herein comprises, in the 5' to 3' direction, exons 1-10 of KMT2A and exons 2-5 MAML2.

In some embodiments, a KMT2A-MAML2 fusion nucleic acid molecule provided herein comprises, in the 5' to 3' direction, a fusion of exon 11 of KMT2A with exon 2 of MAML2. In some embodiments, a KMT2A-MAML2 fusion nucleic acid molecule provided herein comprises, in the 5' to 3' direction, exons 1-11 of KMT2A and exons 2-5 MAML2.

The nucleotide sequences of reference sequence KMT2A transcript variant 2 (NM_005933; SEQ ID NO: 1) and of MAML2 (NM_032427; SEQ ID NO: 2) are provided herein in Table 9.

The nucleotide sequence of KMT2A transcript variant 1 (NM_001197104; SEQ ID NO: 5) is provided in Table 9.

TABLE 9

Sequences.

| Description | | SEQ ID NO |
|---|---|---|
| NM_005933.4 KMT2A, transcript variant 2, mRNA | GCTTCACTTCACGGGGCGAACATGGCGCACAGCTGTC GGTGGCGCTTCCCCGCCCGACCCGGGACCACCG GGGGCGGCGGCGGCGGGGCGCGCCGGGGCCTAGGG GGCGCCCCGCGGCAACGCGTCCCGGCCCTGCTGCT TCCCCCCGGGCCCCCGGTCGGCGGTGGCGGCCCCGG GGCGCCCCCCTCCCCCCCGGCTGTGGCGGCCGCG GCGGCGGCGGCGGGGAAGCAGCGGGGCTGGGGTTCCA GGGGGAGCGGCCGCCGCCGCCTCAGCAGCCTCCTCGT CGTCCGCCTCGTCTTCGTCTTCGTCATCGTCCTCAGCC TCTTCAGGGCCGGCCCTGCTCCGGGTGGGCCC GGGCTTCGACGCGGCCTCTGCAGGTCTCGGCCGCCATC GGCACCAACCTGCGCCGGTTCCGGGCCGTGTTT GGGGAGAGCGGCGGGGGAGGCGGCAGCGGAGAGGA TGAGCAATTCTTAGGTTTTGGCTCAGATGAAGAAG | SEQ ID NO: 1 |

TABLE 9-continued

| Sequences. | |
| --- | --- |
| Description | SEQ ID NO |

TCAGAGTGCGAAGTCCCACAAGGTCTCCTTCAGTTAA
AACTAGTCCTCGAAAACCTCGTGGGAGACCTAG
AAGTGGCTCTGACCGAAATTCAGCTATCCTCTCAGAT
CCATCTGTGTTTTCCCCTCTAAATAAATCAGAG
ACCAAATCTGGAGATAAGATCAAGAAGAAAGATTCT
AAAAGTATAGAAAAGAAGAGAGGAAGACCTCCCA
CCTTCCCTGGAGTAAAAATCAAAATAACACATGGAA
AGGACATTTCAGAGTTACCAAAGGGAAACAAAGA
AGATAGCCTGAAAAAAATTAAAAGGACACCTTCTGC
TACGTTTCAGCAAGCCACAAAGATTAAAAAATTA
AGAGCAGGTAAACTCTCTCCTCTCAAGTCTAAGTTTA
AGACAGGGAAGCTTCAAATAGGAAGGAAGGGGG
TACAAATTGTACGACCGAGACGAAGGCCTCCATCAA
CAGAAAGGATAAAGACCCCTTCGGGTCTCCTCAT
TAATTCTGAACTGGAAAAGCCCCAGAAAGTCCGGAA
AGACAAGGAAGGAACACCTCCACTTACAAAAGAA
GATAAGACAGTTGTCAGACAAAGCCCTCGAAGGATT
AAGCCAGTTAGGATTATTCCTTCTTCAAAAAGGA
CAGATGCAACCATTGCTAAGCAACTCTTACAGAGGG
CAAAAAAGGGGGCTCAAAAGAAAATTGAAAAAGA
AGCAGCTCAGCTGCAGGGAAGAAAGGTGAAGACACA
GGTCAAAAATATTCGACAGTTCATCATGCCTGTT
GTCAGTGCTATCTCCTCGCGGATCATTAAGACCCCTC
GGCGGTTTATAGAGGATGAGGATTATGACCCTC
CAATTAAAATTGCCCGATTAGAGTCTACACCGAATAG
TAGATTCAGTGCCCCGTCCTGTGGATCTTCTGA
AAAATCAAGTGCAGCTTCTCAGCACTCCTCTCAAATG
TCTTCAGACTCCTCTCGATCTAGTAGCCCCAGT
GTTGATACCTCCACAGACTCTCAGGCTTCTGAGGAGA
TTCAGGTACTTCCTGAGGAGCGGAGCGATACCC
CTGAAGTTCATCCTCCACTGCCCATTTCCCAGTCCCC
AGAAAATGAGAGTAATGATAGGAGAAGCAGAAG
GCCCACCCTGAGTGCCTTACCATGGGAAGAACGAGA
AAAGATTTTGTCTTCCATGGGGAATGATGACAAG
TCATCAATTGCTGGCTCAGAAGATGCTGAACCTCTTG
CTCCACCCATCAAACCAATTAAACCTGTCACTA
GAAACAAGGCACCCCAGGAACCTCCAGTAAAGAAAG
GACGTCGATCGAGGCGGTGTGGGCAGTGTCCCGG
CTGCCAGGTGCCTGAGGACTGTGGTGTTTGTACTAAT
TGCTTAGATAAGCCCAAGTTTGGTGGTCGCAAT
ATAAAGAAGCAGTGCTGCAAGATGAGAAAATGTCAG
AATCTACAATGGATGCCTTCCAAAGCCTACCTGC
AGAAGCAAGCTAAAGCTGTGAAAAAGAAAGAGAAA
AAGTCTAAGACCAGTGAAAAGAAAGACAGCAAAGA
GAGCAGTGTTGTGAAGAACGTGGTGGACTCTAGTCA
GAAACCTACCCCATCAGCAAGAGAGGATCCTGCC
CCAAAGAAAAGCAGTAGTGAGCCTCCTCCACGAAAG
CCCGTCGAGGAAAAGAGTGAAGAAGGGAATGTCT
CGGCCCCTGGGCCTGAATCCAAACAGGCCACCACTCC
AGCTTCCAGGAAGTCAAGCAAGCAGGTCTCCCA
GCCAGCACTGGTCATCCCGCCTCAGCCACCTACTACA
GGACCGCCAAGAAAAGAAGTTCCCAAAACCACT
CCTAGTGAGCCCAAGAAAAAGCAGCCTCCACCACCA
GAATCAGGTCCAGAGCAGAGCAAACAGAAAAAAG
TGGCTCCCCGCCCAAGTATCCCTGTAAAACAAAAACC
AAAAGAAAAGGAAAAACCACCTCCGGTCAATAA
GCAGGAGAATGCAGGCACTTTGAACATCCTCAGCAC
TCTCTCCAATGGCAATAGTTCTAAGCAAAAAATT
CCAGCAGATGGAGTCCACAGGATCAGAGTGGACTTT
AAGGAGGATTGTGAAGCAGAAAATGTGTGGGAGA
TGGGAGGCTTAGGAATCTTGACTTCTGTTCCTATAAC
ACCCAGGGTGGTTTGCTTTCTCTGTGCCAGTAG
TGGGCATGTAGAGTTTGTGTATTGCCAAGTCTGTTGT
GAGCCCTTCCACAAGTTTTGTTTAGAGGAGAAC
GAGCGCCCTCTGGAGGACCAGCTGGAAAATTGGTGT
TGTCGTCGTTGCAAATTCTGTCACGTTTGTGGAA
GGCAACATCAGGCTACAAAGCAGCTGCTGGAGTGTA
ATAAGTGCCGAAACAGCTATCACCCTGAGTGCCT
GGGACCAAACTACCCCACCAAACCCACAAAGAAGAA
GAAAGTCTGGATCTGTACCAAGTGTGTTCGCTGT
AAGAGCTGTGGATCCACAACTCCAGGCAAAGGGTGG
GATGCACAGTGGTCTCATGATTTCTCACTGTGTC
ATGATTGCGCCAAGCTCTTTGCTAAAGGAAACTTCTG
CCCTCTCTGTGACAAATGTTATGATGATGATGA
CTATGAGAGTAAGATGATGCAATGTGGAAAGTGTGA
TCGCTGGGTCCATTCCAAATGTGAGAATCTTTCA

TABLE 9-continued

Sequences.

| Description | SEQ ID NO |
|---|---|
| GATGAGATGTATGAGATTCTATCTAATCTGCCAGAAA | |
| GTGTGGCCTACACTTGTGTGAACTGTACTGAGC | |
| GGCACCCTGCAGAGTGGCGACTGGCCCTTGAAAAAG | |
| AGCTGCAGATTTCTCTGAAGCAAGTTCTGACAGC | |
| TTTGTTGAATTCTCGGACTACCAGCGATTTGCTACGCT | |
| ACCGGCAGGCTGCCAAGCCTCCAGACTTAAAT | |
| CCCGAGACAGAGGAGAGTATACCTTCCCGCAGCTCC | |
| CCCGAAGGACCTGATCCACCAGTTCTTACTGAGG | |
| TCAGCAAACAGGATGATCAGCAGCCTTTAGATCTAG | |
| AAGGAGTCAAGAGGAAGATGGACCAAGGGAATTA | |
| CACATCTGTGTTGGAGTTCAGTGATGATATTGTGAAG | |
| ATCATTCAAGCAGCCATTAATTCAGATGGAGGA | |
| CAGCCAGAAATTAAAAAAGCCAACAGCATGGTCAAG | |
| TCCTTCTTCATTCGGCAAATGGAACGTGTTTTTC | |
| CATGGTTCAGTGTCAAAAGTCCAGGTTTTGGGAGCC | |
| AAATAAAGTATCAAGCAACAGTGGGATGTTACC | |
| AAACGCAGTGCTTCCACCTTCACTTGACCATAATTAT | |
| GCTCAGTGGCAGGAGCGAGAGGAAAACAGCCAC | |
| ACTGAGCAGCCTCCTTTAATGAAGAAAATCATTCCAG | |
| CTCCCAAACCCAAAGGTCCTGGAGAACCAGACT | |
| CACCAACTCCTCTGCATCCTCCTACACCACCAATTTT | |
| GAGTACTGATAGGAGTCGAGAAGACAGTCCAGA | |
| GCTGAACCCACCCCCAGGCATAGAAGACAATAGACA | |
| GTGTGCGTTATGTTTGACTTATGGTGATGACAGT | |
| GCTAATGATGCTGGTCGTTTACTATATATTGGCCAAA | |
| ATGAGTGGACACATGTAAATTGTGCTTTGTGGT | |
| CAGCGGAAGTGTTTGAAGATGATGACGGATCACTAA | |
| AGAATGTGCATATGGCTGTGATCAGGGGCAAGCA | |
| GCTGAGATGTGAATTCTGCCAAAAGCCAGGAGCCAC | |
| CGTGGGTTGCTGTCTCACATCCTGCACCAGCAAC | |
| TATCACTTCATGTGTTCCCGAGCCAAGAACTGTGTCT | |
| TTCTGGATGATAAAAAAGTATATTGCCAACGAC | |
| ATCGGGATTTGATCAAAGGCGAAGTGGTTCCTGAGA | |
| ATGGATTTGAAGTTTTCAGAAGAGTGTTTGTGGA | |
| CTTTGAAGGAATCAGCTTGAGAAGGAAGTTTCTCAAT | |
| GGCTTGGAACCAGAAAATATCCACATGATGATT | |
| GGGTCTATGACAATCGACTGCTTAGGAATTCTAAATG | |
| ATCTCTCCGACTGTGAAGATAAGCTCTTTCCTA | |
| TTGGATATCAGTGTTCCAGGGTATACTGGAGCACCAC | |
| AGATGCTCGCAAGCGCTGTGTATATACATGCAA | |
| GATAGTGGAGTGCCGTCCTCCAGTCGTAGAGCCGGAT | |
| ATCAACAGCACTGTTGAACATGATGAAAACAGG | |
| ACCATTGCCCATAGTCCAACATCTTTTACAGAAAGTT | |
| CATCAAAAGAGAGTCAAAACACAGCTGAAATTA | |
| TAAGTCCTCCATCACCAGACCGACCTCCTCATTCACA | |
| AACCTCTGGCTCCTGTTATTATCATGTCATCTC | |
| AAAGGTCCCCAGGATTCGAACACCCAGTTATTCTCCA | |
| ACACAGAGATCCCCTGGCTGTCGACCGTTGCCT | |
| TCTGCAGGAAGTCCTACCCCAACCACTCATGAAATAG | |
| TCACACTAGGTGATCCTTTACTCTCCTCTGGAC | |
| TTCGAAGCATTGGCTCCAGGCGTCACAGTACCTCTTC | |
| CTTATCACCCCAGCGGTCCAAACTCCGGATAAT | |
| GTCTCCAATGAGAACTGGGAATACTTACTCTAGGAAT | |
| AATGTTTCCTCAGTCTCCACCACCGGGACCGCT | |
| ACTGATCTTGAATCAAGTGCCAAAGTAGTTGATCATG | |
| TCTTAGGGCCACTGAATTCAAGTACTAGTTTAG | |
| GGCAAAACACTTCCACCTCTTCAAATTTGCAAAGGAC | |
| AGTGGTTACTGTAGGCAATAAAAACAGTCACTT | |
| GGATGGATCTTCATCTTCAGAAATGAAGCAGTCCAGT | |
| GCTTCAGACTTGGTGTCCAAGAGCTCCTCTTTA | |
| AAGGGAGAGAAGACCAAAGTGCTGAGTTCCAAGAGC | |
| TCAGAGGGATCTGCACATAATGTGGCTTACCCTG | |
| GAATTCCTAAACTGGCCCCACAGGTTCATAACACAAC | |
| ACCTAGAGAACTGAATGTTAGTAAAATCGGCTC | |
| CTTTGCTGAACCCTCTTCAGTGTCGTTTTCTTCTAAAG | |
| AGGCCCTCTCCTTCCCACACCTCCATTTGAGA | |
| GGGCAAAGGAATGATCGAGACCAACACACAGATTCT | |
| ACCCAATCAGCAAACTCCTCTCCAGATGAAGATA | |
| CTGAAGTCAAAACCTTGAAGCTATCTGGAATGAGCA | |
| ACAGATCATCCATTATCAACGAACATATGGGATC | |
| TAGTTCCAGAGATAGGAGACAGAAAGGGAAAAAATC | |
| CTGTAAAGAAACTTTCAAAGAAAAGCATTCCAGT | |
| AAATCTTTTTTGGAACCTGGTCAGGTGACAACTGGTG | |
| AGGAAGGAAACTTGAAGCCAGAGTTTATGGATG | |
| AGGTTTTGACTCCTGAGTATATGGGCCAACGACCATG | |
| TAACAATGTTTCTTCTGATAAGATTGGTGATAA | |

TABLE 9-continued

Sequences.

| Description | SEQ ID NO |
|---|---|

AGGCCTTTCTATGCCAGGAGTCCCCAAAGCTCCACCC
ATGCAAGTAGAAGGATCTGCCAAGGAATTACAG
GCACCACGGAAACGCACAGTCAAAGTGACACTGACA
CCTCTAAAAATGGAAAATGAGAGTCAATCCAAAA
ATGCCCTGAAAGAAAGTAGTCCTGCTTCCCCTTTGCA
AATAGAGTCAACATCTCCCACAGAACCAATTTC
AGCCTCTGAAAATCCAGGAGATGGTCCAGTGGCCCA
ACCAAGCCCCAATAATACCTCATGCCAGGATTCT
CAAAGTAACAACTATCAGAATCTTCCAGTACAGGAC
AGAAACCTAATGCTTCCAGATGGCCCCAAACCTC
AGGAGGATGGCTCTTTTAAAAGGAGGTATCCCCGTCG
CAGTGCCCGTGCACGTTCTAACATGTTTTTTGG
GCTTACCCCACTCTATGGAGTAAGATCCTATGGTGAA
GAAGACATTCCATTCTACAGCAGCTCAACTGGG
AAGAAGCGAGGCAAGAGATCAGCTGAAGGACAGGT
GGATGGGGCCGATGACTTAAGCACTTCAGATGAAG
ACGACTTATACTATTACAACTTCACTAGAACAGTGAT
TTCTTCAGGTGGAGAGGAACGACTGGCATCCCA
TAATTTATTTCGGGAGGAGGAACAGTGTGATCTTCCA
AAAATCTCACAGTTGGATGGTGTTGATGATGGG
ACAGAGAGTGATACTAGTGTCACAGCCACAACAGG
AAAAGCAGCCAGATTCCAAAAAGAAATGGTAAAG
AAAATGGAACAGAGAACTTAAAGATTGATAGACCTG
AAGATGCTGGGGAGAAAGAACATGTCACTAAGAG
TTCTGTTGGCCACAAAAATGAGCCAAAGATGGATAA
CTGCCATTCTGTAAGCAGAGTTAAAACACAGGGA
CAAGATTCCTTGGAAGCTCAGCTCAGCTCATTGGAGT
CAAGCCGCAGAGTCCACACAAGTACCCCCTCCG
ACAAAAATTTACTGGACACCTATAATACTGAGCTCCT
GAAATCAGATTCAGACAATAACAACAGTGATGA
CTGTGGGAATATCCTGCCTTCAGACATTATGGACTTT
GTACTAAAGAATACTCCATCCATGCAGGCTTTG
GGTGAGAGCCCAGAGTCATCTTCATCAGAACTCCTGA
ATCTTGGTGAAGGATTGGGTCTTGACAGTAATC
GTGAAAAAGACATGGGTCTTTTTGAAGTATTTTCTCA
GCAGCTGCCTACAACAGAACCTGTGGATAGTAG
TGTCTCTTCdCTATCTCAGCAGAGGAACAGTTTGAG
TTGCCTCTAGAGCTACCATCTGATCTGTCTGTC
TTGACCACCCGGAGTCCCACTGTCCCCAGCCAGAATC
CCAGTAGACTAGCTGTTATCTCAGACTCAGGGG
AGAAGAGAGTAACCATCACAGAAAAATCTGTAGCCT
CCTCTGAAAGTGACCCAGCACTGCTGAGCCCAGG
AGTAGATCCAACTCCTGAAGGCCACATGACTCCTGAT
CATTTTATCCAAGGACACATGGATGCAGACCAC
ATCTCTAGCCCTCCTTGTGGTTCAGTAGAGCAAGGTC
ATGGCAACAATCAGGATTTAACTAGGAACAGTA
GCACCCCTGGCCTTCAGGTACCTGTTTCCCCAACTGT
TCCCATCCAGAACCAGAAGTATGTGCCCAATTC
TACTGATAGTCCTGGCCCGTCTCAGATTTCCAATGCA
GCTGTCCAGACCACTCCACCCCACCTGAAGCCA
GCCACTGAGAAACTCATAGTTGTTAACCAGAACATGC
AGCCACTTTATGTTCTCCAAACTCTTCCAAATG
GAGTGACCCAAAAAATCCAATTGACCTCTTCTGTTAG
TTCTACACCCAGTGTGATGGAGACAAATACTTC
AGTATTGGGACCCATGGGAGGTGGTCTCACCCTTACC
ACAGGACTAAATCCAAGCTTGCCAACTTCTCAA
TCTTTGTTCCCTTCTGCTAGCAAAGGATTGCTACCCAT
GTCTCATCACCAGCACTTACATTCCTTCCCTG
CAGCTACTCAAAGTAGTTTCCCACCAAACATCAGCAA
TCCTCCTTCAGGCCTGCTTATTGGGGTTCAGCC
TCCTCCGGATCCCCAACTTTTGGTTTCAGAATCCAGC
CAGAGGACAGACCTCAGTACCACAGTAGCCACT
CCATCCTCTGGACTCAAGAAAAGACCCATATCTCGTC
TACAGACCCGAAAGAATAAAAAACTTGCTCCCT
CTAGTACCCCTTCAAACATTGCCCCTTCTGATGTGGTT
TCTAATATGACATTGATTAACTTCACACCCTC
CCAGCTTCCTAATCATCCAAGTCTGTTAGATTTGGGG
TCACTTAATACTTCATCTCACCGAACTGTCCCC
AACATCATAAAAAGATCTAAATCTAGCATCATGTATT
TTGAACCGGCACCCCTGTTACCACAGAGTGTGG
GAGGAACTGCTGCCACAGCGGCAGGCACATCAACAA
TAAGCCAGGATACTAGCCACCTCACATCAGGGTC
TGTGTCTGGCTTGGCATCCAGTTCCTCTGTCTTGAATG
TTGTATCCATGCAAACTACCACAACCCCTACA
AGTAGTGCGTCAGTTCCAGGACACGTCACCTTAACCA
ACCCAAGGTTGCTTGGTACCCCAGATATTGGCT

TABLE 9-continued

| Sequences. | |
|---|---|
| Description | SEQ ID NO |

CAATAAGCAATCTTTTAATCAAAGCTAGCCAGCAGA
GCCTGGGGATTCAGGACCAGCCTGTGGCTTTACC
GCCAAGTTTCAGGAATGTTTCCACAACTGGGGACATCA
CAGACCCCCTCTACTGCTGCAATAACAGCGGCA
TCTAGCATCTGTGTGGTCCCCTCCACTCAGACTACGG
GCATAACAGCCGCTTCACCTTCTGGGGAAGCAG
ACGAACACTATCAGCTTCAGCATGTGAACCAGCTCCT
TGCCAGCAAAACTGGGATTCATTCTTCCCAGCG
TGATCTTGATTCTGCTTCAGGGCCCCAGGTATCCAAC
TTTACCCAGACGGTAGACGCTCCTAATAGCATG
GGACTGGAGCAGAACAAGGCTTTATCCTCAGCTGTGC
AAGCCAGCCCGACCTCTCCTGGGGGTTCTCGAT
CCTCTCCATCTTCTGGACAGCGGTCAGCAAGCCCTTC
AGTGCCGGGTCCCACTAAACCCAAACCAAAAAC
CAAACGGTTTCAGCTGCCTCTAGACAAAGGGAATGG
CAAGAAGCACAAAGTTTCCCATTTGCGGACCAGT
TCTTCTGAAGCACACATTCCAGACCAAGAAACGACAT
CCCTGACCTCAGGCACAGGGACTCCAGGAGCAG
AGGCTGAGCAGCAGGATACAGCTAGCGTGGAGCAGT
CCTCCCAGAAGGAGTGTGGGCAACCTGCAGGGCA
AGTCGCTGTTCTTCCGGAAGTTCAGGTGACCCAAAAT
CCAGCAAATGAACAAGAAAGTGCAGAACCTAAA
ACAGTGGAAGAAGAGGAAAGTAATTTCAGCTCCCCA
CTGATGCTTTGGCTTCAGCAAGAACAAAAGCGGA
AGGAAAGCATTACTGAGAAAAAACCCAAGAAAGGAC
TTGTTTTTGAAATTTCCAGTGATGATGGCTTTCA
GATCTGTGCAGAAAGTATTGAAGATGCCTGGAAGTC
ATTGACAGATAAAGTCCAGGAAGCTCGATCAAAT
GCCCGCCTAAAGCAGCTCTCATTTGCAGGTGTTAACG
GTTTGAGGATGCTGGGGATTCTCCATGATGCAG
TTGTGTTCCTCATTGAGCAGCTGTCTGGTGCCAAGCA
CTGTCGAAATTACAAATTCCGTTTCCACAAGCC
AGAGGAGGCCAATGAACCCCCCTTGAACCCTCACGG
CTCAGCCAGGGCTGAAGTCCACCTCAGGAAGTCA
GCATTTGACATGTTTAACTTCCTGGCTTCTAAACATC
GTCAGCCTCCTGAATACAACCCCAATGATGAAG
AAGAGGAGGAGGTACAGCTGAAGTCAGCTCGGAOGG
CAACTAGCATGGATCTGCCAATGCCCATGCGCTT
CCGGCACTTAAAAAAGACTTCTAAGGAGGCAGTTGG
TGTCTACAGGTCTCCCATCCATGGCCGGGGTCTT
TTCTGTAAGAGAAACATTGATGCAGGTGAGATGGTG
ATTGAGTATGCCGGCAACGTCATCCGCTCCATCC
AGACTGACAAGCGGGAAAAGTATTACGACAGCAAGG
GCATTGGTTGCTATATGTTCCGAATTGATGACTC
AGAGGTAGTGGATGCCACCATGCATGGAAATGCTGC
ACGCTTCATCAATCACTCGTGTGAGCCTAACTGC
TATTCTCGGGTCATCAATATTGATGGGCAGAAGCACA
TTGTCATCTTTGCCATGCGTAAGATCTACCGAG
GAGAGGAACTCACTTACGACTATAAGTTCCCCATTGA
GGATGCCAGCAACAAGCTGCCCTGCAACTGTGG
CGCCAAGAAATGCCGGAAGTTCCTAAACTAAAGCTG
CTCTTCTCCCCCAGTGTTGGAGTGCAAGGAGGCG
GGGCCATCCAAAGCAACGCTGAAGGCCTTTTCCAGC
AGCTGGGAGCTCCCGGATTGCGTGGCACAGCTGA
GGGGCCTCTGTGATGGCTGAGCTCTCTTATGTCCTAT
ACTCACATCAGACATGTGATCATAGTCCCAGAG
ACAGAGTTGAGGTCTCGAAGAAAAGATCCATGATCG
GCTTTCTCCTGGGGCCCCTCCAATTGTTTACTGT
TAGAAAGTGGGAATGGGGTCCCTAGCAGACTTGCCT
GGAAGGAGCCTATTATAGAGGGTTGGTTATGTTG
GGAGATTGGGCCTGAATTTCTCCACAGAAATAAGTTG
CCATCCTCAGGTTGGCCCTTTCCCAAGCACTGT
AAGTGAGTGGGTCAGGCAAAGCCCCAAATGGAGGGT
TGGTTAGATTCCTGACAGTTTGCCAGCCAGGCCC
CACCTACAGCGTCTGTCGAACAAACAGAGGTCTGGT
GGTTTTCCCTACTATCCTCCCACTCGAGAGTTCA
CTTCTGGTTGGGAGACAGGATTCCTAGCACCTCCGGT
GTCAAAAGGCTGTCATGGGGTTGTGCCAATTAA
TTACCAAACATTGAGCCTGCAGGCTTTGAGTGGGAGT
GTTGCCCCCAGGAGCCTTATCTCAGCCAATTAC
CTTTCTTGACAGTAGGAGCGGCTTCCCTCTCCCATTCC
CTCTTCACTCCCTTTTCTTCCTTTCCCCTGTC
TTCATGCCACTGCTTTCCCATGCTTCTTTCGGGTTGTA
GGGGAGACTGACTGCCTGCTCAAGGACACTCC
CTGCTGGGCATAGGATGTGCCTGCAAAAAGTTCCCTG
AGCCTGTAAGCACTCCAGGTGGGGAAGTGGACA

TABLE 9-continued

| Sequences. | |
| --- | --- |
| Description | SEQ ID NO |

GGAGCCATTGGTCATAACCAGACAGAATTTGGAAAC
ATTTTCATAAAGCTCCATGGAGAGTTTTAAAGAA
ACATATGTAGCATGATTTTGTAGGAGAGGAAAAAGA
TTATTTAAATAGGATTTAAATCATGCAACAACGA
GAGTATCACAGCCAGGATGACCCTTGGGTCCCATTCC
TAAGACATGGTTACTTTATTTTCCCCTTGTTAA
GACATAGGAAGACTTAATTTTTAAACGGTCAGTGTCC
AGTTGAAGGCAGAACACTAATCAGATTTCAAGG
CCCACAACTTGGGGACTAGACCACCTTATGTTGAGGG
AACTCTGCCACCTGCGTGCAACCCACAGCTAAA
GTAAATTCAATGACACTACTGCCCTGATTACTCCTTA
GGATGTGGTCAAAACAGCATCAAATGTTTCTTC
TCTTCCTTTCCCCAAGACAGAGTCCTGAACCTGTTAA
ATTAAGTCATTGGATTTTACTCTGTTCTGTTTA
CAGTTTACTATTTAAGGTTTTATAAATGTAAATATATT
TTGTATATTTTTCTATGAGAAGCACTTCATAG
GGAGAAGCACTTATGACAAGGCTATTTTTTAAACCGC
GGTATTATCCTAATTTAAAAGAAGATCGGTTTT
TAATAATTTTTTATTTTCATAGGATGAAGTTAGAGAA
AATATTCAGCTGTACACACAAAGTCTGGTTTTT
CCTGCCCAACTTCCCCCTGGAAGGTGTACTTTTTGTTG
TTTAATGTGTAGCTTGTTTGTGCCCTGTTGAC
ATAAATGTTTCCTGGGTTTGCTCTTTGACAATAAATG
GAGAAGGAAGGTCACCCAACTCCATTGGGCCAC
TCCCCTCCTTCCCCTATTGAAGCTCCTCAAAAGGCTA
CAGTAATATCTTGATACAACAGATTCTCTTCTT
TCCCGCCTCTCTCCTTTCCGGCGCAACTTCCAGAGTG
GTGGGAGACGGCAATCTTTACATTTCCCTCATC
TTTCTTACTTCAGAGTTAGCAAACAACAAGTTGAATG
GCAACTTGACATTTTTGCATCACCATCTGCCTC
ATAGGCCACTCTTTCCTTTCCCTCTGCCCACCAAGTCC
TCATATCTGCAGAGAACCCATTGATCACCTTG
TGCCCTCTTTTGGGGCAGCCTGTTGAAACTGAAGCAC
AGTCTGACCACTCACGATAAAGCAGATTTTTCT
CTGCCTCTGCCACAAGGTTTCAGAGTAGTGTAGTCCA
AGTAGAGGGTGGGGCACCCTTCTCTCGCCGCAA
GAAGCCCATTCCTATGGAAGTCTAGCAAAGCAATAC
GACTCAGCCCAGCACTCTCTGCCCCAGGACTCAT
GGCTCTGCTGTGCCTTCCATCCTGGGCTCCCTTCTCTC
CTGTGACCTTAAGAACTTTGTCTGGTGGCTTT
GCTGGAACATTGTCACTGTTTTCACTGTCATGCAGGG
AGCCCAGCACTGTGGCCAGGATGGCAGAGACTT
CCTTGTCATCATGGAGAAGTGCCAGCAGGGGACTGG
GAAAAGCACTCTACCCAGACCTCACCTCCCTTCC
TCCTTTTGCCCATGAACAAGATGCAGTGGCCCTAGGG
GTTCCACTAGTGTCTGCTTTCCTTTATTATTGC
ACTGTGTGAGGTTTTTTTGTAAATCCTTGTATTCCTAT
TTTTTTTAAAGAAAAAAAAAAAAAACCTTAAGCT
GCATTTGTTACTGAAATGATTAATGCACTGATGGGTC
CTGAATTCACCTTGAGAAAGACCCAAAGGCCAG
TCAGGGGGTGGGGGGAACTCAGCTAAATAGACCTAG
TTACTGCCCTGCTAGGCCATGCTGTACTGTGAGC
CCCTCCTCACTCTCTACCAACCCTAAACCCTGAGGAC
AGGGGAGGAACCCACAGCTTCCTTCTCCTGCCA
GCTGCAGATGGTTTGCCTTGCCTTTCCACCCCCTAATT
GTCAACCACAAAAATGAGAAATTCCTCTTCTA
GCTCAGCCTTGAGTCCATTGCCAAATTTTCAGCACAC
CTGCCAGCAACTTGGGGGAATAAGCGAAGGTTT
CCCTACAAGAGGGAAAGAAGGCAAAAACGGCACAG
CTATCTCCAAACACATCTGAGTTCATTTCAAAAGT
GACCAAGGGAATCTCCGCACAAAAGTGCAGATTGAG
GAATTGTGATGGGTCATTCCCAAGAATCCCCCAA
GGGGCATCCCAAATCCCTGAGGAGTAACAGCTGCAA
ACCTGGTCAGTTCTCAGTGAGAGCCAGCTCACTT
ATAGCTTTGCTGCTAGAACCTGTTGTGGCTGCATTTC
CTGGTGGCCAGTGACAACTGTGTAACCAGAATA
GCTGCATGGCGCTGACCCTTTGGCCGGAACTTGGTCT
CTTGGCTCCCTCCTTGGCCACCCACCACCTCTC
GCACAGCCCCTCTGTTTTTACACCAATAACAAGAATT
AAGGGGGAAGCCCTGGCAGCTATACGTTTTCAA
CCAGACTCCTTTGCCGGGACCCAGCCCGCCACCCTGC
TCGCCTCCGTCAAACCCCCGGCCAATGCAGTGA
GCACCATGTAGCTCCCTTGATTTAAAAAAAATAAAAA
ATAAAAAAAAAAGGAAAAAAAAAATACAACACAC
ACACAAAAATAAAAAAAAATATTCTAATGAATGTATC
TTTCTAAAGGACTGACGTTCAATCAAATATCTGA

TABLE 9-continued

Sequences.

| Description | | SEQ ID NO |
|---|---|---|
| | AAATACTAAAGGTCAAAACCTTGTCAGATGTTAACTT | |
| | GAAATCAAGTTGTTTTTGTTTTTAAGGAAAAGCGGGT | |
| | CATTGCAAAGGGCTGGGTGTAATTTTATGTTTC | |
| | ATTTCCTTCATTTTAAAGCAATACAAGGTTATGGAGC | |
| | AGATGGTTTTGTGCCGAATCATGAATACTAGTC | |
| | AAGTCACACACTCTGGAAACTTGCAACTTTTTGTTTG | |
| | TnTGGTTTTCAAATAAATATAAATATGATATA | |
| | TATAGGAACTAATATAGTAATGCACCATGTAACAAA | |
| | GCCTAGTTCAGTCCATGGCTTTTAATTCTCTTAA | |
| | CACTATAGATAAGGATTGTGTTACAGTTGCTAGTAGC | |
| | GGCAGGAAGATGTCAGGCTCACTTTCCTCTGAT | |
| | TCCCGAAATGGGGGGAACCTCTAACCATAAAGGAAT | |
| | GGTAGAACAGTCCATTCCTCGGATCAGAGAAAAA | |
| | TGCAGACATGGTGTCACCTGGATTTTTTTCTGCCCAT | |
| | GAATGTTGCCAGTCAGTACCTGTCCTCCTTGTT | |
| | TCTCTATTTTTGGTTATGAATGTTGGGGTTACCACCTG | |
| | CATTTAGGGGAAAATTGTGTTCTGTGCTTTCC | |
| | TGGTATCTTGTTCCGAGGTACTCTAGTTCTGTCTTTCA | |
| | ACCAAGAAAATAGAATTGTGGTGTTTCTTTTA | |
| | TTGAACTTTTAACAGTCTCTTTAGTAAATACAGGTAG | |
| | TTGAATAATTGTTTCAAGAGCTCAACAGATGAC | |
| | AAGCTTCTTTTCTAGAAATAAGACATTTTTTGACAAC | |
| | TTTATCATGTATAACAGATCTGTTTTTTTTCCT | |
| | TGTGTTCTTCCAAGCTTCTGGTTAGAGAAAAAGAGAA | |
| | AAAAAAAAAAGGAAAATGTGTCTAAAGTCCATC | |
| | AGTGTTAACTCCCTGTGACAGGGATGAAGGAAAATA | |
| | CTTTAATAGTTCAAAAAATAATAATGCTGAAAGC | |
| | TCTCTACGAAAGACTGAATGTAAAAGTAAAAAGTGT | |
| | ACATAGTTGTAAAAAAAAGGAGTTTTTAAACATG | |
| | TAATTAATAAACATGTCAAGTTTATTGCTGC | |
| | A | |
| | | |
| NM_032427.4 | ACTCTCTCTCTTTCTCTCCCTCTCCTATCGGAGCACAA | SEQ ID NO: 2 |
| MAML2, mRNA | TGAAAGCCTGTGTATCGCCGTGACTCCGGGCG | |
| | CGAGCCAGTGTCAGCAAAGCGGCTAACAACAGACGA | |
| | GAAAGAGAAAGGAAAATACAAGCTACTTTTTTTT | |
| | TCCATCTATAAAGCGGAGCAAATACAGGAGATAGAA | |
| | CCAGATTGCTTATTGCGAGTCCAGACCCTCAGAT | |
| | CCACTGGCCGGGGATGGAATGTACAAAAGTGGACAG | |
| | AAAAGTGGCTGGACATGACTCGGTGCAATTTGCT | |
| | GGAAGTTTGTAAGTTTGACCATCGTTTGTAAATTACT | |
| | CTCGGAAGAGTTTGTCTCTCTTGATACTGTATT | |
| | AGAATAGAGCCGGGGGTGAGGAATAGAAACGTAAGC | |
| | GGGAAAGAAAAAAATGTGTTGAAGGATCTCTCTC | |
| | AGTGGCTAGCGACTTAAGATTGCTTTTCATTTAAGGC | |
| | TAGGAAACCTTAGAGGGAGTGAGGATTTTACCG | |
| | GTGATTGGATTAGCTGAAGAAAAAAGCATGGTCCAA | |
| | AAGTCCAATTACTGACATTGTTAACAGTTGAAAA | |
| | GCTGTCTCCCTCTTTTGGGAGAAGACAACATCCTACA | |
| | GTACCCCAAAGAGGAGAAAACACCGGAGCGAAA | |
| | GGAAAGGGAGGAAAAATTAAAAGCCAAAAGACAGT | |
| | CTCCCTTGATTTTTGCACATTTTGAACAGTGACTT | |
| | AAACATCTTCTGAAACAGCACTGTTTTGTTTTGTTTTG | |
| | GTTTTTTATTTAACCTGAGGAAAAGTCAAGGC | |
| | TGCTGGTTACATAGACATGGTAGAAATGTGTTTCTCT | |
| | GCAGAAACATCCCCATAAAGAATTGTCGGAAAC | |
| | AACTAGGTGAGGGGGAGTCCTCTCTATTAATACCTCT | |
| | CTCAATACCTTTTGCTGTGTGTTTCTGTCTCTT | |
| | GCTGGACAATCCCTGAATTCTTGATCTAACCCCCAGA | |
| | TCGTGTGTTTACAAAGTACCTAGTGGCTCTTGT | |
| | CAGGTTGGTGGAGGAAAAAAAATCCACCAACTCTGT | |
| | CCAACTTCTCCAGAGCTGTCAAATGCAATTAGAG | |
| | TAAGTTAATCAGGGTTTGTTTCCAACTTATCCTCCCCC | |
| | CAGTTGGTTTCTATTCTTTCTCCCCACCCTCT | |
| | TTTTACTAACTCCCCTCCCCCACAACTTCTCCACGGCT | |
| | CCCCCACAACCTCTGAAGACCTCTATTCATGT | |
| | GGCCCTGAACACTGAGCTCACATTGTCAAAAACAGA | |
| | CTTGCCTGCAATAGCCAGCAGTAGCCTCTTTCCA | |
| | CCTCACCATCCCAGAGGCAGCAATCATTGTGTCCGGT | |
| | AAGATGGGGGACACAGCGCCCCCGCAGGCCCCC | |
| | GCAGGAGGGCTAGGGGGGGCCTCTGGGGCGGGGCTC | |
| | CTTGGAGGGGGCTCAGTCACCCCGAGAGTGCACA | |
| | GTGCTATCGTGGAGCGCCTCCGGGCTCGGATCGCTGT | |
| | CTGCCGCCAACACCACCTGAGCTGTGAAGGACG | |
| | ATATGAACGAGGTAGGGCCGAGAGCTCAGACCGGGA | |
| | AAGAGAAAGCACCTTGCAGCTCCTGAGCCTTGTA | |

TABLE 9-continued

Sequences.

| Description | SEQ ID NO |
|---|---|

CAGCATGGCCAGGGGGCAAGGAAAGCTGGCAAACAC
ACCAAGGCCACCGCCACTGCTGCCACCACTACAG
CCCCTCCACCGCCCCCTGCTGCCCCTCCTGCGGCCTC
CCAAGCAGCAGCAACAGCAGCCCCACCGCCCCC
ACCAGACTATCACCATCACCACCAGCAGCACCTGCTG
AACAGTAGCAATAATGGTGGCAGTGGTGGGATA
AACGGAGAGCAGCAGCCGCCCGGTCAACCCCAGGG
GACCAGAGGAACTCAGCCCTGATTGCGCTCCAGG
GTTCCTTGAAAAGAAAACAGGTAGTTAACCTATCTCC
TGCCAACAGCAAGCGACCCAATGGCTTTGTGGA
CAACTCATTTCTTGATATCAAAAGAATTCGTGTTGGG
GAGAATCTCTCTGCAGGACAAGGTGGCCTCCAA
ATAAACAATGGACAAAGTCAGATTATGTCAGGGACC
TTGCCTATGAGCCAAGCACCCCTGCGAAAGACTA
ACACTCTGCCATCCCATACACATTCTCCTGGCAATGG
CCTGTTTAACATGGGCTTAAAGGAGGTAAAGAA
GGAGCCAGGAGAGACTCTGTCTTGCAGTAAGCACAT
GGATGGCCAAATGACCCAAGAGAATATTTTTCCT
AATAGGTACGGAGACGACCCTGGAGAACAACTGATG
GATCCTGAGCTGCAGGAACTGTTCAATGAACTGA
CCAACATATCTGTGCCTCCCATGAGTGACCTTGAACT
GGAGAACATGATCAATGCCACCATAAAGCAGGA
TGACCCATTTAACATTGACTTGGGTCAGCAAAGCCAG
AGGAGCACACCTAGGCCCTCCTTACCCATGGAG
AAAATAGTGATCAAAAGTGAATACTCACCGGGCTTG
ACTCAGGGCCCCTCAGGCTCTCCTCAGCTGAGGC
CCCCATCAGCTGGCCCCGCATTCTCCATGGCCAACTC
TGCCCTCTCCACTTCGTCTCCAATCCCTTCAGT
CCCTCAGAGCCAGGCTCAGCCTCAGACAGGCTCCGG
AGCAAGCCGGGCCTTGCCAAGCTGGCAGGAAGTA
TCCCATGCCCAGCAGCTCAAACAGATAGCTGCTAATC
GTCAGCAGCATGCCCGGATGCAGCAGCACCAGC
AGCAGCACCAGCCTACCAACTGGTCAGCCTTGCCCTC
TTCTGCTGGACCATCACCAGGTCCATTTGGGCA
GGAGAAAATCCCCAGCCCTTCTTTTGGTCAGCAGACA
TTCAGCCCACAGAGCTCCCCCATGCCTGGGGTA
GCTGGCGGCAGCGGCCAGTCGAAAGTAATGGCTAAC
TACATGTACAAGGCCGGCCCCTCAGCCCAGGGTG
GGCACCTAGATGTCCTCATGCAGCAAAAGCCTCAGG
ATCTCAGTCGAAGTTTTATTAACAACCCGCACCC
AGCCATGGAGCCCCGTCAGGGCAACACCAAGCCTTT
GTTTCATTTTAACTCAGATCAAGCGAACCAGCAG
ATGCCTTCTGTTTTGCCTTCCCAGAACAAGCCTTCTCT
CCTACACTACACCCAACAGCAACAGCAGCAAC
AGCAGCAGCAGCAGCAGCAGCAGCAGCAGCAGCAGC
AGCAACAGCAGCAGCAGCAGCAACAGCAACAGCA
ACACCAACAGCAGAGTTCAATTTCAGCTCAACAACA
GCAACAGCAGCAGAGCTCAATTTCAGCCCAACAG
CAGCAGCAGCAGCAACAACAGCAGCAGCAGCAGCAA
CAACAACAGCAACAACAGCAGCAGCAGCAGCAGC
AACAACCATCTTCTCAGCCTGCCCAATCTCTACCAAG
CCAGCCTTTGCTAAGGTCACCTTTGCCACTTCA
GCAAAAGCTCCTACTTCAGCAAATGCAGAATCAGCC
CATTGCAGGAATGGGATACCAAGTCTCCCAACAA
CAGAGACAGGATCAACACTCTGTGGTAGGCCAGAAC
ACAGGCCCCAGTCCAAGTCCTAACCCCTGCTCAA
ATCCAAACACTGGAAGTGGTTACATGAACTCCCAGC
AATCACTGTTGAATCAGCAATTGATGGGAAAGAA
GCAGACTCTACAGAGGCAGATCATGGAGCAGAAACA
GCAACTTCTTCTCCAGCAGCAGATGCTGGCTGAC
GCGGAGAAAATTGCTCCACAAGATCAGATAAACCGA
CATTTGTCAAGGCCACCTCCAGATTATAAAGACC
AAAGAAGAAATGTGGGCAATATGCAACCAACTGCTC
AGTATTCTGGTGGCTCATCCACAATAAGCTTAAA
CTCTAACCAGGCTTTGGCAAACCCAGTTTCAACACAC
ACCATTTTAACTCCCAATTCCAGCCTCCTGTCT
ACTTCTCACGGGACAAGAATGCCATCATTATCTACAG
CAGTTCAGAATATGGGGATGTATGGAAATCTGC
CTTGTAATCAACCTAACACATACAGTGTCACTTCAGG
AATGAATCAATTGACCCAACAGAGAAACCCAAA
GCAATTGTTAGCAAATCAAAACAACCCTATGATGCCA
CGGCCACCTACCTTAGGGCCAAGTAATAATAAC
AATGTAGCCACTTTTGGAGCTGGATCTGTTGGTAATT
CACAACAATTGAGACCAAATTTAACCCATAGTA
TGGCAAGCATGCCACCACAGAGAACATCAAACGTAA
TGATCACATCCAACACAACTGCACCAAACTGGGC

TABLE 9-continued

| Sequences. | |
| --- | --- |
| Description | SEQ ID NO |

CTCTCAAGAAGGAACAAGCAAACAGCAAGAAGCCCr
GACGTCTGCAGGAGTCCGCTTCCCCACAGGTACA
CCTGCAGCCTATACCCCAAATCAGTCACTGCAACAGG
CAGTAGGTAGCCAGCAATTTTCCCAGAGGGCAG
TGGCTCCTCCTAACCAGTTAACACCAGCAGTGCAAAT
GAGACCCATGAACCAAATGAGCCAAACACTAAA
TGGGCAAACCATGGGTCCCCTCAGGGGTCTGAATCTC
AGACCCAATCAGCTAAGCACACAGATTTTGCCT
AATTTGAATCAGTCAGGAACAGGGTTGAATCAGTCG
AGGACGGGCATCAACCAGCCACCATCCCTGACGC
CCAGCAATTTTCCTTCACCCAACCAAAGTTCCAGGGC
TTTTCAAGGAACTGACCACAGCAGTGACTTAGC
TTTTGACTTCCTCAGCCAACAAAATGATAACATGGGC
CCTGCCCTAAACAGTGATGCTGATTTCATTGAT
TCTTTATTGAAGACAGAGCCTGGTAATGATGACTGGA
TGAAAGACATCAATCTTGATGAAATCTTGGGGA
ACAATTCCTAAAGAAGAAAGGGAAGACAATTTACAA
ACTCCAAGCACTAAAAGGCAGTATATTACAGAAA
CTCTGTAGAGGCTGAACTGTTGATGTTCAGGTGGACT
ACATGAAGATAACATGCTTAAAAATGGAAAGCA
GAAAGTAACTGCAGTGATGAACATTTTGGTCCAAATT
CTTGTTTTAAATCTTACACCTGAAAGTAAAATA
TTGGGATCACTTTTCCCTGTCTAAACTCCAGGATACA
GTATCCAATTTATCCAAACAGAACTGTGGTGTC
AATGTGTAATTAATTGTGTAAAATAGCCTTCCCAAGT
TTCTTTTTCCCTGGAAAATAAAAAAGGTAATAG
AACTTGTAGTTTATTTAAACCCCATGTCATGAGGAGG
TACTAGTTCCAAGCAACAAACTCCTTAATTTGC
TCTAATAGATAGGTATGGTTTAATCTTTCCATTGTGTC
TTTTCATTTAATTTTCCTGAAGCTTGCAGGAT
AGATTGAAATGTTATAGGTTTGTTTGGAGTAACCAAA
CAGTATGCAAATTAAGAAAAAGCCAGAGAACCT
AGAAAACATCCAGTGGATTACAGAATTTCTTCCCCAT
ATTCACTCCTCACTTTTACAATTTTCCCACAAT
CCTCTACTTCAGTGGGATGCTGTGTCTAGTGATTAAA
CAAAAATATAGAGCTGTGCAATTTGATTTTGGC
TTCCACAACGAATATCTGAATCCATTCCAAATGAAAT
TTTAGATATAACAAAGACTTGTCCTAATCATAC
TGAAATATTGGTGCACACCTCTCTGCATTAGATTTCA
CTTTTTTAAAAAACCCAGTGGACATTGCTATAA
ATAAGATTTATTTGGCTACAAATAACCTGGGATGTTG
CTTATTATGATTGATGCCTGCTGGTTTGTTCCC
AAGCTGAGTGAAATTGAACCTCGTCCTCCCTACTCAT
TTTGATGACTGAGGCTGGTTTATAAGAAAAGGA
AGTTTGGAGAAGAAAACCGAGATTAGAAAATATCAT
GTTTTGGTTGGAGATAAGAACCAGGGATGGCAAG
TACCAGTGTGTACAAATGTATTTCACGGAGTTTGAAG
GAACGCATAATCAAGAGGGAAAACAATTTGTCC
TTCATTGGACGTATTATTTGGATTTGGGTGAGCAACA
AAATGGAATGTGGTCTGTTAGGAGCATTCTGTT
TGTTCTTTTGTCCCTGATGTGATGAATCATTGCCACAT
GCTAGATGGACTCTTCATATCCAGGTTTTGTC
CCTCAGGGCTGAGCACTGTATTAAAGAGTTTTTGTTG
AGTCATTTAACCTTAGTGTCCACATCCAGATCA
GCTGTAAAATGGGGAAGACGTGTGCTGATTTGGAAT
GAATGCAAAATATCACTATCATTTTCCTAATTAC
AGAGGAGGAAAGGTTATCTTCAGCCCTTTCAGTTCTA
TGCTCACATATTCAAATATCAAATGTAATTTAG
CTGAAGTTATTTAATAATCAAGTGTTTCAATATCTGTT
CAAAGAAAAAGAACACACTTTGAAAATTCTGC
AAAGCTGTCTCCCAGTCTTTAAAATGTCTGGAAGCAC
TCTCCTTCTTTACAATACCAACATCACTGGCCC
AGAATCTTCCCTGTGCTAGTTTGTAAATATAAATAAA
TTACTTGTTTTGTAAACTTTTGTAAAGAATATT
TTGGTAGAAATACTTCAAACATATTCTTTGGGTTATA
TTTATACATATGTGAAATAAATATACTATCAAA
AGGTTATATTTTATACAAAAAGTAAATTGCTACCTTT
TGTATGCTAATATGCAAAGTTTTGTATAATATG
ATGGTTTATTTTTAGCTCTACACTTAAACCATAGGTG
GTTGAGTGGGAACTTTTGAAAACTATCAAGAGG
CTTGTTAGACAAATTTATATTCTGAAACCTCAATAAG
AAAGCATTCCAGGTTTCAATCCTTGTTTTTTGT
CCTGCTCCCAAATTCTTTTTTAAACCCATAGTTCTTGT
GTCTTATTTGATTCTTCTGCTGTGCACATTGT
ATTGGTCCTTGTTGCATGTAGTCTACTGTGTGTTTTCC
GATTTTATAAGGCAGCATTTCTCCATACAAAA

TABLE 9-continued

| Sequences. | | |
|---|---|---|
| Description | | SEQ ID NO |

|  | AGAAAAAAAATGATGTACATATAAACGCTTTTGTTGT<br>ATGGCTCCTCCATGTTACTGTATATATCTGCCA<br>GCACTTCCCAGTTACACTCCTGTGAGTCAGCTTATTTT<br>TACCCTAACATAAATAGTATGTTTTGTACTAG<br>TTATCAAATTTAAGAGATAAAGCAATCAGAATGTTTG<br>GATTTTCTTCTATCTTAATGTGAATTTCATAAT<br>TAATGTCTATTTATTCAGCTATTCATTAAAATACAGG<br>ATTCTTTGGGAAAA | |
| NP_005924.2<br>KMT2A isoform 2<br>acid sequence | MAHSCRWRFPARPGITGGGGGGGRRGLGGAPRORVPA<br>LLLPPGPPVGGGGPGAPPSPPAVAAAAAAAGSS<br>GAGVPGGAAAASAASSSSASSSSSSSSSASSGPALLRVG<br>PGFDAALQVSAAIGTNLRRFRAVFGESGGGG<br>GSGEDEQFLGFGSDEEVRVRSPTRSPSVKTSPRKPRGRP<br>RSGSDRNSAILSDPSVFSPLNKSETKSGDKI<br>KKKDSKSIEKKRGRPPTFPGVKIKITHGKDISELPKGNKE<br>DSLKKIKRTPSATFQQATKIKKLRAGKLSP<br>LKSKFKTGKLQIGRKGVQIVRRRGRPPSTERIKTPSGLLI<br>NSELEKPQKVRKDKEGTPPLTKEDKTVVRQ<br>SPRRIKPVRHPSSKRTDATIAKQEEQRAKKGAQKKIEKE<br>AAQLQGRKVKTQVKNIRQFIMPVVSAISSR<br>IIKTPRRFIEDEDYDPPIKIARLESTPNSRFSAPSCGSSEKS<br>SAASQHSSQMSSDSSRSSSPSVDTSTDS<br>QASEEIQVLPEERSDTPEVHPPLPISQSPENESNDRRSRR<br>YSVSERSFGSRTTKKLSTLQSAPQQQTSSS<br>PPPPLLTPPPPLQPASSISDHTPWLMPPTIPLASPFLPASTA<br>PMQGKRKSILREPTFRWTSLKHSRSEPQ<br>YFSSAKYAKEGLIRKPIFDNFRPPPLTPEDVGFASGFSAS<br>GTAASARLFSPLHSGTRFDMHKRSPLLRAP<br>RFTPSEAHSRIFESVTLPSNRTSAGTSSSGVSNRKRKRKV<br>FSPIRSEPRSPSHSMRTRSGRLSSSELSPL<br>TPPSSVSSSLSISVSPLATSALNPTFTFPSHSLTQSGESAE<br>KNORPRKQTSAPAEPFSSSSPTPEFPWFT<br>PGSQTERGRNKDKAPEELSKDRDADKSVEKDKSRERDR<br>EREKENKRESRKEKRKRGSEIQSSSALYPVGR<br>VSKEKVVGEDVATSSSAKKATGRKKSSSHDSGTDITSV<br>TLGDTTAVKTKILIKKGRGNLEKTNLDLGPTA<br>PSLEKEKTLCLSTPSSSTVKHSTSSIGSMLAQADKLPMT<br>DKRVASLLKKAKAQLCKIEKSKSLKQTDQPK<br>AQGGQESDSSETSVRGPRIKMVCRRAAVALGRKRAVFPD<br>DMPTLSALPWEEREKILSSMGNDDKSSIAGSE<br>DAEPLAPPIKPIKPVTRNKAPQEPPVKKGRRSRRCGQCP<br>GCQVPEDCGVCTNCLDKPKFGGRNIKKQCCK<br>MRKCQNLQWMPSKAYLQKQAKAVKKKEKKSKTSEKK<br>DSKESSVVKNVVDSSQKPTPSAREDPAPKKSSSE<br>PPPRKPVEEKSEEGNVSAPGPESKQATTPASRKSSKQVS<br>QPALVIPPQPPTIGPPRKEVPKTTPSEPKKK<br>QPPPPESGPEQSKQKKVAPRPSIPVKQKPKEKEKPPPVN<br>KQENAGTLNILSTLSNGNSSKQKIPADGVHR<br>IRVDFKEDCEAENVWEMGGLGILTSVPITPRVVCFLCAS<br>SGHVEFVYCQVCCEPFHKFCLEENERPLEDQ<br>LENWCCRRCKFCHVCGRQHQATKQLLECNKCRNSYHP<br>ECLGPNYPTKPTKKKKVWICTKCVRCKSCGSTT<br>PGKGVVDAQWSHDFSLCHDCAKLFAKGNFCPLCDKCY<br>DDDDYESKIVIMQCGKCDRWVHSKCENLSDEMYEIL<br>SNLPESVAYTCVNCTERHPAEWRLALEKELQISLKQVL<br>TALLNSRTTSHLLRYRQAAKPPDLNPETEESI<br>PSRSSPEGPDPPVLTEVSKQDDQQPLDLEGVKRKMDQG<br>NYTSVLEFSDDIVKIIQAAINSDGGQPEIKKA<br>NSMVKSFFIRQMERVFPWFSVRKSRFWEPNKVSSNSGM<br>LPNAVLPPSLDHNYAQWQEREENSFFTEQPPLM<br>KKIIPAPKPKGPGEPDSPTPLHPPTPPILSTDRSREDSPEL<br>NPPPGIEDNRQCALCLTYGDDSANDAGRL<br>LYIGQNEWTHVNCALWSAEVFEDDDGSLKNVHMAVIR<br>GKQLRCEFCQKPGATVGCCLTSCTSNYHFMCSR<br>AKNCVFLDDKKVYCQRHRDLIKGEVVPENGFEVFRRVF<br>VDFEGISLRRKFLNGLEPENIHMMIGSMFIDC<br>LGILNDLSDCEDKLFPIGYQCSRVYWSTTDARKRCVYT<br>CKIVECRPPVVEPDINSTVEHDFNRTIAHSPT<br>SFTESSSKESQNTAEIISPPSPDRPPHSQTSGSCYYHVISK<br>VPRIRTPSYSPTORSPGCRPLPSAGSPTP<br>TFHEIVTVGDPLLSSGLRSIGSRRHSTSSLSPQRSKLRIMS<br>PMRTGNTYSRNNVSSVSTTGTATDLESSA<br>KVVDHVLGPLNSSTSLGQNTSTSSNLQRTVVTVGNKNS<br>HLDGSSSSEMKQSSASDLVSKSSSLKGEKTKV<br>LSSKSSEGSAMNVAYPGIPKLAPQVHNTTSRELNVSKIG | SEQ ID NO: 3 |

TABLE 9-continued

| Description | Sequences. | SEQ ID NO |
| --- | --- | --- |
| | SFAEPSSVSFSSKEALSFPHLHLRGQRNDRD<br>QHTDSTQSANSSPDEDTEVKTLKLSGMSNRSSIINEHMG<br>SSSRDRRQKGKKSCKETFKEKHSSKSFLEPG<br>QVTFGEEGNLKPEFMDEVLTPEYMGORPCNNVSSDKIG<br>DKGLSMPGVPKAPPMQVEGSAKELQAPRKRTV<br>KVTLTPLKMENESQSKNALKESSPASPLQIESTSPTEPIS<br>ASENPGDGPVAQPSPNNTSCQDSQSNNYQN<br>LPVQDRNLYILPDGPKPQEDGSFKRRYPRRSARARSNMF<br>FGLTPLYGVRSYGEEDIPFYSSSTGKKRGKRS<br>AEGQVDGADDLSTSDEDDLYYYNFTRTVISSGGEERLA<br>SFINLFREEEQCDLPKISQLDGVDDGTESDTSV<br>TATTRKSSQIPKRNGKENGTENLKIDRPEDAGEKEHVTK<br>SSVGHKNEPKMDNCHSVSRVKTQGQDSLEAQ<br>LSSLESSRRVHTSTPSDKNLLDTYNTELLKSDSDNNNSD<br>DCGNILPSDIMDFVLKNTPSMQALGESPESS<br>SSELLNLGEGLGLDSNREKDMGLFEVFSQQLPTTEPVDS<br>SVSSSISAEEQFELPLELPSDLSVLTTRSPT<br>VPSQNPSRLAVISDSGEKRVTITEKSVASSESDPALLSPG<br>VDPTPEGHMTPDHFIQGHMPADHISSPPCG<br>SVEQGHGNNQDLTRNSSTPGLQVPVSPTVPIQNQKYVP<br>NSTDSPGPSQISNAAVQTTPPHLKPATEKLIV<br>VNQNMQPLYVLQTLPNGVTQKIQLTSSVSSTPSVMETN<br>TSVLGPMGGGLTLTTGLNPSLPTSQSLFPSAS<br>KGLLPMSHHQHLHSFPAATQSSFPPNISNPPSGLLIGVQP<br>PPDPQLLVSESSQRTDESTTVATPSSGLKK<br>RPISRLQTRKNKKLAPSSTPSNIAPSDVVSNMFLINFTPS<br>QLPNHPSLLDLGSLNTSSHRTVPNIIKRSK<br>SSIMYFEPAPLLPQSVGGTAATAAGTSTISQDTSHLTSGS<br>VSGLASSSSVLNVVSMQMTPTSSASVPG<br>HVTLTNPRLLGTPDIGSISNLLIKASQQSLGIQDQPVALP<br>PSSGMFPQLGTSQTPSTAAITAASSICVLP<br>STQTTGITAASPSGEADEHYQLQHVNQLLASKTGIHSSQ<br>RDLDSASGPQVSNFTQTVDAPNSMGLFQNKA<br>LSSAVQASPTSPGGSPSSPSSGQRSASPSVPGPTKPKPKT<br>KRFQLPLDKGNGKKHKVSHLRTSSSEAHIP<br>DQETTSLTSGTGTPGAEAEQQDTASVEQSSQKECGQPA<br>GQVAVLPEVQVTQNPANEQESAEPKTVEEEES<br>NFSSPLMLWLQQEQKRKESITEKKPKKGLVFEISSDDGF<br>QICAESIEDAWKSLTDKVQEARSNARLKQLS<br>FAGVNGLRMLGILHDAVVFLIEQLSGAKHCRNYKFRFH<br>KPEEANEPPLNPHGSARAEVHLRKSAFDMFNF<br>LASKHRQPPEYNPNDEEEEEVQLKSARRATSMDLPMPM<br>RFRHLKKTSKEAVGVYRSPIHGRGLFCKRNID<br>AGEMVIEYAGNVIRSIQTDKREKYYDSKGIGCYMFRID<br>DSEVVDATMHGNAARFINHSCEPNCYSRVINI<br>DGQKHIVIFAMRKIYRGEELTYDYKFPIEDASNKLPCNC<br>GAKKCRKFLN | |
| NP_115803.1<br>MAML2 amino<br>acid sequence | MGDTAPPQAPAGGLGGASGAGLLGGGSVTPRVHSAIVE<br>RLRARIAVCRQHHLSCEGRYERGRAESSDRER<br>ESTLQLLSLVQHGQGARKAGKHTKATATAATTTAPPPP<br>PAAPPAASQAAATAAPPPPPPDYHHHHQQHLLN<br>SSNNGGSGGINGEQQPPASTPGDQRNSALIALQGSLKRK<br>QWNLSPANSKRPNGFVDNSFLDIKRIRVGE<br>NLSAGQGGLQINNGQSQIMSGTLPMSQAPLRKTNTLPS<br>HTHSPGNGLFNMGLKEVKKEPGETLSCSKHMD<br>GQMTQENIFPNRYGDDPGEQLMDPELQELFNELTNISVP<br>PMSDLELENMINATIKQDDPFNIDLGQQSQR<br>STPRPSLPMEKIVIKSEYSPGLTQGPSGSPQLRPPSAGPAF<br>SMANSALSTSSPIPSVPQSQAQPQTGSGA<br>SRALPSWQEVSHAQQLKQIAANRQQHARMQQHQQQH<br>QPTNWSALPSSAGPSPGPFGQEKIPSPSFGQQTF<br>SPQSSPMPGVAGGSGQSKVMANYMYKAGPSAQGGHL<br>DVLMQQKPQDLSRSFINNPHPAMEPRQGNTKPLF<br>HFNSDQANQQMPSVLPSQNKPSLLHYTQQQQQQQQQ<br>QQQQQQQQQQQQQQQQQQQQQQQQQSSISAQQQQ<br>QQQQSSISAQQQQQQQQQQQQQQQQQQQQQQQQQP<br>SSQPAQSLPSQPLLRSPLPLQQKLLLQQMQNQPI<br>AGMGYQVSQQQRQDQHSVVGQNTGPSPSPNPCSNPNT<br>GSGYMNSQQSLLNQQLMGKKQTLQRQIMEQKQQ<br>LLLQQQMLADAEKIAPQDQINRHLSRPPPDYKDQRRNV<br>GNMQPTAQYSGGSSTISLNSNQALANPVSTHT<br>ILTPNSSLLSTSHGTRMPSLSTAVQNMGMYGNLPCNQP<br>NTYSVTSGMNQLTQQRNPKQLLANQNNPMMPR<br>PPTLGPSNNNNVATFGAGSVGNSQQLRPNLTHSMASMP<br>PQRTSNVMITSNTTAPNWASQEGTSKQQEALT | SEQ ID NO: 4 |

TABLE 9-continued

| Description | Sequences. | SEQ ID NO |
|---|---|---|
| | SAGVRFPTGTPAAYTPNQSLQQAVGSQQFSQRAVAPPN QLTPAVQMRPMNQMSQTLNGQTMGPLRGLNLR PNQLSTQILPNLNQSGTGLNQSRTGINQPPSLTPSNFPSP NQSSRAFQGTDHSSDLAFDFLSQQNDNMGP ALNSDADFIDSLLKTEPGNDDWMKDINLDEILGNNS | |
| NM_001197104.2 KMT2A, transcript variant 1, mRNA | GCTTCACTTCACGGGGCGAACATGGCGCACAGCTGTC GGTGGCGCTTCCCCGCCCGACCCGGGACCACCG GGGGCGGCGGCGGCGGGGGGGCGCCGGGGCCTAGGG GGCGCCCCGCGGCAACGCGTCCCGGCCCTGCTGCT TCCCCCCGGGCCCCCGGTCGGCGGTGGCGGCCCCGG GGCGCCCCCCTCCCCCCCGGCTGTGGCGGCCGCG GCGGCGGCGGCGGGAAGCAGCGGGGCTGGGGTTCCA GGGGGGAGCGGCCGCCGCCTCAGCAGCCTCCTCGT CGTCCGCCTCGTCTTCGTCTTCGTCATCGTCCTCAGCC TCTTCAGGGCCGGCCCTGCTCCGGGTGGGCCC GGGCTTCGACGCGGCGCTGCAGGTCTCGGCCGCCATC GGCACCAACCTGCGCCGGTTCCGGGCCGTGTTT GGGGAGAGCGGCGGGGGAGGCGGCAGCGGAGAGGA TGAGCAATTCTTAGGTTTTGGCTCAGATGAAGAAG TCAGAGTGCGAAGTCCCACAAGGTCTCCTTCAGTTAA AACTAGTCCTCGAAAACCTCGTGGGAGACCTAG AAGTGGCTCTGACCGAAATTCAGCTATCCTCTCAGAT CCATCTGTGTTTTCCCCTCTAAATAAATCAGAG ACCAAATCTGGAGATAAGATCAAGAAGAAAGATTCT AAAAGTATAGAAAAGAAGAGAGAGGAAGACCTCCCA CCTTCCCTGGAGTAAAAATCAAAATAACACATGGAA AGGACATTTCAGAGTTACCAAAGGGAAACAAAGA AGATAGCCTGAAAAAAATTAAAAGGACACCTTCTGC TACGTTTCAGCAAGCCACAAAGATTAAAAAATTA AGAGCAGGTAAACTCTCTCCTCTCAAGTCTAAGTTTA AGACAGGGAAGCTTCAAATAGGAAGGAAGGGGG TACAAATTGTACGACGGAGAGGAAGGCCTCCATCAA CAGAAAGGATAAAGACCCCTTCGGGTCTCCTCAT TAATTCTGAACTGGAAAAGCCCCAGAAAGTCCGGAA AGACAAGGAAGGAACACCTCCACTTACAAAAGAA GATAAGACAGTTGTCAGACAAAGCCCTCGAAGGATT AAGCCAGTTAGGATTATTCCTTCTTCAAAAAGGA CAGATGCAACCATTGCTAAGCAACTCTTACAGAGGG CAAAAAAGGGGGCTCAAAAGAAAATTGAAAAAGA AGCAGCTCAGCTGCAGGGAAGAAAGGTGAAGACACA GGTCAAAAATATTCGACAGTTCATCATGCCTGTT GTCAGTGCTATCTCCTCGCGGATCATTAAGACCCCTC GGCGGTTTATAGAGGATGAGGATTATGACCCTC CAATTAAAAATTGCCCGATTAGAGTCTACACCGAATAG TAGATTCAGTGCCCCGTCCTGTGGATCTTCTGA AAAATCAAGTGCAGCTTCTCAGCACTCCTCTCAAATG TCTTCAGACTCCTCTCGATCTAGTAGCCCCACT GTTGATACCTCCACAGACTCTCAGGCTTCTGAGGAGA TTCAGGTACTTCCTGAGGAGCGGGAGCGATACCC CTGAAGTTCATCCTCCACTGCCCATTTCCCAGTCCCC AGAAAATGAGAGTAATGATAGGAGAAGCAGAAG GTATTCAGTGTCGGAGAGAAGTTTTGGATCTAGAACG ACGAAAAAATTATCAACTCTACAAAGTGCCCCC CAGCAGCAGACCTCCTCGTCTCCACCTCCACCTCTGC TGACTCCACCGCCACCACTGCAGCCAGCCTCCA GTATCTCTGACCACACACCTTGGCTTATGCCTCCAAC AATCCCCTTAGCATCACCATTTTTGCCTGCTTC CACTGCTCCTATGCAAGGGAAGGGAAAATCTATTTTG CGAGAACCGACATTTAGGTGGACTTCTTTAAAG CATTCTAGGTCAGAGCCACAATACTTTTCCTCAGCAA AGTATGCCAAAGAAGGTCTTATTCGCAAACCAA TATTTGATAATTTCCGACCCCCTCCACTAACTCCCGA GGACGTTGGCTTTGCATCTGGTTTTTCTGCATC TGGTACCGCTGCTTCAGCCCGATTGTTTTCGCCACTCC ATTCTGGAACAAGGTTTGATATGCACAAAAGG AGCCCTCTTCTGAGAGCTCCAAGATTTACTCCAAGTG AGGCTCACTCTAGAATATTTGAGTCTGTAACCT TGCCTAGTAATCGAACTTCTGCTGGAACATCTTCTTC AGGAGTATCCAATAGAAAAAGGAAAAGAAAGT GTTTAGTCCTATTCGATCTGAACCAAGATCTCCTTCTC ACTCCATGAGGACAAGAAGTGGAAGGCTTAGT AGTTCTGAGCTCTCACCTCTCACCCCCCCGTCTTCTGT CTCTTCCTCGTTAAGCATTTCTGTTAGTCCTC TTGCCACTAGTGCCTTAAACCCAACTTTTACTTTTCCT TCTCATTCCCTGACTCAGTCTGGGGAATCTGC | SEQ ID NO: 5 |

TABLE 9-continued

| | |
|---|---|
| Sequences. | |

| Description | SEQ ID NO |
|---|---|

```
AGAGAAAAATCAGAGACCAAGGAAGCAGACTAGTCJC
TCCGGCAGAGCCATTTTCATCAAGTAGTCCTACT
CCTCTCTTCCCTTGGTTTACCCCAGGCTCTCAGACTGA
AAGAGGGAGAAATAAAGACAAGGCCCCCGAGG
AGCTGTCCAAAGATCGAGATGCTGACAAGAGCGTGG
AGAAGGACAAGAGTAGAGAGAGAGACCGGGAGAG
AGAAAAGGAGAATAAGCGGGAGTCAAGGAAAGAGA
AAAGGAAAAAGGGATCAGAAATTCAGAGTAGTTCT
GCTTTGTATCCTGTGGGTAGGGTTTCCAAAGAGAAGG
TTGTTGGTGAAGATGTTGCCACTTCATCTTCTG
CCAAAAAAGCAACAGGGCGGAAGAAGTCTTCATCAC
ATGATTCTGGGACTGATATTACTTCTGTGACTCT
TGGGGATACAACAGCTGTCAAAACCAAAATACTTAT
AAAGAAAGGGAGAGGAAATCTGGAAAAAACCAAC
TTGGACCTCGGCCCAACTGCCCCATCCCTGGAGAAGG
AGAAAACCCTCTGCCTTTCCACTCCTTCATCTA
GCACTGTTAAACATTCCACTTCCTCCATAGGCTCCAT
GTTGGCTCAGGCAGACAAGCTTCCAATGACTGA
CAAGAGGGTTGCCAGCCTCCTAAAAAAGGCCAAAGC
TCAGCTCTGCAAGATTGAGAAGAGTAAGAGTCTT
AAACAAACCGACCAGCCCAAAGCACAGGGTCAAGAA
AGTGACTCATCAGAGACCTCTGTGCGAGGACCCC
GGATTAAACATGTCTGCAGAAGAGCAGCTGTTGCCCT
TGGCCGAAAACGAGCTGTGTTTCCTGATGACAT
GCCCACCCTGAGTGCCTTACCATGGGAAGAACGAGA
AAGATTTTGTCTTCCATGGGGAATGATGACAAG
TCATCAATTGCTGGCTCAGAAGATGCTGAACCTCTTG
CTCCACCCATCAAACCAATTAAACCTGTCACTA
GAAACAAGGCACCCCAGGAACCTCCAGTAAAGAAAG
GACGTCGATCGAGGCGGTGTGGGCAGTGTCCCGG
CTGCCAGGTGCCTGAGGACTGTGGTGTTTGTACTAAT
TGCTTAGATAAGCCCAAGTTTGGTGGTCGCAAT
ATAAAGAAGCAGTGCTGCAAGATGAGAAAATGTCAG
AATCTACAATGGATGCCTTCCAAAGCCTACCTGC
AGAAGCAAGCTAAAGCTGTGAAAAAGAAAGAGAAA
AAGTCTAAGACCAGTGAAAAGAAAGACAGCAAAGA
GAGCAGTGTTGTGAAGAACGTGGTGGACTCTAGTCA
GAAACCTACCCCATCAGCAAGAGAGGATCCTGCC
CCAAAGAAAAGCAGTAGTGAGCCTCCTCCACGAAAG
CCCGTCGAGGAAAAGAGTGAAGAAGGGAATGTCT
CGGCCCCTGGGCCTGAATCCAAACAGGCCACCACTCC
AGCTTCCAGGAAGTCAAGCAAGCAGGTCTCCCA
GCCAGCACTGGTCATCCCGCCTCAGCCACCTACTACA
GGACCGCCAAGAAAGAAGTTCCCAAAACCACT
CCTAGTGAGCCCAAGAAAAAGCAGCCTCCACCACCA
GAATCAGGTCCAGAGCAGAGCAAACAGAAAAAAG
TGGCTCCCCGCCCAAGTATCCCTGTAAAACAAAAACC
AAAAGAAAAGGAAAAACCACCTCCGGTCAATAA
GCAGGAGAATGCAGGCACTTTGAACATCCTCAGCAC
TCTCTCCAATGGCAATAGTTCTAAGCAAAAAATT
CCAGCAGATGGAGTCCACAGGATCAGAGTGGACTTT
AACGAGGATTGTGAAGCAGAAAATGTGTGGGAGA
TGGGAGGCTTAGGAATTTTGACTTCTGTTCCTATAAC
ACCCAGGGTGGTTTGCTTTCTCTGTGCCAGTAG
TGGGCATGTAGAGTTTGTGTATTGCCAAGTCTGTTGT
GAGCCCTTCCACAAGTTTTGTTTAGAGGAGAAC
GAGCGCCCTCTGGAGGACCAGCTGGAAAATTGGTGT
TGTCGTCGTTGCAAATTCTGTCACGTTTGTGGAA
GGCAACATCAGGCTACAAAGCAGCTGCTGGAGTGTA
ATAAGTGCCGAAACAGCTATCACCCTGAGTGCCT
GGGACCAAACTACCCCACCAAACCCACAAAGAAGAA
GAAAGTCTGGATCTGTACCAAGTGTGTTCGCTGT
AAGAGCTGTGGATCCACAACTCCAGGCAAAGGGTGG
GATGCACAGTGGTCTCATGATTTCTCACTGTGTC
ATGATTGCGCCAAGCTCTTTGCTAAAGGAAACTTCTG
CCCTCTCTGTGACAAATGTTATGATGATGATGA
CTATGAGAGTAAGATGATGCAATGTGGAAAGTGTGA
TCGCTGGGTCCATTCCAAATGTGAGAATCTTTCA
GGTACAGAAGATGAGATGTATGAGATTCTATCTAATC
TGCCAGAAAGTGTGGCCTACACTTGTGTGAACT
GTACTGAGCGGCACCCTGCAGAGTGGCGACTGGCCC
TTGAAAAAGAGCTGCAGATTTCTCTGAAGCAAGT
TCTGACAGCTTTGTTGAATTCTCGGACTACCAGCCAT
TTGCTACGCTACCGGCAGGCTGCCAAGCCTCCA
GACTTAAATCCCGAGACAGAGGAGAGTATACCTTCC
CGCAGCTCCCCCGAAGGACCTGATCCACCAGTTC
```

TABLE 9-continued

| Sequences. | |
|---|---|
| Description | SEQ ID NO |

```
TTACTGAGGTCAGCAAACAGGATGATCAGCAGCCTTT
AGATCTAGAAGGAGTCAAGAGGAAGATGGACCA
AGGGAATTACACATCTGTGTTGGAGTTCAGTGATGAT
ATTGTGAAGATCATTCAAGCAGCCATTAATTCA
GATGGAGGACAGCCAGAAATTAAAAAAGCCAACAGC
ATGGTCAAGTCCTTCTTCATTCGGCAAATGGAAC
GTGTTTTTCCATGGTTCAGTGTCAAAAAGTCCAGGTT
TTGGGAGCCAAATAAAGTATCAAGCAACAGTGG
GATGTTACCAAACGCAGTGCTTCCACCTTCACTTGAC
CATAATTATGCTCAGTGGCAGGAGCGAGAGGAA
AACAGCCACACTGAGCAGCCTCCTTTAATGAAGAAA
ATCATTCCAGCTCCCAAACCCAAAGGTCCTGGAG
AACCAGACTCACCAACTCCTCTGCATCCTCCTACACC
ACCAATTTTGAGTACTGATAGGAGTCGAGAAGA
CAGTCCAGAGCTGAACCCACCCCCAGGCATAGAAGA
CAATAGACAGTGTGCGTTATGTTTGACTTATGGT
GATGACAGTGCTAATGATGCTGGTCGTTTACTATATA
TTGGCCAAAATGAGTGGACACATGTAAATTGTG
CTTTGTGGTCAGCGGAAGTGTTTGAAGATGATGACGG
ATCACTAAAGAATGTGCATATGGCTGTGATCAG
GGGCAAGCAGCTGAGATGTGAATTCTGCCAAAAGCC
AGGAGCCACCGTGGGTTGCTGTCTCACATCCTGC
ACCAGCAACTATCACTTCATGTGTTCCCGAGCCAAGA
ACTGTGTCTTTCTGGATGATAAAAAAGTATATT
GCCAACGACATCGGGATTTGATCAAAGGCGAAGTGG
TTCCTGAGAATGGATTTGAAGTTTTCAGAAGAGT
GTTTGTGGACTTTGAAGGAATCAGCTTGAGAAGGAA
GTTTCTCAATGGCTTGGAACCAGAAAATATCCAC
ATGATGATTGGGTCTATGACAATCGACTGCTTAGGAA
TTCTAAATGATCTCTCCGACTGTGAAGATAAGC
TCTTTCCTATTGGATATCAGTGTTCCAGGGTATACTG
GAGCACCACAGATGCTCGCAAGCGCTGTGTATA
TACATGCAAGATAGTGGAGTGCCGTCCTCCAGTCCTA
GAGCCGGATATCAACAGCACTGTTGAACATGAT
GAAAACAGGACCATTGCCCATAGTCCAACATCTTTTA
CAGAAAGTTCATCAAAAGAGAGTCAAAACACAG
CTGAAATTATAAGTCCTCCATCACCAGACCGACCTCC
TCATTCACAAACCTCTGGCTCCTGTTATTATCA
TGTCATCTCAAAGGTCCCCAGGATTCGAACACCCAGT
TATTCTCCAACACAGAGATCCCCTGGCTGTCGA
CCGTTGCCTTCTGCAGGAAGTCCTACCCCCAACCACTC
ATGAAATAGTCACAGTAGGTGATCCTTTACTCT
CCTCTGGACTTCGAAGCATTGGCTCCAGGCGTCACAG
TACCTCTTCCTTATCACCCCAGCGGTCCAAACT
CCGGATAATGTCTCCAATGAGAACTGGGAATACTTAC
TCTAGGAATAATGTTTCCTCAGTCTCCACCACC
GGGACCGCTACTGATCTTGAATCAAGTGCCAAAGTA
GTTGATCATGTCTTAGGGCCACTGAATTCAAGTA
CTAGTTTAGGGCAAAACACTTCCACCTCTTCAAATTT
GCAAAGGACAGTGGTTACTGTAGGCAATAAAAA
CAGTCACTTGGATGGATCTTCATCTTCAGAAATGAAG
CAGTCCAGTGCTTCAGACTTGGTGTCCAAGAGC
TCCTCTTTAAAGGGAGAGAAGACCAAAGTGCTGAGT
TCCAAGAGCTCAGAGGGATCTGCACATAATGTGG
CTTACCCTGGAATTCCTAAACTGGCCCCACAGGTTCA
TAACACAACATCTAGAGAACTGAATGTTAGTAA
AATCGGCTCCTTTGCTGAACCCTCTTCAGTGTCGTTT
CTTCTAAAGAGGCCCTCTCCTTCCCACACCTC
CATTTGAGAGGGCAAAGGAATGATCGAGACCAACAC
ACAGATTCTACCCAATCAGCAAACTCCTCTCCAG
ATGAAGATACTGAAGTCAAAACCTTGAAGCTATCTG
GAATGAGCAACAGATCATCCATTATCAACGAACA
TATGGGATCTAGTTCCAGAGATAGGAGACAGAAAGG
GAAAAAATCCTGTAAAGAAACTTTCAAAGAAAAG
CATTCCAGTAAATCTTTTTTGGAACCTGGTCAGGTGA
CAACTGGTGAGGAAGGAAACTTGAAGCCAGAGT
TTATGGATGAGGTTTTGACTCCTGAGTATATGGGCCA
ACGACCATGTAACAATGTTTCTTCTGATAAGAT
TGGTGATAAAGGCCTTTCTATGCCAGGAGTCCCCAAA
GCTCCACCCATGCAAGTAGAAGGATCTGCCAAG
GAATTACAGGCACCACGGAAACGCACAGTCAAAGTG
ACACTGACACCTCTAAAAAATGGAAAATGAGAGTC
AATCCAAAAATGCCCTGAAAGAAAGTAGTCCTGCTTC
CCCTTTGCAAATAGAGTCAACATCTCCCACAGA
ACCAATTTCAGCCTCTGAAAATCCAGGAGATGGTCCA
GTGGCCCAACCAAGCCCCAATAATACCTCATGC
```

TABLE 9-continued

Sequences.

| Description | SEQ ID NO |
|---|---|

CAGGATTCTCAAAGTAACAACTATCAGAATCTTCCAG
TACAGGACAGAAACCTAATGCTTCCAGATGGCC
CCAAACCTCAGGAGGATGGCTCTTTTAAAAGGAGGT
ATCCCCGTCGCAGTGCCCGTGCACGTTCTAACAT
TATGGTGAAGAAGACATTCCATTCTACAGCAGC
TCAACTGGGAAGAAGCGAGGCAAGAGATCAGCTGAA
GGACAGGTGGATGGGGCCGATGACTTAAGCACTT
CAGATGAAGACGACTTATACTATTACAACTTCACTAG
AACAGTGATTTCTTCAGGTGGAGAGGAACGACT
GGCATCCCATAATTTATTTCGGGAGGAGOAACAGTGT
GATCTTCCAAAAATCTCACAGTTGGATGGTGTT
GATGATGGGACAGAGAGTGATACTAGTGTCACAGCC
ACAACAAGGAAAAGCAGCCAGATTCCAAAAAGAA
ATGGTAAAGAAAATGGAACAGAGAACTTAAAGATTG
ACAGACCTGAAGATGCTGGGGAGAAAGAACATGT
CACTAAGAGTTCTGTTGGCCACAAAAATGAGCCAAA
GATGGATAACTGCCATTCTGTAAGCAGAGTTAAA
ACACAGGGACAAGATTCCTTGGAAGCTCAGCTCAGC
TCATTGGAGTCAAGCCGCAGAGTCCACACAAGTA
CCCCCTCCGACAAAAATTTACTGGACACCTATAATAC
TGAGCTCCTGAAATCAGATTCAGACAATAACAA
CAGTGATGACTGTGGGAATATCCTGCCTTCAGACATT
ATGGACTTTGTACTAAAGAATACTCCATCCATG
CAGGCTTTGGGTGAGAGCCCAGAGTCATCTTCATCAG
AACTCCTGAATCTTGGTGAAGGATTGGGTCTTG
ACAGTAATCGTGAAAAAGACATGGGTCTTTTTGAAGT
ATTTTCTCAGCAGCTGCCTACAACAGAACCTGT
GGATAGTAGTGTCTCTTCCTCTATCTCAGCAGAGGAA
CAGTTTGAGTTGCCTCTAGAGCTACCATCTGAT
CTGTCTGTCTTGACCACCCGGAGTCCCACTGTCCCCA
GCCAGAATCCCAGTAGACTAGCTGTTATCTCAG
ACTCAGGGGAGAAGAGAGTAACCATCACAGAAAAAT
CTGTAGCCTCCTCTGAAAGTGACCCAGCACTGCT
GAGCCCAGGAGTAGATCCAACTCCTGAAGGCCACAT
GACTCCTGATCATTTTATCCAAGGACACATGGAT
GCAGACCACATCTCTAGCCCTCCTTGTGGTTCAGTAG
AGCAAGGTCATGGCAACAATCAGGATTTAACTA
GGAACAGTAGCACCCCTGGCCTTCAGGTACCTGTTTC
CCCAACTGTTCCCATCCAGAACCAGAAGTATGT
GCCCAATTCTACTGATAGTCCTGGCCCGTCTCAGATT
TCCAATGCAGCTGTCCAGACCACTCCACCCCAC
CTGAAGCCAGCCACTGAGAAACTCATAGTTGTTAACC
AGAACATGCAGCCACTTTATGTTCTCCAAACTC
TTCCAAATGGAGTGACCCAAAAAATCCAATTGACCTC
TTCTGTTAGTTCTACACCCAGTGTGATGGAGAC
AAATACTTCAGTATTGGGACCCATGGGAGGTGGTCTC
ACCCTTACCACAGGACTAAATCCAAGCTTGCCA
ACTTCTCAATCTTTGTTCCCTTCTGCTAGCAAAGGATT
GCTACCCATGTCTCATCACCAGCACTTACATT
CCTTCCCTGCAGCTACTCAAAGTAGTTTCCCACCAAA
CATCAGCAATCCTCCTTCAGGCCTGCTTATTGG
GGTTCAGCCTCCTCCGGATCCCCAACTTTTGGTTTCA
GAATCCAGCCAGAGGACAGACCTCAGTACCACA
GTAGCCACTCCATCCTCTGGACTCAAGAAAAGACCCA
TATCTCGTCTACAGACCCGAAAGAATAAAAAAC
TTGCTCCCTCTAGTACCCCTTCAAACATTGCCCCTTCT
GATGTGGTTTCTAATATGACATTGATTAACTT
CACACCCTCCCAGCTTCCTAATCATCCAAGTCTGTTA
GATTTGGGGTCACTTAATACTTCATCTCACCGA
ACTGTCCCCAACATCATAAAAAGATCTAAATCTAGCA
TCATGTATTTTGAACCGGCACCCCTGTTACCAC
AGAGTGTGGGAGGAACTGCTGCCACAGCGGCAGGCA
CATCAACAATAAGCCAGGATACTAGCCACCTCAC
ATCAGGGTCTGTGTCTGGCTTGGCATCCAGTTCCTCT
GTCTTGAATGTTGTATCCATGCAAACTACCACA
ACCCCTACAAGTAGTGCGTCAGTTCCAGGACACGTCA
CCTTAACCAACCCAAGGTTGCTTGGTACCCCAG
ATATTGGCTCAATAAGCAATCTTTTAATCAAAGCTAG
CCAGCAGAGCCTGGGGATTCAGGACCAGCCTGT
GGCTTTACCGCCAAGTTCAGGAATGTTTCCACAACTG
GGGACATCACAGACCCCCTCTACTGCTGCAATA
ACAGCGGCATCTAGCATCTGTGTGCTCCCCTCCACTC
AGACTACGGGCATAACAGCCGCTTCACCTTCTG
GGGAAGCAGACGAACACTATCAGCTTCAGCATGTGA
ACCAGCTCCTTGCCAGCAAAACTGGGATTCATTC
TTCCCAGCGTGATGTGATTCTGCTTCAGGGGCCCCAG

TABLE 9-continued

| Sequences. | |
|---|---|
| Description | SEQ ID NO |

GTATCCAACTTTACCCAGACGGTAGACGCTCCT
AATAGCATCGGACTGGAGCACAACAAGGCTTTATCC
TCAGCTGTGCAAGCCAGCCCCACCTCTCCTGGGG
GTTCTCCATCCTCTCCATCTTCTGGACAGCGGTCAGC
AAGCCCTTCAGTGCCGGGTCCCACTAAACCCAA
ACCAAAAACCAAACGGTTTCAGCTGCCTCTAGACAA
AGGGAATGGCAAGAAGCACAAAGTTTCCCATTTG
CGGACCAGTTCTTCTGAAGCACACATTCCAGACCAAG
AAACGACATCCCTGACCTCAGGCACAGGGACTC
CAGGAGCAGAGGCTGAGCAGCAGGATACAGCTAGCG
TGGAGCAGTCCTCCCAGAAGGAGTGTGGGCAACC
TGCAGGGCAAGTCGCTGTTCTTCCGGAAGTTCAGGTG
ACCCAAAATCCAGCAAATGAACAAGAAAGTGCA
GAACCTAAAACAGTGGAAGAAGAGGAAAGTAATTTC
AGCTCCCCACTGATGCTTTGGCTTCAGCAAGAAC
AAAAGCGGAAGGAAAGCATTACTGAGAAAAAACCCA
AGAAAGGACTTGTTTTTGAAATTTCCAGTGATGA
TGGCTTTCAGATCTGTGCAGAAAGTATTGAAGATGCC
TGGAAGTCATTGACAGATAAAGTCCAGGAAGCT
CGATCAAATGCCCGCCTAAAGCAGCTCTCATTTGCAG
GTGTTAACGGTTTGAGGATGCTGGGGATTCTCC
ATGATGCAGTTGTGTTCCTCATTGAGCAGCTGTCTGG
TGCCAAGCACTGTCGAAATTACAAATTCCGTTT
CCACAAGCCAGAGGAGGCCAATGAACCCCCCTTGAA
CCCTCACGGCTCAGCCAGGGCTGAAGTCCACCTC
AGGAAGTCAGCATTTGACATGTTTAACTTCCTGGCTT
CTAAACATCGTCAGCCTCCTGAATACAACCCCA
ATGATGAAGAAGAGGAGGAGGTACAGCTGAAGTCAG
CTCGGAGGGCAACTAGCATGGATCTGCCAATGCC
CATGCGCTTCCGGCACTTAAAAAAGACTTCTAAGGAG
GCAGTTGGTGTCTACAGGTCTCCCATCCATGGC
CGGGGTCTTTTCTGTAAGAGAAACATTGATGCAGGTG
AGATGGTGATTGAGTATGCCGGCAACGTCATCC
GCTCCATCCAGACTGACAAGCGGGAAAAGTATTACG
ACAGCAAGGGCATTGGTTGCTATATGTTCCGAAT
TGATGACTCAGAGGGTAGTGGATGCCACCATGCATGG
AAATGCTGCACGCTTCATCAATCACTCGTGTGAG
CCTAACTGCTATTCTCGGGTCATCAATATTGATGGGC
AGAAGCACATTGTCATCTTTGCCATGCGTAAGA
TCTACCGAGGAGAGGAACTCACTTACGACTATAAGTT
CCCCATTGAGGATGCCAGCAACAAGCTGCCCTG
CAACTGTGGCGCCAAGAAATGCCGGAAGTTCCTAAA
CTAAAGCTGCTCTTCTCCCCCAGTGTTGGAGTGC
AAGGAGGCGGGGCCATCCAAAGCAACGCTGAAGGCC
TTTTCCAGCAGCTGGGAGCTCCCGGATTGCGTGG
CACAGCTGAGGGGCCTCTGTGATGGCTGAGCTCTCTT
ATGTCCTATACTCACATCAGACATGTGATCATA
GTCCCAGAGACAGAGTTGAGGTCTCGAAGAAAAGAT
CCATGATCGGCTTTCTCCTGGGGCCCCTCCAATT
GTTTACTGTTAGAAAGTGGGAATGGGGTCCCTAGCAG
ACTTGCCTGGAAGGAGCCTATTATAGAGGGTTG
GTTATGTTGGGAGATTGGGCCTGAATTTCTCCACAGA
AATAAGTTGCCATCCTCAGGTTGGCCCTTTCCC
AAGCACTGTAAGTGAGTGGGTCAGGCAAAGCCCCAA
ATGGAGGGTTGGTTAGATTCCTGACAGTTTGCCA
GCCAGGCCCCACCTACAGCGTCTGTCGAACAAACAG
AGGTCTGGTGGTTTTCCCTACTATCCTCCCACTC
GAGAGTTCACTTCTGGTTGGGAGACAGGATTCCTAGC
ACCTCCGGTGTCAAAAGGCTGTCATGGGGTTGT
GCCAATTAATTACCAAACATTGAGCCTGCAGGCTTTG
AGTGGGAGTGTTGCCCCCAGGAGCCTTATCTCA
GCCAATTACCTTTCTTGACAGTAGGAGCGGCTTCCCT
CTCCCATTCCCTCTTCACTCCCTTTTCTTCCTT
TCCCCTGTCTTCATGCCACTGCTTTCCCATGCTTCTTT
CGGGTTGTAGGGGAGACTGACTGCCTGCTCAA
GGACACTCCCTGCTGGGCATAGGATGTGCCTGCAAA
AAGTTCCCTGAGCCTGTAAGCACTCCAGGTGGGG
AAGTGGACAGGAGCCATTGGTCATAACCAGACAGAA
TTTGGAAACATTTTCATAAAGCTCCATGGAGAGT
TTTAAAGAAACATATGTAGCATGATTTTGTAGGAGAG
GAAAAAGATTATTTAAATAGGATTTAAATCATG
CAACAACGAGAGTATCACAGCCAGGATGACCCTTGG
GTCCCATTCCTAAGACATGGTTACTTTATTTTCC
CCTTGTTAAGACATAGGAAGACTTAATTTTTAAACGG
TCAGTGTCCAGTTGAAGGCAGAACACTAATCAG
ATTTCAAGGCCCACAACTTGGGGACTAGACCACCTTA

TABLE 9-continued

Sequences.

| Description | | SEQ ID NO |
|---|---|---|
| | TGTTGAGGGAACTCTGCCACCTGCGTGCAACCC | |
| | ACAGCTAAAGTAAATTCAATGACACTACTGCCCTGAT | |
| | TACTCCTTAGGATGTGGTCAAAACAGCATCAAA | |
| | TGTTTCTTCTCTTCCTTTCCCCAAGACAGAGTCCTGAA | |
| | CCTGTTAAATTAAGTCATTGGATTTTACTCTG | |
| | TTCTGTTTACAGTTTACTATTTAAGGTTTTATAAATGT | |
| | AAATATATTTTGTATATTTTTCTATGAGAAGC | |
| | ACTTCATAGGGAGAAGCACTTATGACAAGGCTATTTT | |
| | TTAAACCGCGGTATTATCCTAATTTAAAAGAAG | |
| | ATCGGTTTTTAATAATTTTTTATTTTCATAGGATGAAG | |
| | TTAGAGAAATATTCAGCTGTACACACAAAGT | |
| | CTGGTTTTTCCTGCCCAACTTCCCCCTGGAAGGTGTA | |
| | CTTTTTGTTGTTTAATGTGTAGCTTGTTTGTGC | |
| | CCTGTTGACATAAATGTTTCCTGGGTTTGCTCTTTGAC | |
| | AATAAATGGAGAAGGAAGGTCACCCAACTCCA | |
| | TTGGGCCACTCCCCTCCTTCCCCTATTGAAGCTCCTCA | |
| | AAAGGCTACAGTAATATCTTGATACAACAGAT | |
| | TCTCTTCTTTCCCGCCTCTCTCCTTTCCGGCGCAACTT | |
| | CCAGAGTGGTGGGAGACGGCAATCTTTACATT | |
| | TCCCTCATCTTTCTTACTTCAGAGTTAGCAAACAACA | |
| | AGTTGAATGGCAACTTGACATTTTTGCATCACC | |
| | ATCTGCCTCATAGGCCACTCTTTCCTTTCCCTCTGCCC | |
| | ACCAAGTCCTCATATCTGCAGAGAACCCATTG | |
| | ATCACCTTGTGCCCTCTTTTGGGGCAGCCTGTTGAAA | |
| | CTGAAGCACAGTCTGACCACTCACGATAAAGCA | |
| | GATTTTTCTCTGCCTCTGCCACAAGGTTTCAGAGTAG | |
| | TGTAGTCCAAGTAGAGGGTGCGGCACCCTTTTC | |
| | TCGCCGCAAGAAGCCCATTCCTATGGAAGTCTAGCAA | |
| | AGCAATACGACTCAGCCCAGCACTCTCTGCCCC | |
| | AGGACTCATGGCTCTGCTGTGCCTTCCATCCTGGGCT | |
| | CCCTTCTCTCCTGTGACCTTAAGAACTTTGTCT | |
| | GGTGGCTTTGCTGGAACATTGTCACTGTTTTCACTGTC | |
| | ATGCAGGGAGCCCAGCACTGTGGCCAGGATGG | |
| | CAGAGACTTCCTTGTCATCATGGAGAAGTGCCAGCAG | |
| | GGGACTGGGAAAAGCACTCTACCCAGACCTCAC | |
| | CTCCCTTCCTCCTTTTTGCCCATGAACAAGATGCAGTG | |
| | GCCCTAGGGGTTCCACTAGTGTCTGCTTTCCTT | |
| | TATTCCTATTTTTTTAAAGAAAAAAAAAAAA | |
| | CCTTAAGCTGAATTTGTTACTGAAATGATTAATGCAC | |
| | TGATGGGTCCTGAATTCACCTTGAGAAAGACCC | |
| | AAAGGCCAGTCAGGGGGTGGGGGGAACTCAGCTAAA | |
| | TAGACCTAGTTACTGCCCTGCTAGGCCATGCTGT | |
| | ACTGTGAGCCCCTCCTCACTCTCTACCAACCCTAAAC | |
| | CCTGAGGACAGGGGAGGAACCCACAGCTTCCTT | |
| | CTCCTGCCAGCTGCAGATGGTTTGCCTTGCCTTTCCAC | |
| | CCCCTAATTGTCAACCACAAAAATGAGAAATT | |
| | CCTCTTCTAGCTCAGCCTTGAGTCCATTGCCAAATTTT | |
| | CAGCACACCTGCCAGCAACTTGGGGGAATAAG | |
| | CGAAGGTTTCCCTACAAGAGGGAAAGAAGGCAAAAA | |
| | CGGCACAGCTATCTCCAAACACATCTGAGTTCAT | |
| | TTCAAAAGTGACCAAGGGAATCTCCGCACAAAAGTG | |
| | CAGATTGAGGAATTGTGATGGGTCATTCCCAAGA | |
| | ATCCCCCAAGGGGCATCCCAAATCCCTGAGGAGTAA | |
| | CAGCTGCAAACCTGGTCAGTTCTCAGTGAGAGCC | |
| | AGCTCACTTATAGCTTTGCTGCTAGAACCTGTTGTGG | |
| | CTGCATTTCCTGGTGGCCACTGACAACTGTGTA | |
| | ACCAGAATAGCTGCATGGCGCTGACCCTTTGGCCGGA | |
| | ACTTGGTCTCTTGGCTCCCTCCTTGGCCACCCA | |
| | CCACCTCTCGCACAGCCCCTCTGTTTTTACACCAATA | |
| | ACAAGAATTAAGGGGGAAGCCCTGGCAGCTATA | |
| | CGTTTTCAACCAGACTCCTTTGCCOGGACCCAGCCCG | |
| | CCACCCTGCTCGCCTCCGTCAAACCCCCGGCCA | |
| | ATGCAGTGAGCACCATGTAGCTCCCTTGATTTAAAAA | |
| | AAATAAAAAATAAAAAAAAAAGGAAAAAAAAAT | |
| | ACAACACACACACAAAAATAAAAAAAAATATTCTAAT | |
| | GAATGTATCTTTCTAAAGGACTGACGTTCAATCA | |
| | AATATCTGAAAATACTAAAGGTCAAAACCTTGTCAG | |
| | ATGTTAACTTCTAAGTTCGGTTTGGGATTTTTTT | |
| | TTTTTAATAGAAATCAAGTTGTTTTTGTTTTTAAGGAA | |
| | AAGCGGGTCATTGCAAAGGGCTGGGTGTAATT | |
| | TTATGTTTCATTTCCTTCATTTTAAAGCAATACAAGGT | |
| | TATGGAGCAGATGGTTTTGTGCCGAATCATGA | |
| | ATACTAGTCAAGTCACACACTCTGGAAACTTGCAACT | |
| | TTTTGTTTGTTTTGGTTTTCAAATAAATATAAA | |
| | TATGATATATATAGGAACTAATATAGTAATGCACCAT | |
| | GTAACAAAGCCTAGTTCAGTCCATGGCTTTTAA | |

TABLE 9-continued

| Sequences. | |
| --- | --- |
| Description | SEQ ID NO |

|  |  |
| --- | --- |
|   | TTCTCTTAACACTATAGATAAGGATTGTGTTACAGTT<br>GCTAGTAGCGGCAGGAAGATGTCAGGCTCACTT<br>TCCTCTGATTCCCGAAATGGGGGGAACCTCTAACCAT<br>AAAGGAATGGTAGAACAGTCCATTCCTCGGATC<br>AGAGAAAAATGCAGACATGGTGTCACCTGGATTTTTT<br>TCTGCCCATGAATGTTGCCAGTCAGTACCTGTC<br>CTCCTTGTTTCTCTATTTTTGGTTATGAATGTTGGGGT<br>TACCACCTGCATTTAGGGGAAAATTGTGTTCT<br>GTGCTTTCCTGGTATCTTGTTCCGAGGTACTCTAGTTC<br>TGTCTTTCAACCAAGAAAATAGAATTGTGGTG<br>TTTCTTTTATTGAACTTTTAACAGTCTCTTTACTAAAT<br>ACAGGTAGTTGAATAATTGTTTCAAGAGCTCA<br>ACAGATGACAAGCTTCTTTTCTAGAAATAAGACATTT<br>TTTGACAACTTTATCATGTATAACAGATCTGTT<br>TTTTTTCCTTGTGTTCTTCCAAGCTTCTGGTTAGAGAA<br>AAAGAGAAAAAAAAAAAAGGAAAATGTGTCTA<br>AAGTCCATCAGTGTTAACTCCCTGTGACAGGGATGAA<br>GGAAAATACTTTAATAGTTCAAAAAATAATAAT<br>GCTGAAAGCTCTCTACGAAAGACTGAATGTAAAAGT<br>AAAAAGTGTACATAGTTGTAAAAAAAAGGAGTTT<br>TTAAACATGTTTATTTTCTATGCACTTTTTTTTATTTA<br>AGTGATAGTTTAATTAATAAACATGTCAAGTT<br>TATTGCTGCA |
| NP_001184033.1<br>KMT2A isoform 1<br>amino acid<br>sequence | MAHSCRWRFPARPGTTGGGGGGGRRGLGGAPRQRVPA<br>LLLLPPGPPVGGGGPGAPPSPPAVAAAAAAAGSS<br>GAGVPGGAAAASAASSSSASSSSSSSSSASSGPALLRVG<br>PGFDAALQVSAAIGTNLRRFRAVFGESGGGG<br>GSGEDEQFLGFGSDEEVRVRSPTRSPSVKTSPRKPRGRP<br>RSGSDRNSAILSDPSVFSPLNKSETKSGDKI<br>KKKDSKSIEKKRGRPPTFPGVKIKITHGKDISELPKGNKE<br>DSLKKIKRTPSATFQQATKIKKLRAGKLSP<br>LKSKFKTGKLQIGRKGVQIVRRRGRPPSTERIKTPSGLLI<br>NSELEKPQKVRKDKEGTPPLTKEDKTVVRQ<br>SPRRIKPVRIIPSSKRTDATIAKQLLQRAkKGAQKKIEKE<br>AAQLQGRKVKTQVKNIRQFIMPVVSAISSR<br>IIKTPRRFIEDEDYDPPIKIARLESTPNSRFSAPSCGSSEKS<br>SAASQHSSQMSSDSSRSSSPSVDTSTDS<br>QASEEIQVLPEERSDTPEVHPPLPISQSPENESNDRRSRR<br>YSVSERSFGSRTTKKLSTLQSAPQQQTSSS<br>PPPPLLTPPPPLQPASSISDHTPWLMPPTIPLASPFEPASTA<br>PMQGKRKSILREPTFRWTSLKHSRSEPQ<br>YFSSAKYAKEGLIRKPIFDNFRPPPLTPEDVGFASGFSAS<br>GTAASARLFSPLHSGTRFDMHKRSPLLRAP<br>RFTPSEAHSRIFESVTLPSNRTSAGTSSSGVSNRKRKRKV<br>FSPIRSEPRSPSHSMRTRSGRLSSSELSPL<br>TPPSSVSSSLSISVSPLATSALNPTFTFPSHSLTQSGESAE<br>KNQRPRKQTSAPAEPFSSSSPTPLFPWFT<br>PGSQTERGRNKDKAPEEESKDRDADKSVEKDKSRERDR<br>EREKENKRESRKEKRKKGSEIQSSSALYPVGR<br>VSKEKVVGEDVATSSSAKKATGRKKSSSHDSGTDITSV<br>TLGDTTAVKTKILIKKGRGNLEKTNLDLGPTA<br>PSLEKEKTLCLSTPSSSTVKHSTSSIGSMLAQADKLPMT<br>DKRVASLLKKAKAQLCKIEKSKSLKQTDQPK<br>AQGQESDSSETSVRGPRIKHVCRRAAVALGRKRAVFPD<br>DMPTLSALPWEEREKILSSMGNDDKSSIAGSE<br>DAEPLAPPIKPIKPVTRNKAPQEPPVKKGRRSRRCGQCP<br>GCQVPEDCGVCTNCLDKPKFGGRNIKKQCCK<br>MRKCQNLQVVMPSKAYLQKQAKAVKKKEKKSKTSEKK<br>DSKESSWKNWDSSQKPTPSAREDPAPKKSSSE<br>PPPRKPVEEKSEEGNVSAPGPESKQATTPASRKSSKQVS<br>QPALVIPPQPPTTGPPRKEVPKTTPSEPKKK<br>QPPPPESGPEQSKQKKVAPRPSIPVKQKPKEKEKPPPVN<br>KQENAGTLNILSTLSNGNSSKQKIPADGVHR<br>IRVDFKEDCEAENVWEMGGLGILTSVPITPRVVCFLCAS<br>SGHVEFVYCQVCCEPFHKFCLEENERPLEDQ<br>LENWCCRRCKFCHVCGRQHQATKQLLECNKCRNSYHP<br>ECLGPNYPTKPTKKKKVWICTKCVRCKSCGSTT<br>PGKGWDAQWSHDFSLCHDCAKLFAKGNFCPLCDKCY<br>DDDDYESKMMQCGKCDRWVIISKCENLSGTEDEMY<br>EILSNLPESVAYTCVNCTERHPAEWRLALEKELQISLKQ<br>VLTALLNSRTTSHLLRYRQAAKPPDLNPETE<br>ESIPSRSSPEGPDPPVLTEVSKQDDQQPLDLEGVKRKMD<br>QGNYTSVLEFSDDIVKHQAAINSDGGQPEI<br>KKANSMVKSFFIRQMERVFPWFSVKKSRFWEPNKVSSN<br>SGMLPNAVLPPSLDHNYAQWQEREENSHTEQP | SEQ ID NO: 6 |

TABLE 9-continued

Sequences.

| Description | SEQ ID NO |
|---|---|
| PLMKKIIPAPKPKGPGEPDSPTPLHPPTPPILSTDRSREDS | |
| PELNPPPGIEDNRQCALCLTYGDDSANDA | |
| GRLLYIGQNEWTHVNCALWSAEVFEDDDGSLKNVHM | |
| AVIRGKQLRCEFCQKPGATVGCCLTSCTSNYHFM | |
| CSRAKNCVFLDDKKVYCQRHRDLIKGEVVPENGFEVFR | |
| RVFVDFEGISLRRKFLNGLEPENIHMMIGSMT | |
| IDCLGILNDLSDCEDKLFPIGYQCSRVYWSTTDARKRCV | |
| YTCKIVECRPPVVEPDINSTVEHDENRTIAH | |
| SPTSFTESSSKESQNTAEIISPPSPDRPPHSQTSGSCYYHVI | |
| SKVPRIRTPSYSPTQRSPGCRPLPSAGS | |
| PTPTTHEIVTVGDPLLSSGLRSIGSRRHSTSSLSPQRSKLR | |
| HMSPMRTGNTYSRNNVSSVSTIGTATQLE | |
| SSAKVVDHVLGPLNSSTSLGQNTSTSSNLQRTWTVGN | |
| KNSHLDGSSSSEMKQSSASDLVSKSSSLKGEK | |
| TKVLSSKSSEGSAHNVAYPGIPKLAPQVHNTTSRELNVS | |
| KIGSFAEPSSVSFSSKEALSFPHLHLRGQRN | |
| DRDQHTDSTQSANSSPDEDTEVKTLKLSGMSNRSSIINE | |
| UMGSSSRDRRQKGKKSCKETFKEKIISSKSFL | |
| EPGQVTTGEEGNLKPEFMDEVLTPEYMGQRPCNNVSSD | |
| KIGDKGLSMPGVPKAPPMQVEGSAKELQAPRK | |
| RTVKVTLTPLKMENESQSKNALKESSPASPLQIESTSPTE | |
| PISASENPGDGPVAQPSPNNTSCQDSQSNN | |
| YQNLPVQDRNLMLPDGPKPQEDGSFKRRYPRRSARARS | |
| NMFFGLTPLYGVRSYGEEDIPFYSSSTGKKRG | |
| KRSAEGQVDGADDLSTSDEDDLYYYNFIRTVISSGGEE | |
| RLASHNLFREEEQCDLPKISQLDGVDDGTESD | |
| TSVTATTRKSSQIPKRNGKENGTENLKIDRPEDGEKEH | |
| VTKSSVGHKNEPKMDNCHSVSRVKTQGQDSL | |
| EAQLSSLESSRRVHTSTPSDKNLLDTYNTELLKSDSDNN | |
| NSDDCGNILPSDIMDFVLKNTPSMQALGESP | |
| ESSSSELLNLGEGLGLDSNREKDMGLFEVFSQQLPTTEP | |
| VDSSVSSSISAEEQFELPLELPSDLSVLTTR | |
| SPTVPSQNPSRLAVISDSGEKRVTITEKSVASSESDPALL | |
| SPGVDPTPEGHMTPDHFIQGIIMDADHISSP | |
| PCGSVEQGHGNNQDLTRNSSTPGLQVPVSPTVPIQNQK | |
| YVPNSTDSPGPSQISNAAVQTTPPHLKPATEK | |
| LIVVNQNMQPLYVLQTLPNGVTQKIQLTSSVSSTPSVME | |
| TNTSVLGPMGGGLTLTTGLNPSLPTSQSLFP | |
| SASKGLLPMSHHQHLHSFPAATQSSFPPNISNPPSGLLIG | |
| VQPPPDPQLLVSESSQRTDLSTTVATPSSG | |
| LKKRPISRLQTRKNKKLAPSSTPSNIAPSDVVSNMTLINF | |
| TPSQLPNHPSLLDLGSLNTSSHRTVPNIIK | |
| RSKSSIMYFEPAPLLPQSVGGTAATAAGTSTISQDTSHLT | |
| SGSVSGLASSSSVLNVVSMQTTTTPTSSAS | |
| VPGHVTLTNPRLLGTPDIGSISNLLIKASQQSLGIQDQPV | |
| ALPPSSGMFPQLGTSQTPSTAAITAASSIC | |
| VLPSTQTTGITAASPSGEADEHYQLQHVNQLLASKTGIH | |
| SSQRDLDSASGPQVSNFTQTYDAPNSMGLEQ | |
| NKALSSAVQASPTSPGGSPSSPSSGQRSASPSVPGPTKPK | |
| PKTKRFQLPLDKGNGKKHKVSHLRTSSSEA | |
| HIPDQETTSLTSGTGTPGAEAEQQDTASVEQSSQKECGQ | |
| PAGQVAVLPEVQVTQNPANEQESAEPKTVEE | |
| EESNFSSPLMLWLQQEQKRKESITEKKPKKGLVFEISSD | |
| DGFQICAESIEDAWKSLTDKVQEARSNARLK | |
| QLSFAGVNGLRMLGILHDAVVFLIEQLSGAKHCRNYKF | |
| RFHKPEEANEPPLNPHGSARAEVHLRKSAFDYI | |
| FNFLASKHRQPPEYNPNDEEEEEVQLKSARRATSMDLP | |
| MPMRFRHLKKTSKEAVGVYRSPIHGRGLFCKR | |
| NIDAGEMVIEYAGNVIRSIQTDKREKYYDSKGIGCYMF | |
| RIDDSEVVDATMHGNAARFINHSCEPNCYSRV | |
| INIDGQKHIVIFAMRKIYRGEELTYDYKFPIEDASNKLPC | |
| NCGAKKCRKFLN | |

In some embodiments, a KMT2A-MAML2 fusion nucleic acid molecule comprises at least a portion of a KMT2A sequence of SEQ ID NO: 1 or SEQ ID NO: 5 and at least a portion of a MAML2 sequence of SEQ ID NO: 2, or a sequence having at least about 85% (e.g., any of at least about 85%, at least about 90%, at least 95%, at least about 96%, at least about 97%, at least about 98%, at least about 99%, or 100%) sequence identity to the portion of the KMT2A sequence of SEQ ID NO: 1 or SEQ ID NO: 5 and the portion of the MAML2 sequence of SEQ ID NO: 2.

In some embodiments, the KMT2A-MAML2 fusion nucleic acid molecule comprises: exon 7 or a portion thereof, intron 7 or a portion thereof, exon 8 or a portion thereof, intron 8 or a portion thereof, exon 9 or a portion thereof, intron 9 or a portion thereof, exon 10 or a portion thereof, intron 10 or a portion thereof, exon 11 or a portion thereof, or intron 11 or a portion thereof, of KMT2A and intron 1 or a portion thereof, exon 2 or a portion thereof, intron 2 or a portion thereof, exon 3 or a portion thereof, intron 3 or a portion thereof, or exon 4, of MAML2; and a KMT2A-MAML2 breakpoint that fuses exon 7 or the portion thereof, intron 7 or the portion thereof, exon 8 or the portion thereof, intron 8 or the portion thereof, exon 9 or the portion thereof, intron 9 or the portion thereof, exon 10 or the portion thereof, intron 10 or the portion thereof, exon 11 or the portion thereof, or intron 11 or the portion thereof, of KMT2A to intron 1 or the portion thereof, exon 2 or the portion thereof, intron 3 or the portion thereof, exon 3 or the portion thereof, or exon 4, of MAML2.

In some embodiments, the KMT2A-MAML2 fusion nucleic acid molecule comprises 5 or more nucleotides from exon 7, intron 7, exon 8, intron 8, exon 9, intron 9, exon 10, intron 10, exon 11, or intron 11 of KMT2A on the 5' end of the KMT2A-MAML2 breakpoint, and 5 or more nucleotides from intron 1, exon 2, intron 2, exon 3, intron 3, or exon 4, of MAML2 on the 3' end of the KMT2A-MAML2 breakpoint.

In some embodiments, the KMT2A-MAML2 fusion nucleic acid molecule comprises: (a) exon 7 or the portion thereof, exon 8 or the portion thereof, exon 9 or the portion thereof, exon 10 or the portion thereof, or exon 11 or the portion thereof, of KMT2A fused to exon 2 or the portion thereof, exon 3 or the portion thereof, or exon 4 or the portion thereof, of MAML2; (b) intron 7, 8, 9, 10, or 11, or the portion thereof, of KMT2A fused to intron 1, 2, or 3, or the portion thereof, of MAML2; (c) exon 7 or the portion thereof, exon 8 or the portion thereof, exon 9 or the portion thereof, exon 10 or the portion thereof, or exon 11 or the portion thereof, of KMT2A fused to intron 1, 2, or 3, or the portion thereof, of MAML2; or (d) intron 7, 8, 9, 10, or 11, or the portion thereof, of KMT2A fused to exon 2 or the portion thereof, exon 3 or the portion thereof, or exon 4 or the portion thereof, of MAML2. In some embodiments, the KMT2A-MAML2 fusion nucleic acid molecule comprises a nucleotide sequence comprising, in the 5' to 3' direction: (a) exons 1-6 and exon 7, or a portion of exon 7, of KMT2A and exon 2 or a portion thereof and exons 3-5, exon 3 or a portion thereof and exons 4-5, or exons 4-5, of MAML2; (b) exons 1-7 and exon 8, or a portion of exon 8, of KMT2A and exon 2 or a portion thereof and exons 3-5, exon 3 or a portion thereof and exons 4-5, or exons 4-5, of MAML2; (c) exons 1-8 and exon 9, or a portion of exon 9, of KMT2A and exon 2 or a portion thereof and exons 3-5, exon 3 or a portion thereof and exons 4-5, or exons 4-5, of MAML2; (d) exons 1-9 and exon 10, or a portion of exon 10, of KMT2A and exon 2 or a portion thereof and exons 3-5, exon 3 or a portion thereof and exons 4-5, or exons 4-5, MAML2; or (e) exons 1-10 and exon 11, or a portion of exon 11, of KMT2A and exon 2 or a portion thereof and exons 3-5, exon 3 or a portion thereof and exons 4-5, or exons 4-5, of MAML2.

In some embodiments, the KMT2A-MAML2 breakpoint comprises a nucleotide sequence comprising a fusion of the nucleotide sequence of SEQ ID NO: 7, or a nucleotide sequence at least about 85% (e.g., any of about 85%, 86%, 87%, 88%, 89%, 90%/o, 91%, 92%, 93%, 94%, 95%, 96%, 97%, 98%, 99%, or 100%) identical thereto, fused to the nucleotide sequence of SEQ ID NO: 8, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 9, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 10, or a nucleotide sequence at least about 85%

(e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 11, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 12, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 13, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 14, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 15, or a nucleotide sequence at least about 85% (e.g., any of about 85%, 86%, 87%, 88%, 89%, 90%, 91%, 92%, 93%, 94%, 95%, 96%, 97%, 980, 99%, or 100%) identical thereto, fused to the nucleotide sequence of SEQ ID NO: 16, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 17, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 18, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 19, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 20, or a nucleotide sequence at least about 85% (e.g., any of about 85%, 86%, 87%, 88%, 89%, 90%, 91%, 92%, 93%, 940%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 21, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 22, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 23, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 24, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 25, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 26, or a nucleotide sequence at least about 85% (e.g., any of about 85%, 86%, 870, 88%, 89%, 90%, 91%, 92%, 93%, 94%, 95%, 96%, 97%, 98%, 99%, or 100%) identical thereto. In some embodiments, the KMT2A-MAML2 breakpoint comprises a nucleotide sequence comprising a fusion of the nucleotide sequence of SEQ ID NO: 27, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto, fused to the nucleotide sequence of SEQ ID NO: 28, or a nucleotide sequence at least about 85% (e.g., any of about 85%, 86%, 87%, 88%, 89%, 90%, 91%, 92%, 93%, 94%, 95%, 96%, 97%, 98%, 99%, or 100%) identical thereto.

In some embodiments, the KMT2A-MAML2 fusion nucleic acid molecule is an isolated nucleic acid molecule. The isolated nucleic acid molecule may be free of sequences (such as protein-encoding sequences) that naturally flank the nucleic acid (i.e., sequences located at the 5' and 3' ends of the nucleic acid) in the genomic DNA of the organism from which the nucleic acid is derived. For example, in various embodiments, the fusion nucleic acid molecule can contain less than about 5 kB, less than about 4 kB, less than about 3 kB, less than about 2 kB, less than about 1 kB, less than about 0.5 kB or less than about 0.1 kB of nucleotide sequences which naturally flank the nucleic acid molecule in genomic DNA of the cell from which the nucleic acid is derived.

KMT2A-MAML2 Fusion Polypeptides

Also provided herein are KMT2A-MAML2 fusion polypeptides.

In some embodiments, the KMT2A-MAML2 fusion polypeptide comprises an amino acid sequence encoded by a nucleic acid molecule comprising exon 7 or a portion thereof of KMT2A and exon 2 of MAML2, and a KMT2A-MAML2 breakpoint that fuses exon 7 or the portion thereof of KMT2A to exon 2 of MAML2. In some embodiments, the KMT2A-MAML2 fusion polypeptide comprises an amino acid sequence at least about 85% (e.g., any of at least about 85%, at least about 90%, at least about 95%, at least about 96%, at least about 97%, at least about 98%, at least about 99%, or 100%) identical to the amino acid sequence encoded by a nucleic acid molecule comprising exon 7 or a portion thereof of KMT2A and exon 2 of MAML2, and a KMT2A-MAML2 breakpoint that fuses exon 7 or the portion thereof of KMT2A to exon 2 of MAML2. In some embodiments, the KMT2A-MAML2 breakpoint fuses the 3' end of exon 7 of KMT2A to the 5' end of exon 2 of MAML2. In some embodiments, the KMT2A-MAML2 breakpoint fuses the 3' end of a portion of exon 7 of KMT2A to the 5' end of exon 2 of MAML2. In some embodiments, the nucleic acid molecule comprises exon 7 or a portion thereof of KMT2A fused to exon 2 of MAML2. In some embodiments, the 3' end of exon 7 of KMT2A is fused to the 5' end of exon 2 of MAML2. In some embodiments, the 3' end of a portion of exon 7 of KMT2A is fused to the 5' end of exon 2 of MAML2.

In some embodiments, the KMT2A-MAML2 fusion polypeptide comprises an amino acid sequence encoded by a nucleic acid molecule comprising, in the 5' to 3' direction, exons 1-6 and exon 7, or a portion thereof, of KMT2A and exons 2-5 of MAML2. In some embodiments, the KMT2A-MAML2 fusion polypeptide comprises an amino acid sequence encoded by a nucleic acid molecule comprising, in the 5' to 3' direction, exons 1-6 and exon 7 of KMT2A and exons 2-5 of MAML2. In some embodiments, the KMT2A-MAML2 fusion polypeptide comprises an amino acid sequence encoded by a nucleic acid molecule comprising, in the 5' to 3' direction, exons 1-6 and a portion of exon 7 of KMT2A and exons 2-5 of MAML2.

In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the nucleic acid molecule comprising, in the 5' to 3' direction, exons 1-6 and exon 7, or a portion thereof, of KMT2A and exons 2-5 of MAML2. In some embodiments, the KMT2A-MAML2 fusion polypeptide comprises an amino acid sequence at least about 85% (e.g., any of at least about 85%, at least about 90%, at least about 95%, at least about 96%, at least about 97%, at least about 98%, at least about 99%, or 100%) identical to the nucleic acid molecule comprising, in the 5' to 3' direction, exons 1-6 and exon 7 of KMT2A and exons 2-5 of MAML2. In some embodiments, the KMT2A-MAML2 fusion polypeptide comprises an amino acid sequence at least about 85% (e.g., any of at least about 85%, at least about 900%, at least 95%, at least about 96%, at least about 97%, at least about 98%, at least about 99%, or 100%) identical to the nucleic acid molecule comprising, in the 5' to 3' direction, exons 1-6 and a portion of exon 7 of KMT2A and exons 2-5 of MAML2.

In some embodiments, the KMT2A-MAML2 fusion polypeptide comprises an amino acid sequence encoded by a nucleic acid molecule comprising exon 8 or a portion thereof of KMT2A and exon 2 of MAML2, and a KMT2A-MAML2 breakpoint that fuses exon 8 or the portion thereof of KMT2A to exon 2 of MAML2. In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the amino acid sequence encoded by a nucleic acid molecule comprising exon 8 or a portion thereof of KMT2A and exon 2 of MAML2, and a KMT2A-MAML2 breakpoint that fuses exon 8 or the portion thereof of KMT2A to exon 2 of MAML2. In some embodiments, the KMT2A-MAML2 breakpoint fuses the 3' end of exon 8 of KMT2A to the 5' end of exon 2 of MAML2. In some embodiments, the KMT2A-MAML2 breakpoint fuses the 3' end of a portion of exon 8 of KMT2A to the 5' end of exon 2 of MAML2. In some embodiments, the nucleic acid molecule comprises exon 8 or a portion thereof of KMT2A fused to exon 2 of MAML2. In some embodiments, the 3' end of exon 8 of KMT2A is fused to the 5' end of exon 2 of MAML2. In some embodiments, the 3' end of a portion of exon 8 of KMT2A is fused to the 5' end of exon 2 of MAML2.

In some embodiments, the KMT2A-MAML2 fusion polypeptide comprises an amino acid sequence encoded by a nucleic acid molecule comprising, in the 5' to 3' direction, exons 1-7 and exon 8, or a portion thereof, of KMT2A and exons 2-5 of MAML2. In some embodiments, the KMT2A-MAML2 fusion polypeptide comprises an amino acid sequence encoded by a nucleic acid molecule comprising, in the 5' to 3' direction, exons 1-7 and exon 8 of KMT2A and exons 2-5 of MAML2. In some embodiments, the KMT2A-MAML2 fusion polypeptide comprises an amino acid sequence encoded by a nucleic acid molecule comprising, in the 5' to 3' direction, exons 1-7 and a portion of exon 8 of KMT2A and exons 2-5 of MAML2.

In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the nucleic acid molecule comprising, in the 5' to 3' direction, exons 1-7 and exon 8, or a portion thereof, of KMT2A and exons 2-5 of MAML2. In some embodiments, the KMT2A-MAML2 fusion polypeptide comprises an amino acid sequence at least about 85% identical to the nucleic acid molecule comprising, in the 5' to 3' direction, exons 1-7 and exon 8 of KMT2A and exons 2-5 of MAML2. In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the nucleic acid molecule comprising, in the 5' to 3' direction, exons 1-7 and a portion of exon 8 of KMT2A and exons 2-5 of MAML2.

In some embodiments, the KMT2A-MAML2 fusion polypeptide comprises an amino acid sequence encoded by a nucleic acid molecule comprising exon 9 or a portion thereof of KMT2A and exon 2 of MAML2, and a KMT2A-MAML2 breakpoint that fuses exon 9 or the portion thereof of KMT2A to exon 2 of MAML2. In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the amino acid sequence encoded by a nucleic acid molecule comprising exon 9 or a portion thereof of KMT2A and exon 2 of MAML2, and a KMT2A-MAML2 breakpoint that fuses exon 9 or the portion thereof of KMT2A to exon 2 of MAML2. In some embodiments, the KMT2A-MAML2 breakpoint fuses the 3' end of exon 9 of KMT2A to the 5' end of exon 2 of MAML2. In some embodiments, the KMT2A-MAML2 breakpoint fuses the 3' end of a portion of exon 9 of KMT2A to the 5' end of exon 2 of MAML2. In some embodiments, the nucleic acid molecule comprises exon 9 or a portion thereof of KMT2A fused to exon 2 of MAML2. In some embodiments, the 3' end of exon 9 of KMT2A is fused to the 5' end of exon 2 of MAML2. In some embodiments, the 3' end of a portion of exon 9 of KMT2A is fused to the 5' end of exon 2 of MAML2.

In some embodiments, the KMT2A-MAML2 fusion polypeptide comprises an amino acid sequence encoded by a nucleic acid molecule comprising, in the 5' to 3' direction, exons 1-8 and exon 9, or a portion thereof, of KMT2A and exons 2-5 of MAML2. In some embodiments, the KMT2A-MAML2 fusion polypeptide comprises an amino acid sequence encoded by a nucleic acid molecule comprising, in the 5' to 3' direction, exons 1-8 and exon 9 of KMT2A and exons 2-5 of MAML2. In some embodiments, the KMT2A-MAML2 fusion polypeptide comprises an amino acid sequence encoded by a nucleic acid molecule comprising, in the 5' to 3' direction, exons 1-8 and a portion of exon 9 of KMT2A and exons 2-5 of MAML2.

In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the nucleic acid molecule comprising, in the 5' to 3' direction, exons 1-8 and exon 9, or a portion thereof, of KMT2A and exons 2-5 of MAML2. In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the nucleic acid molecule comprising, in the 5' to 3' direction, exons 1-8 and exon 9 of KMT2A and exons 2-5 of MAML2. In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the nucleic acid molecule comprising, in the 5' to 3' direction, exons 1-8 and a portion of exon 9 of KMT2A and exons 2-5 of MAML2.

In some embodiments, the KMT2A-MAML2 fusion polypeptide comprises an amino acid sequence encoded by a nucleic acid molecule comprising exon 10 or a portion thereof of KMT2A and exon 2 of MAML2, and a KMT2A-MAML2 breakpoint that fuses exon 10 or the portion thereof of KMT2A to exon 2 of MAML2. In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the amino acid sequence encoded by a nucleic acid molecule comprising exon 10 or a portion thereof of KMT2A and exon 2 of MAML2, and a KMT2A-MAML2 breakpoint that fuses exon 10 or the portion thereof of KMT2A to exon 2 of MAML2. In some embodiments, the KMT2A-MAML2 breakpoint fuses the 3' end of exon 10 of KMT2A to the 5' end of exon 2 of MAML2. In some embodiments, the KMT2A-MAML2 breakpoint fuses the 3' end of a portion of exon 10 of KMT2A to the 5' end of exon 2 of MAML2. In some embodiments, the nucleic acid molecule comprises exon 10 or a portion thereof of KMT2A fused to exon 2 of MAML2. In some embodiments, the 3' end of exon 10 of KMT2A is fused to the 5' end of exon 2 of MAML2. In some embodiments, the 3' end of a portion of exon 10 of KMT2A is fused to the 5' end of exon 2 of MAML2.

In some embodiments, the KMT2A-MAML2 fusion polypeptide comprises an amino acid sequence encoded by a nucleic acid molecule comprising, in the 5' to 3' direction, exons 1-9 and exon 10, or a portion thereof, of KMT2A and exons 2-5 of MAML2. In some embodiments, the KMT2A-MAML2 fusion polypeptide comprises an amino acid sequence encoded by a nucleic acid molecule comprising, in the 5' to 3' direction, exons 1-9 and exon 10 of KMT2A and exons 2-5 of MAML2. In some embodiments, the KMT2A-MAML2 fusion polypeptide comprises an amino acid sequence encoded by a nucleic acid molecule comprising, in the 5' to 3' direction, exons 1-9 and a portion of exon 10 of KMT2A and exons 2-5 of MAML2.

In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 1000%) identical to the nucleic acid molecule comprising, in the 5' to 3' direction, exons 1-9 and exon 10, or a portion thereof, of KMT2A and exons 2-5 of MAML2. In some embodiments, the KMT2A-

MAML2 fusion polypeptide comprises an amino acid sequence at least about 85% (e.g., any of at least about 85%, at least about 900%, at least 95%, at least about 96%, at least about 97%, at least about 98%, at least about 99%, or 100%) identical to the nucleic acid molecule comprising, in the 5' to 3' direction, exons 1-9 and exon 10 of KMT2A and exons 2-5 of MAML2. In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the nucleic acid molecule comprising, in the 5' to 3' direction, exons 1-9 and a portion of exon 10 of KMT2A and exons 2-5 of MAML2.

In some embodiments, the KMT2A-MAML2 fusion polypeptide comprises an amino acid sequence encoded by a nucleic acid molecule comprising exon 11 or a portion thereof of KMT2A and exon 2 of MAML2, and a KMT2A-MAML2 breakpoint that fuses exon 11 or the portion thereof of KMT2A to exon 2 of MAML2. In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the amino acid sequence encoded by a nucleic acid molecule comprising exon 11 or a portion thereof of KMT2A and exon 2 of MAML2, and a KMT2A-MAML2 breakpoint that fuses exon 11 or the portion thereof of KMT2A to exon 2 of MAML2. In some embodiments, the KMT2A-MAML2 breakpoint fuses the 3' end of exon 11 of KMT2A to the 5' end of exon 2 of MAML2. In some embodiments, the KMT2A-MAML2 breakpoint fuses the 3' end of a portion of exon 11 of KMT2A to the 5' end of exon 2 of MAML2. In some embodiments, the nucleic acid molecule comprises exon 11 or a portion thereof of KMT2A fused to exon 2 of MAML2. In some embodiments, the 3' end of exon 11 of KMT2A is fused to the 5' end of exon 2 of MAML2. In some embodiments, the 3' end of a portion of exon 11 of KMT2A is fused to the 5' end of exon 2 of MAML2.

In some embodiments, the KMT2A-MAML2 fusion polypeptide comprises an amino acid sequence encoded by a nucleic acid molecule comprising, in the 5' to 3' direction, exons 1-10 and exon 11, or a portion thereof, of KMT2A and exons 2-5 of MAML2. In some embodiments, the KMT2A-MAML2 fusion polypeptide comprises an amino acid sequence encoded by a nucleic acid molecule comprising, in the 5' to 3' direction, exons 1-10 and exon 11 of KMT2A and exons 2-5 of MAML2. In some embodiments, the KMT2A-MAML2 fusion polypeptide comprises an amino acid sequence encoded by a nucleic acid molecule comprising, in the 5' to 3' direction, exons 1-10 and a portion of exon 11 of KMT2A and exons 2-5 of MAML2.

In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the nucleic acid molecule comprising, in the 5' to 3' direction, exons 1-10 and exon 11, or a portion thereof, of KMT2A and exons 2-5 of MAML2. In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the nucleic acid molecule comprising, in the 5' to 3' direction, exons 1-10 and exon 11 of KMT2A and exons 2-5 of MAML2. In some embodiments, the KMT2A-MAML2 fusion polypeptide comprises an amino acid sequence at least about 85% (e.g., any of at least about 85%, at least about 90%, at least 95%, at least about 96%, at least about 97%, at least about 98%, at least about 99%, or 100%) identical to the nucleic acid molecule comprising, in the 5' to 3' direction, exons 1-10 and a portion of exon 11 of KMT2A and exons 2-5 of MAML2.

In some embodiments, the KMT2A-MAML2 fusion polypeptide comprises 5 or more amino acids (e.g., any of 5 or more, 10 or more, 15 or more, or 20 or more amino acids) encoded by the 3' end of exon 7 or the portion thereof, the 3' end of exon 8 or the portion thereof, the 3' end of exon 9 or the portion thereof, the 3' end of exon 10 or the portion thereof, or the 3' end of exon 11 or the portion thereof, of KMT2A fused to 5 or more amino acids (e.g., any of 5 or more, 10 or more, 15 or more, or 20 or more amino acids) encoded by the 5' end of exon 2 of MAML2 or a portion thereof.

In some embodiments, in vivo expression of a KMT2A-MAML2 fusion polypeptide provided herein (e.g., in one or more cells) results in modulation in the expression of one or more genes in the NOTCH pathway. In some embodiments, the one or more genes in the NOTCH pathway are PTCRA, ID1, PDCD6, MEIS1, MCL1, HES1, or FLIP. In some embodiments, the one or more genes in the NOTCH pathway are NOTCH1, NOTCH2, NOTCH3, or NOTCH4. In some embodiments, the one or more genes in the NOTCH pathway are ADAM17, S2, JAG1, JAG2, DLL1, DLL3, DLL4, LFNG, MFNG, RFNG, NOTCH1, NOTCH2, NOTCH3, NOTCH4, DVL1, DVL2, DVL3, NUMB, NUMBL, DTX2, DTX3L, DTX1, DTX3, DTX4, S3, PSENEN, PSEN1, PSEN2, NCSTN, APH1A, APH1B, the gamma-Secretase complex, MAML3, MAML2, MAML1, CREBBP, EP300, KAT2A, KAT2B, SNW1, RBPJL, RBPJ, HES1, HES5, HEY1, HEY2, HEYL, PTCRA, NCOR2, CTBP1, CTBP2, CIR1, HDAC1, HDAC2, HR, TLE1, TLE2, TLE3, TLE4, ATXN1L, or ATXN1. In some embodiments, in vivo expression of a KMT2A-MAML2 fusion polypeptide provided herein (e.g., in one or more cells) results in modulation in the expression of one or more genes in the Ras/MAPK signaling pathway. In some embodiments, in vivo expression of a KMT2A-MAML2 fusion polypeptide provided herein (e.g., in one or more cells) results in modulation in the expression of BAG3, FLIP, FASTK or one or more HOX genes, such as HOXA5, HOXA9, HOXA10. See, e.g., Metzler et al. 2008. In some embodiments, a KMT2A-MAML2 fusion polypeptide provided herein comprises a histone methyltransferase activity. In some embodiments, a KMT2A-MAML2 fusion polypeptide provided herein comprises a constitutive histone methyltransferase activity. In some embodiments, the histone methyltransferase activity comprises methylation of histone H3 at lysine-4 (H3K4). In some embodiments, the histone methyltransferase activity comprises methylation of histone H3 at lysine-4 (H3K4) on homeobox (HOX) gene promoters. In some embodiments, the histone methyltransferase activity comprises positively regulating the expression of homeobox (HOX) genes (see, e.g., Milne et al. 2002). Methods of measuring histone methyltransferase activity are known in the art, including, without limitation, antibodies that specifically bind to methylated H3K4, immunoblots, immunoassays, chromatin immunoprecipitation, mass spectrometry, in vitro enzyme activity assays.

In some embodiments, a KMT2A-MAML2 fusion polypeptide provided herein comprises an amino acid sequence encoded by an in-frame fusion of an exon of KMT2A with an exon of MAML2. In some embodiments, a KMT2A-MAML2 fusion polypeptide provided herein comprises an amino acid sequence encoded by at least one exon of KMT2A and at least one exon of MAML2. In some embodiments, a KMT2A-MAML2 fusion polypeptide provided herein comprises an amino acid sequence encoded by at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, or 36 exons of KMT2A and at least 1, at least 2, at least 3, at least 4, or 5 exons of MAML2.

In some embodiments, a KMT2A-MAML2 fusion polypeptide provided herein comprises an amino acid sequence encoded by a KMT2A-MAML2 fusion nucleic acid molecule described herein or a fragment thereof.

In some embodiments, a KMT2A-MAML2 fusion polypeptide provided herein comprises an amino acid sequence encoded by a KMT2A-MAML2 fusion nucleic acid molecule comprising, in the 5' to 3' direction, a fusion of exon 7 of KMT2A with exon 2 of MAML2. In some embodiments, a KMT2A-MAML2 fusion polypeptide provided herein comprises an amino acid sequence encoded by a KMT2A-MAML2 fusion nucleic acid molecule comprising, in the 5' to 3' direction, exons 1-7 of KMT2A and exons 2-5 MAML2.

In some embodiments, a KMT2A-MAML2 fusion polypeptide provided herein comprises an amino acid sequence encoded by a KMT2A-MAML2 fusion nucleic acid molecule comprising, in the 5' to 3' direction, a fusion of exon 8 of KMT2A with exon 2 of MAML2. In some embodiments, a KMT2A-MAML2 fusion polypeptide provided herein comprises an amino acid sequence encoded by a KMT2A-MAML2 fusion nucleic acid molecule comprising, in the 5' to 3' direction, exons 1-8 of KMT2A and exons 2-5 MAML2.

In some embodiments, a KMT2A-MAML2 fusion polypeptide provided herein comprises an amino acid sequence encoded by a KMT2A-MAML2 fusion nucleic acid molecule comprising, in the 5' to 3' direction, a fusion of exon 9 of KMT2A with exon 2 of MAML2. In some embodiments, a KMT2A-MAML2 fusion polypeptide provided herein comprises an amino acid sequence encoded by a KMT2A-MAML2 fusion nucleic acid molecule comprising, in the 5' to 3' direction, exons 1-9 of KMT2A and exons 2-5 MAML2.

In some embodiments, a KMT2A-MAML2 fusion polypeptide provided herein comprises an amino acid sequence encoded by a KMT2A-MAML2 fusion nucleic acid molecule comprising, in the 5' to 3' direction, a fusion of exon 10 of KMT2A with exon 2 of MAML2. In some embodiments, a KMT2A-MAML2 fusion polypeptide provided herein comprises an amino acid sequence encoded by a KMT2A-MAML2 fusion nucleic acid molecule comprising, in the 5' to 3' direction, exons 1-10 of KMT2A and exons 2-5 MAML2.

In some embodiments, a KMT2A-MAML2 fusion polypeptide provided herein comprises an amino acid sequence encoded by a KMT2A-MAML2 fusion nucleic acid molecule comprising, in the 5' to 3' direction, a fusion of exon 11 of KMT2A with exon 2 of MAML2 In some embodiments, a KMT2A-MAML2 fusion polypeptide provided herein comprises an amino acid sequence encoded by a KMT2A-MAML2 fusion nucleic acid molecule comprising, in the 5' to 3' direction, exons 1-11 of KMT2A and exons 2-5 MAML2.

The amino acid sequences corresponding to the nucleotide sequences of reference sequence KMT2A transcript variant 2 (NM_005933; SEQ ID NO: 1) and of MAML2 (NM_032427; SEQ ID NO: 2) are provided in Table 9 as SEQ ID NO: 3 and SEQ ID NO: 4, respectively.

The amino acid sequence corresponding to the nucleotide sequence of KMT2A transcript variant 1 (NM_001197104; SEQ ID NO: 5) is provided as SEQ ID NO: 6 in Table 9.

In some embodiments, a KMT2A-MAML2 fusion polypeptide provided herein comprises an amino acid sequence encoded by a KMT2A-MAML2 fusion nucleic acid molecule comprising at least a portion of a KMT2A sequence of SEQ ID NO: 1 or SEQ ID NO: 5 and at least a portion of a MAML2 sequence of SEQ ID NO: 2, or an amino acid sequence having at least about 85% (e.g., any of at least about 85%, at least about 90%, at least 95%, at least about 96%, at least about 97%, at least about 98%, at least about 990%, or 100%) sequence identity to the amino acid sequence encoded by a KMT2A-MAML2 fusion nucleic acid molecule comprising the portion of the KMT2A sequence of SEQ ID NO: 1 or SEQ ID NO: 5 and the portion of the MAML2 sequence of SEQ ID NO: 2.

In some embodiments, a KMT2A-MAML2 fusion polypeptide provided herein comprises at least a portion of a KMT2A amino acid sequence of SEQ ID NO: 3 or SEQ ID NO: 6 and at least a portion of a MAML amino acid sequence of SEQ ID NO: 4, or an amino acid sequence having at least about 85% (e.g., any of at least about 85%, at least about 90%, at least 95%, at least about 96%, at least about 97%, at least about 98%, at least about 99%, or 100%) sequence identity to a portion of the KMT2A amino acid sequence of SEQ ID NO: 3 or SEQ ID NO: 6 and a portion of the MAML amino acid sequence of SEQ ID NO: 4.

In some embodiments, a fusion polypeptide provided herein is isolated from cells or tissue sources according to methods known in the art. In some embodiments, a fusion polypeptide provided herein can be synthesized chemically using standard peptide synthesis techniques. In some embodiments, a fusion polypeptide provided herein is isolated or purified such that it is substantially free of cellular material or other contaminating proteins from the cell or tissue source from which the protein is derived, or substantially free of chemical precursors or other chemicals when chemically synthesized.

In some embodiments, a fusion polypeptide provided herein is fused to a label or a tag. In some embodiments, the label or tag is a radiolabel, a fluorescent label, an enzymatic label, a sequence tag, biotin, or other ligands. Examples of labels or tags include, but are not limited to, 6×His-tag, biotin-tag. Glutathione-S-transferase (GST)-tag. Green fluorescent protein (GFP)-tag, c-myc-tag, FLAG-tag, Thioredoxin-tag, Glu-tag, Nus-tag, V5-tag, calmodulin-binding protein (CBP)-tag, Maltose binding protein (MBP)-tag, Chitin-tag, alkaline phosphatase (AP)-tag, HRP-tag, Biotin Caboxyl Carrier Protein (BCCP)-tag, Calmodulin-tag, S-tag, Strep-tag, haemoglutinin (HA)-tag, digoxigenin (DIG)-tag, DsRed, RFP, Luciferase, Short Tetracysteine Tags, Halo-tag, Strep-tag, and Nus-tag. In some embodiments, the label or tag comprises a detection agent, such as a fluorescent molecule or an affinity reagent or tag.

Methods of Detecting KMT2A-MAML2 Fusions

In some aspects, provided herein are methods of detecting the presence of a KMT2A-MAML2 fusion. e.g., in a sample. In some embodiments, the methods of detecting the presence of a KMT2A-MAML2 fusion comprise detecting a KMT2A-MAML2 fusion nucleic acid molecule described herein in a sample. In some embodiments, the methods of detecting the presence of a KMT2A-MAML2 fusion comprise detecting a KMT2A-MAML2 fusion polypeptide described herein in a sample. In some embodiments, the sample is obtained from an individual, such as an individual having a cancer. In some embodiments, the cancer is an epithelial neoplasm. In some embodiments, the epithelial neoplasm is a thymoma. In some embodiments, the methods of detecting the presence of a KMT2A-MAML2 fusion nucleic acid molecule provided herein comprise selectively enriching for one or more nucleic acids comprising KMT2A or MAML2 nucleotide sequences to produce an enriched sample. In some embodiments, the methods of detecting the presence of a KMT2A-MAML2 fusion polypeptide provided herein comprise selectively enriching for one or more polypeptides comprising KMT2A or MAML2 amino acid sequences to produce an enriched sample.

Detection of KMT2A-MAML2 Gene Fusion Nucleic Acids

Provided herein are methods of detecting a KMT2A-MAML2 fusion nucleic acid molecule of the disclosure.

In some embodiments, a KMT2A-MAML2 fusion nucleic acid molecule provided herein is detected using any suitable method known in the art, such as a nucleic acid hybridization assay, an amplification-based assay (e.g., polymerase chain reaction. PCR), a PCR-RFLP assay, real-time PCR, sequencing (e.g., Sanger sequencing or next-generation sequencing), a screening analysis (e.g., using karyotype methods), fluorescence in situ hybridization (FISH), break away FISH, spectral karyotyping, multiplex-FISH, comparative genomic hybridization, in situ hybridization, single specific primer-polymerase chain reaction (SSP-PCR), HPLC, or mass-spectrometric genotyping. Methods of analyzing samples, e.g., to detect a fusion nucleic acid molecule, are described in U.S. Pat. No. 9,340,830 and in WO2012092426A1, which are hereby incorporated by reference in their entirety.

In Situ Hybridization Methods

In some embodiments, a KMT2A-MAML2 fusion nucleic acid molecule provided herein is detected using an in situ hybridization method, such a fluorescence in situ hybridization (FISH) method.

In some embodiments, FISH analysis is used to identify the chromosomal rearrangement resulting in the fusions as described above. In some embodiments, FISH analysis is used to identify an RNA molecule comprising a KMT2A-MAML2 breakpoint described herein. Methods for performing FISH are known in the art and can be used in nearly any type of tissue. In FISH analysis, nucleic acid probes which are detectably labeled, e.g. fluorescently labeled, are allowed to bind to specific regions of DNA, e.g., a chromosome, or an RNA, e.g., an mRNA, and then examined, e.g., through a microscope. See, for example, U.S. Pat. No. 5,776,688. DNA or RNA molecules are first be fixed onto a slide, the labeled probe is then hybridized to the DNA or RNA molecules, and then visualization is achieved, e.g., using enzyme-linked label-based detection methods known in the art. Generally, the resolution of FISH analysis is on the order of detection of 60 to 100000 nucleotides, e.g., 60 base pairs (bp) up to 100 kilobase pairs of DNA. Nucleic acid probes used in FISH analysis comprise single stranded nucleic acids. Such probes are typically at least about 50 nucleotides in length. In some embodiments, probes comprise about 100 to about 500 nucleotides. Probes that hybridize with centromeric DNA and locus-specific DNA or RNA are available commercially, for example, from Vysis, Inc. (Downers Grove, Ill.), Molecular Probes, Inc. (Eugene, Oreg.) or from Cytocell (Oxfordshire, UK). Alternatively, probes can be made non-commercially from chromosomal or genomic DNA or other sources of nucleic acids through standard techniques. Examples of probes, labeling and hybridization methods are known in the art.

Several variations of FISH methods are known in the art and suitable for use according to the methods of the disclosure, including single-molecule RNA FISH, Fiber FISH, Q-FISH, Flow-FISH, MA-FISH, break-away FISH, hybrid fusion-FISH, and multi-fluor FISH or mFISH.

In some embodiments, "break-away FISH", is used in the methods provided herein. In break-away FISH, at least one probe targeting a fusion junction or breakpoint and at least one probe targeting an individual gene of the fusion, e.g., at one or more exons and or introns of the gene, are utilized. In normal cells (i.e., cells not having a fusion nucleic acid molecule described herein), both probes are observed (or a secondary color is observed due to the close proximity of the two genes of the gene fusion); and in cells having a fusion nucleic acid molecule described herein, only a single gene probe is observed due to the presence of a rearrangement resulting in the fusion nucleic acid molecule.

Array-Based Methods

In some embodiments, a KMT2A-MAML2 fusion nucleic acid molecule provided herein is detected using an array-based method, such as array-based comparative genomic hybridization (CGH) methods. In array-based CGH methods, a first sample of nucleic acids (e.g., from a sample, such as from a tumor) is labeled with a first label, while a second sample of nucleic acids (e.g., a control, such as from a healthy cell/tissue) is labeled with a second label. In some embodiments, equal quantities of the two samples are mixed and co-hybridized to a DNA microarray of several thousand evenly spaced cloned DNA fragments or oligonucleotides, which have been spotted in triplicate on the array. After hybridization, digital imaging systems are used to capture and quantify the relative fluorescence intensities of each of the hybridized fluorophores. The resulting ratio of the fluorescence intensities is proportional to the ratio of the copy numbers of DNA sequences in the two samples. In some embodiments, where there are chromosomal deletions or multiplications, differences in the ratio of the signals from the two labels are detected and the ratio provides a measure of the copy number. Array-based CGH can also be performed with single-color labeling. In single color CGH, a control (e.g., control nucleic acid sample, such as from a healthy cell/tissue) is labeled and hybridized to one array and absolute signals are read, and a test sample (e.g., a nucleic acid sample obtained from an individual or from a tumor) is labeled and hybridized to a second array (with identical content) and absolute signals are read. Copy number differences are calculated based on absolute signals from the two arrays.

Amplification-Based Methods

In some embodiments, a KMT2A-MAML2 fusion nucleic acid molecule provided herein is detected using an amplification-based method. As is known in the art, in such amplification-based methods, a sample of nucleic acids, such as a sample obtained from an individual or from a tumor, is used as a template in an amplification reaction (e.g., Polymerase Chain Reaction (PCR) using one or more oligonucleotides or primers, e.g., such as one or more oligonucleotides or primers provided herein. The presence of a KMT2A-MAML2 fusion nucleic acid molecule provided herein in the sample can be determined based on the presence or absence of an amplification product. Quantitative amplification methods are also known in the art and may be used according to the methods provided herein. Methods of measurement of DNA copy number at microsatellite loci using quantitative PCR analysis are known in the art. The known nucleotide sequence for genes is sufficient to enable one of skill in the art to routinely select primers to amplify any portion of the gene. Fluorogenic quantitative PCR can also be used. In fluorogenic quantitative PCR, quantitation is based on amount of fluorescence signals, e.g., TaqMan and Sybr green.

Other amplification methods suitable for use according to the methods provided herein include, e.g., ligase chain reaction (LCR), transcription amplification, self-sustained sequence replication, dot PCR, and linker adapter PCR.

Sequencing

In some embodiments, a KMT2A-MAML2 fusion nucleic acid molecule provided herein is detected using a sequencing method. Any method of sequencing known in the art can be used to detect a KMT2A-MAML2 fusion nucleic acid molecule provided herein. Exemplary sequencing methods that may be used to detect a KMT2A-MAML2 fusion nucleic acid molecule provided herein include those based on techniques developed by Maxam and Gilbert or Sanger. Automated sequencing procedures may be used, e.g., including sequencing by mass spectrometry.

In some embodiments, a KMT2A-MAML2 fusion nucleic acid molecule provided herein is detected using next-generation sequencing (NGS). Next-generation sequencing includes any sequencing method that determines the nucleotide sequence of either individual nucleic acid molecules or clonally expanded proxies for individual nucleic acid molecules in a highly parallel fashion (e.g., greater than 10 molecules may be sequenced simultaneously). Next generation sequencing methods suitable for use according to the methods provided herein are known in the art and include, without limitation, massively parallel short-read sequencing, template-based sequencing, pyrosequencing, real-time sequencing comprising imaging the continuous incorporation of dye-labeling nucleotides during DNA synthesis, nanopore sequencing, sequencing by hybridization, nano-transistor array based sequencing, polony sequencing, scanning tunneling microscopy (STM)-based sequencing, or nanowire-molecule sensor based sequencing. See. e.g., Metzker, M. (2010) *Nature Biotechnology Reviews* 11:31-46, which is hereby incorporated by reference. Exemplary NGS methods and platforms that may be used to detect a KMT2A-MAML2 fusion nucleic acid molecule provided herein include, without limitation, the HeliScope Gene Sequencing system from Helicos BioSciences (Cabmridge, MA, USA), the PacBio RS system from Pacific Biosciences (Menlo Park, CA, USA), massively parallel short-read sequencing such as the Solexa sequencer and other methods and platforms from Illumina Inc. (San Diego, CA, USA), 454 sequencing from 454 LifeSciences (Branford, CT, USA), Ion Torrent sequencing from ThermoFisher (Waltham, MA, USA), or the SOLiD sequencer from Applied Biosystems (Foster City, CA, USA). Additional exemplary methods and platforms that may be used to detect a KMT2A-MAML2 fusion nucleic acid molecule provided herein include, without limitation, the Genome Sequencer (GS) FLX System from Roche (Basel, CHE), the G.007 polonator system, and the Solexa Genome Analyzer, HiSeq 2500, HiSeq3000, HiSeq 4000, and NovaSeq 6000 platforms from Illumina Inc. (San Diego, CA, USA).

Detection Reagents

In some aspects, provided herein are reagents for detecting a KMT2A-MAML2 fusion nucleic acid molecule provided herein or a fragment thereof, e.g., according to the methods of detection provided herein. In some embodiments, a detection reagent provided herein comprises a nucleic acid molecule, e.g., a DNA, RNA, or mixed DNA/RNA molecule, comprising a nucleotide sequence which is complementary to a nucleotide sequence on a target nucleic acid, e.g., a nucleic acid that comprises a KMT2A-MAML2 fusion nucleic acid molecule described herein or a fragment or portion thereof Baits Provided herein are baits suitable for the detection of a KMT2A-MAML2 fusion nucleic acid molecule provided herein.

In some embodiments, the bait comprises a capture nucleic acid molecule configured to hybridize to a target nucleic acid molecule comprising a KMT2A-MAML2 fusion nucleic acid molecule provided herein. In some embodiments, the capture nucleic acid molecule is configured to hybridize to the KMT2A-MAML2 fusion nucleic acid molecule of the target nucleic acid molecule.

In some embodiments, the capture nucleic acid molecule is configured to hybridize to a fragment of the KMT2A-MAML2 fusion nucleic acid molecule of the target nucleic acid molecule. In some embodiments, the fragment comprises (or is) between about 5 and about 25 nucleotides, between about 5 and about 300 nucleotides, between about 100 and about 300 nucleotides, between about 130 and about 230 nucleotides, or between about 150 and about 200 nucleotides. In some embodiments, the capture nucleic acid molecule is between about 5 and about 25 nucleotides, between about 5 and about 300 nucleotides, between about 100 and about 300 nucleotides, between about 130 and about 230 nucleotides, or between about 150 and about 200 nucleotides. In some embodiments, the fragment comprises (or is) about 100 nucleotides, about 125 nucleotides, about 150 nucleotides, about 175 nucleotides, about 200 nucleotides, about 225 nucleotides, about 250 nucleotides, about 275 nucleotides, or about 300 nucleotides in length. In some embodiments, the capture nucleic acid molecule is about 100 nucleotides, about 125 nucleotides, about 150 nucleotides, about 175 nucleotides, about 200 nucleotides, about 225 nucleotides, about 250 nucleotides, about 275 nucleotides, or about 300 nucleotides in length.

In some embodiments, the capture nucleic acid molecule is configured to hybridize to the KMT2A-MAML2 breakpoint, and may further hybridize to between about 10 and about 100 nucleotides or more, e.g., any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides flanking either side of the KMT2A-MAML2 breakpoint. In some embodiments, a capture nucleic acid molecule provided herein hybridizes to the KMT2A-MAML2 breakpoint between exon 7 of KMT2A and exon 2 of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, a capture nucleic acid molecule provided herein hybridizes to the KMT2A-MAML2 breakpoint between exon 8 of KMT2A and exon 2 of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides).

In some embodiments, a capture nucleic acid molecule provided herein hybridizes to the KMT2A-MAML2 breakpoint between exon 9 of KMT2A and exon 2 of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, a capture nucleic acid molecule provided herein hybridizes to the KMT2A-MAML2 breakpoint between exon 10 of KMT2A and exon 2 of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, a capture nucleic acid molecule provided herein hybridizes to the KMT2A-MAML2 breakpoint between exon 11 of KMT2A and exon 2 of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides).

In some embodiments, the capture nucleic acid molecule is configured to hybridize to a nucleotide sequence comprising a nucleotide sequence in an intron or an exon of KMT2A or MAML2, or in a KMT2A-MAML2 breakpoint joining the introns or exons of KMT2A and MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the capture nucleic acid molecule is configured to hybridize to a nucleotide sequence comprising a nucleotide sequence in an intron of KMT2A or MAML2 or in a KMT2A-MAML2 breakpoint joining the introns of KMT2A and MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides).

In some embodiments, the capture nucleic acid molecule is configured to hybridize to the KMT2A-MAML2 breakpoint joining an intron of KMT2A and an intron of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the capture nucleic acid molecule is configured to hybridize to the KMT2A-MAML2 breakpoint joining an intron of KMT2A and an exon of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the capture nucleic acid molecule is configured to hybridize to the KMT2A-MAML2 breakpoint joining an exon of KMT2A and an exon of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 10), or more nucleotides). In some embodiments, the capture nucleic acid molecule is configured to hybridize to the KMT2A-MAML2 breakpoint joining an exon of KMT2A and an intron of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides).

In some embodiments, the capture nucleic acid molecule is a DNA, RNA, or a DNA/RNA molecule. In some embodiments, the capture nucleic acid molecule comprises any of between about 50 and about 1000 nucleotides, between about 50 and about 500 nucleotides, between about 100 and about 500 nucleotides, between about 100 and about 300 nucleotides, between about 130 and about 230 nucleotides, or between about 150 and about 200 nucleotides. In some embodiments, the capture nucleic acid molecule comprises any of between about 50 nucleotides and about 100 nucleotides, about 100 nucleotides and about 150 nucleotides, about 150 nucleotides and about 200 nucleotides, about 200 nucleotides and about 250 nucleotides, about 250 nucleotides and about 300 nucleotides, about 300 nucleotides and about 350 nucleotides, about 350 nucleotides and about 400 nucleotides, about 400 nucleotides and about 450 nucleotides, about 450 nucleotides and about 500 nucleotides, about 500 nucleotides and about 550 nucleotides, about 550 nucleotides and about 600 nucleotides, about 600 nucleotides and about 650 nucleotides, about 650 nucleotides and about 700 nucleotides, about 700 nucleotides and about 750 nucleotides, about 750 nucleotides and about 800 nucleotides, about 800 nucleotides and about 850 nucleotides, about 850 nucleotides and about 900 nucleotides, about 900 nucleotides and about 950 nucleotides, or about 950 nucleotides and about 1000 nucleotides. In some embodiments, the capture nucleic acid molecule comprises about 150 nucleotides. In some embodiments, the capture nucleic acid molecule is about 150 nucleotides.

In some embodiments, a bait provided herein comprises a DNA, RNA, or a DNA/RNA molecule. In some embodiments, a bait provided herein includes a label or a tag. In some embodiments, the label or tag is a radiolabel, a fluorescent label, an enzymatic label, a sequence tag, biotin, or another ligand. In some embodiments, a bait provided herein includes a detection reagent such as a fluorescent marker. In some embodiments, a bait provided herein includes (e.g., is conjugated to) an affinity tag, e.g., that allows capture and isolation of a hybrid formed by a bait and a nucleic acid hybridized to the bait. In some embodiments, the affinity tag is an antibody, an antibody fragment, biotin, or any other suitable affinity tag or reagent known in the art. In some embodiments, a bait is suitable for solution phase hybridization.

Baits can be produced and used according to methods known in the art, e.g., as described in WO2012092426A1, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

In some embodiments, a bait provided herein comprises a target-specific bait sequence (e.g., a capture nucleic acid molecule described herein) and universal tails on each end. In some embodiments, a bait provided herein comprises an oligonucleotide comprising about 200 nucleotides, of which about 170 nucleotides are target-specific (e.g., a capture nucleic acid molecule described herein) and the other 30 nucleotides (e.g., 15 nucleotides on each end of the bait) are universal arbitrary tails, e.g., suitable for PCR amplification.

In some embodiments, a bait provided herein hybridizes to a nucleotide sequence comprising a nucleotide sequence in an intron or an exon of one gene of a fusion molecule described herein (e.g., KMT2A), in an intron or an exon of the other gene of a fusion molecule described herein (e.g., MAML2), or a KMT2A-MAML2 breakpoint joining the introns and/or exons.

In some embodiments, a bait provided herein hybridizes to a nucleotide sequence comprising a nucleotide sequence in an intron of one gene of a fusion molecule described herein (e.g., KMT2A), in an intron of the other gene of a fusion molecule described herein (e.g., MAML2), or a KMT2A-MAML2 breakpoint joining the introns. In some embodiments, a bait provided herein hybridizes to a nucleotide sequence comprising a nucleotide sequence in an intron of one gene of a fusion molecule described herein (e.g., KMT2A), in an exon of the other gene of a fusion molecule described herein (e.g., MAML2), or a KMT2A-MAML2 breakpoint joining the intron and exon. In some embodiments, a bait provided herein hybridizes to a nucleotide sequence comprising a nucleotide sequence in an exon of one gene of a fusion molecule described herein (e.g., KMT2A), in an exon of the other gene of a fusion molecule described herein (e.g., MAML2), or a KMT2A-MAML2 breakpoint joining the exons. In some embodiments, a bait provided herein hybridizes to a nucleotide sequence comprising a nucleotide sequence in an exon of one gene of a fusion molecule described herein (e.g., KMT2A), in an intron of the other gene of a fusion molecule described herein (e.g., MAML2), or a KMT2A-MAML2 breakpoint joining the intron and the exon.

The baits described herein can be used for selection of exons and short target sequences. In some embodiments, a bait is between about 100 nucleotides and 300 nucleotides. In some embodiments, a bait is between about 130 nucleotides and 230 nucleotides. In some embodiments, a bait is between about 150 nucleotides and 200 nucleotides. In some embodiments, the target-specific sequences in the baits, e.g., a capture nucleic acid molecule described herein, e.g., for selection of exons and short target sequences, are between about 40 nucleotides and 1000 nucleotides. In some embodiments, the target-specific sequence e.g., a capture nucleic acid molecule described herein, is between about 70 nucleotides and about 300 nucleotides. In some embodiments, the target-specific sequence, e.g., a capture nucleic acid molecule described herein, is between about 100 nucleotides and about 200 nucleotides. In some embodiments, the target-specific sequence, e.g., a capture nucleic acid molecule described herein, is between about 120 nucleotides and about 170 nucleotides.

In some embodiments, a bait of the disclosure distinguishes a nucleic acid, e.g., a genomic or transcribed nucleic acid, e.g., a cDNA or RNA, having a KMT2A-MAML2 breakpoint described herein, from a reference nucleotide sequence, e.g., a nucleotide sequence not having the breakpoint. In some embodiments, a bait of the disclosure distinguishes a nucleic acid, e.g., a genomic or transcribed nucleic acid, e.g., a cDNA or RNA, having a KMT2A-MAML2 breakpoint between exon 7 of KMT2A and exon 2 of MAML2, from a reference nucleotide sequence, e.g., a nucleotide sequence not having the breakpoint. In some embodiments, a bait of the disclosure distinguishes a nucleic acid, e.g., a genomic or transcribed nucleic acid, e.g., a cDNA or RNA, having a KMT2A-MAML2 breakpoint between exon 8 of KMT2A and exon 2 of MAML2, from a reference nucleotide sequence, e.g., a nucleotide sequence not having the breakpoint. In some embodiments, a bait of the disclosure distinguishes a nucleic acid, e.g., a genomic or transcribed nucleic acid, e.g., a cDNA or RNA, having a KMT2A-MAML2 breakpoint between exon 9 of KMT2A and exon 2 of MAML2, from a reference nucleotide sequence, e.g., a nucleotide sequence not having the breakpoint. In some embodiments, a bait of the disclosure distinguishes a nucleic acid, e.g., a genomic or transcribed nucleic acid, e.g., a cDNA or RNA, having a KMT2A-MAML2 breakpoint between exon 10 of KMT2A and exon 2 of MAML2, from a reference nucleotide sequence, e.g., a nucleotide sequence not having the breakpoint. In some embodiments, a bait of the disclosure distinguishes a nucleic acid, e.g., a genomic or transcribed nucleic acid, e.g., a cDNA or RNA, having a KMT2A-MAML2 breakpoint between exon 11 of KMT2A and exon 2 of MAML2, from a reference nucleotide sequence, e.g., a nucleotide sequence not having the breakpoint.

In some embodiments, the bait hybridizes to the KMT2A-MAML2 breakpoint, and a sequence on either side of the KMT2A-MAML2 breakpoint (e.g., any of 1, 2, 3, 4, 5, 6, 7, 8, 9, or 10 nucleotides on either side of the KMT2A-MAML2 breakpoint, or any of between 1 and about 5, about 5 and about 10, about 10 and about 15, about 15 and about 20, about 20 and about 25, about 25 and about 30, about 30 and about 35, about 35 and about 40, about 40 and about 45, about 45 and about 50, about 50 and about 55, about 55 and about 60, about 60 and about 65, about 70 and about 75, about 75 and about 80, about 80 and about 85, about 85 and about 90, about 90 and about 95, or about 95 and about 100, or more nucleotides on either side of the KMT2A-MAML2 breakpoint).

Probes

Also provided herein are probes, e.g., nucleic acid molecules, suitable for the detection of a KMT2A-MAML2 fusion nucleic acid molecule provided herein. In some embodiments, a probe provided herein comprises a nucleic acid sequence configured to hybridize to a target nucleic acid molecule comprising a KMT2A-MAML2 fusion nucleic acid molecule provided herein. In some embodiments, the probe comprises a nucleic acid sequence configured to hybridize to the KMT2A-MAML2 fusion nucleic acid molecule of the target nucleic acid molecule.

In some embodiments, the probe comprises a nucleic acid sequence configured to hybridize to a fragment or portion of the KMT2A-MAML2 fusion nucleic acid molecule of the target nucleic acid molecule. In some embodiments, the fragment or portion comprises between about 5 and about 25 nucleotides, between about 5 and about 300 nucleotides, between about 100 and about 300 nucleotides, between about 130 and about 230 nucleotides, or between about 150 and about 200 nucleotides.

In some embodiments, the probe comprises a nucleic acid sequence configured to hybridize to the KMT2A-MAML2 breakpoint between KMT2A and MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the probe comprises a nucleic acid sequence that hybridizes to the KMT2A-MAML2 breakpoint between exon 7 of KMT2A and exon 2 of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the probe comprises a nucleic acid sequence that hybridizes to the KMT2A-MAML2 breakpoint between exon 8 of KMT2A and exon 2 of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the probe comprises a nucleic acid sequence that hybridizes to the KMT2A-MAML2 breakpoint between exon 9 of KMT2A and exon 2 of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the probe comprises a nucleic acid sequence that hybridizes to the KMT2A-MAML2 breakpoint between exon 10 of KMT2A and exon 2 of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the probe comprises a nucleic acid sequence that hybridizes to the KMT2A-MAML2 breakpoint between exon 11 of KMT2A and exon 2 of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides).

In some embodiments, the probe comprises a nucleic acid sequence configured to hybridize to a nucleotide sequence comprising a nucleotide sequence in an intron or an exon of KMT2A or MAML2, or in a KMT2A-MAML2 breakpoint joining the introns or exons of KMT2A and MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the probe comprises a nucleic acid sequence configured to hybridize to a nucleotide sequence comprising a nucleotide sequence in an intron of KMT2A or MAML2 or in a KMT2A-MAML2 breakpoint joining the introns of KMT2A and MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the probe comprises a nucleic acid sequence configured to hybridize to the KMT2A-MAML2 breakpoint joining an intron of KMT2A and an intron of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the probe comprises a nucleic acid sequence configured to hybridize to the KMT2A-MAML2 breakpoint joining an intron of KMT2A and an exon of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the probe comprises a nucleic acid sequence configured to hybridize to the KMT2A-MAML2 breakpoint joining an exon of KMT2A and an intron of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides). In some embodiments, the probe comprises a nucleic acid sequence configured to hybridize to the KMT2A-MAML2 breakpoint joining an exon of KMT2A and an exon of MAML2 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides).

In some embodiments, the probe comprises a nucleic acid molecule which is a DNA, RNA, or a DNA/RNA molecule. In some embodiments, the probe comprises a nucleic acid molecule comprising any of between about 10 and about 20 nucleotides, between about 12 and about 20 nucleotides, between about 10 and about 1000 nucleotides, between about 50 and about 500 nucleotides, between about 100 and about 500 nucleotides, between about 100 and about 300 nucleotides, between about 130 and about 230 nucleotides, or between about 150 and about 200 nucleotides. In some embodiments, the probe comprises a nucleic acid molecule comprising any of about 10 nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, or about 30 nucleotides. In some embodiments, the probe comprises a nucleic acid molecule comprising any of between about 40 nucleotides and about 50 nucleotides, about 50 nucleotides and about 100 nucleotides, about 100 nucleotides and about 150 nucleotides, about 150 nucleotides and about 200 nucleotides, about 200 nucleotides and about 250 nucleotides, about 250 nucleotides and about 300 nucleotides, about 300 nucleotides and about 350 nucleotides, about 350 nucleotides and about 400 nucleotides, about 400 nucleotides and about 450 nucleotides, about 450 nucleotides and about 500 nucleotides, about 500 nucleotides and about 550 nucleotides, about 550 nucleotides and about 600 nucleotides, about 600 nucleotides and about 650 nucleotides, about 650 nucleotides and about 700 nucleotides, about 700 nucleotides and about 750 nucleotides, about 750 nucleotides and about 800 nucleotides, about 800 nucleotides and about 850 nucleotides, about 850 nucleotides and about 900 nucleotides, about 900 nucleotides and about 950 nucleotides, or about 950 nucleotides and about 1000 nucleotides. In some embodiments, the probe comprises a nucleic acid molecule comprising about between about 12 and about 20 nucleotides. In some embodiments, the probe comprises a nucleic acid molecule comprising about 17 nucleotides. In some embodiments, the probe comprises a nucleic acid molecule comprising about 18 nucleotides. In some embodiments, the probe comprises a nucleic acid molecule comprising about 19 nucleotides. In some embodiments, the probe comprises a nucleic acid molecule comprising about 20 nucleotides.

In some embodiments, a probe provided herein comprises a DNA. RNA, or a DNA/RNA molecule. In some embodiments, a probe provided herein includes a label or a tag. In some embodiments, the label or tag is a radiolabel (e.g., a radioisotope), a fluorescent label (e.g., a fluorescent compound), an enzymatic label, an enzyme co-factor, a sequence tag, biotin, or other another ligand. In some embodiments, a probe provided herein includes a detection reagent such as a fluorescent marker. In some embodiments, a probe provided herein includes (e.g., is conjugated to) an affinity tag, e.g., that allows capture and isolation of a hybrid formed by a probe and a nucleic acid hybridized to the probe. In some embodiments, the affinity tag is an antibody, an antibody fragment, biotin, or any other suitable affinity tag or reagent known in the art. In some embodiments, a probe is suitable for solution phase hybridization.

In some embodiments, probes provided herein may be used according to the methods of detection of KMT2A-MAML2 fusion nucleic acid molecules provided herein. For example, a probe provided herein may be used for detecting a KMT2A-MAML2 fusion nucleic acid molecule provided herein in sample, e.g., a sample obtained from an individual. In some embodiments, the probe may be used for identifying cells or tissues which express a KMT2A-MAML2 fusion nucleic acid molecule provided herein, e.g., by measuring levels of a KMT2A-MAML2 fusion nucleic acid molecule. In some embodiments, the probe may be used for detecting levels of a KMT2A-MAML2 fusion nucleic acid molecule, e.g., mRNA levels, in a sample of cells from an individual.

In some embodiments, a probe provided herein specifically hybridizes to a nucleic acid comprising a rearrangement (e.g., a deletion, inversion, insertion, duplication, or other rearrangement) resulting in a KMT2A-MAML2 fusion nucleic acid molecule described herein.

In some embodiments, a probe of the disclosure distinguishes a nucleic acid, e.g., a genomic or transcribed nucleic acid, e.g., a cDNA or RNA, having a KMT2A-MAML2 breakpoint described herein, from a reference nucleotide sequence, e.g., a nucleotide sequence not having the breakpoint. In some embodiments, a probe of the disclosure distinguishes a nucleic acid, e.g., a genomic or transcribed nucleic acid, e.g., a cDNA or RNA, having a KMT2A-MAML2 breakpoint between exon 7 of KMT2A and exon 2 of MAML2, from a reference nucleotide sequence, e.g., a nucleotide sequence not having the breakpoint. In some embodiments, a probe of the disclosure distinguishes a nucleic acid, e.g., a genomic or transcribed nucleic acid, e.g., a cDNA or RNA, having a KMT2A-MAML2 breakpoint between exon 8 of KMT2A and exon 2 of MAML2, from a reference nucleotide sequence, e.g., a nucleotide sequence not having the breakpoint. In some embodiments, a probe of the disclosure distinguishes a nucleic acid, e.g., a genomic or transcribed nucleic acid, e.g., a cDNA or RNA, having a KMT2A-MAML2 breakpoint between exon 9 of KMT2A and exon 2 of MAML2, from a reference nucleotide sequence, e.g., a nucleotide sequence not having the breakpoint. In some embodiments, a probe of the disclosure distinguishes a nucleic acid, e.g., a genomic or transcribed nucleic acid, e.g., a cDNA or RNA, having a KMT2A-MAML2 breakpoint between exon 10 of KMT2A and exon 2 of MAML2, from a reference nucleotide sequence, e.g., a nucleotide sequence not having the breakpoint. In some embodiments, a probe of the disclosure distinguishes a nucleic acid, e.g., a genomic or transcribed nucleic acid, e.g., a cDNA or RNA, having a KMT2A-MAML2 breakpoint between exon 11 of KMT2A and exon 2 of MAML2, from a reference nucleotide sequence, e.g., a nucleotide sequence not having the breakpoint.

Also provided herein are isolated pairs of allele specific probes, wherein, for example, the first probe of the pair specifically hybridizes to a KMT2A-MAML2 fusion nucleic acid molecule, e.g., to the KMT2A-MAML2 breakpoint, described herein and the second probe of the pair specifically hybridizes to a corresponding wild type sequence (e.g., a wild type KMT2A or MAML2 nucleic acid molecule). Probe pairs can be designed and produced for any of the fusion nucleic acid molecules described herein and are useful in detecting a somatic mutation in a sample. In some embodiments, a first probe of a pair specifically hybridizes to a mutation (e.g., the KMT2A-MAML2 breakpoint of an inversion, duplication, deletion, insertion or translocation resulting in a KMT2A-MAML2 fusion nucleic acid molecule described herein), and a second probe of a pair specifically hybridizes to a sequence upstream or downstream of the mutation.

In some embodiments, one or more probes provided herein are suitable for use in in situ hybridization methods, e.g., as described above, such as FISH.

Chromosomal probes, e.g., for use in the FISH methods described herein, are typically about 50 to about $10^5$ nucleotides. Longer probes typically comprise smaller fragments of about 100 to about 500 nucleotides. Probes that hybridize with centromeric DNA and locus-specific DNA are available commercially, for example, from Vysis, Inc. (Downers Grove, Ill.), Molecular Probes, Inc. (Eugene, Oreg.) or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, chromosome (e.g., human chromosome) along with the normal chromosome complement of the host, and chromosomes purified by flow cytometry or microdissection. The region of interest can be isolated through cloning, or by site-specific amplification via the polymerase chain reaction (PCR). Probes of the disclosure may also hybridize to RNA molecules, e.g., mRNA, such as an RNA comprising a KMT2A-MAML2 breakpoint provided herein.

In some embodiments, probes, such as probes for use in the FISH methods described herein, are used for determining whether a cytogenetic abnormality is present in one or more cells, e.g., in a region of a chromosome or an RNA bound by one or probes provided herein, such as a cytogenetic abnormality that results in a KMT2A-MAML2 fusion nucleic acid molecule described herein. Examples of such cytogenetic abnormalities include, without limitation, deletions (e.g., deletions of entire chromosomes or deletions of fragments of one or more chromosomes), duplications (e.g., of entire chromosomes, or of regions smaller than an entire chromosome), translocations (e.g., non-reciprocal translocations, balanced translocations), intra-chromosomal inversions, point mutations, deletions, gene copy number changes, germ-line mutations, and gene expression level changes.

In some embodiments, probes, such as probes for use in the FISH methods described herein, are labeled such that a chromosomal region or a region on an RNA to which they hybridize can be detected. Probes typically are directly labeled with a fluorophore, allowing the probe to be visualized without a secondary detection molecule. Probes can also be labeled by nick translation, random primer labeling or PCR labeling. Labeling is done using either fluorescent (direct)- or hapten (indirect)-labeled nucleotides. Representative, non-limiting examples of labels include: AMCA-6-dUTP, CascadeBlue-4-dUTP, Fluorescein-12-dUTP. Rhodamine-6-dUTP, TexasRed-6-dUTP, Cy3-6-dUTP, Cy5-dUTP. Biotin (BIO)-11-dUTP, Digoxygenin (DIG)-11-dUTP and Dinitrophenyl (DNP)-11-dUTP. Probes can also be indirectly labeled with biotin or digoxygenin, or labeled with radioactive isotopes such as P and $^3$H, and secondary detection molecules or further processing is performed to visualize the probes. For example, a probe labeled with biotin can be detected by avidin conjugated to a detectable marker, e.g., avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase. Probes can also be prepared such that a fluorescent or other label is added after hybridization of the probe to its target (e.g., on a chromosome), to detect the probe hybridized to a chromosome. For example, probes can be used that have antigenic molecules incorporated into the DNA. After hybridization, these antigenic molecules are detected using specific antibodies reactive with the antigenic molecules. Such antibodies can themselves incorporate a fluorochrome, or can be detected using a second antibody with a bound fluorochrome.

For fluorescent probes used in fluorescence in situ hybridization (FISH) techniques. e.g., as described herein, fluorescence can be viewed with a fluorescence microscope equipped with an appropriate filter for each fluorophore, or by using dual or triple band-pass filter sets to observe multiple fluorophores. Alternatively, techniques such as flow cytometry can be used to examine the hybridization pattern of the chromosomal probes.

In some embodiments, the probe hybridizes to the KMT2A-MAML2 breakpoint, and a sequence on either side of the KMT2A-MAML2 breakpoint (e.g., any of 1, 2, 3, 4, 5, 6, 7, 8, 9, or 10 nucleotides on either side of the KMT2A-MAML2 breakpoint, or any of between 1 and about 5, about 5 and about 10, about 10 and about 15, about 15 and about 20, about 20 and about 25, about 25 and about 30, about 30 and about 35, about 35 and about 40, about 40 and about 45, about 45 and about 50, about 50 and about 55, about 55 and about 60, about 60 and about 65, about 70 and about 75, about 75 and about 80, about 80 and about 85, about 85 and about 90, about 90 and about 95, or about 95 and about 100, or more nucleotides on either side of the KMT2A-MAML2 breakpoint).

Oligonucleotides

In some aspects, provided herein are oligonucleotides, e.g., useful as primers. In some embodiments, an oligonucleotide, e.g., a primer, provided herein comprises a nucleic acid sequence configured to hybridize to a target nucleic acid molecule comprising a KMT2A-MAML2 fusion nucleic acid molecule provided herein. In some embodiments, the oligonucleotide comprises a nucleic acid sequence configured to hybridize to the KMT2A-MAML2 fusion nucleic acid molecule of the target nucleic acid molecule. In some embodiments, the oligonucleotide comprises a nucleic acid sequence configured to hybridize to a fragment of the KMT2A-MAML2 fusion nucleic acid molecule of the target nucleic acid molecule.

In some embodiments, the oligonucleotide comprises a nucleic acid sequence configured to hybridize to the KMT2A-MAML2 breakpoint (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence that hybridizes to the KMT2A-MAML2 breakpoint between exon 7 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence that hybridizes to the KMT2A-MAML2 breakpoint between exon 8 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence that hybridizes to the KMT2A-MAML2 breakpoint between exon 9 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence that hybridizes to the KMT2A-MAML2 breakpoint between exon 10 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence that hybridizes to the KMT2A-MAML2 breakpoint between exon 11 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides).

In some embodiments, the oligonucleotide comprises a nucleic acid sequence configured to hybridize to a nucleotide sequence comprising a nucleotide sequence in an intron or an exon of KMT2A or MAML2, or in a KMT2A-MAML2 breakpoint joining the introns or exons of KMT2A and MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence configured to hybridize to a nucleotide sequence comprising a nucleotide sequence in an intron of KMT2A or MAML2 or in a KMT2A-MAML2 breakpoint joining the introns of KMT2A and MAML2 (e.g., plus or minus any of between about 10 and about 12, about 12 and about 15, about 15 and about 17, about 17 and about 20, about 20 and about 25, or about 25 and about 30, or more nucleotides).

In some embodiments, the oligonucleotide comprises a nucleic acid sequence configured to hybridize to the KMT2A-MAML2 breakpoint joining an intron of KMT2A and an intron of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence configured to hybridize to the KMT2A-MAML2 breakpoint joining an intron of KMT2A and an exon of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence con-figured to hybridize to the KMT2A-MAML2 breakpoint joining an exon of KMT2A and an intron of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence configured to hybridize to the KMT2A-MAML2 breakpoint joining an exon of KMT2A and an exon of MAML2 (e.g., plus or minus any of between about 10 and about 12, about 12 and about 15, about 15 and about 17, about 17 and about 20, about 20 and about 25, or about 25 and about 30, or more nucleotides).

In some embodiments, the oligonucleotide comprises a nucleic acid sequence corresponding to a KMT2A-MAML2 fusion nucleic acid molecule provided herein. In some embodiments, the oligonucleotide comprises a nucleic acid sequence corresponding to a fragment or a portion of a KMT2A-MAML2 fusion nucleic acid molecule provided herein. In some embodiments, the fragment or portion comprises between about 10 and about 30 nucleotides, between about 12 and about 20 nucleotides, or between about 12 and about 17 nucleotides.

In some embodiments, the oligonucleotide comprises a nucleic acid sequence complementary to a KMT2A-MAML2 fusion nucleic acid molecule provided herein. In some embodiments, the oligonucleotide comprises a nucleic acid sequence complementary to a fragment or a portion of a KMT2A-MAML2 fusion nucleic acid molecule provided herein. In some embodiments, the fragment or portion comprises between about 10 and about 30 nucleotides, between about 12 and about 20 nucleotides, or between about 12 and about 17 nucleotides.

In some embodiments, the oligonucleotide comprises a nucleic acid sequence corresponding to a KMT2A-MAML2 breakpoint between KMT2A and MAML2 (e.g., plus or minus any of between about 10 and about 12, about 12 and about 15, about 15 and about 17, about 17 and about 20, about 20 and about 25, or about 25 and about 30, or more nucleotides) provided herein. In some embodiments, the oligonucleotide comprises a nucleic acid sequence corre-sponding to the KMT2A-MAML2 breakpoint between exon 7 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence corresponding to the KMT2A-MAML2 breakpoint between exon 8 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence cor-responding to the KMT2A-MAML2 breakpoint between exon 9 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence corresponding to the KMT2A-MAML2 breakpoint between exon 10 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence corresponding to the KMT2A-MAML2 break-point between exon 11 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides).

In some embodiments, the oligonucleotide comprises a nucleic acid sequence complementary to a KMT2A-MAML2 breakpoint between KMT2A and MAML2 (e.g., plus or minus any of between about 10 and about 12, about 12 and about 15, about 15 and about 17, about 17 and about 20, about 20 and about 25, or about 25 and about 30, or more nucleotides) provided herein. In some embodiments, the oligonucleotide comprises a nucleic acid sequence comple-mentary to the KMT2A-MAML2 breakpoint between exon 7 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence complementary to the KMT2A-MAML2 breakpoint between exon 8 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence complementary to the KMT2A-MAML2 breakpoint between exon 9 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence complementary to the KMT2A-MAML2 breakpoint between exon 10 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence complementary to the KMT2A-MAML2 break-point between exon 11 of KMT2A and exon 2 of MAML2 (e.g., plus or minus any of between about 10 and about 12, about 12 and about 15, about 15 and about 17, about 17 and about 20, about 20 and about 25, or about 25 and about 30, or more nucleotides).

In some embodiments, the oligonucleotide comprises a nucleic acid sequence corresponding to a nucleotide sequence in an intron or an exon of KMT2A or MAML2, or to a KMT2A-MAML2 breakpoint joining the introns or exons of KMT2A and MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence corresponding to a nucleotide sequence in an intron of KMT2A or MAML2 or to a KMT2A-MAML2 breakpoint joining the introns of KMT2A and MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucle-otide comprises a nucleic acid sequence corresponding to a to a KMT2A-MAML2 breakpoint joining an intron of KMT2A and an intron of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence corresponding to a to a KMT2A-MAML2 breakpoint joining an exon of KMT2A and an intron of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence corresponding to a to a KMT2A-MAML2 breakpoint joining an intron of KMT2A and an exon of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence corresponding to a to a KMT2A-MAML2 breakpoint joining an exon of KMT2A and an exon of MAML2 (e.g., plus or minus any of between about 10 and about 12, about 12 and about 15, about 15 and about 17, about 17 and about 20, about 20 and about 25, or about 25 and about 30, or more nucleotides).

In some embodiments, the oligonucleotide comprises a nucleic acid sequence complementary to a nucleotide sequence in an intron or an exon of KMT2A or MAML2, or to a KMT2A-MAML2 breakpoint joining the introns or exons of KMT2A and MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence complementary to a nucleotide sequence in an intron of KMT2A or MAML2 or to a KMT2A-MAML2 breakpoint joining the introns of KMT2A and MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence complementary to a to a KMT2A-MAML2 breakpoint joining an intron of KMT2A and an intron of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence complementary to a to a KMT2A-MAML2 breakpoint joining an exon of KMT2A and an intron of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence complementary to a to a KMT2A-MAML2 breakpoint joining an intron of KMT2A and an exon of MAML2 (e.g., plus or minus any of between about 10 and about 12, about 12 and about 15, about 15 and about 17, about 17 and about 20, about 20 and about 25, or about 25 and about 30, or more nucleotides). In some embodiments, the oligonucleotide comprises a nucleic acid sequence complementary to a to a KMT2A-MAML2 breakpoint joining an exon of KMT2A and an exon of MAML2 (e.g., plus or minus any of between about 10 and about 12, about 12 and about 15, about 15 and about 17, about 17 and about 20, about 20 and about 25, or about 25 and about 30, or more nucleotides).

In some embodiments, an oligonucleotide, e.g., a primer, provided herein comprises a nucleotide sequence that is sufficiently complementary to its target nucleotide sequence such that the oligonucleotide specifically hybridizes to a nucleic acid molecule comprising the target nucleotide sequence, e.g., under high stringency conditions. In some embodiments, an oligonucleotide, e.g., a primer, provided herein comprises a nucleotide sequence that is sufficiently complementary to its target nucleotide sequence such that the oligonucleotide specifically hybridizes to a nucleic acid molecule comprising the target nucleotide sequence under conditions that allow a polymerization reaction (e.g., PCR) to occur.

In some embodiments, an oligonucleotide, e.g., a primer, provided herein may be useful for initiating DNA synthesis via PCR (polymerase chain reaction) or a sequencing method. In some embodiments, the oligonucleotide may be used to amplify a nucleic acid molecule comprising a KMT2A-MAML2 fusion nucleic acid molecule or fragment thereof provided herein. e.g., using PCR. In some embodiments, the oligonucleotide may be used to sequence a nucleic acid molecule comprising a KMT2A-MAML2 fusion nucleic acid molecule or fragment thereof provided herein. In some embodiments, the oligonucleotide may be used to amplify a nucleic acid molecule comprising a KMT2A-MAML2 breakpoint provided herein, e.g., using PCR. In some embodiments, the oligonucleotide may be used to sequence a nucleic acid molecule comprising a KMT2A-MAML2 breakpoint provided herein.

In some embodiments, pairs of oligonucleotides, e.g., pairs of primers, are provided herein, which are configured to hybridize to a nucleic acid molecule comprising a KMT2A-MAML2 fusion nucleic acid molecule or fragment thereof provided herein for use in directing amplification of a the fusion nucleic acid molecule or fragment thereof, e.g., using a PCR reaction. In some embodiments, pairs of oligonucleotides, e.g., pairs of primers, are provided herein, which are configured to hybridize to a nucleic acid molecule comprising a KMT2A-MAML2 breakpoint provided herein for use in directing amplification of a the fusion nucleic acid molecule or fragment thereof, e.g., using a PCR reaction.

In some embodiments, an oligonucleotide, e.g., a primer, provided herein is a single stranded nucleic acid molecule, e.g., for use in sequencing or amplification methods. In some embodiments, an oligonucleotide provided herein is a double stranded nucleic acid molecule. In some embodiments, a double stranded oligonucleotide is treated, e.g., denatured, to separate its two strands prior to use, e.g., in sequencing or amplification methods. Oligonucleotides provided herein comprise a nucleotide sequence of sufficient length to hybridize to their target, e.g., a KMT2A-MAML2 fusion nucleic acid molecule or fragment thereof provided herein, and to prime the synthesis of extension products, e.g., during PCR or sequencing.

In some embodiments, an oligonucleotide provided herein comprises at least three deoxyribonucleotides or ribonucleotides. In some embodiments, an oligonucleotide provided herein comprises at least about eight deoxyribonucleotides or ribonucleotides. In some embodiments, an oligonucleotide provided herein comprises at least about 20 deoxyribonucleotides or ribonucleotides. In some embodiments, an oligonucleotide provided herein comprises at least about 30 deoxyribonucleotides or ribonucleotides. In some embodiments, an oligonucleotide provided herein comprises between about 10 and about 30 deoxyribonucleotides or ribonucleotides. In some embodiments, an oligonucleotide provided herein comprises between about 10 and about 25 deoxyribonucleotides or ribonucleotides. In some embodiments, an oligonucleotide provided herein comprises between about 10 and about 20 deoxyribonucleotides or ribonucleotides. In some embodiments, an oligonucleotide provided herein comprises between about 10 and about 15 deoxyribonucleotides or ribonucleotides. In some embodiments, an oligonucleotide provided herein comprises between about 12 and about 20 deoxyribonucleotides or ribonucleotides. In some embodiments, an oligonucleotide provided herein comprises between about 17 and about 20 deoxyribonucleotides or ribonucleotides. In some embodiments, the length of an oligonucleotide provided herein is determined according to methods known in the art, e.g., based on factors such as the specific application (e.g., PCR, sequencing library preparation, sequencing), reaction conditions (e.g., buffers, temperature), and the nucleotide composition of the nucleotide sequence of the oligonucleotide or of its target complementary sequence.

In some embodiments, an oligonucleotide, e.g., a primer, of the disclosure distinguishes a nucleic acid, e.g., a genomic or transcribed nucleic acid, e.g., a cDNA or RNA, having a KMT2A-MAML2 breakpoint described herein from a reference nucleotide sequence, e.g., a nucleotide sequence not having the breakpoint. In some embodiments, an oligonucleotide, e.g., a primer, of the disclosure distinguishes a nucleic acid, e.g., a genomic or transcribed nucleic acid, e.g., a cDNA or RNA, having a KMT2A-MAML2 breakpoint between exon 7 of KMT2A and exon 2 of MAML2, from a reference nucleotide sequence, e.g., a nucleotide sequence not having the breakpoint. In some embodiments, an oligonucleotide, e.g., a primer, of the disclosure distinguishes a nucleic acid, e.g., a genomic or transcribed nucleic acid, e.g., a cDNA or RNA, having a KMT2A-MAML2 breakpoint between exon 8 of KMT2A and exon 2 of MAML2, from a reference nucleotide sequence, e.g., a nucleotide sequence not having the breakpoint. In some embodiments, an oligonucleotide, e.g., a primer, of the disclosure distinguishes a nucleic acid, e.g., a genomic or transcribed nucleic acid, e.g., a cDNA or RNA, having a KMT2A-MAML2 breakpoint between exon 9 of KMT2A and exon 2 of MAML2, from a reference nucleotide sequence, e.g., a nucleotide sequence not having the breakpoint. In some embodiments, an oligonucleotide, e.g., a primer, of the disclosure distinguishes a nucleic acid, e.g., a genomic or transcribed nucleic acid, e.g., a cDNA or RNA, having a KMT2A-MAML2 breakpoint between exon 10 of KMT2A and exon 2 of MAML2, from a reference nucleotide sequence, e.g., a nucleotide sequence not having the breakpoint. In some embodiments, an oligonucleotide, e.g., a primer, of the disclosure distinguishes a nucleic acid, e.g., a genomic or transcribed nucleic acid, e.g., a cDNA or RNA, having a KMT2A-MAML2 breakpoint between exon 11 of KMT2A and exon 2 of MAML2, from a reference nucleotide sequence, e.g., a nucleotide sequence not having the breakpoint.

In one aspect, provided herein is a primer or primer set for amplifying a nucleic acid comprising a cytogenetic abnormality such as a chromosomal inversion, deletion, translocation, or duplication resulting in a fusion molecule described herein. In another aspect, provided herein is a primer or primer set for amplifying a nucleic acid comprising a chromosomal inversion, insertion, deletion, translocation, or duplication resulting in a fusion molecule described herein. In certain aspects, provided herein are allele-specific oligonucleotides, e.g., primer, where a first oligonucleotide of a pair specifically hybridizes to a mutation (e.g., the KMT2A-MAML2 breakpoint of an inversion, duplication, deletion, insertion or translocation resulting in a KMT2A-MAML2 fusion nucleic acid molecule described herein), and a second oligonucleotide of a pair specifically hybridizes to a sequence upstream or downstream of the mutation.

In some embodiments, the oligonucleotide, e.g., the primer, hybridizes to the KMT2A-MAML2 breakpoint, and a sequence on either side of the KMT2A-MAML2 breakpoint (e.g., any of 1, 2, 3, 4, 5, 6, 7, 8, 9, or 10 nucleotides on either side of the KMT2A-MAML2 breakpoint, or any of between 1 and about 5, about 5 and about 10, about 10 and about 15, about 15 and about 20, about 20 and about 25, about 25 and about 30, about 30 and about 35, about 35 and about 40, about 40 and about 45, about 45 and about 50, about 50 and about 55, about 55 and about 60, about 60 and about 65, about 70 and about 75, about 75 and about 80, about 80 and about 85, about 85 and about 90, about 90 and about 95, or about 95 and about 100, or more nucleotides on either side of the KMT2A-MAML2 breakpoint).

Nucleic Acid Samples

In some embodiments, a KMT2A-MAML2 fusion nucleic acid molecule is detected in a sample comprising nucleic acids, e.g., genomic DNA, cDNA, or mRNA. In some embodiments, the sample is obtained from an individual having an epithelial neoplasm, such as a thymoma. A variety of materials (such as tissues) can be the source of the nucleic acid samples used in the methods provided herein. For example, the source of the sample can be solid tissue as from a fresh, frozen and/or preserved organ, tissue sample, biopsy, resection, smear, or aspirate; blood or any blood constituents; bodily fluids such as cerebral spinal fluid, amniotic fluid, urine, saliva, sputum, peritoneal fluid or interstitial fluid; or cells from any time in gestation or development of an individual. In some embodiments, the source of the sample is blood or blood constituents. In some embodiments, the source of the sample is a tumor sample. In some embodiments, the sample is or comprises biological tissue or fluid. In some embodiments, the sample can contain compounds that are not naturally intermixed with the tissue in nature such as preservatives, anticoagulants, buffers, fixatives, nutrients, antibiotics or the like. In some embodiments, a KMT2A-MAML2 fusion nucleic acid molecule is detected in a sample comprising genomic or subgenomic DNA fragments or RNA, such as mRNA isolated from a sample, e.g., a tumor sample, a normal adjacent tissue (NAT) sample, a tissue sample, or a blood sample obtained from an individual. In some embodiments, the sample comprises cDNA derived from an mRNA sample or from a sample comprising mRNA. In some embodiments, the tissue is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

In some embodiments, the sample comprises cell-free DNA (cfDNA). CfDNA can be used as a biomarker, for example, for non-invasive prenatal testing (NIPT), organ transplant, cardiomyopathy, microbiome, and cancer. In some embodiments, the sample comprises cell-free RNA (cfRNA).

In some embodiments, the sample comprises circulating tumor DNA (ctDNA). In some embodiments, the sample comprises circulating tumor cells (CTCs). In some embodiments, CTCs apoptose and are a source of ctDNA in the blood/lymph.

In some embodiments, a sample may be or comprise bone marrow; a bone marrow aspirate blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as ductal lavages or bronchoalveolar lavages; aspirates; scrapings;

bone marrow specimens; tissue biopsy specimens; surgical specimens; feces, other body fluids, secretions, and/or excretions; and/or cells therefrom, etc. In some embodiments, a biological sample is or comprises cells obtained from an individual.

In some embodiments, a sample is a primary sample obtained directly from a source of interest by any appropriate means. For example, in some embodiments, a primary biological sample is obtained by a method chosen from biopsy (e.g., fine needle aspiration or tissue biopsy), surgery, collection of body fluid (e.g., blood, lymph, or feces), etc. In some embodiments, as will be clear from context, the term "sample" refers to a preparation that is obtained by processing (e.g., by removing one or more components of and/or by adding one or more agents to) a primary sample. Such a processed sample may comprise, for example nucleic acids or proteins extracted from a sample or obtained by subjecting a primary sample to techniques such as amplification or reverse transcription of mRNA, isolation and/or purification of certain components, etc.

In an embodiment, the sample is one or more cells associated with a tumor, e.g., tumor cells or tumor-infiltrating lymphocytes (TIL). In one embodiment, the sample includes one or more premalignant or malignant cells. In an embodiment, the sample is acquired from a hematologic malignancy (or pre-malignancy). e.g., a hematologic malignancy (or pre-malignancy) described herein. In an embodiment, the sample is acquired from a cancer, such as an epithelial neoplasm. e.g., a thymoma, described herein. In some embodiments, the sample is acquired from a solid tumor, a soft tissue tumor or a metastatic lesion. In other embodiments, the sample includes tissue or cells from a surgical margin. In another embodiment, the sample includes one or more circulating tumor cells (CTCs) (e.g., a CTC acquired from a blood sample). In an embodiment, the sample is a cell not associated with a tumor, e.g., a non-tumor cell or a peripheral blood lymphocyte.

In some embodiments, the sample comprises tumor nucleic acids, such as nucleic acids from a tumor or a cancer sample, e.g., genomic DNA, or cDNA derived from RNA, from a tumor or cancer sample. In certain embodiments, a tumor nucleic acid sample is purified or isolated (e.g., it is removed from its natural state).

In some embodiments, the sample is a control nucleic acid sample or a reference nucleic acid sample, e.g., genomic DNA, or cDNA derived from RNA, not containing a gene fusion described herein. In certain embodiments, the reference or control nucleic acid sample is a wild type or a non-mutated sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

In some embodiments, a KMT2A-MAML2 fusion nucleic acid molecule is detected in a sample comprising cell-free DNA (cfDNA), cell-free RNA, or circulating tumor DNA (ctDNA).

Detection of KMT2A-MAML2 Fusion Polypeptides

Also provided herein are methods of detecting a KMT2A-MAML2 fusion polypeptide provided herein or a fragment thereof. A KMT2A-MAML2 fusion polypeptide provided herein may be detected or measured, e.g., in a sample obtained from an individual, using any method known in the art, such as using antibodies (e.g., an antibody described herein), mass spectrometry (e.g., tandem mass spectrometry), a reporter assay (e.g., a fluorescence-based assay), immunoblots such as a Western blot, immunoassays such as enzyme-linked immunosorbent assays (ELISA), immuno-histochemistry, other immunological assays (e.g., fluid or gel precipitin reactions, immunodiffusion, immunoelectro-phoresis, radioimmunoassay (RIA), immunofluorescent assays), and analytic biochemical methods (e.g., electrophoresis, capillary electrophoresis, high performance liquid chromatography (HPLC), thin layer chromatography (TLC), hyperdiffusion chromatography).

In some embodiments, a KMT2A-MAML2 fusion polypeptide provided herein or a fragment thereof can be distinguished from a reference polypeptide, e.g., a non-mutant or wild type KMT2A and/or MAML2 protein, by reaction with a detection reagent, e.g., a substrate, e.g., a substrate for catalytic activity, e.g., methylation, or with an antibody or fragment thereof that reacts differentially with a mutant protein or polypeptide (e.g., a KMT2A-MAML2 fusion polypeptide provided herein or a fragment thereof) as compared to a reference protein or polypeptide.

In some embodiments, methods of detection of a KMT2A-MAML2 fusion polypeptide described herein or a fragment thereof are provided, comprising contacting a sample, e.g., a sample described herein, comprising a fusion polypeptide described herein, with a detection reagent provided herein (e.g., an antibody of the disclosure), and determining if the fusion polypeptide is present in the sample.

Protein Samples

In some embodiments, a sample for use according to the methods of detection of a KMT2A-MAML2 fusion polypeptide described herein is a solid tissue, e.g., from a fresh, frozen and/or preserved organ, tissue sample, biopsy (e.g., a tumor biopsy), resection, smear, or aspirate; blood or any blood constituents; bodily fluids such as cerebral spinal fluid, amniotic fluid, urine, saliva, sputum, peritoneal fluid or interstitial fluid; or cells such as tumor cells. In some embodiments, the source of the sample is blood or blood constituents. In some embodiments, the source of the sample is a tumor sample. In some embodiments, the sample is or comprises biological tissue or fluid. In some embodiments, the sample is preserved as a frozen sample or as a formaldehyde- or paraformaldehyde-fixed paraffin-embedded (FFPE) tissue preparation. In some embodiments, the sample comprises circulating tumor cells (CTCs).

In some embodiments, a sample for use according to the methods of detection of a KMT2A-MAML2 fusion polypeptide described herein is a sample of proteins isolated or obtained from a solid tissue, e.g., from a fresh, frozen and/or preserved organ, tissue sample, biopsy (e.g., a tumor biopsy), resection, smear, or aspirate; from blood or any blood constituents; from bodily fluids such as cerebral spinal fluid, amniotic fluid, urine, saliva, sputum, peritoneal fluid or interstitial fluid; or from cells such as tumor cells. In some embodiments, the sample is a sample of proteins isolated or obtained from a preserved sample, such as a frozen sample or as a formaldehyde- or paraformaldehyde-fixed paraffin-embedded (FFPE) tissue preparation. In some embodiments, the sample is a sample of proteins isolated or obtained from circulating tumor cells (CTCs). In some embodiments, the sample can contain compounds that are not naturally inter-mixed with the tissue in nature such as preservatives, anticoagulants, buffers, fixatives, nutrients, antibiotics or the like.

In some embodiments, a sample may be or comprise bone marrow; a bone marrow aspirate blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs, vaginal swabs; oral swabs; nasal swabs; washings or lavages such as ductal lavages or bronchoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual.

In some embodiments, a sample is a primary sample obtained directly from a source of interest by any appropriate means. For example, in some embodiments, a primary biological sample is obtained by a method chosen from biopsy (e.g., fine needle aspiration or tissue biopsy), surgery, collection of body fluid (e.g., blood, lymph, or feces), etc. In some embodiments, as will be clear from context, the term "sample" refers to a preparation that is obtained by processing (e.g., by removing one or more components of and/or by adding one or more agents to) a primary sample. Such a processed sample may comprise, for example proteins extracted from a sample or obtained by subjecting a primary sample to techniques such as isolation and/or purification of certain components, etc.

In an embodiment, the sample is one or more cells associated with a tumor, e.g., tumor cells or tumor-infiltrating lymphocytes (TIL). In one embodiment, the sample includes one or more premalignant or malignant cells. In an embodiment, the sample is acquired from a hematologic malignancy (or pre-malignancy), e.g., a hematologic malignancy (or pre-malignancy) described herein. In an embodiment, the sample is acquired from a cancer described herein, such as an epithelial neoplasm, e.g., a thymoma. In some embodiments, the sample is acquired from a solid tumor, a soft tissue tumor or a metastatic lesion. In other embodiments, the sample includes tissue or cells from a surgical margin. In another embodiment, the sample includes one or more circulating tumor cells (CTCs) (e.g., a CTC acquired from a blood sample). In an embodiment, the sample is a cell not associated with a tumor, e.g., a non-tumor cell or a peripheral blood lymphocyte.

Antibodies

Provided herein are antibodies or antibody fragments that specifically bind to a KMT2A-MAML2 fusion polypeptide provided herein or a portion thereof. The antibody may be of any suitable type of antibody, including, but not limited to, a monoclonal antibody, a polyclonal antibody, a multispecific antibody (e.g., a bispecific antibody), or an antibody fragment, so long as the antibody or antibody fragment exhibits a specific antigen binding activity.

In some embodiments, a KMT2A-MAML2 fusion polypeptide provided herein, or a fragment thereof, is used as an immunogen to generate one or more antibodies of the disclosure, e.g., using standard techniques for polyclonal and monoclonal antibody preparation. In some embodiments, a KMT2A-MAML2 fusion polypeptide provided herein, is used to provide antigenic peptide fragments (e.g., comprising any of at least about 8, at least about 10, at least about 15, at least about 20, at least about 30 or more amino acids) for use as immunogens to generate one or more antibodies of the disclosure, e.g., using standard techniques for polyclonal and monoclonal antibody preparation.

As is known in the art, an antibody of the disclosure may be prepared by immunizing a suitable (i.e., immunocompetent) subject such as a rabbit, goat, mouse, or other mammal or vertebrate. An appropriate immunogenic preparation can contain, for example, recombinantly-expressed or chemically-synthesized polypeptides, e.g., a KMT2A-MAML2 fusion polypeptide provided herein, or a fragment thereof. The preparation can further include an adjuvant, such as Freund's complete or incomplete adjuvant, or a similar immunostimulatory agent.

In some embodiments, an antibody provided herein is a polyclonal antibody. Methods of producing polyclonal antibodies are known in the art.

In some embodiments, an antibody provided herein is a monoclonal antibody, wherein a population of the antibody molecules contain only one species of an antigen binding site capable of immunoreacting or binding with a particular epitope, e.g., an epitope on a KMT2A-MAML2 fusion polypeptide provided herein. Methods of preparation of monoclonal antibodies are known in the art, e.g., using standard hybridoma techniques originally described by Kohler and Milstein (1975) *Nature* 256:495-497, human B cell hybridoma techniques (see Kozbor et al., 1983, *Immunol. Today* 4:72), EBV-hybridoma techniques (see Cole et al., pp. 77-96 In *Monoclonal Antibodies and Cancer Therapy*, Alan R. Liss, Inc., 1985), or trioma techniques. The technology for producing hybridomas is well known (see generally *Current Protocols in Immunology*. Coligan et al, ed., John Wiley & Sons, New York, 1994). A monoclonal antibody of the disclosure may also be identified and isolated by screening a recombinant combinatorial immunoglobulin library (e.g., an antibody phage display library) with the polypeptide of interest, e.g., a KMT2A-MAML2 fusion polypeptide provided herein or a fragment thereof. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281, and Griffiths et al. (1993) *EMBO J.* 12:725-734. In some embodiments, a monoclonal antibodies of the disclosure are recombinant antibodies, such as chimeric and humanized monoclonal antibodies, comprising both human and non-human portions. Such chimeric and/or humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad Sci. USA* 84:3439-3443; Liu et al. (1987) *J. Immunol.* 139:3521-3526; Sun et al. (1987) *Proc. Natl. Acad Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559; Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060. In some embodiments, a monoclonal antibody of the disclosure is a human monoclonal antibody. In some embodiments, human monoclonal antibodies are prepared using methods known in the art, e.g., using transgenic mice which are incapable of expressing endogenous immunoglobulin heavy and light chains genes, but which can express human heavy and light chain genes. For an overview of this technology for producing human antibodies, see Lonberg and Huszar (1995) *Int. Rev. Immunol.* 13:65-93. For a detailed discussion of this technology for producing human antibodies and human monoclonal antibodies and protocols for producing such antibodies, see e.g., U.S. Pat. Nos. 5,625,126; 5,633,425; 5,569,825; 5,661,016; and 5,545,806.

In some embodiments, the antibody or antibody fragment is an isolated antibody or antibody fragment, which has been separated from a component of its natural environment or a cell culture used to produce the antibody or antibody fragment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC).

Antibody Affinity

In certain embodiments, an antibody provided herein has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M. e.g., from $10^{-9}$M to $10^{-13}$ M). Methods of measuring antibody affinity (e.g., Kd) are known in the art, and include, without limitation, a radiolabeled antigen binding assay (RIA) and a BIACORE® surface plasmon resonance assay. In one embodiment, an RIA is performed with the Fab version of an antibody of interest and its antigen.

Antibody Fragments

In certain embodiments, an antibody provided herein is an antibody fragment. Antibody fragments include, but are not limited to, Fab, Fab', Fab'-SH, F(ab')$_2$, Fv, and single-chain antibody molecules (e.g., scFv) fragments, and other fragments described below.

In certain embodiments, an antibody provided herein is a diabody. Diabodies are antibody fragments with two antigen-binding sites that may be bivalent or bispecific. In certain embodiments, an antibody provided herein is a triabody or a tetrabody.

In certain embodiments, an antibody provided herein is a single-domain antibody. Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells (e.g. *E. coli* or phage), as known in the art and as described herein.

Chimeric and Humanized Antibodies

In certain embodiments, an antibody provided herein is a chimeric antibody. Certain chimeric antibodies. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are known in the art.

Human framework regions that may be used for humanization include but are not limited to: framework regions selected using the "best-fit" method; framework regions derived from the consensus sequence of human antibodies of a particular subgroup of light or heavy chain variable regions; human mature (somatically mutated) framework regions or human germline framework regions; and framework regions derived from screening FR libraries.

Human Antibodies

In certain embodiments, an antibody provided herein is a human antibody. Human antibodies can be produced using various techniques known in the art. For example, human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. Human variable regions from intact antibodies generated by such animals may be further modified, e.g., by combining with a different human constant region. Human antibodies can also be made by hybridoma-based methods known in the art, e.g., using known human myeloma and mouse-human heteromyeloma cell lines for the production of human monoclonal antibodies. Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Library-Derived Antibodies

Antibodies of the disclosure may be isolated by screening combinatorial libraries for antibodies with the desired activity or activities. For example, a variety of methods are known in the art for generating phage display libraries and screening such libraries for antibodies possessing the desired binding characteristics. In certain phage display methods, repertoires of VH and VL genes are separately cloned by polymerase chain reaction (PCR) and recombined randomly in phage libraries, which can then be screened for antigen-binding phage. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization. Finally, naive libraries can also be made synthetically by cloning unrearranged V-gene segments from stem cells, and using PCR primers containing random sequence to encode the highly variable CDR3 regions and to accomplish rearrangement in vitro. Antibodies or antibody fragments isolated from human antibody libraries are considered human antibodies or human antibody fragments herein.

Multi-Specific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for an immune checkpoint protein of the present disclosure and the other is for any other antigen, e.g., a fusion polypeptide provided herein. Bispecific antibodies can be prepared as full length antibodies or antibody fragments. Techniques for making multispecific antibodies are known in the art and include, but are not limited to, recombinant co-expression of two immunoglobulin heavy chain-light chain pairs having different specificities, and "knob-in-hole" engineering. Multi-specific antibodies may also be made by engineering electrostatic steering effects for making antibody Fc-heterodimeric; cross-linking two or more antibodies or fragments; using leucine zippers to produce bi-specific antibodies; using "diabody" technology for making bispecific antibody fragments; using single-chain Fv (sFv) dimers; and preparing trispecific antibodies. Engineered antibodies with three or more functional antigen binding sites, including "Octopus antibodies," are also included in the disclosure. Antibodies or antibody fragments of the disclosure also include "Dual Acting FAbs" or "DAF" comprising an antigen binding site that binds to an immune checkpoint protein as well as another, different antigen.

Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the HVRs and FRs. Amino acid substitutions may be introduced into an antibody of interest and the products screened for a desired activity, e.g., retained/improved antigen binding, decreased immunogenicity, or improved ADCC or CDC.

In certain embodiments, an antibody of the present disclosure is altered to increase or decrease the extent to which the antibody is glycosylated. Addition or deletion of glycosylation sites to an antibody may be conveniently accomplished by altering the amino acid sequence such that one or more glycosylation sites is created or removed. Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Antibody variants with at least one galactose residue in the oligosaccharide attached to the Fc region are also provided. Such antibody variants may have improved CDC function.

In certain embodiments, one or more amino acid modifications may be introduced into the Fc region of an antibody of the present disclosure, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the present disclosure contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks Fc-gamma-R binding (hence likely lacking ADCC activity), but retains FcRn binding ability. The primary cells for mediating ADCC, NK cells, express Fc-gamma-RIII only, whereas monocytes express Fc-gamma-RI, Fc-gamma-RII and Fc-gamma-RIII. Antibodies with reduced effector function include those with substitution of one or more of Fc region residues 238, 265, 269, 270, 297, 327 and 329. Such Fc mutants include Fc mutants with substitutions at two or more of amino acid positions 265, 269, 270, 297 and 327, including the so-called "DANA" Fc mutant with substitution of residues 265 and 297 to alanine. Antibody variants with improved or diminished binding to FcRs are also included in the disclosure. In certain embodiments, an antibody variant comprises an Fc region with one or more amino acid substitutions which improve ADCC, e.g., substitutions at positions 298, 333, and/or 334 of the Fc region (EU numbering of residues). In some embodiments, alterations are made in the Fc region that result in altered (i.e., either improved or diminished) C1q binding and/or Complement Dependent Cytotoxicity (CDC). In some embodiments, antibodies of the disclosure include antibodies with increased half-lives and improved binding to the neonatal Fc receptor (FcRn). Antibodies with increased half-lives and improved binding to the neonatal Fc receptor (FcRn), which is responsible for the transfer of maternal IgGs to the fetus are known in the art. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434.

See also Duncan & Winter. Nature 322:738-40 (1988); U.S. Pat. Nos. 5,648,260; 5,624,821; and WO 94/29351 concerning other examples of Fc region variants.

In certain embodiments, an antibody provided herein is a cysteine engineered antibody, e.g., "thioMAb," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain;

and S400 (EU numbering) of the heavy chain Fc region. Cysteine engineered antibodies may be generated using any suitable method known in the art.

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. In another embodiment, conjugates of an antibody and nonproteinaceous moiety that may be selectively heated by exposure to radiation are provided. In one embodiment, the nonproteinaceous moiety is a carbon nanotube. The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In some embodiments, an antibody or antibody fragment provided herein comprises a label or a tag. In some embodiments, the label or tag is a radiolabel, a fluorescent label, an enzymatic label, a sequence tag, biotin, or other ligands. Examples of labels or tags include, but are not limited to, 6xHis-tag, biotin-tag, Glutathione-S-transferase (GST)-tag. Green fluorescent protein (GFP)-tag, c-myc-tag, FLAG-tag, Thioredoxin-tag, Glu-tag, Nus-tag, V5-tag, calmodulin-binding protein (CBP)-tag, Maltose binding protein (MBP)-tag, Chitin-tag, alkaline phosphatase (AP)-tag, HRP-tag, Biotin Caboxyl Carrier Protein (BCCP)-tag, Calmodulin-tag, S-tag, Strep-tag, haemoglutinin (HA)-tag, digoxigenin (DIG)-tag, DsRed, RFP, Luciferase, Short Tetracysteine Tags, Halo-tag, Strep-tag, and Nus-tag. In some embodiments, the label or tag comprises a detection agent, such as a fluorescent molecule or an affinity reagent or tag. In some embodiments, an isolated antibody molecule provided herein is conjugated to a drug molecule, e.g., an anti-cancer agent described herein, a cytotoxic agent such as mertansine or monomethyl auristatin E (MMAE).

In some embodiments, an antibody of the disclosure can be used to isolate a KMT2A-MAML2 fusion polypeptide provided herein, or a fragment thereof, by standard techniques, such as affinity chromatography or immunoprecipitation. Moreover, such an antibody can be used to detect a fusion polypeptide described herein (e.g., in a cellular lysate or cell supernatant) in order to evaluate the level and pattern of expression of the fusion polypeptide. Detection can be facilitated by coupling the antibody to a detectable substance. This, in some embodiments, an antibody of the disclosure is couple to a detectable substance. Non-limiting examples of detectable substances include, e.g., various enzymes, prosthetic groups, fluorescent materials, luminescent materials, bioluminescent materials, and radioactive materials. Non-limiting examples of suitable enzymes include, e.g., horseradish peroxidase, alkaline phosphatase, β-galactosidase, or acetylcholinesterase; examples of suitable prosthetic group complexes include, e.g., streptavidin/biotin and avidin/biotin; examples of suitable fluorescent materials include, e.g., umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, e.g., luciferase, luciferin, and aequorin, and examples of suitable radioactive materials include, e.g., $^{125}$I, $^{131}$I, $^{35}$S or $^{3}$H.

An antibody of the disclosure may also be used diagnostically to monitor protein levels in tissues or body fluids (e.g., in a tumor cell-containing body fluid) as part of a clinical testing procedure, e.g., for example, to determine the efficacy of a given treatment regimen.

Cancers

In some embodiments, a cancer of the disclosure (e.g., a cancer to be treated according to the methods of the disclosure) includes, without limitation, acute lymphoblastic leukemia ("ALL"), acute myeloid leukemia ("AML"), adenocarcinoma, adenocarcinoma of the lung, adrenocortical cancer, adrenocortical carcinoma, anal cancer (e.g., squamous cell carcinoma of the anus), appendiceal cancer, B-cell derived leukemia, B-cell derived lymphoma. B-cell lymphoma, bladder cancer, brain cancer, breast cancer (e.g., triple negative breast cancer (TNBC) or non-triple negative breast cancer), cancer of the fallopian tube(s), cancer of the testes, carcinoma, cerebral cancer, cervical cancer (e.g., squamous cell carcinoma of the cervix), cholangiocarcinoma, choriocarcinoma, chronic myelogenous leukemia, CNS tumor, colon cancer or colorectal cancer (e.g., colon adenocarcinoma), diffuse intrinsic pontine glioma (DIPG), diffuse large B cell lymphoma ("DLBCL"), embryonal rhabdomyosarcoma (ERMS), endometrial cancer, epithelial cancer, epithelial neoplasm, esophageal cancer (e.g., squamous cell carcinoma of the esophagus), Ewing's sarcoma, eye cancer (e.g., uveal melanoma), eyelid cancer, follicular lymphoma ("FL"), gall bladder cancer, gastric cancer, gastrointestinal cancer, glioblastoma, glioblastoma multiforme, glioma (e.g., lower grade glioma), gullet cancer, head and neck cancer (e.g., squamous cell carcinoma of the head and neck (SCHNC)), hematological cancer, hepatocellular cancer, hepatocellular carcinoma, Hodgkin's lymphoma (HL), intestinum rectum cancer, kidney cancer (e.g., kidney clear cell cancer, kidney chromophobe cancer, kidney clear cell cancer, kidney papillary cancer), large B-cell lymphoma, large intestine cancer, laryngeal cancer, leucosis, leukemia, liver cancer, lung cancer (e.g., lung adenocarcinoma, lung squamous cell cancer, or non-small cell lung cancer), lymphoma, mammary gland cancer, melanoma (e.g., metastatic malignant melanoma), Merkel cell carcinoma, Mesothelioma, monocytic leukemia, multiple myeloma, myeloma, myogenic sarcoma, nasopharyngeal cancer, neuroblastic-derived CNS tumor (e.g., neuroblastoma (NB)), neuroma, non-Hodgkin's lymphoma (NHL), non-small cell lung cancer (NSCLC), oral cancer, oral cavity cancer, osteosarcoma, ovarian cancer, ovarian carcinoma, pancreatic adenocarcinoma, pancreatic cancer, peritoneal cancer, pheochromocytoma, primary mediastinal B-cell lymphoma, primary peritoneal cancer, prostate cancer (e.g., hormone refractory prostate adenocarcinoma), rectal cancer (rectum carcinoma), relapsed or refractory classic Hodgkin's Lymphoma (cHL), renal cancer (e.g., clear cell carcinoma), salivary gland cancer (e.g., salivary gland tumor), skin cancer, small cell lung cancer, small intestine cancer, soft tissue sarcoma, squamous carcinoma such as squamous cell carcinoma, squamous cell carcinoma (e.g., of the lung; of the anogenital region including anus), squamous cell carcinoma of the anus, squamous cell carcinoma of the cervix, squamous cell carcinoma of the esophagus, squamous cell carcinoma of the head and neck, squamous cell carcinoma of the head and neck (SCHNC), squamous cell carcinoma of the lung, squamous cell carcinoma of the lung, squamous cell carcinoma of the penis, squamous cell carcinoma of the vagina, squamous cell carcinoma of the vulva, stomach cancer. T-cell derived leukemia, T-cell lymphoma, testicular cancer, testicular tumor, thymic cancer, thymoma, thyroid cancer (thyroid carcinoma), tongue cancer, tunica conjunctiva cancer, urinary bladder cancer, urothelial cell carcinoma, uterine cancer (e.g., uterine endometrial cancer or uterine sarcoma such as uterine carcinosarcoma), uterine endometrial cancer, uterus cancer, uveal melanoma, vaginal cancer (e.g., squamous cell carcinoma of the vagina), vulvar cancer (e.g., squamous cell carcinoma of the vulva), or Wilms' tumor.

In some embodiments, a cancer of the disclosure (e.g., a cancer to be treated according to the methods of the disclosure) includes a cancer that is recurrent or refractory to a prior anti-cancer therapy.

In some embodiments, a cancer of the disclosure (e.g., a cancer to be treated according to the methods of the disclosure) includes, without limitation, a microsatellite stable (MSS), has high microsatellite instability (MSI-H) or low microsatellite instability (MSI-L). In some embodiments, the cancer is characterized by microsatellite instability, is MSI-H, has high tumor mutational burden (TMB) or low TMB, has high TMB and is MSS or MSI-L, has high TMB and is MSI-H, has a defective DNA mismatch repair system, has a defect in a DNA mismatch repair gene, is a hypermutated cancer, is a homologous recombination deficient (HRD) or homologous recombination repair (HRR) deficient cancer, comprises a mutation in polymerase delta (POLD), or comprises a mutation in polymerase epsilon (POLE).

In some embodiments, a cancer of the disclosure (e.g., a cancer to be treated according to the methods of the disclosure) includes, without limitation, a hematological cancer, such as diffuse large B cell lymphoma ("DLBCL"), Hodgkin's lymphoma ("HL"), Non-Hodgkin's lymphoma ("NHL"), follicular lymphoma ("FL"), acute myeloid leukemia ("AML"), acute lymphoblastic leukemia ("ALL"), or multiple myeloma ("MM"). In embodiments, a cancer is a blood-borne cancer such as acute lymphoblastic leukemia ("ALL"), acute lymphoblastic B-cell leukemia, acute lymphoblastic T-cell leukemia, acute myeloblastic leukemia ("AML"), acute lymphoblastic leukemia ("ALL"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia and multiple myeloma; acute and chronic leukemias such as lymphoblastic, myelogenous, lymphocytic, and myelocytic leukemias. In embodiments, a hematological cancer is a lymphoma (e.g., Hodgkin's lymphoma (e.g., relapsed or refractory classic Hodgkin's Lymphoma (cHL), non-Hodgkin's lymphoma, diffuse large B-cell lymphoma, or precursor T-lymphoblastic lymphoma), lymphoepithelial carcinoma, or malignant histiocytosis.

In some embodiments, a cancer of the disclosure (e.g., a cancer to be treated according to the methods of the disclosure) includes, without limitation, a lymphoma such as Hodgkin's disease, non-Hodgkin's Lymphoma, Multiple myeloma, Waldenstrom's macroglobulinemia, Heavy chain disease and Polycythemia vera.

In some embodiments, a cancer of the disclosure (e.g., a cancer to be treated according to the methods of the disclosure) includes, without limitation, a squamous cell carcinoma. In embodiments, a cancer is squamous cell carcinoma of the lung. In embodiments, a cancer is squamous cell carcinoma of the esophagus. In embodiments, a cancer is squamous cell carcinoma of the anogenital region (e.g., of the anus, penis, cervix, vagina, or vulva). In embodiments, a cancer is head and neck squamous cell carcinoma (HN-SCC).

In some embodiments, a cancer of the disclosure (e.g., a cancer to be treated according to the methods of the disclosure) includes, without limitation, a CNS or brain cancer such as neuroblastoma (NB), glioma, diffuse intrinsic pontine glioma (DIPG), pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain tumor, meningioma, spinal tumor, or medulloblastoma. In embodiments, a cancer is a CNS tumor.

In some embodiments, a cancer of the disclosure (e.g., a cancer to be treated according to the methods of the disclosure) includes, without limitation, a solid tumor, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma. Ewing's tumor, leiomyosarcoma, rhabdomyosarcoma, osteosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms tumor, cervical cancer, uterine cancer, testicular cancer, non-small cell lung cancer (NSCLC), small cell lung carcinoma, bladder carcinoma, lung cancer, epithelial carcinoma, skin cancer, melanoma, neuroblastoma (NB), or retinoblastoma.

Epithelial Neoplasms

In some embodiments, a cancer of the disclosure (e.g., a cancer to be treated according to the methods of the disclosure) is an epithelial neoplasm or cancer. Epithelial neoplasms include cancers that develop from the epithelium or related tissues in the skin, hollow viscera, and other organs. Epithelial cancers include, but are not limited to, breast cancer, lung cancer, liver cancer, buccal cancer, stomach cancer, carcinomas, colon cancer, thymus cancer (e.g., thymoma), nasopharyngeal cancer, dermal cancer, renal cancer, brain tumor, prostate cancer, ovarian cancer, cervical cancer, endometrial cancer, intestinal cancer, pancreatic cancer, bladder cancer, squamous cell carcinoma, epidermoid carcinoma, malignant skin adnexal tumors, glandular epithelium cancers (e.g., liver, kidney, bile ducts), adenomas (e.g., hepatic adenomas, renal tubular adenomas, bile duct adenomas), adenocarcinomas, hepatomas, hepatocellular carcinomas, renal cell carcinomas, hypemephromas, cholangiocarcinomas, cancers of the transitional epithelium, transitional cell papilloma, transitional cell carcinoma, hydatidiform mole, choriocarcinoma, testis cancers, seminoma, and embryonal cell carcinomas.

Thymomas

In some embodiments, a cancer of the disclosure (e.g., a cancer to be treated according to the methods of the disclosure) is a thymoma. Thymomas are neoplasms arising from or exhibiting thymic epithelial differentiation. The etiology and pathogenesis of thymoma remain largely unknown. The most significant prognostic factors in thymoma are World Health Organization (WHO) histologic type, tumor stage, and completeness of surgical resection. WHO histologic types A (oval or fusiform-shaped cells) and AB (mixed histology) thymomas are associated with a favorable clinical course, with a 100% 5-year overall survival (Scorsetti M et al., *Critical Reviews in Oncolog/Hematology Thymoma and thymic carcinomas*, Crit Rev Oncol/Hematol, vol. 99, pp. 332-350 (2016)). Types B1, B2, and B3 (epithelioid shape, with progressively decreased lymphoid infiltrate) show progressively worse survival, with type B3 demonstrating a 5-year survival ranging from 43% to 70% (Scorsetti M et al., *Critical Reviews in Oncology/Hematology Thymoma and thymic carcinomas*, Crit Rev Oncol/Hematol, vol. 99, pp. 332-350 (2016)). Surgery is the standard of care for localized tumors, with radiation and chemotherapy reserved for advanced stages (Scorsetti M et al., *Critical Reviews in Oncology/Hematology Thymoma and thymic carcinomas*, Crit Rev Oncol/Hematol, vol. 99, pp. 332-350 (2016)).

Thymomas may be staged according to the Masaoka or the modified Masaoka staging systems. In some embodiments, the thymoma is a Stage I, Stage IIa, Stage IIb, Stage III, Stage IVa, or Stage IVb thymoma (i.e., Stage 1, Stage 2a, Stage 2b, Stage 3, Stage 4a, or Stage 4b), according to the Masaoka Classification or the modified Masaoka classification. In some embodiments, the thymoma is a Stage 2b, Stage 4a, Stage 4b, or unknown stage thymoma, according to the Modified Masaoka Classification. In some embodiments, the thymoma is a Stage IIb. Stage IVa. Stage IVb, or unknown stage thymoma, according to the Modified Masaoka Classification. In some embodiments, the thymoma is a Stage I, Stage II (e.g., Stage IIa or Stage IIb), Stage III, Stage IV (e.g., Stage IVa or Stage IVb), continuous or unknown stage thymoma, according to the Modified Masaoka Classification. Stage I thymomas are characterized by grossly and microscopically completely encapsulated tumors. Stage IIa thymomas are characterized by microscopic transcapsular invasion. Stage IIb thymomas are characterized by macroscopic invasion into thymic or surrounding fatty tissue, or grossly adherent to but not breaking through mediastinal pleura or pericardium. Stage III thymomas are characterized by macroscopic invasion into neighboring organs (i.e., pericardium, great vessel, or lung). Stage IVa thymomas are characterized by pleural or pericardial metastases. Stage IVb thymomas are characterized by lymphogenous or hematogenous metastasis. See, e.g., Detterbeck et al., *The Masaoka-Koga Stage Classification for Thymic Malignancies: Clarification and Definition of Terms*, J Thoracic Oncology, vol. 6, no. 7s3, pp. s1710-1716 (2011).

Thymomas may be further classified according to their histology. In some embodiments, the thymoma has a Type A, Type atypical A, Type AB. Type B1, Type B2, or Type B3 histology subtype, according to the World Health Organization (WHO) classification. In some embodiments, the thymoma is a metaplastic thymoma, a micronodular thymoma with lymphoid stroma (MNT), a microscopic thymoma, a sclerosing thymoma, or a lipofibroadenoma. In some embodiments, the thymoma has a B2 or B3 histology subtype, according to the WHO classification. In some embodiments, the thymoma has a B2-B3 histology subtype, according to the WHO classification. In some embodiments, the thymoma has a B2 or B3+C (B3+carcinoma) histology subtype, according to the WHO classification.

Type A thymomas are characterized by oval or fusiform-shaped cells. In some embodiments, Type A thymomas comprise bland, spindle shaped epithelial cells (at least focally); and paucity or absence of immature (TdT+) T cells throughout the tumor. In some cases, Type A thymomas comprise polygonal epithelial cells and/or CD20+ epithelial cells. Atypical Type A variant thymomas are characterized by the criteria of type A thymoma and comedo-type tumor necrosis; increased mitotic count (>4/2 $mm^2$); and nuclear crowding. In some cases, atypical Type A thymomas comprise polygonal epithelial cells and/or CD20+ epithelial cells. Type AB thymomas are characterized by a mixed histology. In some embodiments, Type AB thymomas comprise bland, spindle shaped epithelial cells (at least focally); and abundance of immature (TdT+) T cells focally or throughout tumor. In some cases, Type AB thymomas comprise polygonal epithelial cells and/or CD20+ epithelial cells. Type B1, B2, and B3 thymomas are characterized by epithelioid shape, with progressively decreased lymphoid infiltrate. In some embodiments, Type B1 thymomas comprise a thymus-like architecture and cytology, such as abundance of immature T cells and areas of medullary differentiation (medullary islands); and paucity of polygonal or dendritic epithelia cells without clustering (i.e., <3 contiguous epithelial cells). In some cases, Type B1 thymomas comprise Hassall's corpuscles and/or perivascular spaces. In some embodiments, Type B2 thymomas comprise increased numbers of single or clustered polygonal or dendritic epithelial cells intermingled with abundant immature T cells. In some cases, Type B2 thymomas comprise medullary islands; Hassall's corpuscles; and/or perivascular spaces. In some embodiments, Type B3 thymomas comprise sheets of polygonal slightly to moderately atypical epithelial cells; absent or rare intercellular bridges; and paucity or absence of intermingled TdT+ T cells. In some cases, Type B3 thymomas comprise Hassall's corpuscles and/or perivascular spaces. In some embodiments, MNT thymomas comprise nodules of bland spindle or oval epithelial cells surrounded by an epithelial cell-free lymphoid stroma. In some cases, MNT thymomas comprise lymphoid follicles; and/or monoclonal B cells and/or plasma cells. In some embodiments, metaplastic thymomas comprise biphasic tumors composed of solid areas of epithelial cells in a background of bland-looking spindle cells and absence of immature T cells. In some cases, metaplastic thymomas thymomas comprise pleomorphism of epithelial cells; and/or actin, keratin, or EMA-positive spindle cells. See, e.g., Marx et al., *Introduction to The* 2015 *World Health Organization Classification of Tumors of the Lung, Pleura, Thymus, and Heart*, J Thorac Oncol, vol. 10, no. 9, pp. P1240-1242 (2016).

Expression Vectors, Host Cells and Recombinant Cells

Provided herein are vectors comprising KMT2A-MAML2 fusion nucleic acid molecules, baits, probes, or oligonucleotides described herein, or fragments thereof.

In some embodiments, a vector provided herein comprises a KMT2A-MAML2 fusion nucleic acid molecule described herein, or a nucleic acid molecule encoding a KMT2A-MAML2 fusion polypeptide described herein.

In some embodiments, a vector provided herein is a nucleic acid molecule capable of transporting another nucleic acid to which it has been linked (e.g., KMT2A-MAML2 fusion nucleic acid molecules, baits, probes, or oligonucleotides described herein, or fragments thereof). In some embodiments, a vector is a plasmid, a cosmid or a viral vector. The vector can be capable of autonomous replication or it can integrate into a host DNA. Viral vectors include, e.g., replication defective retroviruses, adenoviruses and adeno-associated viruses.

In some embodiments, a vector provided herein comprises a KMT2A-MAML2 fusion nucleic acid in a form suitable for expression of the nucleic acid in a host cell. In some embodiments, the vector includes one or more regulatory sequences operatively linked to the nucleotide sequence to be expressed. In some embodiments, the one or more regulatory sequences include promoters (e.g., promoters derived from polyoma, Adenovirus 2, cytomegalovirus and Simian Virus 40), enhancers, and other expression control elements (e.g., polyadenylation signals). In some embodiments, a regulatory sequence directs constitutive expression of a nucleotide sequence and/or tissue-specific expression of a nucleotide sequence and/or inducible expression of a nucleotide sequence. Examples of inducible regulatory sequences include, without limitation, promoters regulated by a steroid hormone, by a polypeptide hormone, or by a heterologous polypeptide, such as a tetracycline-inducible promoter. Examples of tissue- or cell-type-specific regulatory sequences include, without limitation, the albumin promoter, lymphoid-specific promoters, promoters of T cell receptors or immunoglobulins, neuron-specific promoters, pancreas-specific promoters, mammary gland-specific promoters, and developmentally-regulated promoters. In some embodiments, a vector provided herein comprises a KMT2A-MAML2 fusion nucleic acid molecule described herein, or a nucleic acid molecule encoding a KMT2A-MAML2 fusion polypeptide described herein, in the sense or the anti-sense orientation. In some embodiments, a vector (e.g., an expression vector) provided herein is introduced into host cells to thereby produce a fusion polypeptide, e.g., a KMT2A-MAML2 fusion polypeptide described herein, or a fragment or mutant forms thereof.

In some embodiments, the design of a vector provided herein depends on such factors as the choice of the host cell to be transformed, the level of expression desired, and the like. In some embodiments, expression vectors are designed for the expression of a KMT2A-MAML2 fusion polypeptide described herein in prokaryotic or eukaryotic cells, such as E. coli cells, insect cells (e.g., using baculovirus expression vectors), yeast cells, or mammalian cells. In some embodiments, a vector described herein is transcribed and translated in vitro, for example using T7 promoter regulatory sequences and T7 polymerase. In some embodiments, a vector (e.g., an expression vector) provided herein comprises a KMT2A-MAML2 fusion nucleic acid molecule described herein, wherein the nucleotide sequence of the KMT2A-MAML2 fusion nucleic acid molecule described herein has been altered (e.g., codon optimized) so that the individual codons for each encoded amino acid are those preferentially utilized in the host cell.

Also provided herein are host cells, e.g., comprising KMT2A-MAML2 fusion nucleic acid molecules, baits, probes, vectors, or oligonucleotides, or KMT2A-MAML2 fusion polypeptides describes herein. In some embodiments a host cell (e.g., a recombinant host cell or recombinant cell) comprises a vector described herein (e.g., an expression vector described herein). In some embodiments, a KMT2A-

MAML2 fusion nucleic acid molecule, bait, probe, vector, or oligonucleotide provided herein comprises sequences which allow it to integrate into the host cell's genome (e.g., through homologous recombination at a specific site). In some embodiments, a host cell provided herein is a prokaryotic or eukaryotic cell. Non limiting examples of host cells include, without limitation, bacterial cells (e.g., E. coli), insect cells, yeast cells, or mammalian cells (e.g., human cells, rodent cells, mouse cells, rabbit cells, pig cells, Chinese hamster ovary cells (CHO) or COS cells, e.g., COS-7 cells, CV-1 origin SV40 cells). A host cell described herein includes the particular host cell, as well as the progeny of such a cell. Because certain modifications may occur in succeeding generations due to either mutation or environmental influences, such progeny may not, in fact, be identical to the parent host cell.

KMT2A-MAML2 fusion nucleic acid molecules, baits, probes, vectors, or oligonucleotides described herein may be introduced into host cells using any suitable method known in the art, such as conventional transformation or transfection techniques (e.g., using calcium phosphate or calcium chloride co-precipitation, DEAE-dextran-mediated transfection, lipofection, or electroporation).

Also provided herein are methods of producing a KMT2A-MAML2 fusion polypeptide described herein, e.g., by culturing a host cell described herein (e.g., into which a recombinant expression vector encoding a polypeptide has been introduced) in a suitable medium such that the fusion polypeptide is produced. In another embodiment, the method further includes isolating a fusion polypeptide from the medium or the host cell.

Methods of Diagnosing or Assessing

In some aspects, provided herein are methods of diagnosing or assessing a KMT2A-MAML2 fusion in a cancer, such as an epithelial neoplasm. e.g., a thymoma, in an individual. In some embodiments, the methods comprise detecting a KMT2A-MAML2 fusion nucleic acid molecule or polypeptide provided herein in a sample obtained from the individual. In some embodiments, the KMT2A-MAML2 fusion nucleic acid molecule or polypeptide described herein is detected in a sample obtained from the individual using any method known in the art, such as one or more of the methods of detection of KMT2A-MAML2 fusion nucleic acid molecules or polypeptides described herein. In some embodiments, the methods further comprise providing a diagnosis or an assessment of the KMT2A-MAML2 fusion nucleic acid molecule or polypeptide. In some embodiments, the diagnosis or assessment identifies the presence or absence of the KMT2A-MAML2 fusion nucleic acid molecule or polypeptide in the sample. In some embodiments, the diagnosis or assessment identifies the cancer, such as an epithelial neoplasm, e.g., a thymoma, as likely to respond to an anti-cancer therapy. e.g., an anti-cancer therapy provided herein. In some embodiments, the presence of the KMT2A-MAML2 fusion nucleic acid molecule or polypeptide in the sample identifies the cancer, such as an epithelial neoplasm, e.g., a thymoma, as likely to response to an anti-cancer therapy, e.g., an anti-cancer therapy provided herein.

In some aspects, provided herein are methods of diagnosing or assessing a cancer in an individual. In some embodiments, the methods of diagnosing or assessing cancer comprise detecting a KMT2A-MAML2 fusion provided herein in a sample obtained from the individual.

In some embodiments, the methods of diagnosing or assessing cancer, such as an epithelial neoplasm, e.g., a thymoma, comprise detecting a KMT2A-MAML2 fusion nucleic acid molecule or polypeptide described herein in a sample obtained from the individual. In some embodiments, the methods comprise detecting a KMT2A-MAML2 fusion nucleic acid molecule or polypeptide described herein in a sample obtained from the individual using any method known in the art, such as one or more of the methods of detection of KMT2A-MAML2 fusion nucleic acid molecules or polypeptides described herein. In some embodiments, detection of a KMT2A-MAML2 fusion nucleic acid molecule or polypeptide described herein, or a fragment thereof, in a sample obtained from the individual identifies the cancer as likely to respond to an anti-cancer therapy, e.g., an anti-cancer therapy provided herein. In some embodiments, the presence of a KMT2A-MAML2 fusion nucleic acid molecule or polypeptide described herein, or a fragment thereof, in a sample obtained from the individual identifies the cancer as likely to respond to an anti-cancer therapy, e.g., an anti-cancer therapy provided herein. In some embodiments, the methods further comprise providing a diagnosis or an assessment of the cancer or of the KMT2A-MAML2 fusion nucleic acid molecule or polypeptide. In some embodiments, the diagnosis or assessment identifies the cancer as likely to respond to an anti-cancer therapy, e.g., an anti-cancer therapy provided herein. In some embodiments, the diagnosis or assessment identifies the presence or absence of the KMT2A-MAML2 fusion nucleic acid molecule in the sample.

In some embodiments, the cancer is a cancer provided herein. In some embodiments, the cancer is an epithelial neoplasm. e.g., an epithelial neoplasm provided herein. In some embodiments, the epithelial neoplasm is a thymoma. In some embodiments, the thymoma is a Stage I, Stage IIa, Stage IIb, Stage III, Stage IVa, or Stage IVb thymoma, according to the Masaoka Classification. In some embodiments, the thymoma is a Stage 2b, Stage 4a. Stage 4b, or unknown stage thymoma, according to the Modified Masaoka Classification. In some embodiments, the thymoma is a Stage I, Stage II, Stage III, Stage IV, continuous or unknown stage thymoma, according to the Modified Masaoka Classification. See, e.g., Detterbeck et al., *The Masaoka-Koga Stage Classification for Thymic Malignancies: Clarification and Definition of Terms*, J Thoracic Oncology, vol. 6, no. 7s3, pp. s1710-1716 (2011).

In some embodiments, the thymoma has an A, AB, B1, B2, or B3 histology subtype, according to the World Health Organization (WHO) classification. In some embodiments, the thymoma has a B2 or B3 histology subtype, according to the WHO classification. In some embodiments, the thymoma has a B2-B3 histology subtype, according to the WHO classification. In some embodiments, the thymoma has a B2 or B3+C (B3+carcinoma) histology subtype, according to the WHO classification. See, e.g., Marx et al., *Introduction to The* 2015 *World Health Organization Classification of Tumors of the Lung. Pleura, Thymus, and Heart*, J Thorac Oncol, vol. 10, no. 9, pp. P1240-1242 (2016). In some embodiments, the thymoma is recurrent. In some embodiments, the thymoma is metastatic. In some embodiments, the thymoma further comprises one or more mutations in another gene, such as TP53. ARID1A, TERT, or SF3B1. In some embodiments, the individual has received a prior anti-cancer treatment. In some embodiments, the prior anti-cancer treatment is one or more of a chemotherapy, surgical resection, radiation, MGCD516, BBI608, paclitaxel, or sunitinib.

Methods Selecting a Treatment

In some aspects, provided herein are methods of identifying an individual having cancer, e.g., an epithelial neoplasm such as a thymoma, who may benefit from an anti-cancer therapy, e.g., an anti-cancer therapy provided herein. In some embodiments, the methods comprise detecting a KMT2A-MAML2 fusion nucleic acid molecule or polypeptide provided herein in a sample obtained from the individual. In some embodiments, the presence of the KMT2A-MAML2 fusion nucleic acid molecule or polypeptide in the sample identifies the individual as one who may benefit from a treatment comprising an anti-cancer therapy, e.g., an anti-cancer therapy provided herein. In some embodiments, the presence of the KMT2A-MAML2 fusion nucleic acid molecule in the sample identifies the individual as one who may benefit from a treatment comprising an anti-cancer therapy, e.g., an anti-cancer therapy provided herein. In some embodiments, the presence of the KMT2A-MAML2 fusion polypeptide in the sample identifies the individual as one who may benefit from a treatment comprising an anti-cancer therapy, e.g., an anti-cancer therapy provided herein. In some embodiments, the KMT2A-MAML2 fusion nucleic acid molecule or polypeptide is detected using any suitable method known in the art or described herein. In some embodiments, the sample obtained from the individual comprises fluid (e.g., blood or serum), cells, or tissue (e.g., a tumor tissue). In some embodiments, the sample is a nucleic acid sample, e.g., a sample comprising cell-free DNA (cfDNA) or cell-free RNA or circulating tumor DNA (ctDNA). In some embodiments, the sample is a protein sample.

Also provided herein are methods of identifying or selecting a treatment, a therapy, or one or more treatment options for an individual having a cancer, such as an epithelial neoplasm, e.g., a thymoma. In some embodiments, the cancer, such as an epithelial neoplasm (e.g., a thymoma) comprises a KMT2A-MAML2 fusion nucleic acid molecule or a KMT2A-MAML2 fusion polypeptide provided herein. In some embodiments, the methods comprise detecting a KMT2A-MAML2 fusion nucleic acid molecule or polypeptide provided herein in a sample obtained from an individual having a cancer, such as an epithelial neoplasm, e.g., a thymoma. In some embodiments, the KMT2A-MAML2 fusion nucleic acid molecule or polypeptide is detected using any suitable method known in the art or described herein. In some embodiments, the sample obtained from the individual comprises fluid (e.g., blood or serum), cells, or tissue (e.g., a tumor tissue). In some embodiments, the sample is a nucleic acid sample, e.g., a sample comprising cell-free DNA (cfDNA), cell-free RNA, or circulating tumor DNA (ctDNA). In some embodiments, the sample is a protein sample. In some embodiments, detection of a KMT2A-MAML2 fusion nucleic acid molecule or polypeptide provided herein in a sample obtained from an individual having a cancer, such as an epithelial neoplasm, e.g., a thymoma, identifies the individual as one who may benefit from an anti-cancer treatment, e.g., an anti-cancer therapy provided herein. In some embodiments, the presence of a KMT2A-MAML2 fusion nucleic acid molecule or polypeptide provided herein in a sample obtained from an individual having a cancer, such as an epithelial neoplasm, e.g., a thymoma, identifies the individual as one who may benefit from an anti-cancer treatment, such as an anti-cancer therapy provided herein. In some embodiments, responsive to detection of a KMT2A-MAML2 fusion nucleic acid molecule or polypeptide provided herein in a sample obtained from an individual having a cancer, such as an epithelial neoplasm, e.g., a thymoma, the individual is classified as a candidate to receive an anti-cancer treatment, such as an anti-cancer therapy provided herein. In some embodiments, responsive to detection of a KMT2A-MAML2 fusion nucleic acid molecule or polypeptide provided herein in a sample obtained from an individual having a cancer, such as an epithelial neoplasm. e.g., a thymoma, the individual is classified or identified as likely to respond to an anti-cancer treatment, such as an anti-cancer therapy provided herein.

In some embodiments, the methods of selecting or identifying a treatment, a therapy, or one or more treatment options for an individual having a cancer, such as an epithelial neoplasm, e.g., a thymoma, comprise acquiring knowledge of a KMT2A-MAML2 fusion nucleic acid molecule or polypeptide provided herein in a sample obtained from an individual having an epithelial neoplasm, e.g., a thymoma. In some embodiments, the methods of selecting or identifying a treatment, a therapy, or one or more treatment options for an individual having a cancer, such as an epithelial neoplasm, e.g., a thymoma, comprise acquiring knowledge of the presence of a KMT2A-MAML2 fusion nucleic acid molecule or polypeptide provided herein in a sample obtained from an individual having an epithelial neoplasm, e.g., a thymoma. In some embodiments, the knowledge of the presence of the KMT2A-MAML2 fusion nucleic acid molecule or polypeptide is acquired using any suitable method known in the art or described herein. In some embodiments, the sample obtained from the individual comprises fluid (e.g., blood or serum), cells, or tissue (e.g., a tumor tissue). In some embodiments, the sample is a nucleic acid sample, e.g., a sample comprising mRNA, genomic DNA, cell-free DNA (cfDNA) or circulating tumor DNA (ctDNA). In some embodiments, the sample is a protein sample. In some embodiments, acquiring knowledge of the presence of a KMT2A-MAML2 fusion nucleic acid molecule or polypeptide provided herein in a sample obtained from an individual having a cancer, such as an epithelial neoplasm, e.g., a thymoma, identifies the individual as one who may benefit from an anti-cancer treatment, such as an anti-cancer therapy provided herein. In some embodiments, responsive to acquisition of knowledge of a KMT2A-MAML2 fusion nucleic acid molecule or polypeptide provided herein in a sample obtained from an individual having a cancer, such as an epithelial neoplasm, e.g., a thymoma, the individual is classified as a candidate to receive an anti-cancer treatment, such as an anti-cancer therapy provided herein. In some embodiments, responsive to acquisition of knowledge of a KMT2A-MAML2 fusion nucleic acid molecule or polypeptide provided herein in a sample obtained from an individual having a cancer, such as an epithelial neoplasm. e.g., a thymoma, the individual is classified or identified as likely to respond to an anti-cancer treatment, such as an anti-cancer therapy provided herein. In some embodiments, responsive to acquisition of knowledge of the presence of a KMT2A-MAML2 fusion nucleic acid molecule or polypeptide provided herein in a sample obtained from an individual having a cancer, such as an epithelial neoplasm. e.g., a thymoma, the individual is classified as a candidate to receive an anti-cancer treatment, such as an anti-cancer therapy provided herein. In some embodiments, responsive to acquisition of knowledge of the presence of a KMT2A-MAML2 fusion nucleic acid molecule or polypeptide provided herein in a sample obtained from an individual having a cancer, such as an epithelial neoplasm, e.g., a thymoma, the individual is classified or identified as likely to respond to an anti-cancer treatment, such as an anti-cancer therapy provided herein.

In some embodiments, the methods of selecting or identifying a treatment, a therapy, or one or more treatment options for an individual having a cancer, such as an epithelial neoplasm, e.g., a thymoma, further comprise generating a report, e.g., as described herein. In some embodiments, the report comprises one or more treatment options identified or selected, e.g., based, at least in part, on the detection of a KMT2A-MAML2 fusion nucleic acid molecule or polypeptide provided herein in a sample obtained from an individual having a cancer, such as an epithelial neoplasm, e.g., a thymoma. In some embodiments, the report comprises one or more treatment options identified or selected, e.g., based, at least in part, on the presence of a KMT2A-MAML2 fusion nucleic acid molecule or polypeptide provided herein in a sample obtained from an individual having a cancer, such as an epithelial neoplasm. e.g., a thymoma. In some embodiments, the report comprises one or more treatment options identified or selected, e.g., based, at least in part, on acquiring knowledge of the presence of a KMT2A-MAML2 fusion nucleic acid molecule or polypeptide provided herein in a sample obtained from an individual having a cancer, such as an epithelial neoplasm, e.g., a thymoma. In some embodiments, the report comprises one or more treatment options identified or selected, e.g., based, at least in part, on acquiring knowledge of a KMT2A-MAML2 fusion nucleic acid molecule or polypeptide provided herein in a sample obtained from an individual having a cancer, such as an epithelial neoplasm, e.g., a thymoma. In some embodiments, the one or more treatment options include an anti-cancer therapy provided herein.

In some embodiments, the cancer is a cancer provided herein. In some embodiments, the cancer is an epithelial neoplasm, e.g., an epithelial neoplasm provided herein. In some embodiments, the epithelial neoplasm is a thymoma. In some embodiments, the thymoma is a Stage I, Stage IIa, Stage IIb, Stage III, Stage IVa, or Stage IVb thymoma, according to the Masaoka Classification. In some embodiments, the thymoma is a Stage 2b, Stage 4a, Stage 4b, or unknown stage thymoma, according to the Modified Masaoka Classification. In some embodiments, the thymoma is a Stage I, Stage II, Stage III, Stage IV, continuous or unknown stage thymoma, according to the Modified Masaoka Classification. See, e.g., Detterbeck et al., *The Masaoka-Koga Stage Classification for Thymic Malignancies: Clarification and Definition of Terms*, J Thoracic Oncology, vol. 6, no. 7s3, pp. s1710-1716 (2011).

In some embodiments, the thymoma has an A, AB, B1, B2, or B3 histology subtype, according to the World Health Organization (WHO) classification. In some embodiments, the thymoma has a B2 or B3 histology subtype, according to the WHO classification. In some embodiments, the thymoma has a B2-B3 histology subtype, according to the WHO classification. In some embodiments, the thymoma has a B2 or B3+C (B3+carcinoma) histology subtype, according to the WHO classification. See, e.g., Marx et al., *Introduction to The* 2015 *World Health Organization Classification of Tumors of the Lung. Pleura, Thymus, and Heart.* J Thorac Oncol, vol. 10, no. 9, pp. P1240-1242 (2016). In some embodiments, the thymoma is recurrent. In some embodiments, the thymoma is metastatic. In some embodiments, the thymoma further comprises one or more mutations in another gene, such as TP53. ARID1A, TERT, or SF3B1. In some embodiments, the individual has received a prior anti-cancer treatment. In some embodiments, the prior anti-cancer treatment is one or more of a chemotherapy, surgical resection, radiation. MGCD516, BB1608, paclitaxel, or sunitinib.

Methods of Treatment

Also provided herein are methods of treating or delaying progression of a cancer in an individual, such as an epithelial neoplasm, e.g., a thymoma. In some embodiments, the individual has a cancer, such as an epithelial neoplasm (e.g., a thymoma) comprising a KMT2A-MAML2 fusion nucleic acid molecule or polypeptide provided herein. In some embodiments, the methods of treating or delaying progression of a cancer, such as an epithelial neoplasm, e.g., a thymoma, in an individual comprise administering to the individual a therapeutically effective amount of an anti-cancer therapy, such as an anti-cancer therapy provided herein. In some embodiments, the methods of treating or delaying progression of a cancer, such as an epithelial neoplasm, e.g., a thymoma, in an individual comprise administering to the individual an effective amount of an anti-cancer therapy, such as an anti-cancer therapy provided herein.

In some embodiments, the methods of treating or delaying progression of a cancer, such as an epithelial neoplasm, e.g., a thymoma, in an individual comprise, responsive to knowledge of a KMT2A-MAML2 fusion nucleic acid molecule or polypeptide provided herein in a sample obtained from the individual, administering to the individual an effective amount, e.g., a therapeutically effective amount of an anti-cancer therapy, such as an anti-cancer therapy provided herein. In some embodiments, the methods of treating or delaying progression of a cancer, such as an epithelial neoplasm, e.g., a thymoma, in an individual comprise, responsive to knowledge of the presence of a KMT2A-MAML2 fusion nucleic acid molecule or polypeptide provided herein in a sample obtained from the individual, administering to the individual an effective amount, e.g., a therapeutically effective amount of an anti-cancer therapy, such as an anti-cancer therapy provided herein.

In some embodiments, the methods of treating or delaying progression of a cancer, such as an epithelial neoplasm. e.g., a thymoma, in an individual comprise detecting a KMT2A-MAML2 fusion nucleic acid molecule or polypeptide provided herein in a sample obtained from the individual. In some embodiments, the methods further comprise administering to the individual an effective amount of, e.g., a therapeutically effective amount of, an anti-cancer therapy, such as an anti-cancer therapy provided herein. In some embodiments, the KMT2A-MAML2 fusion nucleic acid molecule or polypeptide is detected using any suitable method known in the art or described herein. In some embodiments, the sample obtained from the individual comprises fluid (e.g., blood or serum), cells, or tissue (e.g., a tumor tissue). In some embodiments, the sample is a nucleic acid sample, e.g., a sample comprising cell-free DNA (cfDNA), cell-free RNA, or circulating tumor DNA (ctDNA). In some embodiments, the sample is a protein sample. In some embodiments, responsive to detection of a KMT2A-MAML2 fusion nucleic acid molecule or polypeptide provided herein in a sample obtained from the individual, the individual is administered a therapeutically effective amount of an anti-cancer therapy, such as an anti-cancer therapy provided herein.

In some embodiments, the methods of treating or delaying progression of a cancer, such as an epithelial neoplasm, e.g., a thymoma, in an individual comprise acquiring knowledge of the presence of a KMT2A-MAML2 fusion nucleic acid molecule or polypeptide provided herein in a sample obtained from the individual. In some embodiments, the methods of treating or delaying progression of a cancer, such as an epithelial neoplasm, e.g., a thymoma, in an individual comprise acquiring knowledge of a KMT2A-MAML2 fusion nucleic acid molecule or polypeptide provided herein in a sample obtained from the individual. In some embodiments, the knowledge of the presence of a KMT2A-

MAML2 fusion nucleic acid molecule or polypeptide is acquired using any suitable method known in the art or described herein. In some embodiments, the knowledge of the KMT2A-MAML2 fusion nucleic acid molecule or polypeptide is acquired using any suitable method known in the art or described herein. In some embodiments, the sample obtained from the individual comprises fluid (e.g., blood or serum), cells, or tissue (e.g., a tumor tissue). In some embodiments, the sample is a nucleic acid sample, e.g., a sample comprising cell-free DNA (cfDNA), cell-free RNA, or circulating tumor DNA (ctDNA). In some embodiments, the sample is a protein sample. In some embodiments, responsive to acquisition of knowledge of the presence of a KMT2A-MAML2 fusion nucleic acid molecule or polypeptide provided herein in a sample obtained from the individual, the individual is administered an effective amount, e.g., a therapeutically effective amount of an anti-cancer therapy, such as an anti-cancer therapy provided herein. In some embodiments, responsive to acquisition of knowledge of a KMT2A-MAML2 fusion nucleic acid molecule or polypeptide provided herein in a sample obtained from the individual, the individual is administered an effective amount, e.g., a therapeutically effective amount of an anti-cancer therapy, such as an anti-cancer therapy provided herein.

In some embodiments, the cancer is a cancer provided herein. In some embodiments, the cancer is an epithelial neoplasm, e.g., an epithelial neoplasm provided herein. In some embodiments, the epithelial neoplasm is a thymoma. In some embodiments, the thymoma is a Stage I, Stage IIa, Stage IIb, Stage III, Stage IVa, or Stage IVb thymoma, according to the Masaoka Classification. In some embodiments, the thymoma is a Stage 2b, Stage 4a, Stage 4b, or unknown stage thymoma, according to the Modified Masaoka Classification. In some embodiments, the thymoma is a Stage I, Stage II, Stage III, Stage IV, continuous or unknown stage thymoma, according to the Modified Masaoka Classification. See, e.g., Detterbeck et al., *The Masaoka-Koga Stage Classification for Thymic Malignancies: Clarification and Definition of Terms*, J Thoracic Oncology, vol. 6, no. 7s3, pp. s1710-1716 (2011).

In some embodiments, the thymoma has an A, AB, B1, B2, or B3 histology subtype, according to the World Health Organization (WHO) classification. In some embodiments, the thymoma has a B2 or B3 histology subtype, according to the WHO classification. In some embodiments, the thymoma has a B2-B3 histology subtype, according to the WHO classification. In some embodiments, the thymoma has a B2 or B3+C (B3+carcinoma) histology subtype, according to the WHO classification. See, e.g., Marx et al., *Introduction to The* 2015 *World Health Organization Classification of Tumors of the Lung, Pleura, Thymus, and Heart*, J Thorac Oncol, vol. 10, no. 9, pp. P1240-1242 (2016). In some embodiments, the thymoma is recurrent. In some embodiments, the thymoma is metastatic. In some embodiments, the thymoma further comprises one or more mutations in another gene, such as TP53, ARID1A, TERT, or SF3B1. In some embodiments, the individual has received a prior anti-cancer treatment. In some embodiments, the prior anti-cancer treatment is one or more of a chemotherapy, surgical resection, radiation, MGCD516, BB1608, paclitaxel, or sunitinib.

Additional Mutations

In some embodiments, a cancer, such as an epithelial neoplasm (e.g., a thymoma), comprising a KMT2A-MAML2 fusion provided herein also comprises one or more mutations in another gene. In some embodiments, a cancer, such as an epithelial neoplasm (e.g., a thymoma), comprising a KMT2A-MAML2 fusion provided herein also comprises one or more mutations in TP53, TERT, ARID1A, and/or SF3B1. In some embodiments, the cancer also comprises a TP53 mutation, such as an E286D amino acid substitution. In some embodiments, the cancer also comprises an ARID1A mutation, such as an R1528 amino acid substitution. In some embodiments, the cancer also comprises an SF3B1 mutation, such as a K700E amino acid substitution. In some embodiments, the cancer also comprises a TERT promoter variant, such as c.-124C>T.

In some embodiments, a cancer, such as an epithelial neoplasm (e.g., a thymoma), comprising a KMT2A-MAML2 fusion provided herein is tested for the presence of one or more substitutions, deletions, indels, rearrangements and copy number alterations in one or more genes, such as one or more genes provided in Table 1. In some embodiments, the presence of one or more substitutions, deletions, indels, rearrangements, and copy number alterations in the one or more genes is determined using any method known in the art, such as sequencing or an RNA-based assay, e.g., Solid Fusion Assay from One Massachusetts general (MGH), e.g., Solid Fusion Assay V2. In some embodiments, the cancer comprises one or more substitutions, deletions, indels, rearrangements, and copy number alterations in one or more genes provided in Table 1, or within the exonic or intronic regions of the one or more genes provided in Table 1.

TABLE 1

Genes (exons) for Additional Variant Assays

Genes with full coding, exonic regions for detection of substitutions, indels, and copy number alterations.

| | | | | | | |
|---|---|---|---|---|---|---|
| ALK (19-22, intron 19) | NRG1 (1-3, 6) | ERG (2-11) | FGR (2) | MYB (7-9, 11-16) | PDGFRB (8-14) | RSPO2 (1, 2) |
| BRAF(7-12, 15) | NUTM1 (3) | ESR1 (3-6) | INSR (12-22) | NOTCH1(2, 4, 26-31, internal exon 3-27 deletion) | PIK3CA (2) | RSPO3 (2) |
| BRD4 (10, 11) | RET (8-13) | ETV1 (3-13) | JAZF1 (2-4) | NOTCH2 (5-7, 26-28) | PKN1 (10-13) | TERT (2) |
| EGFR (2-7 exon skipping/vIII variant, 7-9, 16, 20, 24, 25) | ROS1 (31-37) | ETV4 (2, 4-10) | MAST1 (7-9, 18-21) | NTRK1 (8, 10-13) | PPARG (1-3) | TFE3 (2-8) |
| EWSR1 (4-14) | AKT3 (1-3) | ETV5 (2, 3, 7-9) | MAST2 (2, 3, 5, 6) | NTRK2 (11-17) | PRKCA (4-6) | TFEB (1, 2) |
| FGER2(2, 8-10, 17) | ARHGAP26 (2, 10-12) | ETV6 (1-7) | MET (13, 15) | NTRK3 (13-16) | PRKCB (3) | THADA (28) |
| MAML2 (2, 3) | AXL (19, 20) | FGFR1 (2, 8-10, 17) | MSMB (2-4) | NUMBL (3) | RAF1 (4-7, 9-12) | TMPRSS2 (1-6) |
| MET (exon 14 skipping) | BRD3 (9-12) | FGFR3 (8-10, 17, intron, 17) | MUSK (7-9, 11-14) | PDGFRA (7, exon 8 deletion, 10-14) | RELA (3, 4) | |

In some embodiments, a cancer, such as an epithelial neoplasm (e.g., a thymoma), comprising a KMT2A-MAML2 fusion provided herein is tested for the presence of one or more substitutions, deletions, indels, rearrangements, and copy number alterations in one or more genes, such as one or more genes provided in Table 2. In some embodiments, the presence of one or more substitutions, deletions, indels, rearrangements, and copy number alterations in the one or more genes is determined using any method known in the art, such as sequencing or a DNA-based assay, e.g., SNAPSHOT-NGS-V2 Assay. In some embodiments, the cancer comprises one or more substitutions, deletions, indels, rearrangements, and copy number alterations in one or more genes provided in Table 2, or within the exonic regions of the one or more genes provided in Table 2.

TABLE 2

Genes (exons) in for Additional Variant Assays
Genes with full coding exonic regions for detection of substitutions, indels, and copy number alterations.

| ABL1 (4-7) | BRAF (11, 15) | CSF1R (7, 22) | ERBB4 (3-4, 6-9, 15, 23) | FOXL2 (1) | IDH2 (4) |
|---|---|---|---|---|---|
| AKT1 (3, 6) | BRCA1 (2-23) | CTNNB1 (3) | ESR1 (8) | GNA11 (5) | JAK2 (11, 13-14, 16, 19) |
| ALK (21-23, 25) | BRCA2 (2-27) | DAXX (1-8) | EZH2 (16) | GNAQ (4-5) | JAK3 (4, 13, 16) |
| APC (16) | CCNE1 (3-8, 10, 12) | DDR2 (12-18) | FBX 7 (1-11) | GNAS (6-9) | KDR (6-7, 11, 19, 21, 26-27, 30) |
| ARID1A (1-20) | CDH1 (1-16) | DDX3X (1-17) | FGFR1 (4, 7-8, 13, 15, 17) | H3F3A (2) | KEAP1 (2-6) |
| ATM (1-63) | CDK4 (2-7) | EGFR (3, 7, 15, 18-21) | FGFR2 (7, 9, 12, 14) | HNF1A (3-4) | KIT (2, 8-11, 13-15, 17-18) |
| ATRX (1-35) | CDKN2A (1-3) | ERBB2 (8, 10, 19-21, 24) | FGFR3 (7-9, 14-16, 18) | HRAS (2-3) | KRAS (2-5) |

TABLE 2-continued

Genes (exons) in for Additional Variant Assays
Genes with full coding exonic regions for detection of substitutions, indels, and copy number alterations.

| AURKA (2, 5-8) | CIC (1-20) | ERBB3 (2-3, 7-8) | FLT3 (11, 14, 16, 20) | IDH1 (3-4) | MAP2K1 (2, 3, 6-7) |
|---|---|---|---|---|---|

In some embodiments, a cancer, such as an epithelial neoplasm (e.g., a thymoma), comprising a KMT2A-MAML2 fusion provided herein is tested for the presence of one or more substitutions, deletions, indels, rearrangements, and copy number alterations in one or more genes, such as one or more genes provided in Tables 3-6. In some embodiments, the presence of one or more substitutions, deletions, indels, rearrangements, and copy number alterations in the one or more genes is determined using any method known in the art, such as sequencing or an F1CDx or F1H assay (see, e.g., Frampton et al. *Development and validation of a clinical cancer genomic profiling test based on massively parallel DNA sequencing.* Nat Biotechnol. 2013; Sun et al. *A computational approach to distinguish somatic vs. germline origin of genomic alterations from deep sequencing of cancer specimens without a matched normal. PLoS Pathog.* 2018; Chalmers et al. *Analysis of* 100,000 *human cancer genomes reveals the landscape of tumor mutational burden. Genome Med.* 2017; Forbes et al. *COSMIC: Exploring the world's knowledge of somatic mutations in human cancer.* Nucleic Acids Res. 2015). In some embodiments, the cancer comprises one or more substitutions, deletions, indels, rearrangements, and copy number alterations in one or more genes provided in Tables 3-4, or within the exonic regions of the one or more genes provided in Table 3 or within the intronic regions of the one or more genes provided in Table 4. In some embodiments, the cancer comprises one or more substitutions, deletions, indels, rearrangements, and copy number alterations in one or more genes provided in Tables 5-6, or within the exonic regions of the one or more genes provided in Table 5 or within the intronic regions of the one or more genes provided in Table 6.

TABLE 3

Genes for Additional Variant Assays
Genes with full coding exonic regions for detection of substitutions, indels, and copy number alterations.

| ABL1 | ACVR1B | AKT1 | AKT2 | AKT3 | ALK | AMER1 | APC | AR | ARAF | ARFRP1 | ARID1A |
|---|---|---|---|---|---|---|---|---|---|---|---|
| BARD1 | BCL2 | BCL2L1 | BCL2L2 | BCL6 | BCOR | BCORL1 | BRAF | BRCA1 | BRCA2 | BRD4 | BRIP1 |
| CCND1 | CCND2 | CCND3 | CCNE1 | CD22 | CD274 | CD70 | CD79A | CD79B | CDC73 | CDH1 | CDK12 |
| CEBPA | CHEK1 | CHEK2 | CIC | CREBBP | CRKL | CSF1R | CSF3R | CTCF | CTNNA1 | CTNNB1 | CUL3 |
| EPHA3 | EPHB1 | ERBB2 | ERBB3 | ERBB4 | ERG | ERRFI1 | ESR1 | EZH2 | FAM123B | FAM46C | FANCA |
| FGF23 | FGF3 | FGF4 | FGF6 | FGFR1 | FGFR2 | FGFR3 | FGFR4 | FH | FLCN | FLT1 | FLT3 |
| GNA13 | GNAQ | GNAS | GRM3 | GSK3B | H3F3A | HDAC1 | HGF | HNF1A | HRAS | HSD3B1 | ID3 |
| IRS2 | AK1 | AK2 | AK3 | UN | KDM A | KDM C | KDM6A | KDR | KEAP1 | KEL | KIT |
| MAP2K4 | MAP3K1 | MAPK1 | MCL1 | MDM2 | MDM4 | MED12 | MEF2B | MEN1 | MET | MITF | MLH1 |
| MTOR | MUTYH | MYC | MYCL | MYCN | MYD88 | NF1 | NF2 | NFE2L2 | NFKBIA | NKX2-1 | NOTCH1 |
| NTRK2 | NTRK3 | P2RY8 | PALB2 | PARK2 | PAX | PBRM1 | PDCD1 | PDCD1LG2 | PDGFRA | PDGFRB | PDK1 |
| PPP2R1A | PRDM1 | PRKAR1A | PRKCI | PRKN | PTCH1 | PTEN | PTPNI1 | PTPRO | QKI | RAC1 | RAD21 |
| ROS1 | RPTOR | SDHA | SDHB | SDHC | SDHD | SETD2 | SF3B1 | SGK1 | SMAD2 | SMAD4 | SMARCA4 |
| SRC | STAG2 | STAT3 | STK11 | SUFU | SYK | TBX3 | TERC | TET2 | TGFBR2 | TNFAIP3 | TNFRSFI4 |
| WT1 | WTX | XPO1 | ZNF217 | ZNF703 | ATM | ATR | ATRX | AURKA | AURKB | AXL | BAP1 |
| BTG2 | BTK | C11orf30 | CALR | CARD11 | CBFB | CBL | CDK6 | CDK8 | CDKN1A | CDKN1B | CDKN2A |
| CDKN2B | CDKN2C | DAXX | DDR2 | DNMT3A | DOT1L | EED | EGFR | EP300 | FANCG | FANCL | FAS |
| FBXW7 | FGF10 | EGF14 | FGF19 | FUBP1 | GABRA6 | GATA3 | GATA4 | GATA6 | GID4 | GNA11 | IDH2 |
| IGF1R | IKBKE | IKZF1 | INPP4B | IRF2 | IRF4 | KMT2A | KMT2A | KRAS | LYN | MAF | MAP2K1 |
| MAP2K | MPL | MRE11 | MRE11A | MSH2 | MSH3 | MSH6 | MTAP | NOTCH3 | NPM1 | NRAS | NSD2 |
| NSD3 | NT C2 | NTRK1 | PIK3C | PIK3CB | PIK3R1 | PIM1 | PMS2 | POLD1 | POLE | RAF1 | RARA |
| RB1 | RBM10 | RET | RICTO | RNF43 | SMO | SNCAIP | SOCS1 | SOX2 | SOX9 | SPEN | SPOP |
| TSC1 | TSC2 | U2AF1 | VEGFA | VHL | WHSC1 | WHSC1L1 | | | | | |

TABLE 4

Genes for Additional Variant Assays
Genes with select intronic regions

| | | | | | | | | | | | |
|---|---|---|---|---|---|---|---|---|---|---|---|
| ALK | BCL2 | BCR | BRAF | BRCA1 | BRCA2 | EGFR | ETV4 | ETV | ETV6 | EWSR1 | FGFR1 |
| NTRK1 | NTRK2 | NUTM1 | PDGFRA | RAF1 | RARA | RET | ROS1 | SLC34A2 | TERT | TMPRSS2 | |
| FGFR3 | KIT | KMT2A | MSH2 | MYB | MYC | NOTCH2 | | | | | |

TABLE 5

Genes for Additional Valiant Assays
Genes with full coding exonic regions for detection of substitutions, indels, and copy number alterations.

| | | | | | |
|---|---|---|---|---|---|
| ABI1 | ACTB | ADGRA2 | AKT1 | AKT2 | AKT3 |
| ALK | AMER1 | APC | APH1A | AR | ARAF |
| ATRX | AURKA | AURKB | AXIN1 | AXL | B2M |
| BAP1 | BARD1 | BCL10 | BCL11B | BCL2 | BCL2L2 |
| BRD4 | BRIP1 | BRSK1 | BTG1 | BTG2 | BTK |
| BTLA | C11orf30 | C17orf39 | CAD | CARD11 | CBFB |
| CD36 | CDS | CD70 | CD79A | CD79B | CDC73 |
| CDH1 | CDK12 | CDK4 | CDK6 | CDK | CDKN1B |
| CKS1B | CPS1 | CREBBP | CRKL | CRLF2 | CSF1R |
| CSF3R | CTCF | CTNNA1 | CTNNB1 | CUX1 | CXCR4 |
| DUSP9 | E2A | EBF1 | ECT2L | EED | EGFR |
| ELP2 | EMSY | EP300 | EPHA3 | EPHAS | EPHA7 |
| ETV6 | EXOSC6 | EZH2 | FAF1 | FAM123B | FAM46C |
| FANCA | FANCC | FANCD2 | FANCE | FANCF | FANCG |
| FGF23 | FGF3 | FGF4 | FGF6 | FGFR1 | FGFR2 |
| FGFR3 | FGFR4 | FHIT | FLCN | FLT1 | FLT3 |
| GATA1 | GATA2 | GATA3 | GID4 | GNA11 | GNA12 |
| GNA13 | GNAQ | GNAS | GPR124 | GRAF | GRIN2A |
| HIST1H1E | HIST1H2AC | HIST1H2AG | HIST1H2AL | HIST1H2AM | HIST1H2BC |
| HIST1H2B | HIST1H2BK | HIST1H2BO | HIST1H3B | HNF1A | HRAS |
| IKZF3 | IL7R | INHBA | INPP4B | INPPSD | IRF1 |
| IRF4 | IRF | IRS2 | AK1 | AK2 | AK3 |
| KDR | KEAP1 | KIT | KLHL6 | KMT2A | KMT2C |
| KRAS | LEF1 | LMO1 | LRP1B | LRRK2 | MAF |
| MAP3K6 | MAP3K7 | MAPK1 | MCL1 | MDM2 | MDM4 |
| MED12 | MEF2B | MEF2C | MEN1 | MET | MIB1 |
| MRE11A | MSH2 | MSH3 | MSH6 | MTOR | MUTYH |
| MYC | MYCL | MYCL1 | MYCN | MYD | MYO1A |
| NOD1 | NOTCH1 | NOTCH2 | NPM1 | NRAS | NSD1 |
| NSD2 | NTSC2 | NTRK1 | NTRK2 | NTRK3 | NUP93 |
| PC | PCBP1 | PCLO | PDCD1 | PDCD11 | PDCD1LG2 |
| PDGFRA | PDGFRB | PDK1 | PDL1 | PDL2 | PHF6 |
| PRKAR1A | PRKDC | PRSS | PTCH1 | PTEN | PTPN11 |
| PTPN2 | PTPN6 | PTPRO | RAD21 | RADS0 | RADS1 |
| RNF43 | ROS1 | RPTOR | RUNX1 | RUNXIT1 | S1PR2 |
| SDHA | SDHB | SDHC | SDHD | SERP2 | SETBP1 |
| SMARCA4 | SMARCB1 | SMC1A | SMC3 | SMO | SOCS1 |
| SOCS2 | SOCS3 | SOX10 | SOX2 | SPEN | SPOP |
| STK11 | SUFU | SUZ12 | SYK | TAF1 | TBL1XR1 |
| TCF3 | TCL1 | TCL1A | TET2 | TGFBR2 | TLL2 |
| TOP1 | TPS3 | TP63 | TRAF2 | TRAF3 | TRAFS |
| TSC1 | TSC2 | TUSC3 | TYK2 | U2AF1 | U2AF2 |
| YY1AP1 | ZMYM2 | ZNF217 | ZNF24 | ZNF703 | ZRSR2 |
| ZSCAN3 | ARFRP1 | ARHGAP26 | ARID1A | ARID2 | ASMTL |
| ASXL1 | ATM | ATR | BCL6 | BCOR | BCORL1 |
| BIRC3 | BLM | BRAF | BRCA1 | BRCA2 | CBL |
| CCND1 | CCND2 | CCND3 | CCNE1 | CCT6B | CD22 |
| CD274 | CDKN2A | CDKN2B | CDKN2C | CEBPA | CHEK1 |
| CHEK2 | CIC | CIITA | DAXX | DDR2 | DDX3X |
| DNM2 | DNMT3A | DOT1L | DTX1 | DUSP2 | EPHB1 |
| ERBB2 | ERBB3 | ERBB4 | ERG | ESR1 | ETO |
| ETS1 | FANCL | FAS | FBXO11 | FBXO31 | FBXW7 |
| FGF10 | FGF14 | FGF19 | FLT4 | FLYWCH1 | FOXL2 |
| FOXO1 | FOXO3 | FOXP1 | FRS2 | GADD4SB | GSK3B |
| GTSE1 | HDAC1 | HDAC4 | HDAC7 | HGF | HIST1H1C |
| HIST1H1D | HSP90AA1 | ICK | ID3 | IDH1 | IDH2 |
| IKBKE | IKZF1 | IKZF2 | ARID2 | UN | KAT6A |
| KDM2B | KDM4C | KDMSA | KDMSC | KDM6A | MAFB |
| MAGED1 | MALT1 | MAP2K1 | MAP2K2 | MAP2K4 | MAP3K1 |
| MAP3K14 | MITF | MKI67 | MLH1 | MLL | MLL3 |
| MMSET | MPL | MRE11 | MYST3 | NCOR2 | NCSTN |
| NF1 | NF2 | NFE2L2 | NFKBIA | NKX2-1 | NUP9 |
| P2RY | PAG1 | PAK3 | PALB2 | PASK | PAXS |
| PBRM1 | PIK3CA | PIK3CG | PIK3R1 | PIK3R2 | PIM1 |

TABLE 5-continued

Genes for Additional Valiant Assays
Genes with full coding exonic regions for detection of substitutions, indels, and copy number alterations.

| | | | | | |
|---|---|---|---|---|---|
| POT1 | POU2AF1 | PRDM1 | RAF1 | RARA | RASGEF1A |
| RB1 | RELN | RET | RHOA | RICTOR | SETD2 |
| SF3B1 | SGK1 | SHIP | SHP-1 | SMAD2 | SMAD4 |
| SMARCA1 | SRC | SRSF2 | STAG2 | STAT3 | STAT4 |
| STATSA | STATSB | STAT6 | TMEM30A | TMSB4XP | TMSL3 |
| TNFAIP3 | TNFRSF11A | TNFRSF14 | TNFRSF17 | TNFRSF6 | VHL |
| WDR90 | WHSC1 | WISP3 | WTI | WTX | XBP1 |
| XPO1 | | | | | |

TABLE 6

Genes for Additional Variant Assays
Genes with select intronic regions.

| | | | | | | | | | | |
|---|---|---|---|---|---|---|---|---|---|---|
| ALK | BCL2 | BCL6 | BCR | BRAF | CCND1 | CRLF2 | EGFR | EPOR | ETV1 | ETV4 |
| KMT2A | MLL | MYC | NTRK1 | PDGFRA | PDGFRB | RAF1 | RARA | RET | ROS1 | TMPRSS2 |
| ETV5 | ETV6 | EWSR1 | FGFR2 | IGH | IGK | IGL | JAK1 | JAK2 | TRG | |

Reporting

In certain aspects, provided herein are methods that include generating and/or providing a report about a KMT2A-MAML2 fusion nucleic acid molecule or polypeptide provided herein, or about a cancer of the disclosure, e.g., an epithelial neoplasm such as a thymoma.

In some embodiments, a report according to the present disclosure comprises, e.g., information about the presence or absence of a KMT2A-MAML2 fusion nucleic acid molecule or polypeptide in a sample obtained from an individual, such as an individual having an epithelial neoplasm, e.g., a thymoma. In one embodiment, a report according to the present disclosure indicates that a KMT2A-MAML2 fusion nucleic acid molecule or polypeptide is present in a sample obtained from an individual, such as an individual having an epithelial neoplasm, e.g., a thymoma. In one embodiment, a report according to the present disclosure indicates that a KMT2A-MAML2 fusion nucleic acid molecule or polypeptide is not present in a sample obtained from an individual, such as an individual having an epithelial neoplasm. e.g., a thymoma. In one embodiment, a report according to the present disclosure indicates that a KMT2A-MAML2 fusion nucleic acid molecule or polypeptide has been detected in a sample obtained from an individual, such as an individual having an epithelial neoplasm, e.g., a thymoma. In one embodiment, a report according to the present disclosure indicates that a KMT2A-MAML2 fusion nucleic acid molecule or polypeptide has not been detected in a sample obtained from an individual, such as an individual having an epithelial neoplasm, e.g., a thymoma. In some embodiments, the report comprises an identifier for the individual or patient from which the sample was obtained.

In some embodiments, the report also includes information on the role of a KMT2A-MAML2 fusion described herein, or its wild type counterparts, in disease, such as in cancer, an epithelial neoplasm, or a thymoma. Such information can include, for example, information on prognosis, resistance, potential or suggested therapeutic options, e.g., such as a treatment selected or identified according to the methods provided herein, and/or therapeutic options that should be avoided. The report can include information on the likely effectiveness, acceptability, or the advisability of applying the therapeutic option (e.g., such as a treatment selected or identified according to the methods provided herein) to an individual, e.g., an individual having a KMT2A-MAML2 fusion provided herein and identified in the report. In some embodiments, the report can include information, or a recommendation on, the administration of a drug (e.g., such as a treatment selected or identified according to the methods provided herein), e.g., the administration at a dosage or in a treatment regimen to the patient, e.g., in combination with other treatments (e.g., a second therapeutic agent described herein). In some embodiments, the report comprises information or a recommendation for at least one, at least two, at least three, at least four, at least five, at least six, at least seven, at least eight, at least nine, at least ten, or more treatments (e.g., such as a treatment selected or identified according to the methods provided herein and/or a second therapeutic agent described herein).

Also provided herein are methods of generating a report according to the present disclosure. In some embodiments, a report according to the present disclosure is generated by a method comprising the steps of obtaining a sample, such as a tumor sample, from an individual (e.g., an individual or a patient with an epithelial neoplasm such as a thymoma); detecting a KMT2A-MAML2 fusion nucleic acid molecule or polypeptide in the sample or acquiring knowledge of the presence of a KMT2A-MAML2 fusion nucleic acid molecule or polypeptide in the sample; and generating a report, wherein the report comprises one or more of: information about the presence or absence of a KMT2A-MAML2 fusion nucleic acid molecule or polypeptide in the sample; an identifier for the individual from which the sample was obtained; information on the role of a KMT2A-MAML2 fusion described herein or its wild type counterparts in disease (e.g., such as in cancer, an epithelial neoplasm, or a thymoma); information on prognosis, resistance, or potential or suggested therapeutic options, e.g., such as a treatment selected or identified according to the methods provided herein; information on the likely effectiveness, acceptability, or the advisability of applying a therapeutic option (e.g., such as a treatment selected or identified according to the methods provided herein) to the individual; a recommendation or information on the administration of a drug (e.g., such as a treatment selected or identified according to the methods provided herein); or a recommendation or information on the dosage or treatment regimen of a drug (e.g., such as a treatment selected or identified according to the methods provided herein), e.g., in combination with other treatments (e.g., a second therapeutic agent described herein). In some embodiments, the report generated is a personalized cancer report.

A report according to the present disclosure may be in an electronic, web-based, or paper form. The report may be provided to an individual or a patient (e.g., an individual or a patient with an epithelial neoplasm such as a thymoma), or an individual or entity other than the individual or patient (e.g., other than the individual or patient with an epithelial neoplasm such as a thymoma) such as a caregiver, a physician, an oncologist, a hospital, a clinical, a third party payor, an insurance company, or a government entity. In some embodiments, the report is provided or delivered to an entity, e.g., an entity described herein, within any of about 1 day or more, about 7 days or more, about 14 days or more, about 21 days or more, about 30 days or more, about 45 days or more, about 60 days or more, from obtaining a sample from an individual (e.g., an individual having an epithelial neoplasm such as a thymoma). In some embodiments, the report is provided or delivered to an entity, e.g., an entity described herein, within any of about 1 day or more, about 7 days or more, about 14 days or more, about 21 days or more, about 30 days or more, about 45 days or more, about 60 days or more, from detecting a KMT2A-MAML2 fusion nucleic acid molecule or polypeptide provided herein in a sample obtained from an individual (e.g., an individual having an epithelial neoplasm such as a thymoma). In some embodiments, the report is provided or delivered to an entity, e.g., an entity described herein, within any of about 1 day or more, about 7 days or more, about 14 days or more, about 21 days or more, about 30 days or more, about 45 days or more, about 60 days or more, from acquiring knowledge of the presence of a KMT2A-MAML2 fusion nucleic acid molecule or polypeptide provided herein in a sample obtained from an individual (e.g., an individual having an epithelial neoplasm such as a thymoma).

Therapeutic Agents and Formulations

Certain aspects of the present disclosure relate to anti-cancer therapies. In some embodiments, an anti-cancer therapy of the disclosure includes one or more therapeutic agents, e.g., for treating a disease, disorder, or injury associated with a KMT2A-MAML2 fusion described herein, such as a cancer provided herein (e.g., an epithelial neoplasm, such as a thymoma). In some embodiments, the anti-cancer therapy is selected from a chemotherapeutic agent, an anti-hormonal agent, an antimetabolite chemotherapeutic agent, a kinase inhibitor, a methyltransferase inhibitor, a peptide, a gene therapy, a vaccine, a platinum-based chemotherapeutic agent, an immunotherapy, an antibody, an NOTCH pathway inhibitor, and a checkpoint inhibitor. In some embodiments, the anti-cancer therapy comprises a second agent, such an anti-cancer therapy or agent described herein. In some embodiments, the anti-cancer therapy is administered in combination with the second agent.

In some embodiments, an anti-cancer therapy of the disclosure comprises anti-cancer agent that inhibits activity or expression of a KMT2A-MAML2 fusion polypeptide. In some embodiments, an anti-cancer therapy of the disclosure comprises anti-cancer agent that inhibits activity of a KMT2A-MAML2 fusion polypeptide. In some embodiments, the anti-cancer therapy comprises a NOTCH pathway inhibitor, such as inhibitors of NOTCH1, NOTCH2, DLL4, DLL1, JAG1, NICASTRIN, SAHM1, and γ-Secretase. Suitable NOTCH pathway inhibitors are known in the art. Non-limiting examples of NOTCH pathway inhibitors include neutralizing antibodies, such as OMP-59R5 (anti-Notch2/3 mAb; OncoMed Pharmaceuticals), NRR1 (anti-Notch1 mAb; Genentech and Exelixis; Merck), NRR2 (anti-Notch2 mAb; Genentech and Exelixis), NRR3 (anti-Notch3 mAb; Genentech), OMP-21M18 (anti-DLL4 mAb; OncoMed Pharmaceuticals), DLL1-Fc and JAG1-Fc (Anti-Delta-likeland Jagged 1 Fc chimeric mAbs), A5622A (Anti-nicastrin mAb); decoys, such as soluble forms of Notch1, Dll1, and Jagged 1; γ-Secretase Inhibitors (GSI), such as R04929097 (Roche), MRK-003 (Merck), MRK-0752 (Merck), PF-03084014 (Pfizer), MRK-0752 (Merck), and PF-3084014 (Pfizer); blocking peptides, such as MAM peptide antagonist SAHM1 (Aileron Therapeutics); compounds, such as Genistein, Sulforaphane, Quercetin, Curcumin, and Resveratrol. See, e.g., Espinoza and Miele. Pharmacol Ther (2013) 139(2):95-110. In some embodiments, the anti-cancer therapy comprises an inhibitor of NOTCH1. In some embodiments, the anti-cancer therapy comprises an EGFR inhibitor. In some embodiments, the EGFR inhibitor is gefitinib or cetuximab. In some embodiments, the anti-cancer therapy comprises a methyl transferase inhibitor such as EZM 2302 (EZM2302 or GSK 3359088), 3,5-bis[(3-bromo-4-hydroxyphenyl)methylene]-1-(phenylmethyl)-4-piperidinone), EPZ025654, MM-401 or MM-NC-401 (see, e.g., Cao et al. Mol Cell vol. 53, no. 2, pp. 247-261 (2014)), SNDX-5613 (Syndax Pharmaceuticals, Inc.), MI-3454 (see, e.g., Klossowski et al., J Clin Inv, vol. 130, no. 2, pp. 981-997 (2020)), KO-539 (Kura Oncology), M-808 (Xu et al., J Med Chem, vol. 63, no. 9, pp. 497-5010 (2020)), entospletinib (see, e.g., Walker et al., Cancer Res, (2018)), VTP50469 (see, e.g., Krivtsov et al., Cancer Cell, vol. 36, no. 6, pp. 660-673.E11 (2019)), or a suitable methyl transferase inhibitor known in the art.

In some embodiments, an anti-cancer therapy of the disclosure comprises anti-cancer agent that inhibits expression of a KMT2A-MAML2 fusion polypeptide. In some embodiments, the anti-cancer therapy comprises a dsRNA molecule. As is known in the art, dsRNAs having a duplex structure are effective at inducing RNA interference (RNAi). In some embodiments, the anti-cancer therapy comprises a small interfering ribonucleic acid (siRNA) molecule. As is known in the art, siRNAs are small double stranded RNAs (dsRNAs) that optionally include overhangs. For example, the duplex region of an siRNA is between about 18 and 25 nucleotides, e.g., any of 18, 19, 20, 21, 22, 23, 24, or 25 nucleotides. Typically, the siRNA sequences are exactly complementary to the target mRNA, dsRNAs and siRNAs in particular can be used to silence gene expression in mammalian cells (e.g., human cells). In some embodiments, a dsRNA of the disclosure comprises any of between about 5 and about 10 base pairs, between about 10 and about 12 base pairs, between about 12 and about 15 base pairs, between about 15 and about 20 base pairs, between about 20 and 23 base pairs, between about 23 to about 25 base pairs, between about 25 to about 27 base pairs, or between about 27 to about 30 base pairs, siRNAs may also include short hairpin RNAs (shRNAs) with 29-base-pair stems and 2-nucleotide 3' overhangs. In some embodiments, a dsRNA of the disclosure, e.g., a dsRNA, an siRNA, or an shRNA, comprises a nucleotide sequence that is configured to hybridize to a KMT2A-MAML2 fusion nucleic acid molecule provided herein. In some embodiments, a dsRNA of the disclosure comprises a nucleotide sequence that is configured to hybridize to the KMT2A-MAML2 breakpoint of a KMT2A-MAML2 fusion nucleic acid molecule provided herein.

Methods of designing, optimizing, producing, and using dsRNAs, e.g., a dsRNA, an siRNA, or an shRNA, are known in the art.

In some embodiments, the anti-cancer therapy comprises a chemotherapeutic agent. Chemotherapeutic agents are chemical agent that inhibit the proliferation, growth, life-span and/or metastatic activity of cancer cells. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines (e.g., altretamine, triethylenemelamine, trietylenephosphoramide, triethiylenethiophosphoramide and trimethylolomelamine); acetogenins; delta-9-tetrahydrocannabinol (e.g., dronabinol, MARINOL); beta-lapachone; lapachol; colchicines; betulinic acid; a camptothecin (including the synthetic analogue topotecan (HYCAMTIN®), CPT-11 (irinotecan, CAMP-TOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (e.g., cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium tenuazonic acid; triaziquone; 2,2',2"-trichlorotriethylamine; trichothecenes (e.g., T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; xeloda; ibandronate; topoisomerase inhibitor RFS 2000; difluoromethylomithine (DMFO); retinoids such as retinoic acid; capecitabine; pharmaceutically acceptable salts, acids or derivatives of any of the above; as well as combinations of two or more of the above such as CHOP, an abbreviation for a combined therapy of cyclophosphamide, doxorubicin, vincristine, and prednisone, and FOLFOX, an abbreviation for a treatment regimen with oxaliplatin (ELOXATIN™) combined with 5-FU and leucovovin.

In some embodiments, the anti-cancer therapy comprises an anti-hormonal agent. Anti-hormonal agents are agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene. LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGACE® megestrol acetate. AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

In some embodiments, the anti-cancer therapy comprises an antimetabolite chemotherapeutic agent. Antimetabolite chemotherapeutic agents are agents which are structurally similar to a metabolite, but cannot be used by the body in a productive manner. Many antimetabolite chemotherapeutic agents interfere with the production of the nucleic acids, RNA and DNA. Examples of antimetabolite chemotherapeutic agents include gemcitabine (GEMZAR®), 5-fluorouracil (5-FU), capecitabine (XELODA™), 6-mercaptopurine, methotrexate, 6-thioguanine, pemetrexed, raltitrexed, arabinosylcytosine ARA-C cytarabine (CYTOSAR-U®), dacarbazine (DTIC-DOMED), azocytosine, deoxycytosine, pyridmidene, fludarabine (FLUDARA®), cladrabine, 2-deoxy-D-glucose, etc. In some embodiments, an antimetabolite chemotherapeutic agent is gemcitabine. Gemcitabine HCl is sold by Eli Lilly under the trademark GEMZAR®.

In some embodiments, the anti-cancer therapy comprises a platinum-based chemotherapeutic agent. Platinum-based chemotherapeutic agents are chemotherapeutic agents that comprise an organic compound which contains platinum as an integral part of the molecule. In some embodiments, a chemotherapeutic agent is a platinum agent. In some such embodiments, the platinum agent is selected from cisplatin, carboplatin, oxaliplatin, nedaplatin, triplatin tetranitrate, phenanthriplatin, picoplatin, or satraplatin.

In some embodiments, the anti-cancer therapy comprises a checkpoint inhibitor. As is known in the art, a checkpoint inhibitor targets at least one immune checkpoint protein to alter the regulation of an immune response, e.g., down-modulating or inhibiting an immune response. Immune checkpoint proteins include, e.g., CTLA4, PD-L1, PD-1, PD-L2, VISTA, B7-H2, B7-H3, B7-H4, B7-H6, 2B4, ICOS, HVEM, CEACAM, LAIR1, CD80, CD86, CD276, VTCN1, MHC class I, MHC class II, GALS, adenosine, TGFR, CSF1R, MICA/B, arginase, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, LAG-3, BTLA, IDO, OX40, and A2aR. In some embodiments, a checkpoint inhibitor decreases the activity of a checkpoint protein that negatively regulates immune cell function, e.g., in order to enhance T cell activation and/or an anti-cancer immune response; in other embodiments, a checkpoint inhibitor increases the activity of a checkpoint protein that positively regulates immune cell function, e.g., in order to enhance T cell activation and/or an anti-cancer immune response. In some embodiments, the checkpoint inhibitor is an antibody. In some embodiments, the checkpoint inhibitor is an antibody. Examples of check-point inhibitors include, without limitation, a PD-L1 axis binding antagonist (e.g, an anti-PD-L1 antibody, e.g., atezolizumab (MPDL3280A)), an antagonist directed against a co-inhibitory molecule (e.g., a CTLA4 antagonist (e.g., an anti-CTLA4 antibody), a TIM-3 antagonist (e.g., an anti-TIM-3 antibody), or a LAG-3 antagonist (e.g., an anti-LAG-3 antibody)), or any combination thereof. In some embodiments, a cancer immunotherapy comprises a check-point inhibitor.

In some embodiments, the checkpoint inhibitor is a PD-L1 axis binding antagonist. e.g., a PD-1 binding antago-nist, a PD-L1 binding antagonist, or a PD-L2 binding antagonist. PD-1 (programmed death 1) is also referred to in the art as "programmed cell death 1," "PDCD1," "CD279," and "SLEB2." An exemplary human PD-1 is shown in UmProtKB/Swiss-Prot Accession No. Q15116. PD-L1 (pro-grammed death ligand 1) is also referred to in the art as "programmed cell death 1 ligand 1," "PDCD1 LG1." "CD274," "B7-H." and "PDL1." An exemplary human PD-L1 is shown in UniProtKB/Swiss-Prot Accession No. Q9NZQ7.1. PD-L2 (programmed death ligand 2) is also referred to in the art as "programmed cell death 1 ligand 2," "PDCD1 LG2," "CD273." "B7-DC," "Btdc." and "PDL2." An exemplary human PD-L2 is shown in UniProtKB/Swiss-Prot Accession No Q9BQ51 In some instances, PD-1, PD-L1, and PD-L2 are human PD-1, PD-L1 and PD-L2.

In some instances, the PD-1 binding antagonist is a molecule that inhibits the binding of PD-1 to its ligand binding partners. In a specific aspect the PD-1 ligand bind-ing partners are PD-L1 and/or PD-L2. In another instance, a PD-L1 binding antagonist is a molecule that inhibits the binding of PD-L1 to its binding ligands. In a specific aspect, PD-L1 binding partners are PD-1 and/or B7-1. In another instance, the PD-L2 binding antagonist is a molecule that inhibits the binding of PD-L2 to its ligand binding partners. In a specific aspect, the PD-L2 binding ligand partner is PD-1. The antagonist may be an antibody, an antigen bind-ing fragment thereof, an immunoadhesin, a fusion protein, or oligopeptide. In some embodiments, the PD-1 binding antagonist is a small molecule, a nucleic acid, a polypeptide (e.g., antibody), carbohydrate, a lipid, a metal, or a toxin.

In some instances, the PD-1 binding antagonist is an anti-PD-1 antibody (e.g., a human antibody, a humanized antibody, or a chimeric antibody), for example, as described below. In some instances, the anti-PD-1 antibody is selected from the group consisting of MDX-1 106 (nivolumab). MK-3475 (pembrolizumab). MEDI-0680 (AMP-514). PDR001, REGN2810, MGA-012, JNJ-63723283, BI 754091, and BCB-108. MDX-1 106, also known as MDX-1 106-04. ONO-4538. BMS-936558, or nivolumab, is an anti-PD-1 antibody described in WO 2006/121168. MK-3475, also known as pembrolizumab or lambrolizumab, is an anti-PD-1 antibody described in WO 2009/114335. In some instances, the PD-1 binding antagonist is an immuno-adhesin (e.g., an immunoadhesin comprising an extracellu-lar or PD-1 binding portion of PD-L1 or PD-L2 fused to a constant region (e.g., an Fc region of an immunoglobulin sequence). In some instances, the PD-1 binding antagonist is AMP-224 AMP-224, also known as B7-DCIg, is a PD-L2-Fc fusion soluble receptor described in WO 2010/027827 and WO 2011/066342.

Other examples of anti-PD-1 antibodies include, but are not limited to, MEDI-0680 (AMP-514; AstraZeneca), PDR001 (CAS Registry No. 1859072-53-9; Novartis), REGN2810 (LIBTAYO® or cemiplimab-rwlc; Regeneron), BGB-108 (BeiGene), BGB-A317 (BeiGene), BI 754091, JS-001 (Shanghai Junshi), STI-A1110 (Sorrento), INCSHR-1210 (Incyte), PF-06801591 (Pfizer). TSR-042 (also known as ANBO11; Tesaro/AnaptysBio), AM0001 (ARMO Bio-sciences), ENUM 244C8 (Enumeral Biomedical Holdings), ENUM 388D4 (Enumeral Biomedical Holdings). In some embodiments, the PD-1 binding antagonist is a peptide or small molecule compound. In some embodiments, the PD-1 binding antagonist is AUNP-12 (PierreFabre/Aurigene).

In some embodiments, the PD-L1 binding antagonist is a small molecule that inhibits PD-1. In some embodiments, the PD-L1 binding antagonist is a small molecule that inhibits PD-L1. In some embodiments, the PD-L1 binding antagonist is a small molecule that inhibits PD-L1 and VISTA or PD-L1 and TIM3. In some embodiments, the PD-L1 binding antagonist is CA-170 (also known as AUPM-170). In any of the instances herein, the isolated anti-PD-L1 antibody can bind to a human PD-L1, for example a human PD-L1 as shown in UniProtKB/Swiss-Prot Accession No. Q9NZQ7.1, or a variant thereof. In some embodiments, the PD-L1 binding antagonist is a small molecule, a nucleic acid, a polypeptide (e.g., antibody), carbohydrate, a lipid, a metal, or a toxin.

In some instances, the PD-L1 binding antagonist is an anti-PD-L1 antibody, for example, as described below. In some instances, the anti-PD-L1 antibody is capable of inhibiting binding between PD-L1 and PD-1 and/or between PD-L1 and B7-1. In some instances, the anti-PD-L1 anti-body is a monoclonal antibody. In some instances, the anti-PD-L1 antibody is an antibody fragment selected from the group consisting of Fab, Fab'-SH, Fv. scFv. and (Fab')2 fragments. In some instances, the anti-PD-L1 antibody is a humanized antibody. In some instances, the anti-PD-L1 antibody is a human antibody. In some instances, the anti-PD-L1 antibody is selected from the group consisting of YW243.55 S70, MPDL3280A (atezolizumab). MDX-1 105, and MED14736 (durvalumab), and MSB0010718C (avelumab). Antibody YW243 55.S70 is an anti-PD-L1 described in WO 2010/077634 MDX-1 105, also known as BMS-936559, is an anti-PD-L1 antibody described in WO2007/005874 MEDI4736 (durvalumab) is an anti-PD-L1 monoclonal antibody described in WO2011/066389 and US2013/034559.

Other examples of anti-PD-L1 antibodies include, but are not limited to, MDX-1105 (BMS-936559; Bristol Myers Squibb), LY3300054 (Eli Lilly), STI-A1014 (Sorrento), KN035 (Suzhou Alphamab), FAZ053 (Novartis), or CX-072 (CytomX Therapeutics).

In some embodiments, the checkpoint inhibitor is CT-011, also known as hBAT, hBAT-1 or pidilizumab, an antibody described in WO 2009/101611.

In some embodiments, the checkpoint inhibitor is an antagonist of CTLA4. In some embodiments, the checkpoint inhibitor is a small molecule antagonist of CTLA4. In some embodiments, the checkpoint inhibitor is an anti-CTLA4 antibody. CTLA4 is part of the CD28-B7 immunoglobulin superfamily of immune checkpoint molecules that acts to negatively regulate T cell activation, particularly CD28-dependent T cell responses. CTLA4 competes for binding to common ligands with CD28, such as CD80 (B7-1) and CD86 (B7-2), and binds to these ligands with higher affinity than CD28. Blocking CTLA4 activity (e.g., using an anti-CTLA4 antibody) is thought to enhance CD28-mediated costimulation (leading to increased T cell activation/priming), affect T cell development, and/or deplete Tregs (such as intratumoral Tregs). In some embodiments, the CTLA4 antagonist is a small molecule, a nucleic acid, a polypeptide (e.g., antibody), carbohydrate, a lipid, a metal, or a toxin.

In some embodiments, the anti-CTLA4 antibody is ipilimumab (YERVOY®; CAS Registry Number; 477202-00-9). Ipilimumab, also known as BMS-734016, MDX-010, and MDX-101, is a fully human monoclonal IgG1 kappa anti-CTLA4 antibody (Bristol-Myers Squibb) described in WO2001/14424. Other examples of anti-CTLA4 antibodies include, but are not limited to, APL-509, AGEN1884, and CS1002.

In some aspects, provided herein are therapeutic formulations comprising an anti-cancer therapy provided herein and a pharmaceutically acceptable carrier, excipient, or stabilizer. Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants, or polyethylene glycol (PEG).

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art.

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and $\gamma$ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

A formulation provided herein may also contain more than one active compound, for example, those with complementary activities that do not adversely affect each other. The type and effective amounts of such medicaments depend, for example, on the amount and type of antagonist present in the formulation, and clinical parameters of the individuals. For example, a formulation provided herein may also contain one or more of the agents, e.g., the second agents, described above.

Kits

Also provided herein are kits for detecting a KMT2A-MAML2 fusion nucleic acid molecule provided herein. In some embodiments, a kit provided herein comprises a reagent (e.g., one or more oligonucleotides, primers, probes or baits of the present disclosure) for detecting a KMT2A-MAML2 fusion nucleic acid molecule provided herein. In some embodiments, the kit comprises a reagent (e.g., one or more oligonucleotides, primers, probes or baits of the present disclosure) for detecting a wild-type counterpart of KMT2A-MAML2 fusion nucleic acid molecule provided herein. In some embodiments, the reagent comprises one or more oligonucleotides, primers, probes or baits of the present disclosure capable of hybridizing to a KMT2A-MAML2 fusion nucleic acid molecule provided herein, or to a wild-type counterpart of a KMT2A-MAML2 fusion nucleic acid molecule provided herein.

In some embodiments, the reagent comprises one or more oligonucleotides, primers, probes or baits of the present disclosure capable of distinguishing a KMT2A-MAML2 fusion nucleic acid molecule provided herein from a wild-type counterpart of a KMT2A-MAML2 fusion nucleic acid molecule provided herein. In some embodiments, the kit is for use according to any sequencing or nucleotide detecting assay known in the art or described herein, such sequencing, PCR, or in situ hybridization methods, a nucleic acid hybridization assay, an amplification-based assay, a PCR-RFLP assay, real-time PCR, sequencing, a screening analysis, FISH, spectral karyotyping or MFISH, comparative genomic hybridization, in situ hybridization, sequence-specific priming (SSP) PCR, HPLC, and mass-spectrometric genotyping.

In some embodiments, a kit provided herein further comprises instructions for detecting a KMT2A-MAML2 fusion nucleic acid molecule provided herein, e.g., using one or more oligonucleotides, primers, probes or baits of the present disclosure.

Also provided herein are kits for detecting a KMT2A-MAML2 fusion polypeptide described herein. In some embodiments, a kit provided herein comprises a reagent (e.g., one or more antibodies of the present disclosure) for detecting a KMT2A-MAML2 fusion polypeptide provided herein. In some embodiments, the kit comprises a reagent (e.g., one or more antibodies of the present disclosure) for detecting the wild-type counterpart of KMT2A-MAML2 fusion polypeptide provided herein. In some embodiments, the reagent comprises one or more antibodies of the present disclosure capable of binding to a KMT2A-MAML2 fusion polypeptide provided herein, or to a wild-type counterpart of KMT2A-MAML2 fusion polypeptide provided herein. In some embodiments, the reagent comprises one or more antibodies of the present disclosure capable of distinguishing a KMT2A-MAML2 fusion polypeptide provided herein from a wild-type counterpart of a KMT2A-MAML2 fusion polypeptide provided herein. In some embodiments, the kit is for use according to any protein or polypeptide detection assay known in the art or described herein, such as mass spectrometry (e.g., tandem mass spectrometry), a reporter assay (e.g., a fluorescence-based assay), immunoblots such as a Western blot, immunoassays such as enzyme-linked immunosorbent assays (ELISA), immunohistochemistry, other immunological assays (e.g., fluid or gel precipitin reactions, immunodiffusion, immunoelectrophoresis, radioimmunoassay (RIA), immunofluorescent assays), and analytic biochemical methods (e.g., electrophoresis, capillary electrophoresis, high performance liquid chromatography (HPLC), thin layer chromatography (TLC), hyperdiffusion chromatography).

In some embodiments, the kit further comprises instructions for detecting a KMT2A-MAML2 fusion polypeptide provided herein, e.g., using one or more antibodies of the present disclosure.

The method steps of the described herein are intended to include any suitable method of causing one or more other parties or entities to perform the steps, unless a different meaning is expressly provided or otherwise clear from the context. Such parties or entities need not be under the direction or control of any other party or entity, and need not be located within a particular jurisdiction. Thus for example, a description or recitation of "adding a first number to a second number" includes causing one or more parties or entities to add the two numbers together. For example, if person X engages in an arm's length transaction with person Y to add the two numbers, and person Y indeed adds the two numbers, then both persons X and Y perform the step as recited: person Y by virtue of the fact that he actually added the numbers, and person X by virtue of the fact that he caused person Y to add the numbers. Furthermore, if person X is located within the United States and person Y is located outside the United States, then the method is performed in the United States by virtue of person X's participation in causing the step to be performed.

ENUMERATED EMBODIMENTS

The following enumerated embodiments are representative of some aspects of the invention:

Embodiment 1. An isolated KMT2A-MAML2 fusion nucleic acid molecule comprising a nucleotide sequence chosen from:
(i) a nucleotide sequence comprising one or more, or all of exons of KMT2A, and one or more, or all, of exons of MAML2, as described herein (e.g., comprising any of exons 8, 9, 10 or 11 of KMT2A and exon 2 of MAML2), or a nucleotide sequence at least 85% identical thereto:
(ii) a nucleotide sequence described herein, or a nucleotide sequence at least 85% identical thereto;
(iii) a nucleotide sequence encoding an amino acid sequence described herein, or a nucleotide sequence at least 85% identical thereto:
(iv) a nucleotide sequence comprising all or a portion of the KMT2A-MAML2 fusion nucleic acid molecule Breakpoint 1 and/or Breakpoint 2 depicted herein; or
(v) a fragment of any of (i)-(iv) comprising a nucleotide sequence from a KMT2A gene and a nucleotide sequence from an MAML2 gene.

Embodiment 2. A nucleic acid molecule that is capable of hybridizing to the nucleic acid molecule of embodiment 1.

Embodiment 3. A fragment of the nucleic acid molecule of embodiment 1 or 2, wherein said fragment comprises between 10 and 25 nucleotides, or between 100 and 300 nucleotides.

Embodiment 4. The fragment of embodiment 3, which is a probe or primer that comprises about 5 and 25 nucleotides.

Embodiment 5. The fragment of embodiment 3, which is a bait that comprises between about 100 and 300 nucleotides, 130 and 230 nucleotides, or 150 and 200 nucleotides.

Embodiment 6. A nucleic acid molecule suitable as a probe, primer, bait, or library member, that specifically binds to the nucleic acid molecule of embodiment 1 or 2, or the fragment of any of embodiments 3-5.

Embodiment 7. The nucleic acid molecule of embodiment 1 or 2, or the fragment of any of embodiments 3-5, which is operatively linked to a native or a heterologous regulatory nucleotide sequence.

Embodiment 8. A vector comprising a nucleic acid molecule of embodiment 1 or 2, or a fragment of any of embodiments 3-5.

Embodiment 9. A host cell comprising a vector of embodiment 8.

Embodiment 10. A nucleic acid molecule that specifically reduces or inhibits the expression, or alters a function, of the nucleic acid molecule of embodiment 1 or 2.

Embodiment 11. The nucleic acid molecule of embodiment 10, which is chosen from an antisense molecule, a ribozyme, an siRNA, a guide RNA (gRNA), or a triple helix molecule.

Embodiment 12. An isolated KMT2A-MAML2 fusion polypeptide comprising an amino acid sequence chosen from:
(i) the amino acid sequence encoded by one or more, or all of exons of KMT2A and encoded by one or more, or all, of exons of MAML2, as described herein (e.g., comprising any of exons 8, 9, 10 or 11 of KMT2A and exon 2 of MAML2), or an amino acid sequence at least 85% identical thereto;
(ii) the amino acid sequence encoded by a nucleotide sequence described herein, or an amino acid sequence at least 85% identical thereto;
(iii) the amino acid sequence described herein, or an amino acid sequence at least 85% identical thereto;
(iv) the amino acid sequence encoded by a nucleotide sequence comprising all or a portion of a KMT2A-MAML2 fusion nucleic acid molecule Breakpoint 1 and/or Breakpoint 2 depicted herein; or
(v) a fragment of any of (i)-(iv) comprising an amino acid sequence from a KMT2A polypeptide and an amino acid sequence from an MAML2 polypeptide.

Embodiment 13. The polypeptide of embodiment 12, having a biological activity of KMT2A and/or MAML2.

Embodiment 14. An isolated antibody molecule that specifically binds to the polypeptide of embodiment 12 or 13.

Embodiment 15. A reaction mixture comprising:

a detection reagent capable of detecting a rearrangement associated with a KMT2A gene and/or an MAML2 gene; and a target nucleic acid derived from a cancer, e.g., a cancer described herein, e.g., a thymoma, wherein the target nucleic acid comprises the nucleic acid molecule of any of embodiments 1-3.

Embodiment 16. The reaction mixture of embodiment 15, wherein the detection reagent detects the nucleotide sequence of a KMT2A-MAML2 fusion nucleic acid molecule.

Embodiment 17. The reaction mixture of embodiment 15 or 16, wherein the detection reagent distinguishes the nucleotide sequence of a KMT2A-MAML2 fusion nucleic acid molecule, from a wildtype KMT2A or MAML2 nucleotide sequence, or the nucleotide sequence of a second KMT2A or MAML2 fusion nucleic acid molecule.

Embodiment 18. The reaction mixture of any of embodiments 15-17, wherein the detection reagent comprises a DNA, RNA, or mixed DNA/RNA molecule comprising a nucleotide sequence that is complementary to a KMT2A-MAML2 fusion nucleic acid molecule.

Embodiment 19. The reaction mixture of any of embodiments 15-18, wherein the detection reagent detects the fusion junction of a KMT2A-MAML2 fusion nucleic acid molecule.

Embodiment 20. A method of making a reaction mixture comprising:

combining a detection reagent capable of detecting a rearrangement associated with a KMT2A gene and/or an MAML2 gene with a target nucleic acid derived from a cancer. e.g., a cancer described herein. e.g., a thymoma, wherein the target nucleic acid comprises the nucleic acid molecule of embodiment 1 or 2.

Embodiment 21. A preparation of the nucleic acid molecule of embodiment 1 or 2, or the fragment of any of embodiments 3-5, disposed in a sequencing device, or a sample holder for use in such a device.

Embodiment 22. A preparation of the nucleic acid molecule of embodiment 1 or 2, or the fragment of any of embodiments 3-5, disposed in a device for determining a physical or chemical property (e.g., stability of a duplex, e.g., $T_m$), or a sample holder for use in such a device.

Embodiment 23. A detection reagent comprising a DNA, RNA, or mixed DNA/RNA molecule, comprising a nucleotide sequence that is complementary to the nucleotide sequence of a KMT2A-MAML2 fusion nucleic acid molecule.

Embodiment 24. A kit comprising the detection reagent of embodiment 23 and instructions for use of the detection reagent to detect a KMT2A-MAML2 fusion nucleic acid molecule.

Embodiment 25. A reaction mixture, comprising:

a detection reagent capable of detecting a structural or functional property of a KMT2A-MAML2 fusion polypeptide, e.g., a substrate e.g., a substrate for phosphorylation, or an antibody; and a target protein derived from a cancer, e.g., a cancer described herein, e.g., a thymoma, wherein the target protein comprises the polypeptide of embodiment 12 or 13.

Embodiment 26. A method of making a reaction mixture, comprising:

combining a detection reagent capable of detecting a structural or functional property of a KMT2A-MAML2 fusion polypeptide, e.g., a substrate e.g., a substrate for phosphorylation, or an antibody; with a target protein derived from a cancer, e.g., a cancer described herein. e.g., a thymoma, wherein the target protein comprises the polypeptide of embodiment 12 or 13.

Embodiment 27. A kit comprising the antibody molecule of embodiment 14 and instructions for use of the antibody molecule to detect a KMT2A-MAML2 fusion polypeptide.

Embodiment 28. A method of reducing an activity or expression of the KMT2A-MAML2 fusion polypeptide of embodiment 12 or 13, comprising:

optionally, acquiring knowledge of the presence of the KMT2A-MAML2 fusion polypeptide; and contacting the KMT2A-MAML2 fusion polypeptide, or a cell expressing the KMT2A-MAML2 fusion polypeptide, with an agent that reduces an activity or expression of the KMT2A-MAML2 fusion polypeptide.

Embodiment 29. The method of embodiment 28, wherein the contacting step is effected in vitro.

Embodiment 30. The method of embodiment 28, wherein the contacting step is effected in vivo.

Embodiment 31. The method of embodiment 30, wherein the contacting step is effected in a human or animal subject.

Embodiment 32. An anti-cancer agent for use in treating a cancer in a subject, wherein the use comprises acquiring knowledge of the presence of the KMT2A-MAML2 fusion nucleic acid molecule of any of embodiments 1-3 or a KMT2A-MAML2 fusion polypeptide of embodiment 12 or 13 in the subject.

Embodiment 33. The anti-cancer agent for use of embodiment 32, wherein said anti-cancer agent comprises a targeted therapy.

Embodiment 34. The anti-cancer agent for use of embodiment 33, wherein the targeted therapy is administered responsive to a determination of presence of the KMT2A-MAML2 fusion nucleic acid molecule or KMT2A-MAML2 fusion polypeptide in a sample from said subject.

Embodiment 35. The anti-cancer agent for use of embodiment 32, wherein said use is responsive to acquiring knowledge or information of the presence of the KMT2A-MAML2 fusion nucleic acid molecule or KMT2A-MAML2 fusion polypeptide in said subject.

Embodiment 36. The anti-cancer agent for use of embodiment 32, wherein said use is responsive to acquiring knowledge or information of the presence of the KMT2A-MAML2 fusion nucleic acid molecule or KMT2A-MAML2 fusion polypeptide in said subject from another party.

Embodiment 37. The anti-cancer agent for use of embodiment 32, wherein the use comprises receiving a communication of the presence of the KMT2A-MAML2 fusion nucleic acid molecule or KMT2A-MAML2 fusion polypeptide in the subject.

Embodiment 38. The anti-cancer agent for use of embodiment 32, wherein said use is responsive to an identification of the presence of the KMT2A-MAML2 fusion nucleic acid molecule or KMT2A-MAML2 fusion polypeptide in the subject, wherein said identification arises from collaboration with another party.

Embodiment 39. The anti-cancer agent for use of embodiment 32, comprising determining the presence of the KMT2A-MAML2 fusion nucleic acid molecule or KMT2A-MAML2 fusion polypeptide by sequencing, e.g., next-generation sequencing (NGS).

Embodiment 40. The anti-cancer agent for use of any of embodiments 32-39, wherein said cancer is chosen from a cancer described herein, e.g., a thymoma.

Embodiment 41. The anti-cancer agent for use of embodiment 40, wherein the cancer is a thymoma.

Embodiment 42. The anti-cancer agent for use of embodiment 41, wherein the thymoma is an aggressive type B3 thymoma or an aggressive histological subtype of thymoma.

Embodiment 43. The anti-cancer agent for use of any of embodiments 3242, wherein the anti-cancer agent selectively inhibits a biological activity of the KMT2A-MAML2 fusion polypeptide.

Embodiment 44. The anti-cancer agent for use of any of embodiments 3246, wherein the anti-cancer agent comprises a therapeutic agent chosen from an antisense molecule, a ribozyme, an siRNA, a triple helix-forming oligonucleotide, or a gRNA, each of which hybridizes to a KMT2A-MAML2 fusion nucleic acid molecule, or a transcription regulatory region thereof.

Embodiment 45. The anti-cancer agent for use of any of embodiments 3244, wherein the anti-cancer agent is used in combination with a second therapeutic agent or modality.

Embodiment 46. A method for screening for an agent that inhibits the expression or activity of a KMT2A-MAML2 fusion polypeptide of embodiment 12 or 13, comprising:

optionally, determining if the KMT2A-MAML2 fusion polypeptide, or a nucleic acid molecule encoding the KMT2A-MAML2 fusion polypeptide, is present;

contacting the KMT2A-MAML2 fusion polypeptide, or a host cell expressing the KMT2A-MAML2 fusion polypeptide, with a candidate agent; and detecting a change in a parameter associated with the KMT2A-MAML2 fusion polypeptide.

Embodiment 47. The method of embodiment 46, wherein said parameter is the expression or an activity of the KMT2A-MAML2 fusion polypeptide.

Embodiment 48. The method of embodiment 46 or 47, further comprising comparing a value for the parameter to a reference value.

Embodiment 49. The method of any of embodiments 46-48, further comprising comparing a parameter obtained from contacting a sample with the candidate agent to the same parameter obtained from not contacting a sample with the candidate agent.

Embodiment 50. The method of any of embodiments 46-49, further comprising, if a decrease in the expression or activity of the KMT2A-MAML2 fusion polypeptide is detected, identifying or classifying the candidate agent as an inhibitor.

Embodiment 51. The method of any of embodiments 46-50, wherein said contacting occurs in a cell-free system.

Embodiment 52. The method of any of embodiments 46-50, wherein said contacting is effected in vitro, ex vivo, or in vivo.

Embodiment 53. The method of any of embodiments 46-52, wherein said parameter is chosen from one or more of:

(i) direct binding of the candidate agent to the KMT2A-MAML2 fusion polypeptide:

(ii) a change in a KMT2A or MAML2 biological activity:

(iii) a change in an activity of a cell containing the KMT2A-MAML2 fusion polypeptide, e.g., a change in proliferation, morphology or tumorigenicity of the cell;

(iv) a change in a tumor present in an animal subject, e.g., size, appearance, proliferation, of the tumor; or (v) a change in the level of the KMT2A-MAML2 fusion polypeptide or a nucleic acid molecule encoding the KMT2A-MAML2 fusion polypeptide.

Embodiment 54. A method of determining the presence of a KMT2A-MAML2 fusion nucleic acid molecule or a KMT2A-MAML2 fusion polypeptide, comprising:

directly acquiring knowledge that the KMT2A-MAML2 fusion nucleic acid molecule of embodiment 1 or 2, or the KMT2A-MAML2 fusion polypeptide of embodiment 12 or 13, is present in a sample.

Embodiment 55. The method of embodiment 54, wherein said sample comprises fluid (e.g., blood or serum), cells, or tissue (e.g., a tumor tissue).

Embodiment 56. The method of embodiment 54, wherein the sample is a nucleic acid sample, e.g., a sample comprising cell-free DNA (cfDNA) or circulating tumor DNA (ctDNA).

Embodiment 57. The method of embodiment 54, wherein the sample is a protein sample.

Embodiment 58. The method of any of embodiments 54-57, wherein the sample is acquired from a subject (e.g., a human subject).

Embodiment 59. The method of embodiment 54, wherein the sample comprises a tumor biopsy, a circulating tumor cell, or a circulating tumor nucleic acid.

Embodiment 60. The method of any of embodiments 54-59, wherein the sample is from a subject having a cancer described herein.

Embodiment 61. The method of embodiment 60, wherein the cancer is a thymoma.

Embodiment 62. The method of any of embodiments 54-61, wherein the KMT2A-MAML2 fusion nucleic acid molecule is detected.

Embodiment 63. The method of embodiment 62, wherein the KMT2A-MAML2 fusion nucleic acid molecule is detected by a method chosen from one or more of: a nucleic acid hybridization assay, an amplification-based assay, a PCR-RFLP assay, real-time PCR, sequencing, a screening analysis, FISH, spectral karyotyping or MFISH, comparative genomic hybridization, in situ hybridization, sequence-specific priming (SSP) PCR HPLC, or mass-spectrometric genotyping.

Embodiment 64. The method of embodiment 62 or 63, comprising acquiring a read for a nucleotide position in the KMT2A-MAML2 fusion nucleic acid molecule by sequencing, thereby detecting that the KMT2A-MAML2 fusion nucleic acid molecule is present.

Embodiment 65. The method of embodiment 64, wherein the read acquired is compared to a reference nucleotide sequence, optionally a wildtype KMT2A reference nucleotide sequence or a wildtype MAML2 reference nucleotide sequence.

Embodiment 66. The method of any of embodiments 54-61, wherein the KMT2A-MAML2 fusion polypeptide is detected.

Embodiment 67. The method of embodiment 66, comprising: contacting a sample with a reagent which specifically binds to the KMT2A-MAML2 fusion polypeptide; and detecting the formation of a complex of the KMT2A-MAML2 fusion polypeptide and the reagent.

Embodiment 68. The method of embodiment 67, wherein the reagent is labeled with a detectable moiety to facilitate detection of the bound and unbound reagent.

Embodiment 69. The method of embodiment 68, wherein the reagent is an antibody molecule.

Embodiment 70. A method of evaluating a subject, comprising:

identifying, selecting, or obtaining information or knowledge that the subject has participated in a clinical trial or has been treated for a cancer; and acquiring genotype information that identifies a KMT2A-MAML2 fusion nucleic acid molecule or KMT2A-MAML2 polypeptide described herein in the subject, wherein the presence of the KMT2A-MAML2 fusion nucleic acid molecule or KMT2A-MAML2 fusion polypeptide identifies the subject as having an increased risk for, or having, a cancer associated with the KMT2A-MAML2 fusion nucleic acid molecule or the KMT2A-MAML2 fusion polypeptide.

Embodiment 71. The method of embodiment 70, further comprising providing a report to a party.

Embodiment 72. The method of embodiment 71, wherein the party is the subject, a caregiver, a physician, an oncologist, a hospital, a clinic, a third-party payor, an insurance company or a government office.

Embodiment 73. The method of embodiment 71 or 72, wherein said report is in electronic, web-based, or paper form.

Embodiment 74. The method of any of embodiments 71-73, wherein the report identifies the presence or absence of the KMT2A-MAML2 fusion nucleic acid molecule or the KMT2A-MAML2 fusion polypeptide, and optionally comprises an identifier for the subject from which the KMT2A-MAML2 fusion nucleic acid molecule or the KMT2A-MAML2 fusion polypeptide was obtained.

Embodiment 75. The method of any of embodiments 71-74, wherein said report comprises:

information on the role of the KMT2A-MAML2 fusion nucleic acid molecule or KMT2A-MAML2 fusion polypeptide, in disease;

information on prognosis, resistance, or potential or suggested therapeutic options:

information on the likely effectiveness of a therapeutic option, the acceptability of a therapeutic option, or the advisability of applying the therapeutic option to a subject; or information, or a recommendation on, the administration of a drug.

Embodiment 76. A method for generating a personalized cancer treatment report, comprising:

obtaining a sample from a subject, detecting a KMT2A-MAML2 fusion nucleic acid molecule or a KMT2A-MAML2 fusion polypeptide described herein in the sample;

selecting a treatment based on the KMT2A-MAML2 fusion nucleic acid molecule or the KMT2A-MAML2 fusion polypeptide detected; and providing a report comprising information on the KMT2A-MAML2 fusion nucleic acid molecule or the KMT2A-MAML2 fusion polypeptide detected and the treatment selected.

EXAMPLES

The present disclosure will be more fully understood by reference to the following Examples. They should not, however, be construed as limiting the scope of the present disclosure. All citations throughout the disclosure are hereby expressly incorporated by reference.

Example 1: A Pan-Cancer Landscape Analysis Reveals Recurrent KMT2A-MAML2 Gene Fusions in Aggressive Histologic Subtypes of Adult Thymoma Thymomas are epithelial neoplasms that represent the most common thymic tumors in adults. These tumors have been previously shown to harbor a relatively low mutational burden. As a result, there is a lack of molecular genetic alterations that may be used prognostically or targeted therapeutically for this disease. Described here is a recurrent gene rearrangement in thymoma.

Methods

In a cohort of 41 thymomas, a single thymoma was evaluated by an RNA-based solid fusion assay, and the entire cohort was evaluated by FISH break-apart probe to detect MAML2 rearrangements. In a separate cohort of 255,008 unique advanced cancers, including 242 thymomas, all were sequenced by hybrid-capture-NGS-based comprehensive genomic profiling of 186-406 genes, including KMT2A rearrangements, and a portion were evaluated for RNA of 265 genes. Clinical, molecular, and histologic features of all fusion-positive cases were characterized in both cohorts.

Two cohorts of thymomas were interrogated for KMT2A-MAML2 fusions:

Cohort 1: One Massachusetts general (MGH) Pathology thymoma case underwent solid fusion assay analysis (MGH Solid Fusion Assay; see Table 1, above, for list of gene targets) and single nucleotide variant (SNV) and insertion/deletion (indel) analysis (SNAPSHOT DNA-based Assay; see Table 2, above, for list of gene targets). The solid fusion assay utilized RNA-based fusion-targeted anchored multiplex polymerase chain reaction (PCR) and Illumina (San Diego, CA) sequencing. This case and an additional 40 thymoma cases from MGH Pathology archives were tested with FISH break-apart probe to detect MAML2 rearrangements (n=41). Reviews of pathology reports and histopathology (KG, AL, LRM), and patient clinical data (age at diagnosis, sex, site of tumor biopsy, stage at diagnosis, clinical course) were performed. Approval for this study, including a waiver of additional informed consent and a HIPAA waiver of authorization, was obtained from the Partners Institutional Review Board (Protocol No. 2011P001749).

Cohort 2: Formalin-fixed paraffin-embedded tissue from an additional 242 thymoma cases were tested as part of clinical care by hybridization capture of 186-406 cancer-related genes to detect base substitutions, small indels, gene amplifications (amp), and rearrangements (Foundation-One® [Frampton et al., *Development and validation of a clinical cancer genomic profiling test based on massively parallel DNA sequencing*. Nat Biotechnol, vol. 31, no. 11, pp. 1023-1031 (2013); Sun et al., *A computational approach to distinguish somatic vs. germline origin of genomic alterations from deep sequencing of cancer specimens without a matched normal*, PLoS Comput Biol, vol. 14, no. 2, e1005965 (2018); Chalmers et al., *Analysis of* 100,000 *human cancer genomes reveals the landscape of tumor mutational burden*, Genome Med, vol. 19, no. 9(1), pp. 34 (2017); Forbes et al., *COSMIC: Exploring the world's knowledge of somatic mutations in human cancer*, Nucleic Acids Res, vol. 43, no. D1, pp. D805-D811 (2015)]; see Tables 3-6, above, for a list of gene targets), and a portion were evaluated for RNA of 265 genes. A query of 255,008 cases including all categories of tumor (thymoma and non-thymoma) was performed to identify additional cases of KMT2A-MAML2 fusions. Reviews of pathology reports, histopathology (RPH, AL, LRM), and patient clinical data (age at diagnosis, sex, site of biopsy, stage at diagnosis) were performed on relevant cases. Approval for this study, including a waiver of additional informed consent and a HIPAA waiver of authorization, was obtained from the Western Institutional Review Board (Protocol No. 20152817). Data collection and analysis were performed under institutional review board-approved protocols.

Results

Herein, novel recurrent fusions in 11 cases of types B2 and B3 thymoma, involving the lysine methyltransferase 2A (KMT2A) and mastermind-like transcriptional coactivator 2 (MAML2) genes, are described.

Figure 1B:
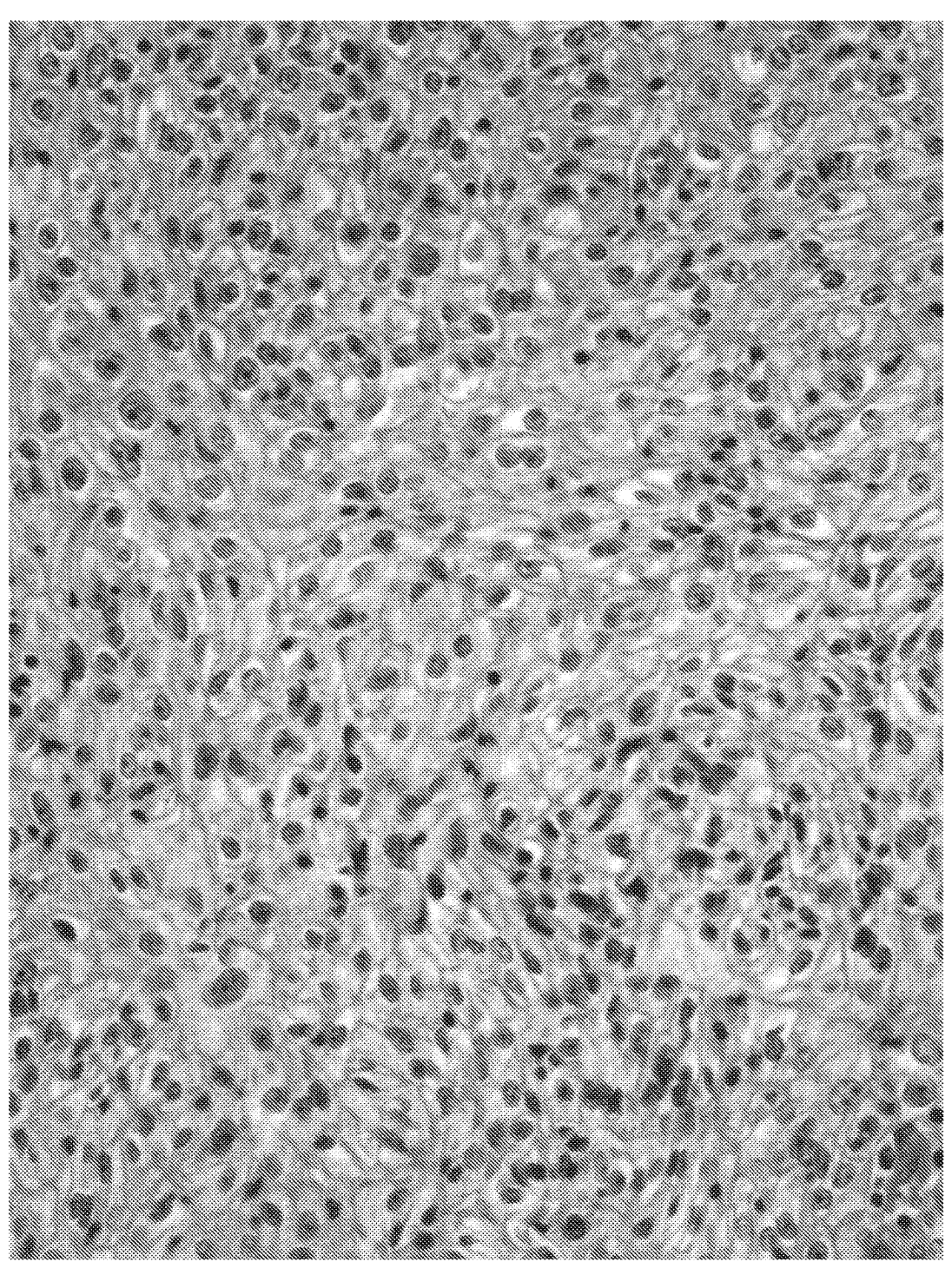
Figure 1C:
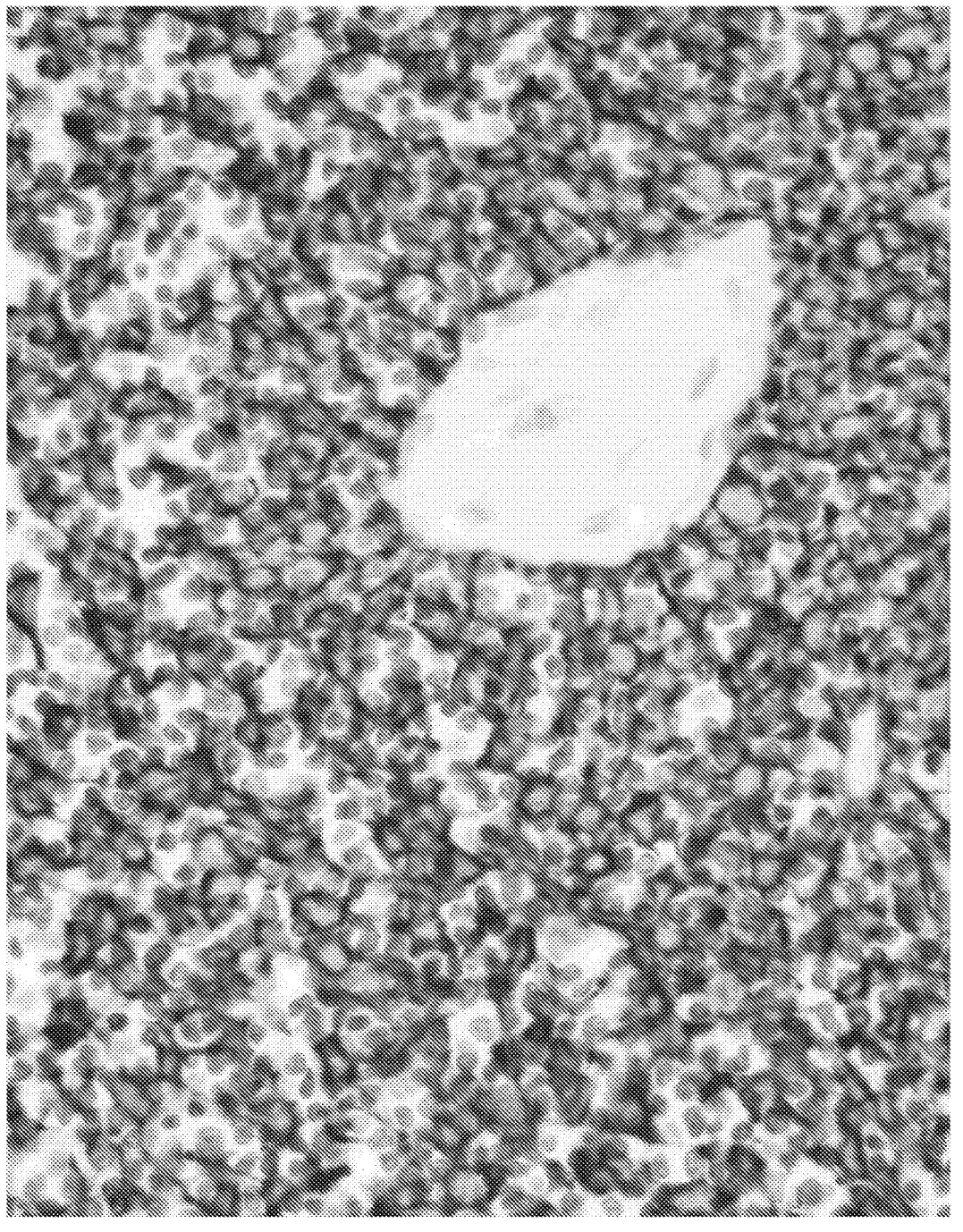
Figure 1D:
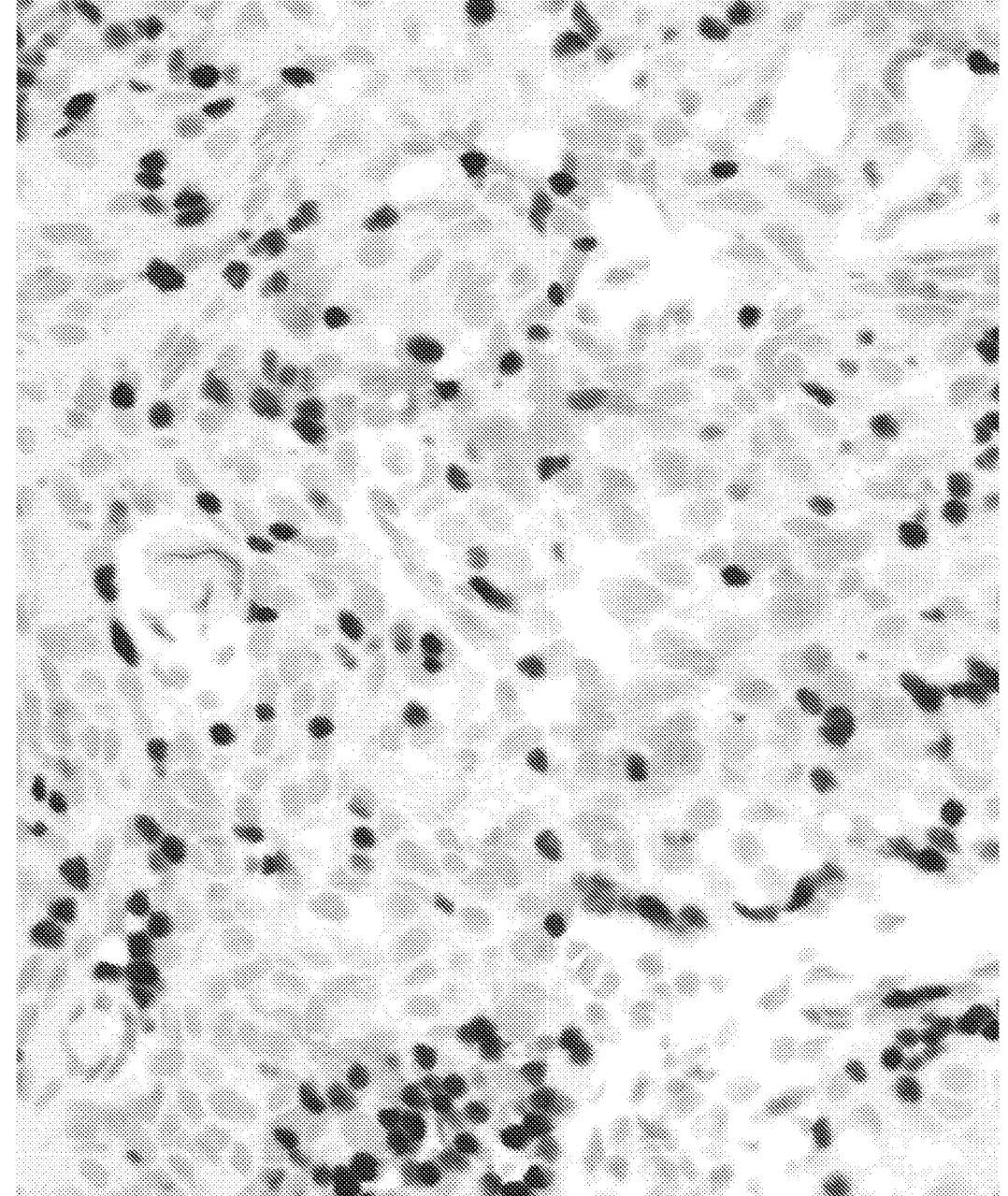

Index Case: Identification of Novel KMT2A-MAML2 Fusion in an Aggressive Type B3 Thymoma A 29-year-old female presented with a thymic mass soon after being diagnosed with myasthenia gravis. Upon surgical resection of the mass, histological review supported a diagnosis of type B2-B3 thymoma with apparently clear surgical margins. The patient's myasthenia gravis symptoms resolved post-operatively. The patient developed recurrent thymoma seven years later, with metastatic involvement of the lung, pericardium, distal left main pulmonary artery, as well as paratracheal lymph nodes (FIG. 1A). The patient received induction chemotherapy and underwent surgical resection (radical thymectomy, radical pericardiectomy, and left pneumonectomy), followed by paratracheal lymph node excision and radiation therapy. Histopathology was diagnostic of type B3 thymoma (FIGS. 1B-1D). The patient's thymoma recurred within one year, with progression despite additional radiation, chemotherapy, and multiple investigational drug therapies (MGCD516, BB1608 with paclitaxel, and sunitinib). Her clinical course was complicated by Good syndrome (a rare combined B- and T-cell immunodeficiency), pure red cell aplasia, paraneoplastic intestinal pseudo-obstruction, and a persistent recurrence of myasthenia gravis. The patient succumbed to complications of her thymoma fifteen years after the initial diagnosis.

Figure 2:
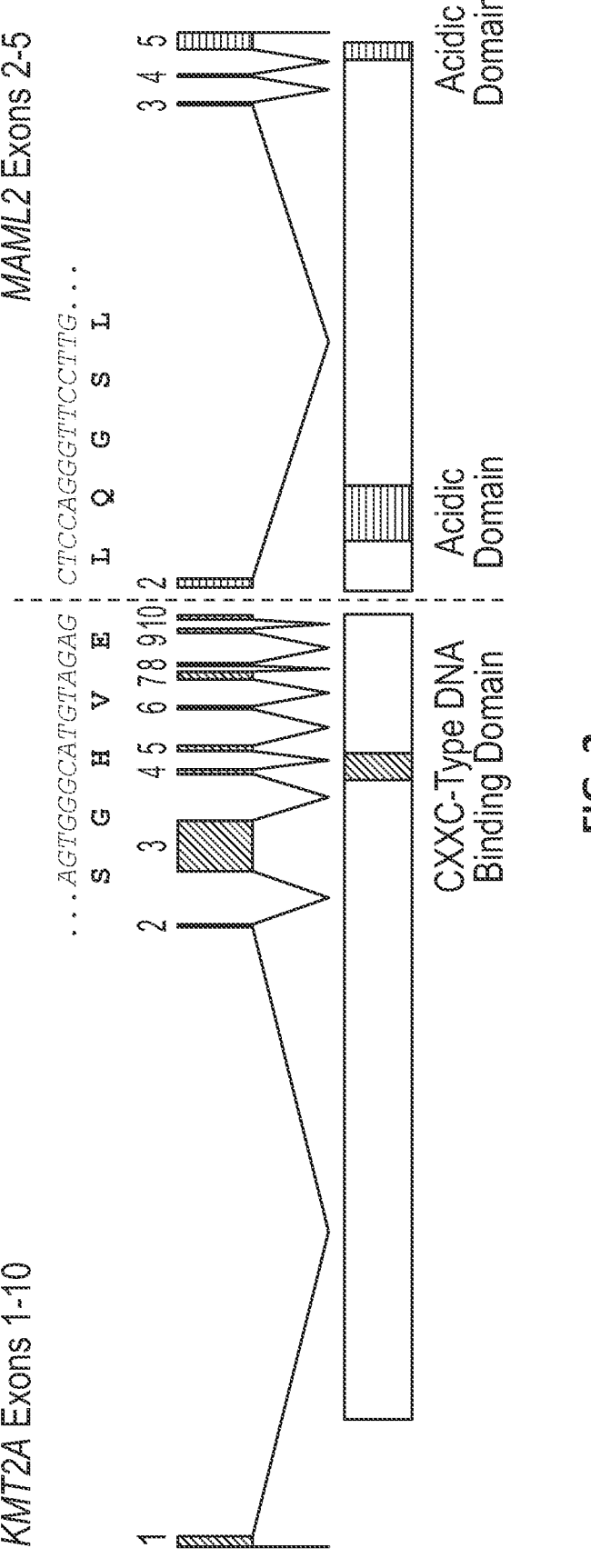
FIG. 2 provides a schematic of an exemplary KMT2A-MAML2 fusion from the index patient described in Example 1 and break-apart FISH probe for MAML2.

Given the unusually aggressive nature of this thymoma, molecular genetic assays were performed on the tumor sample during the care of this patient, in an attempt to identify genetic alterations that could potentially be targetable. This case was found to have an in-frame KMT2A-MAML2 rearrangement using a solid tumor fusion assay (SFA), an RNA-based fusion targeted Anchored Multiplex PCR and Illumina sequencing assay (FIG. 2). This fusion was validated by an orthogonal FISH assay for MAML2, which confirmed the KMT2A-MAML2 fusion.

KMT2A-MAML2 Fusions Occur in Aggressive Histological Subtypes of Thymoma

An additional 40 thymomas (total 41) from the MGH archives were interrogated, which included 2 type A, 1 type A-Micronodular variant (MNT), 1 MNT, 8 type AB, 6 type B1, 2 type B1-B2, 3 type B1-B3, 7 type B2, 7 type B2-B3, and 4 type B3 thymomas, with a total of 23 containing B2 and/or B3 components, were interrogated. The median age of the cohort was 55 years, and 59% were female. MAML2 fusion was not identified in any of the additional 40 thymoma cases beyond the index case.

To determine the frequency of KMT2A-MAML2 fusions in a cohort that is specifically enriched in clinically more aggressive cases of thymoma, the entire set of 242 thymoma cases from the Foundation Medicine archives were reviewed. The cohort included the following thymoma histologic subtypes: 8 type A (3%), 12 type AB (5%), 1 type AB-B1 (<1%), 43 type BI (18%), 10 type B1-B2 (4%), 66 type B2 (27%), 21 type B2-B3 (9%), and 72 type B3 (30%, including two cases with components of thymic carcinoma). An additional 9 (4%) cases were ungraded for technical reasons or unusual case features. The median age of the cohort was 53 years and 51% of patients were female (118/242). An in-frame KMT2A-MAML2 fusion was identified in ten cases (4.9%). The fusion was restricted to the most aggressive histologic thymoma subtypes, including 10/169 (5.9%) thymomas of type B2 or greater (type B2 and type B3), and 0/64 of the remaining thymomas (type A, type AB, type B1). No other known or likely pathogenic alterations were identified in 7/10 cases with KMT2A-MAML2, while a concurrent mutation in TP53, ARID1A, and SF3B1 was identified, each in one case, respectively. The clinical, histological and molecular features of all 11 KMT2A-MAML2 rearranged thymoma cases are shown in Table 7, Table 8, and Table 10. Table 8 shows mRNA breakpoint positions (and therefore represents exon-exon fusions), and Table 10 shows DNA breakpoint positions (which include exon-intron fusions and intron-intron fusions). In the combined cohort of graded thymomas, there is significant association of presence of the fusion with B2 or B3 histology (11/192 vs. 0/82, p=0.0375). A single case with KMT2A-MAML2 fusion showed foci of thymic carcinoma.

TABLE 7

Clinical Characteristics of Patients with KMT2A-MAML2-rearranged Thymomas.

| Characteristic | No. (%) |
|---|---|
| No. of patients | 11 |
| Median age at diagnosis, years (range) | 48 (29-69) |
| Sex | |
| Male | 6 (55) |
| Female | 5 (45) |
| Final staging (Modified Masaoka) | |
| 2b | 2 (18) |
| 4a | 2 (18) |
| 4b | 2 (18) |
| Unknown | 5 (45) |
| Histology | |
| B2 | 4 (36) |
| B3 | 6 (55) |
| B3 + C | 1 (9) |

TABLE 8

| Patient No. | Position of fusion | Histology subtype | Concurrent Genomic Alterations* | Molecular Assay |
|---|---|---|---|---|
| 1 (index) | KMT2A exon 10 to MAML2 exon 2 | B3 | TERT promoter variant c.-124C > T | MGH Solid Fusion, FISH, MGH Snapshot |
| 2 | KMT2A exon 8 to MAML2 exon 2 | B3 | None | FoundationOne |
| 3 | KMT2A exon 8 to MAML2 exon 2 | B3 | None | FoundationOne |
| 4 | KMT2A exon 9 to MAML2 exon 2 | B3 | TP53 p.E286D | FoundationOne |
| 5 | KMT2A exon 9 to MAML2 exon 2 | B3 + C | None | FoundationOne |
| 6 | KMT2A exon 9 to MAML2 exon 2 | B2 | ARID1A p.R1528 | FoundationOne |
| 7 | KMT2A exon 9 to MAML2 exon 2 | B2 | None | FoundationOne |
| 8 | KMT2A exon 10 to MAML2 exon 2 | B3 | None | FoundationOne |
| 9 | KMT2A exon 10 to MAML2 exon 2 | B2 | None | FoundationOne |
| 10 | KMT2A exon 11 to MAML2 exon 2 | B3 | None | FoundationOne |
| 11 | KMT2A exon 11 to MAML2 exon 2 | B2 | SF3B1 p.K700E | FoundationOne |

Molecular Characteristics of KMT2A-MAML2-rearranged Thymomas and mRNA Breakpoints Abbreviations: MGH, Massachusetts General Hospital; FISH, fluorescence in situ hybridization; C, thymic carcinoma.
*Variants of undetermined significant not shown.

A reverse query for KMT2A-MAML2 fusions was performed on >200,000 Foundation Medicine cases of all tumor categories. Only one additional case, diagnosed as plasmacytoma, was identified to harbor a KMT2A-MAML2 fusion. Tis case was reviewed and the original diagnosis was confirmed.

Discussion

In a cohort of nearly 300 cases of thymoma, recurrent fusions of KMT2A and MAML2 in approximately 4% of cases were discovered. This fusions were observed in adult thymomas with aggressive histologic features, as the thymoma cases harboring this fusion in these cohorts were of the more aggressive histologies (Type B2 and type B3, one with foci of thymic carcinoma). The striking restriction of KMT2A-MAML2 fusions to adult thymomas was underscored by the absence of this fusion in >200.000 case of diverse tumor types, with the exception of a single case of plasmacytoma.

KMT2A, first described in 1991, was initially termed mixed-lineage leukemia-1 (MLL-1) owing to its frequent appearance as a translocation partner in myeloid and lymphoid leukemias. See Ziemin-van der Poel et al., *Identification of a gene, MLL, that spans the breakpoint in 11q23 translocations associated with human leukemias*, Proc Natl. Acad. Sci. USA, vol. 88, pp. 10735-1073 (1991)). The 36-exon gene is located at 11q23. The encoded protein binds DNA and methylates histone H3 at lysine-4 (H3K4), to positively regulate other genes including several homeobox (HOX) genes (Milne et al., *MLL targets SET domain methyltransferase activity to Hox gene promoters*, Mol Cell, vol. 10, no. 5, pp. 1107-1117 (2002)).

MAML2 is a 5-exon gene residing on chromosome 11q21. MAML2, and other MAML family proteins, are involved in the NOTCH pathway mediated transcriptional activation (Köchert et al., *High-level expression of Master-mind-like 2 contributes to aberrant activation of the NOTCH signaling pathway in human lymphomas*, Oncogene, vol. 30, no. 15, pp. 1831-1840 (2011)). Recurrent gene rearrangements involving MAML2 have been described in mucoepidermoid carcinoma and clear cell hidradenoma, in which fusion of the first exon of the cAMP response element-binding protein (CREB) regulated transcription coactivator-1 (CRTC1) with MAML2 exons 2-5 leads to NOTCH pathway disruption (Tonon et al., t(11:19)(q21; p13) *translocation in mucoepidermoid carcinoma creates a novel fusion product that disrupts a Notch signaling pathway*, Nat Genet, vol. 33, pp. 208-213 (2003)).

The KMT2A-MAML2 gene fusion results from inv(11)(q21q23), a cytogenetic abnormality first reported in 1998 in a patient with therapy-related acute myeloid leukemia (AML) (Obama et al.. *Secondary monxcytic leukemia with rearrangement of the MU gene occurring during the course of adult T-cell leukemia*. Int J Hematol. 1998). Subsequent reports of the fusion are exceptionally rare, entirely limited to hematologic malignancies. To our knowledge, only 8 cases have been reported, including 2 cases of acute myeloid leukemia (AML), 2 cases of myelodysplastic syndrome (MDS), and 4 cases of acute lymphoblastic leukemia (ALL) (Obama et al., Secondary monocytic leukemia with rearrangement of the MLL gene occurring during the course of adult T-cell leukemia. *Int J Hematol.* 1998; Mariani R A et al.. Genetic Abnormality in T-Cell Therapy—related Acute Lymphoblastic Leukemia 2019; 00(00):21-24; Nemoto et al., *Identification of a novel fusion gene MLL-MAML2 in secondary acute myelogenous leukemia and myelodysplastic syndrome with inv*(11)(*q21q23*), Genes Chromosom Cancer, vol. 46, no. 9 (2007); Tang G et al.. Homozygous inv(11)(q21q23) and MLL gene rearrangement in two patients with myeloid neoplasms. *Int J Clin Exp Pathol.* 2014; Metzler M et al., *Inv*(11)(*q21q23*)*fuses MLL to the Notch co-activator mastermind-like 2 in secondary T-cell acute lymphoblastic leukemia*, Leukemia, vol. 22, no. 9, pp. 1807-1811 (2008); Menu E et al., *First case of B ALL with KMT2A-MAML2 rearrangement: A case report*, BMC Cancer, vol. 17 (2017)).

When reported, fusion proteins among these cases fell into the regions reported in our cohort, with the exception of two cases reported by Metlzer M et al., with MAML2 breakpoints in introns 2 and 3 (Metzler M et al., *Inv*(11)(*q*21*q*23) *fuses MLL to the Notch co-activator mastermind-like 2 in secondary T-cell acute lymphoblastic leukemia*, Leukemia, vol. 22, no. 9, pp. 1807-1811 (2008)).

Prior functional studies of the KMT2A-MAML2 construct have shown evidence of disrupted NOTCH pathway signaling. In addition to describing the fusion in cases of therapy-related myeloid neoplasms, Nemoto et al. performed a luciferase assay demonstrating the KMT2A-MAML2 fusion suppresses promoter activation of the NOTCH1 target gene, HES1 (Nemoto N et al., *Identification of a novel fission gene MLL-MAML2 in secondary acute myelogenous leukemia and myelodysplastic syndrome with inv*(11)(*q*21*q*23), Genes Chromosom Cancer, vol. 46, no. 9 (2007)). Gene expression profiles from two cases of KMT2A-MAML2-positive T-cell ALL cases showed differential expression patterns relative to controls that suggested activation of genes downstream of NOTCH1 (Metzler M et al., *Inv*(11)(*q*21*q*23) *fuses MLL to the Notch co-activator mastermind-like 2 in secondary T-cell acute lymphoblastic leukemia*, Leukemia, vol. 22, no. 9, pp. 1807-1811 (2008)). Another study demonstrated oncogenic activity by KMT2A-MAML2 fusions inserted into cell lines with sleeping-beauty vectors (Wachter K et al., *Functional characterisation of different MLL fusion proteins by using inducible Sleeping Beauty vectors*, Cancer Lett, vol. 352, no. 2, pp. 196-202 (2014)). The sum of these studies demonstrates oncogenic function of the KMT2A-MAML2 fusion may occur via disruption of NOTCH signaling.

In patients with malignancies not amenable to traditional surgical or chemoradiative protocols, targeted therapy offers an additional potential opportunity for disease control. The finding of recurrent KMT2A-MAML2 fusions in a subset of thymomas predisposed to aggressive behavior may offer a future target in patients with high-stage disease refractory to initial therapy. Early data suggests that MAML2 fusion-positive mucoepidermoid carcinoma may respond to targeted therapeutics (O'Neill I D, *Gefitinib as targeted therapy for mucoepidermoid carcinoma of the lung: Possible significance of CRTC1-MAML2 oncogene*, Lung Cancer, vol. 64, no. 1, pp. 129-130 (2009); Chen Z et al., *Aberrantly activated AREG-EGFR signaling is required for the growth and survival of CRTC1-MAML2 fusion-positive mucoepidermoid carcinoma cells*, Oncogene, vol. 33, pp. 3869-3877 (2014); Li S et al., *Pathological complete response to gefitinib in a 10-year-old boy with EGFR-negative pulmonary mucoepidermoid carcinoma: a case report and literature review*, Clin Respir J, vol. 11, no. 3 (2017)).

Overall, the results described in this Example show the presence of a gene fusion of lysine methyltransferase 2A (KMT2A) and mastermind-like transcriptional coactivator 2 (MAML2) in 12 patients [11 with thymoma and one with plasmacytoma] that harbor a gene fusion of lysine methyltransferase 2A (KMT2A) and mastermind-like transcriptional coactivator 2 (MAML2). Fusion breakpoints were identified between exons 8, 9, 10 or 11 of KMT2A and exon 2 of MAML2. Of the thymomas, fifty-five percent were male, with a median age of 48 years at surgery (range, 29 years to 69 years). Concurrent genomic alterations were infrequent. The eleven thymomas were of B2 (n=4) and B3 type (n=7), with a single B3 case showing foci of thymic carcinoma. The frequency of KMT2A-MAML2 fusion was 4% of all thymomas (11/283) and 6% of thymomas of B2 or B3 histology (11/192), with significant association of the fusion with B2 or B3 histology among thymomas (p=0.038).

To our knowledge, KMT2A-MAML2 represents the first recurrent fusion described in thymoma. The fusion is specific to B2 and B3 thymomas, the most aggressive histologic subtypes. The identification of this fusion offers insights into the biology of thymoma and has clinical relevance for patients with disease refractory to conventional therapeutic modalities.

Given the low tumor mutational burden seen in thymoma, identification of this small but significant subset of KMT2A-MAML2-positive tumors provides a therapeutic target for cases not amenable to traditional therapy. This finding illustrates the importance of performing comprehensive genomic profiling to define treatment strategies, including molecular inclusion criteria for clinical trials and more fully informed personalized therapeutic options.

REFERENCES

1. Engels E A. Epidemiology of thymoma and associated malignancies. *J Thorac Oncol.* 2010. doi:10.1097/JTO.0b013e3181f1f62d
2. Scorsetti M, Leo F, Trama A. et al. Critical Reviews in Oncology/Hematology Thymoma and thymic carcinomas. *Crit Rev Oncol/Hematol.* 2016; 99:332-350. doi:10.1016/j.critrevonc.2016.01.012
3. Radovich M, Pickering C R, Felau I, et al. The Integrated Genomic Landscape of Thymic Epithelial Tumors. *Cancer Cell.* 2018:33(2):244-258.e10. doi:10.1016/j.ccell.2018.01.003
4. Petrini I, Meltzer P S, Kim I K, et al. A specific missense mutation in GTF2I occurs at high frequency in thymic epithelial tumors. *Nat Genet.* 2014; 46(8):844-849. doi:10.1038/ng.3016
5. Chen Y. Gharwan H. Thomas A. Novel Biologic Therapies for Thymic Epithelial Tumors. *Front Oncol.* 2014:4 (May):1-3. doi:10.3389/fonc.2014.00103
6. Thomas A, Rajan A, Berman A, et al. Sunitinib in patients with chemotherapy-refractory thymoma and thymic carcinoma: An open-label phase 2 trial. *Lancet Oncol.* 2015. doi:10.1016/S1470-2045(14)71181-7
7. Petrini I, Rajan A, Pham T, et al. Whole Genome and Transcriptome Sequencing of a B3 Thymoma. *PLoS One.* 2013; 8(4). doi:10.1371/journal.pone.0060572
8. Frampton G M, Fichtenholtz A, Otto G A, et al. Development and validation of a clinical cancer genomic profiling test based on massively parallel DNA sequencing. *Nat Biotechnol.* 2013. doi:10.1038/nbt.2696
9. Sun J X, He Y, Sanford E, et al. A computational approach to distinguish somatic vs. germline origin of genomic alterations from deep sequencing of cancer specimens without a matched normal. *PLoS Pathog.* 2018. doi:10.1371/journal.pcbi.1005965
10. Chalmers Z R, Connelly C F, Fabrizio D, et al. Analysis of 100,000 human cancer genomes reveals the landscape of tumor mutational burden. *Genome Med.* 2017. doi:10.1186/s13073-017-0424-2
11. Forbes S A, Beare D, Gunasekaran P, et al. COSMIC: Exploring the world's knowledge of somatic mutations in human cancer. *Nucleic Acids Res.* 2015. doi:10.1093/nar/gku1075
12. Ziemin-van der Poel S, McCabe N R, Gill H J, Espinosa R 3rd, Patel Y, Harden A, Rubinelli P, Smith S D, LeBeau M M, Rowley J D et al. Identification of a gene. MLL, that spans the breakpoint in 11q23 translocations associated with human leukemias. *Proc Natl Acad Sci USA.* 1991.

13. Milne T A, Briggs S D, Brock H W, et al. MLL targets SET domain methyltransferase activity to Hox gene promoters. *Mol Cell.* 2002; 10(5):1107-1117. doi:10.1016/S1097-2765(02)00741-4

14. Winters A C, Bemt K M. MLL-Rearranged Leukemias—An Update on Science and Clinical Approaches. *Front Pediatr.* 2017; 5(February):11-13. doi:I0.3389/fped.2017.00004

15. Köchert K, Ullrich K, Kreher S, et al. High-level expression of Mastermind-like 2 contributes to aberrant activation of the NOTCH signaling pathway in human lymphomas. *Oncogene.* 2011; 30(15):1831-1840. doi:10.1038/onc.2010.544

16. Tonon G, Modi S, Wu L, et al. t(11; 19)(q21; p13) translocation in mucoepidermoid carcinoma creates a novel fusion product that disrupts a Notch signaling pathway. *Nat Genet.* 2003. doi:10.1038/ng1083

17. Obama K, Furukawa Y, Tara M, Niina K. Secondary monocytic leukemia with rearrangement of the MLL gene occurring during the course of adult T-cell leukemia. *Int J Hematol.* 1998.

18. Mariani R A, Silva M, Caparelli E, et al. Genetic Abnormality in T-Cell Therapy—related Acute Lymphoblastic Leukemia. 2019; 00(00):21-24.

19. Nemoto N, Suzukawa K. Shimizu S. et al. Identification of a novel fusion gene MLL-MAML2 in secondary acute myelogenous leukemia and myelodysplastic syndrome with inv(11)(q21q23). *Genes Chromosom Cancer.* 2007. doi:10.1002/gcc.20467

20. Tang G, Lu X, Wang S A, et al. Homozygous inv(11) (q21q23) and MLL gene rearrangement in two patients with myeloid neoplasms. *Int J Clin Exp Pathol.* 2014.

21. Metzler M, Staege M S, Harder L, et al. Inv(11 xq21q23) fuses MLL to the Notch co-activator mastermind-like 2 in secondary T-cell acute lymphoblastic leukemia. *Leukemia.* 2008:22(9):1807-1811. doi:10.1038/leu.2008.50

22. Menu E, Beaufils N, Usseglio F, et al. First case of B ALL with KMT2A-MAML2 rearrangement: A case report. *BMC Cancer.* 2017; 17(1):2-6. doi:10.1186/s12885-017-3368-4

23. Wachter K, Kowarz E, Marschalek R. Functional characterisation of different MLL fusion proteins by using inducible Sleeping Beauty vectors. *Cancer Lett.* 2014; 352(2):196-202. doi:10.1016/j.canlet.2014.06.016

24. O'Neill I D. Gefitinib as targeted therapy for mucoepidermoid carcinoma of the lung: Possible significance of CRTC1-MAML2 oncogene. *Lung Cancer.* 2009; 64(1): 129-130. doi:10.1016/j.lungcan.2009.01.003

25. Chen Z, Chen J, Gu Y, et al. Aberrantly activated AREG-EGFR signaling is required for the growth and survival of CRTC1-MAML2 fusion-positive mucoepidermoid carcinoma cells. *Oncogene.* 2014. doi:10.1038/onc.2013.348

26. Li S, Zhang Z, Tang H, et al. Pathological complete response to gefitinib in a 10-year-old boy with EGFR-negative pulmonary mucoepidermoid carcinoma: a case report and literature review. *Clin Respir J.* 2017. doi:10.1111/crj.12343

KMT2A-MAML2 DNA Breakpoints

| Patient | 5'-Gene | 5'-Sequence | 3'-Gene | 3'-Sequence |
|---|---|---|---|---|
| 3 | KMT2A | AGAGGAAGTAATTCCTTCACATGGA AAGTATCAAACCATGATGATTCCTT (SEQ ID NO: 7) | MAML2 | TTATACACACATACACACATATACATAGAAA AATGTATATAATACATATT (SEQ ID NO: 8) |
| 3 (Reciprocal) | MAML2 | TTTGTTTGCTTGGTTATCTTCTCTTAT ATAACCCAGCACTCTTAGCAAAT (SEQ ID NO: 9) | KMT2A | TATCAAACCATGATGATTCCTTGAGTCAGCA AAACTGTAAGAGAAATTCA (SEQ ID NO: 10) |
| 4 | KMT2A | AAATACTCTGACATTGTGATGTCAC ACTAATTTTATGCTTTTCATCCTTA (SEQ ID NO: 11) | MAML2 | CTTTGGCCAGCCAGCTCTGATTAGGCCCCCA AGCCATTTTTCAGCCCCAA (SEQ ID NO: 12) |
| 5 | KMT2A | AGTCCGTGTCTGAGATTAAAACTTTT TAAAGCAGCAGTTATTTTTGGACT (SEQ ID NO: 13) | MAML2 | TCCATGTTGGCTTTTAAAGTTTCCTCTTAACA AATTTTCAGTGTGAAATC (SEQ ID NO: 14) |
| 6 | KMT2A | TTACATAGTCATTGCTTAATGAATAT GTATTGAATTAAATATATGCCAGT (SEQ ID NO: 15) | MAML2 | ATTGTATCCCAGGTAGAGGATCTTATTTAAA CACACACACACACACACAC (SEQ ID NO: 16) |
| 6 (Reciprocal) | MAML2 | ATGAATTGTGATATTTATTTTTTTTTT AAGTTAAAGAGTACAAAATTGTA (SEQ ID NO: 17) | KMT2A | GAAGGGTATGGTTGATTATGTTTTTCTACAT ATTATTTGACATACTTCTA (SEQ ID NO: 18) |
| 7 | KMT2A | GGAATCTTGACTTCTGTTCCTATAAC ACCCAGGGTGGTTTGCTTTCTCTG (SEQ ID NO: 19) | MAML2 | GAAGCAACTGGGATGAACTATTTATCTTCCT GATCACTGCAAGGAAACAC (SEQ ID NO: 20) |
| 8 | KMT2A | TGTTCCTATAACACCCAGGGTGGTTT GCTTTCTCTGTGCCAGTACTTGGGC (SEQ ID NO: 21) | MAML2 | TCAAGTTGCTTTTGTAATTGGGAAGCTAGGA GGTGATGTATTTTGCTAAG (SEQ ID NO: 22) |
| 9 | KMT2A | TTTCCTAAGTGACCTTTCTCTCTCCA CAGGAGGATTGTGAAGCAGAAAAT (SEQ ID NO: 23) | MAML2 | AATTTCAGTCTCTTCTTACATATGTTTATTGA GGAAGAATTGAAAGGAGC (SEQ ID NO: 24) |
| 10 | KMT2A | GCGCCCTCTGGAGGACCAGCTGGAA AATTGGTGTTGTCGTCGTTGCAAAT (SEQ ID NO: 25) | MAML2 | ATCTGTAAATAAACTATGATTTTTCACCAAA TCTTGGAGTGTATAGGACT (SEQ ID NO: 26) |

| KMT2A-MAML2 DNA Breakpoints | | | | |
| --- | --- | --- | --- | --- |
| Patient | 5'-Gene | 5'-Sequence | 3'-Gene | 3'-Sequence |
| 11 | KMT2A | TTGGAAAATTGGTGTTGTCGTCGTTGC AAATTCTGTCACGTTTGTGGAAGG (SEQ ID NO: 27) | MAML2 | ACCTCAGGTGATCCGCCTGCCTTGGCCTCCC AAAGTACTGGGATTACAAG (SEQ ID NO: 28) |

SEQUENCE LISTING

<160> NUMBER OF SEQ ID NOS: 28

<210> SEQ ID NO 1
<211> LENGTH: 16591
<212> TYPE: DNA
<213> ORGANISM: Homo sapiens

<400> SEQUENCE: 1

```
gcttcacttc acggggcgaa catggcgcac agctgtcggt ggcgcttccc cgcccgaccc        60
gggaccaccg ggggcggcgg cggcggggggg cgccggggcc tagggggcgc cccgcggcaa       120
cgcgtcccgg ccctgctgct tcccccccggg ccccccggtcg gcggtggcgg ccccgggggcg      180 ccccccctccc ccccggctgt ggcggccgcg gcggcggcgg cgggaagcag cggggctggg       240
gttccagggg gagcggccgc cgcctcagca gcctcctcgt cgtccgcctc gtcttcgtct        300
tcgtcatcgt cctcagcctc ttcagggccg gccctgctcc gggtgggccc gggcttcgac        360
gcggcgctgc aggtctcggc cgccatcggc accaacctgc gccggttccg ggccgtgttt        420
ggggagagcg gcgggggagg cggcagcgga gaggatgagc aattcttagg ttttggctca        480
gatgaagaag tcagagtgcg aagtcccaca aggtctcctt cagttaaaac tagtcctcga        540
aaacctcgtg ggagacctag aagtggctct gaccgaaatt cagctatcct ctcagatcca        600
tctgtgtttt ccctctaaa taaatcagag accaaatctg gagataagat caagaagaaa        660
gattctaaaa gtatagaaaa gaagagagga agacctccca ccttccctgg agtaaaaatc        720
aaaataacac atggaaagga catttcagag ttaccaaagg gaaacaaaga agatagcctg        780 aaaaaaaatta aaaggacacc ttctgctacg tttcagcaag ccacaaagat taaaaaatta       840
agagcaggta aactctctcc tctcaagtct aagtttaaga cagggaagct tcaaatagga        900
aggaaggggg tacaaattgt acgacggaga ggaaggcctc catcaacaga aaggataaag        960
accccttcgg gtctcctcat taattctgaa ctggaaaagc cccagaaagt ccggaaagac       1020
aaggaaggaa cacctccact tacaaaagaa gataagacag ttgtcagaca aagccctcga       1080
aggattaagc cagttaggat tattccttct tcaaaaagga cagatgcaac cattgctaag       1140
caactcttac agagggcaaa aaaggggggct caaaagaaaa ttgaaaaaga agcagctcag       1200
ctgcagggaa gaaaggtgaa gacacaggtc aaaaatattc gacagttcat catgcctgtt       1260
gtcagtgcta tctcctcgcg gatcattaag accccctcggc ggtttataga ggatgaggat       1320
tatgaccctc caattaaaat tgcccgatta gagtctacac cgaatagtag attcagtgcc       1380
ccgtcctgtg gatcttctga aaaatcaagt gcagcttctc agcactcctc tcaaatgtct       1440
tcagactcct ctcgatctag tagccccagt gttgatacct ccacagactc tcaggcttct       1500
gaggagattc aggtacttcc tgaggagcgg agcgataccc ctgaagttca tcctccactg       1560
cccatttccc agtccccaga aaatgagagt aatgatagga gaagcagaag gtattcagtg       1620
tcggagagaa gttttggatc tagaacgacg aaaaaattat caactctaca aagtgcccc       1680
```

-continued

```
cagcagcaga cctcctcgtc tccacctcca cctctgctga ctccaccgcc accactgcag   1740
ccagcctcca gtatctctga ccacacacct tggcttatgc ctccaacaat ccccttagca   1800
tcaccatttt tgcctgcttc cactgctcct atgcaaggga agcgaaaatc tattttgcga   1860
gaaccgacat ttaggtggac ttctttaaag cattctaggt cagagccaca atactttttcc  1920 tcagcaaagt atgccaaaga aggtcttatt cgcaaaccaa tatttgataa tttccgaccc   1980
cctccactaa ctccccgagga cgttggcttt gcatctggtt tttctgcatc tggtaccgct   2040
gcttcagccc gattgttttc gccactccat tctggaacaa ggtttgatat gcacaaaagg   2100
agccctcttc tgagagctcc aagatttact ccaagtgagg ctcactctag aatatttgag   2160
tctgtaacct tgcctagtaa tcgaacttct gctggaacat cttcttcagg agtatccaat   2220
agaaaaagga aaagaaaagt gtttagtcct attcgatctg aaccaagatc tccttctcac   2280
tccatgagga caagaagtgg aaggcttagt agttctgagc tctcacctct cacccccccg   2340
tcttctgtct cttcctcgtt aagcattttct gttagtcctc ttgccactag tgccttaaac   2400
ccaactttta cttttccttc tcattccctg actcagtctg gggaatctgc agagaaaaat   2460
cagagaccaa ggaagcagac tagtgctccg gcagagccat tttcatcaag tagtcctact   2520
cctctcttcc cttggtttac cccaggctct cagactgaaa gagggagaaa taaagacaag   2580
gcccccgagg agctgtccaa agatcgagat gctgacaaga gcgtggagaa ggacaagagt   2640
agagagagag accgggagag agaaaaggag aataagcggg agtcaaggaa agagaaaagg   2700
aaaaagggat cagaaattca gagtagttct gctttgtatc ctgtgggtag ggtttccaaa   2760
gagaaggttg ttggtgaaga tgttgccact tcatcttctg ccaaaaaagc aacagggcgg   2820
aagaagtctt catcacatga ttctgggact gatattactt ctgtgactct tggggataca   2880
acagctgtca aaaccaaaat acttataaag aaagggagag gaaatctgga aaaaaccaac   2940
ttggacctcg gcccaactgc cccatccctg gagaaggaga aaaccctctg cctttccact   3000
ccttcatcta gcactgttaa acattccact tcctccatag gctccatgtt ggctcaggca   3060
gacaagcttc caatgactga caagagggtt gccagcctcc taaaaaaggc caaagctcag   3120
ctctgcaaga ttgagaagag taagagtctt aaacaaaccg accagcccaa agcacagggt   3180
caagaaagtg actcatcaga gacctctgtg cgaggacccc ggattaaaca tgtctgcaga   3240
agagcagctg ttgcccttgg ccgaaaacga gctgtgtttc ctgatgacat gcccaccctg   3300
agtgccttac catgggaaga acgagaaaag attttgtctt ccatggggaa tgatgacaag   3360
tcatcaattg ctggctcaga agatgctgaa cctcttgctc cacccatcaa accaattaaa   3420
cctgtcacta gaaacaaggc accccaggaa cctccagtaa agaaaggacg tcgatcgagg   3480
cggtgtgggc agtgtcccgg ctgccaggtg cctgaggact gtggtgtttg tactaattgc   3540
ttagataagc ccaagtttgg tggtcgcaat ataaagaagc agtgctgcaa gatgagaaaa   3600
tgtcagaatc tacaatggat gccttccaaa gcctacctgc agaagcaagc taaagctgtg   3660
aaaaagaaag agaaaaagtc taagaccagt gaaaagaaag acagcaaaga gagcagtgtt   3720
gtgaagaacg tggtggactc tagtcagaaa cctaccccat cagcaagaga ggatcctgcc   3780
ccaaagaaaa gcagtagtga gcctcctcca cgaaagcccg tcgaggaaaa gagtgaagaa   3840
gggaatgtct cggcccctgg gcctgaatcc aaacaggcca ccactccagc ttccaggaag   3900
tcaagcaagc aggtctccca gccagcactg gtcatcccgc ctcagccacc tactacagga   3960
ccgccaagaa aagaagttcc caaaaccact cctagtgagc caagaaaaaa gcagcctcca   4020
ccaccagaat caggtccaga gcagagcaaa cagaaaaaag tggctccccg cccaagtatc   4080
```

-continued

```
cctgtaaaac aaaaaccaaa agaaaaggaa aaaccacctc cggtcaataa gcaggagaat    4140
gcaggcactt tgaacatcct cagcactctc tccaatggca atagttctaa gcaaaaaatt    4200
ccagcagatg gagtccacag gatcagagtg gactttaagg aggattgtga agcagaaaat    4260
gtgtgggaga tgggaggctt aggaatcttg acttctgttc ctataacacc cagggtggtt    4320
tgctttctct gtgccagtag tgggcatgta gagtttgtgt attgccaagt ctgttgtgag    4380
cccttccaca agttttgttt agaggagaac gagcgccctc tggaggacca gctggaaaat    4440
tggtgttgtc gtcgttgcaa attctgtcac gtttgtggaa ggcaacatca ggctacaaag    4500
cagctgctgg agtgtaataa gtgccgaaac agctatcacc ctgagtgcct gggaccaaac    4560
taccccacca aacccacaaa gaagaagaaa gtctggatct gtaccaagtg tgttcgctgt    4620
aagagctgtg gatccacaac tccaggcaaa gggtgggatg cacagtggtc tcatgatttc    4680
tcactgtgtc atgattgcgc caagctcttt gctaaaggaa acttctgccc tctctgtgac    4740
aaatgttatg atgatgatga ctatgagagt aagatgatgc aatgtggaaa gtgtgatcgc    4800
tgggtccatt ccaaatgtga gaatctttca gatgagatgt atgagattct atctaatctg    4860
ccagaaagtg tggcctacac ttgtgtgaac tgtactgagc ggcaccctgc agagtggcga    4920
ctggcccttg aaaaagagct gcagatttct ctgaagcaag ttctgacagc tttgttgaat    4980
tctcggacta ccagccattt gctacgctac cggcaggctg ccaagcctcc agacttaaat    5040
cccgagacag aggagagtat accttcccgc agctcccccg aaggacctga tccaccagtt    5100
cttactgagg tcagcaaaca ggatgatcag cagcctttag atctagaagg agtcaagagg    5160
aagatggacc aagggaatta cacatctgtg ttggagttca gtgatgatat tgtgaagatc    5220
attcaagcag ccattaattc agatggagga cagccagaaa ttaaaaaagc caacagcatg    5280
gtcaagtcct tcttcattcg gcaaatggaa cgtgtttttc catggttcag tgtcaaaaag    5340
tccaggtttt gggagccaaa taaagtatca agcaacagtg ggatgttacc aaacgcagtg    5400
cttccacctt cacttgacca taattatgct cagtggcagg agcgagagga aaacagccac    5460
actgagcagc ctcctttaat gaagaaaatc attccagctc ccaaacccaa aggtcctgga    5520
gaaccagact caccaactcc tctgcatcct cctacaccac caattttgag tactgatagg    5580
agtcgagaag acagtccaga gctgaaccca cccccaggca tagaagacaa tagacagtgt    5640
gcgttatgtt tgacttatgg tgatgacagt gctaatgatg ctggtcgttt actatatatt    5700
ggccaaaatg agtggacaca tgtaaattgt gctttgtggt cagcggaagt gtttgaagat    5760
gatgacggat cactaaagaa tgtgcatatg gctgtgatca ggggcaagca gctgagatgt    5820
gaattctgcc aaaagccagg agccaccgtg ggttgctgtc tcacatcctg caccagcaac    5880
tatcacttca tgtgttccg agccaagaac tgtgtctttc tggatgataa aaaagtatat    5940
tgccaacgac atcgggattt gatcaaaggc gaagtggttc ctgagaatgg atttgaagtt    6000
ttcagaagag tgtttgtgga ctttgaagga atcagcttga gaaggaagtt tctcaatggc    6060
ttggaaccag aaaaatatcca catgatgatt gggtctatga caatcgactg cttaggaatt    6120
ctaaatgatc tctccgactg tgaagataag ctctttccta ttggatatca gtgttccagg    6180
gtatactgga gcaccacaga tgctcgcaag cgctgtgtat atacatgcaa gatagtggag    6240
tgccgtcctc cagtcgtaga gccggatatc aacagcactg ttgaacatga tgaaaacagg    6300
accattgccc atagtccaac atcttttaca gaaagttcat caaaagagag tcaaaacaca    6360
gctgaaatta taagtcctcc atcaccagac cgacctcctc attcacaaac ctctggctcc    6420
```

-continued

```
tgttattatc atgtcatctc aaaggtcccc aggattcgaa cacccagtta ttctccaaca      6480
cagagatccc ctggctgtcg accgttgcct tctgcaggaa gtcctacccc aaccactcat      6540
gaaatagtca cagtaggtga tcctttactc tcctctggac ttcgaagcat tggctccagg      6600
cgtcacagta cctcttcctt atcaccccag cggtccaaac tccggataat gtctccaatg      6660
agaactggga atacttactc taggaataat gtttcctcag tctccaccac cgggaccgct      6720
actgatcttg aatcaagtgc caaagtagtt gatcatgtct tagggccact gaattcaagt      6780
actagtttag ggcaaaacac ttccacctct tcaaatttgc aaaggacagt ggttactgta      6840
ggcaataaaa acagtcactt ggatggatct tcatcttcag aaatgaagca gtccagtgct      6900
tcagacttgg tgtccaagag ctcctcttta aagggagaga agaccaaagt gctgagttcc      6960
aagagctcag agggatctgc acataatgtg gcttaccctg gaattcctaa actggcccca      7020
caggttcata acacaacatc tagagaactg aatgttagta aaatcggctc ctttgctgaa      7080
ccctcttcag tgtcgttttc ttctaaagag gccctctcct tcccacacct ccatttgaga      7140
gggcaaagga atgatcgaga ccaacacaca gattctaccc aatcagcaaa ctcctctcca      7200
gatgaagata ctgaagtcaa aaccttgaag ctatctggaa tgagcaacag atcatccatt      7260
atcaacgaac atatgggatc tagttccaga gataggagac agaaagggaa aaaatcctgt      7320
aaagaaactt tcaaagaaaa gcattccagt aaatcttttt tggaacctgg tcaggtgaca      7380
actggtgagg aaggaaactt gaagccagag tttatggatg aggttttgac tcctgagtat      7440
atgggccaac gaccatgtaa caatgtttct tctgataaga ttggtgataa aggcctttct      7500
atgccaggag tccccaaagc tccacccatg caagtagaag gatctgccaa ggaattacag      7560
gcaccacgga aacgcacagt caaagtgaca ctgacacctc taaaaatgga aaatgagagt      7620
caatccaaaa atgccctgaa agaaagtagt cctgcttccc ctttgcaaat agagtcaaca      7680
tctcccacag aaccaatttc agcctctgaa aatccaggag atggtccagt ggcccaacca      7740
agccccaata tacctcatg ccaggattct caaagtaaca actatcagaa tcttccagta      7800
caggacagaa acctaatgct tccagatggc cccaaacctc aggaggatgg ctcttttaaa      7860
aggaggtatc cccgtcgcag tgcccgtgca cgttctaaca tgtttttggg gcttaccccca     7920 ctctatggag taagatccta tggtgaagaa gacattccat tctacagcag ctcaactggg      7980
aagaagcgag gcaagagatc agctgaagga caggtggatg gggccgatga cttaagcact      8040
tcagatgaag acgacttata ctattacaac ttcactagaa cagtgatttc ttcaggtgga      8100
gaggaacgac tggcatccca taatttattt cgggaggagg aacagtgtga tcttccaaaa      8160
atctcacagt tggatggtgt tgatgatggg acagagagtg atactagtgt cacagccaca      8220
acaaggaaaa gcagccagat tccaaaaaga aatggtaaag aaaatggaac agagaactta      8280
aagattgata gacctgaaga tgctggggag aaagaacatg tcactaagag ttctgttggc      8340
cacaaaaatg agccaaagat ggataactgc cattctgtaa gcagagttaa aacacaggga      8400
caagattcct tggaagctca gctcagctca ttggagtcaa gccgcagagt ccacacaagt      8460
accccctccg acaaaaattt actggacacc tataatactg agctcctgaa atcagattca      8520
gacaataaca acagtgatga ctgtgggaat atcctgcctt cagacattat ggactttgta      8580
ctaaagaata ctccatccat gcaggctttg ggtgagagcc cagagtcatc ttcatcagaa      8640
ctcctgaatc ttggtgaagg attgggtctt gacagtaatc gtgaaaaaga catgggtctt      8700
tttgaagtat tttctcagca gctgcctaca acagaacctg tggatagtag tgtctcttcc      8760
tctatctcag cagaggaaca gtttgagttg cctctagagc taccatctga tctgtctgtc      8820
```

```
ttgaccaccc ggagtcccac tgtccccagc cagaatccca gtagactagc tgttatctca    8880
gactcagggg agaagagagt aaccatcaca gaaaaatctg tagcctcctc tgaaagtgac    8940
ccagcactgc tgagcccagg agtagatcca actcctgaag gccacatgac tcctgatcat    9000
tttatccaag gacacatgga tgcagaccac atctctagcc ctccttgtgg ttcagtagag    9060
caaggtcatg gcaacaatca ggatttaact aggaacagta gcacccctgg ccttcaggta    9120
cctgtttccc caactgttcc catccagaac cagaagtatg tgcccaattc tactgatagt    9180
cctggcccgt ctcagatttc caatgcagct gtccagacca ctccacccca cctgaagcca    9240
gccactgaga aactcatagt tgttaaccag aacatgcagc cactttatgt tctccaaact    9300
cttccaaatg gagtgaccca aaaaatccaa ttgacctctt ctgttagttc tacacccagt    9360
gtgatggaga caaatacttc agtattggga cccatgggag gtggtctcac ccttaccaca    9420
ggactaaatc caagcttgcc aacttctcaa tctttgttcc cttctgctag caaaggattg    9480
ctacccatgt ctcatcacca gcacttacat tccttccctg cagctactca aagtagtttc    9540
ccaccaaaca tcagcaatcc tccttcaggc ctgcttattg gggttcagcc tcctccggat    9600
ccccaacttt tggtttcaga atccagccag aggacagacc tcagtaccac agtagccact    9660
ccatcctctg gactcaagaa aagacccata tctcgtctac agacccgaaa gaataaaaaa    9720
cttgctccct ctagtacccc ttcaaacatt gcccttctg atgtggtttc taatatgaca    9780
ttgattaact tcacaccctc ccagcttcct aatcatccaa gtctgttaga tttggggtca    9840
cttaatactt catctcaccg aactgtcccc aacatcataa aaagatctaa atctagcatc    9900
atgtattttg aaccggcacc cctgttacca cagagtgtgg gaggaactgc tgccacagcg    9960
gcaggcacat caacaataag ccaggatact agccacctca catcagggtc tgtgtctggc    10020
ttggcatcca gttcctctgt cttgaatgtt gtatccatgc aaactaccac aaccccctaca  10080 agtagtgcgt cagttccagg acacgtcacc ttaaccaacc caaggttgct tggtaccccca  10140 gatattggct caataagcaa tctttaatc aaagctagcc agcagagcct ggggattcag   10200
gaccagcctg tggctttacc gccaagttca ggaatgtttc cacaactggg gacatcacag   10260 acccctcta ctgctgcaat aacagcggca tctagcatct gtgtgctccc ctccactcag    10320
actacgggca taacagccgc ttcaccttct ggggaagcag acgaacacta tcagcttcag   10380
catgtgaacc agctccttgc cagcaaaact gggattcatt cttcccagcg tgatcttgat   10440
tctgcttcag ggccccaggt atccaacttt acccagacgg tagacgctcc taatagcatg   10500
ggactggagc agaacaaggc tttatcctca gctgtgcaag ccagccccac ctctcctggg   10560
ggttctccat cctctccatc ttctggacag cggtcagcaa gcccttcagt gccgggtccc   10620
actaaaccca aaccaaaaac caaacggttt cagctgcctc tagacaaagg gaatggcaag   10680
aagcacaaag tttcccattt gcggaccagt tcttctgaag cacacattcc agaccaagaa   10740
acgacatccc tgacctcagg cacagggact ccaggagcag aggctgagca gcaggataca   10800
gctagcgtgg agcagtcctc ccagaaggag tgtgggcaac ctgcagggca agtcgctgtt   10860
cttccggaag ttcaggtgac ccaaaatcca gcaaatgaac aagaaagtgc agaacctaaa   10920
acagtggaag aagaggaaag taatttcagc tccccactga tgctttggct tcagcaagaa   10980
caaaagcgga aggaaagcat tactgagaaa aaacccaaga aaggacttgt ttttgaaatt   11040
tccagtgatg atggctttca gatctgtgca gaaagtattg aagatgcctg gaagtcattg   11100
acagataaag tccaggaagc tcgatcaaat gcccgcctaa agcagctctc atttgcaggt   11160
```

-continued

```
gttaacggtt tgaggatgct ggggattctc catgatgcag ttgtgttcct cattgagcag    11220
ctgtctggtg ccaagcactg tcgaaattac aaattccgtt tccacaagcc agaggaggcc    11280
aatgaacccc ccttgaaccc tcacggctca gccagggctg aagtccacct caggaagtca    11340
gcatttgaca tgtttaactt cctggcttct aaacatcgtc agcctcctga atacaacccc    11400
aatgatgaag aagaggagga ggtacagctg aagtcagctc ggagggcaac tagcatggat    11460
ctgccaatgc ccatgcgctt ccggcactta aaaaagactt ctaaggaggc agttggtgtc    11520
tacaggtctc ccatccatgg ccgggggtctt ttctgtaaga gaaacattga tgcaggtgag    11580
atggtgattg agtatgccgg caacgtcatc cgctccatcc agactgacaa gcgggaaaag    11640
tattacgaca gcaagggcat tggttgctat atgttccgaa ttgatgactc agaggtagtg    11700
gatgccacca tgcatggaaa tgctgcacgc ttcatcaatc actcgtgtga gcctaactgc    11760
tattctcggg tcatcaatat tgatgggcag aagcacattg tcatctttgc catgcgtaag    11820
atctaccgag gagaggaact cacttacgac tataagttcc ccattgagga tgccagcaac    11880
aagctgccct gcaactgtgg cgccaagaaa tgccggaagt tcctaaacta aagctgctct    11940
tctcccccag tgttggagtg caaggaggcg gggccatcca aagcaacgct gaaggccttt    12000
tccagcagct gggagctccc ggattgcgtg gcacagctga ggggcctctg tgatggctga    12060
gctctcttat gtcctatact cacatcagac atgtgatcat agtcccagag acagagttga    12120
ggtctcgaag aaaagatcca tgatcggctt tctcctgggg cccctccaat tgtttactgt    12180
tagaaagtgg gaatggggtc cctagcagac ttgcctggaa ggagcctatt atagagggtt    12240
ggttatgttg ggagattggg cctgaatttc tccacagaaa taagttgcca tcctcaggtt    12300
ggccctttcc caagcactgt aagtgagtgg gtcaggcaaa gccccaaatg gagggttggt    12360
tagattcctg acagtttgcc agccaggccc cacctacagc gtctgtcgaa caaacagagg    12420
tctggtggtt ttccctacta tcctcccact cgagagttca cttctggttg ggagacagga    12480
ttcctagcac ctccggtgtc aaaaggctgt catggggttg tgccaattaa ttaccaaaca    12540
ttgagcctgc aggctttgag tgggagtgtt gcccccagga gccttatctc agccaattac    12600
ctttcttgac agtaggagcg gcttccctct cccattccct cttcactccc ttttcttcct    12660
ttcccctgtc ttcatgccac tgctttccca tgcttctttc gggttgtagg ggagactgac    12720
tgcctgctca aggacactcc ctgctgggca taggatgtgc ctgcaaaaag ttccctgagc    12780
ctgtaagcac tccaggtggg gaagtggaca ggagccattg gtcataacca gacagaattt    12840
ggaaacattt tcataaagct ccatggagag ttttaaagaa acatatgtag catgattttg    12900
taggagagga aaaagattat ttaaatagga tttaaatcat gcaacaacga gagtatcaca    12960
gccaggatga cccttgggtc ccattcctaa gacatggtta ctttattttc cccttgttaa    13020
gacataggaa gacttaattt ttaaacggtc agtgtccagt tgaaggcaga acactaatca    13080
gatttcaagg cccacaactt ggggactaga ccaccttatg ttgagggaac tctgccacct    13140
gcgtgcaacc cacagctaaa gtaaattcaa tgacactact gccctgatta ctccttagga    13200
tgtggtcaaa acagcatcaa atgtttcttc tcttcctttc cccaagacag agtcctgaac    13260
ctgttaaatt aagtcattgg attttactct gttctgttta cagtttacta tttaaggttt    13320
tataaatgta aatatatttt gtatattttt ctatgagaag cacttcatag ggagaagcac    13380
ttatgacaag gctatttttt aaaccgcggt attatcctaa tttaaaagaa gatcggtttt    13440
taataatttt ttattttcat aggatgaagt tagagaaaat attcagctgt acacacaaag    13500
tctggttttt cctgcccaac ttcccctgg aaggtgtact ttttgttgtt taatgtgtag    13560
```

-continued

```
cttgtttgtg ccctgttgac ataaatgttt cctgggtttg ctctttgaca ataaatggag   13620
aaggaaggtc acccaactcc attgggccac tcccctcctt cccctattga agctcctcaa   13680
aaggctacag taatatcttg atacaacaga ttctcttctt tcccgcctct ctcctttccg   13740
gcgcaacttc cagagtggtg ggagacggca atctttacat ttccctcatc tttcttactt   13800
cagagttagc aaacaacaag ttgaatggca acttgacatt tttgcatcac catctgcctc   13860
ataggccact ctttcctttc cctctgccca ccaagtcctc atatctgcag agaacccatt   13920
gatcaccttg tgccctcttt tggggcagcc tgttgaaact gaagcacagt ctgaccactc   13980
acgataaagc agatttttct ctgcctctgc cacaaggttt cagagtagtg tagtccaagt   14040
agagggtggg gcaccctttt ctcgccgcaa gaagcccatt cctatggaag tctagcaaag   14100
caatacgact cagcccagca ctctctgccc caggactcat ggctctgctg tgccttccat   14160
cctgggctcc cttctctcct gtgaccttaa gaactttgtc tggtggcttt gctggaacat   14220
tgtcactgtt ttcactgtca tgcagggagc ccagcactgt ggccaggatg gcagagactt   14280
ccttgtcatc atggagaagt gccagcaggg gactgggaaa agcactctac ccagacctca   14340
cctcccttcc tcctttttgcc catgaacaag atgcagtggc cctaggggtt ccactagtgt   14400
ctgctttcct ttattattgc actgtgtgag gttttttttgt aaatccttgt attcctattt   14460
tttttaaaga aaaaaaaaaa accttaagct gcatttgtta ctgaaatgat taatgcactg   14520
atgggtcctg aattcacctt gagaaagacc caaaggccag tcaggggtg gggggaactc    14580 agctaaatag acctagttac tgccctgcta ggccatgctg tactgtgagc ccctcctcac   14640
tctctaccaa ccctaaaccc tgaggacagg ggaggaaccc acagcttcct tctcctgcca   14700
gctgcagatg gtttgccttg cctttccacc ccctaattgt caaccacaaa aatgagaaat   14760
tcctcttcta gctcagcctt gagtccattg ccaaatttc agcacacctg ccagcaactt    14820
gggggaataa gcgaaggttt ccctacaaga gggaaagaag gcaaaaacgg cacagctatc   14880
tccaaacaca tctgagttca tttcaaaagt gaccaaggga atctccgcac aaaagtgcag   14940
attgaggaat tgtgatgggt cattcccaag aatcccccaa ggggcatccc aaatccctga   15000
ggagtaacag ctgcaaacct ggtcagttct cagtgagagc cagctcactt atagctttgc   15060
tgctagaacc tgttgtggct gcatttcctg gtggccagtg acaactgtgt aaccagaata   15120
gctgcatggc gctgaccctt tggccggaac ttggtctctt ggctccctcc ttggccaccc   15180
accacctctc gcacagcccc tctgttttta caccaataac aagaattaag ggggaagccc   15240
tggcagctat acgtttttcaa ccagactcct ttgccgggac ccagcccgcc accctgctcg   15300
cctccgtcaa accccggcc aatgcagtga gcaccatgta gctcccttga tttaaaaaaa    15360
ataaaaaata aaaaaaaag gaaaaaaaaa tacaacacac acacaaaat aaaaaaaata    15420 ttctaatgaa tgtatctttc taaaggactg acgttcaatc aaatatctga aaatactaaa   15480
ggtcaaaacc ttgtcagatg ttaacttcta agttcggttt gggatttttt ttttttaata   15540
gaaatcaagt tgtttttgtt tttaaggaaa agcgggtcat tgcaaagggc tgggtgtaat   15600
tttatgtttc atttccttca ttttaaagca atacaaggtt atggagcaga tggttttgtg   15660
ccgaatcatg aatactagtc aagtcacaca ctctggaaac ttgcaacttt ttgtttgttt   15720
tggttttcaa ataaatataa atatgatata tataggaact aatatagtaa tgcaccatgt   15780
aacaaagcct agttcagtcc atggctttta attctcttaa cactatagat aaggattgtg   15840
ttacagttgc tagtagcggc aggaagatgt caggctcact ttcctctgat tcccgaaatg   15900
```

-continued

```
gggggaacct ctaaccataa aggaatggta gaacagtcca ttcctcggat cagagaaaaa    15960
tgcagacatg gtgtcacctg gattttttc tgcccatgaa tgttgccagt cagtacctgt     16020
cctccttgtt tctctatttt tggttatgaa tgttggggtt accacctgca tttaggggaa    16080
aattgtgttc tgtgctttcc tggtatcttg ttccgaggta ctctagttct gtctttcaac    16140
caagaaaata gaattgtggt gtttctttta ttgaacttt aacagtctct ttagtaaata    16200
caggtagttg aataattgtt tcaagagctc aacagatgac aagcttcttt tctagaaata    16260 agacatttt tgacaacttt atcatgtata acagatctgt ttttttcct tgtgttcttc     16320 caagcttctg gttagagaaa aagagaaaaa aaaaaaagga aaatgtgtct aaagtccatc    16380
agtgttaact ccctgtgaca gggatgaagg aaaatacttt aatagttcaa aaaataataa    16440
tgctgaaagc tctctacgaa agactgaatg taaaagtaaa aagtgtacat agttgtaaaa    16500
aaaaggagtt tttaaacatg tttattttct atgcactttt ttttatttaa gtgatagttt    16560
aattaataaa catgtcaagt ttattgctgc a                                   16591
```

<210> SEQ ID NO 2
<211> LENGTH: 7121
<212> TYPE: DNA
<213> ORGANISM: Homo sapiens

<400> SEQUENCE: 2

```
actctctctc tttctctccc tctcctatcg gagcacaatg aaagcctgtg tatcgccgtg      60
actccgggcg cgagccagtg tcagcaaagc ggctaacaac agacgagaaa gagaaaggaa     120
aatacaagct acttttttt tccatctata aagcggagca aatacaggag atagaaccag      180
attgcttatt gcgagtccag accctcagat ccactggccg gggatggaat gtacaaaagt     240
ggacagaaaa gtggctggac atgactcggt gcaatttgct ggaagtttgt aagtttgacc     300
atcgtttgta aattactctc ggaagagttt gtctctcttg atactgtatt agaatagagc     360 cggggtgag aatagaaac gtaagcggga aagaaaaaa tgtgttgaag gatctctctc        420
agtggctagc gacttaagat tgcttttcat ttaaggctag gaaaccttag agggagtgag     480
gattttaccg gtgattggat tagctgaaga aaaaagcatg gtccaaaagt ccaattactg     540
acattgttaa cagttgaaaa gctgtctccc tcttttggga gaagacaaca tcctacagta     600
ccccaaagag gagaaaacac cggagcgaaa ggaaagggag gaaaaattaa aagccaaaag     660
acagtctccc ttgattttg cacatttga acagtgactt aaacatcttc tgaaacagca       720 ctgtttgtt ttgttttggt ttttattta acctgaggaa aagtcaaggc tgctggttac       780
atagacatgg tagaaatgtg tttctctgca gaaacatccc cataaagaat tgtcggaaac     840
aactaggtga gggggagtcc tctctattaa tacctctctc aatacctttt gctgtgtgtt     900
tctgtctctt gctggacaat ccctgaattc ttgatctaac ccccagatcg tgtgtttaca     960
aagtacctag tggctcttgt cagcttggtg gaggaaaaaa aatccaccaa ctctgtccaa    1020
cttctccaga gctgtcaaat gcaattagag taagttaatc agggtttgtt tccaacttat    1080
cctcccccca gttggtttct attctttctc cccaccctct ttttactaac tcccctcccc    1140
cacaacttct ccacggctcc cccacaacct ctgaagacct ctattcatgt ggccctgaac    1200
actgagctca cattgtcaaa aacagacttg cctgcaatag ccagcagtag cctctttcca    1260
cctcaccatc ccagaggcag caatcattgt gtccggtaag atgggggaca cagcgccccc    1320
gcaggccccc gcaggagggc tagggggggc ctctggggcg gggctccttg gaggggggctc    1380 agtcaccccg agagtgcaca gtgctatcgt ggagcgcctc cgggctcgga tcgctgtctg    1440
```

-continued

```
ccgccaacac cacctgagct gtgaaggacg atatgaacga ggtagggccg agagctcaga      1500
ccgggaaaga gaaagcacct tgcagctcct gagccttgta cagcatggcc aggggcaag       1560 gaaagctggc aaacacacca aggccaccgc cactgctgcc accactacag cccctccacc      1620 gcccctgct gcccctcctg cggcctccca agcagcagca acagcagccc caccgccccc       1680
accagactat caccatcacc accagcagca cctgctgaac agtagcaata atggtggcag      1740
tggtgggata aacggagagc agcagccgcc cgcttcaacc ccaggggacc agaggaactc      1800
agccctgatt gcgctccagg gttccttgaa aagaaacag gtagttaacc tatctcctgc       1860
caacagcaag cgacccaatg gctttgtgga caactcattt cttgatatca aaagaattcg      1920 tgttgggggag aatctctctg caggacaagg tggcctccaa ataaacaatg gacaaagtca     1980
gattatgtca gggaccttgc ctatgagcca agcacccctg cgaaagacta cactctgcc       2040 atcccataca cattctcctg gcaatggcct gtttaacatg ggcttaaagg aggtaaagaa      2100
ggagccagga gagactctgt cttgcagtaa gcacatggat ggccaaatga cccaagagaa      2160
tatttttcct aataggtacg gagacgaccc tggagaacaa ctgatggatc ctgagctgca      2220
ggaactgttc aatgaactga ccaacatatc tgtgcctccc atgagtgacc ttgaactgga      2280
gaacatgatc aatgccacca taaagcagga tgacccattt aacattgact tgggtcagca     2340
aagccagagg agcacaccta ggccctcctt acccatggag aaaatagtga tcaaaagtga     2400
atactcaccg ggcttgactc agggcccctc aggctctcct cagctgaggc ccccatcagc      2460
tggccccgca ttctccatgg ccaactctgc cctctccact tcgtctccaa tcccttcagt     2520
ccctcagagc caggctcagc ctcagacagg ctccggagca agccgggcct tgccaagctg      2580
gcaggaagta tcccatgccc agcagctcaa acagatagct gctaatcgtc agcagcatgc      2640
ccggatgcag cagcaccagc agcagcacca gcctaccaac tggtcagcct tgccctcttc      2700
tgctggacca tcaccaggtc catttgggca ggagaaaatc cccagccctt cttttggtca     2760
gcagacattc agcccacaga gctcccccat gcctggggta gctggcggca gcggccagtc      2820
gaaagtaatg gctaactaca tgtacaaggc cggcccctca gcccagggtg ggcacctaga      2880
tgtcctcatg cagcaaaagc ctcaggatct cagtcgaagt tttattaaca acccgcaccc     2940
agccatggag ccccgtcagg gcaacaccaa gcctttgttt cattttaact cagatcaagc      3000
gaaccagcag atgccttctg ttttgccttc ccagaacaag ccttctctcc tacactacac      3060
ccaacagcaa cagcagcaac agcagcagca gcagcagcag cagcagcagc agcagcagca     3120
acagcagcag cagcagcaac agcaacagca acagcaacag cagagttcaa tttcagctca      3180
acaacagcaa cagcagcaga gctcaatttc agcccaacag cagcagcagc agcaacaaca     3240
gcagcagcag cagcaacaac aacagcaaca acagcagcag cagcagcagc aacaaccatc      3300
ttctcagcct gcccaatctc taccaagcca gcctttgcta aggtcacctt tgccacttca     3360
gcaaaagctc ctacttcagc aaatgcagaa tcagcccatt gcaggaatgg ataccaagt       3420 ctcccaacaa cagagacagg atcaacactc tgtggtaggc cagaacacag gccccagtcc      3480
aagtcctaac ccctgctcaa atccaaacac tggaagtggt tacatgaact cccagcaatc      3540
actgttgaat cagcaattga tgggaaagaa gcagactcta cagaggcaga tcatggagca     3600
gaaacagcaa cttcttctcc agcagcagat gctggctgac gcggagaaaa ttgctccaca      3660
agatcagata aaccgacatt tgtcaaggcc acctccagat tataaagacc aaagaagaaa      3720
tgtgggcaat atgcaaccaa ctgctcagta ttctggtggc tcatccacaa taagcttaaa     3780
```

-continued

```
ctctaaccag gctttggcaa acccagtttc aacacacacc attttaactc ccaattccag    3840
cctcctgtct acttctcacg ggacaagaat gccatcatta tctacagcag ttcagaatat    3900
ggggatgtat ggaaatctgc cttgtaatca acctaacaca tacagtgtca cttcaggaat    3960
gaatcaattg acccaacaga gaaacccaaa gcaattgtta gcaaatcaaa acaaccctat    4020
gatgccacgg ccacctacct tagggccaag taataataac aatgtagcca cttttggagc    4080
tggatctgtt ggtaattcac aacaattgag accaaattta acccatagta tggcaagcat    4140
gccaccacag agaacatcaa acgtaatgat cacatccaac acaactgcac caaactgggc    4200
ctctcaagaa ggaacaagca aacagcaaga agccctgacg tctgcaggag tccgcttccc    4260
cacaggtaca cctgcagcct ataccccaaa tcagtcactg caacaggcag taggtagcca    4320
gcaattttcc cagagggcag tggctcctcc taaccagtta acaccagcag tgcaaatgag    4380
acccatgaac caaatgagcc aaacactaaa tgggcaaacc atgggtcccc tcaggggtct    4440
gaatctcaga cccaatcagc taagcacaca gattttgcct aatttgaatc agtcaggaac    4500
agggttgaat cagtcgagga cgggcatcaa ccagccacca tccctgacgc ccagcaattt    4560
tccttcaccc aaccaaagtt ccagggcttt tcaaggaact gaccacagca gtgacttagc    4620
ttttgacttc ctcagccaac aaaatgataa catgggccct gccctaaaca gtgatgctga    4680
tttcattgat tctttattga agacagagcc tggtaatgat gactggatga aagacatcaa    4740
tcttgatgaa atcttgggga acaattccta aagaagaaag ggaagacaat ttacaaactc    4800
caagcactaa aaggcagtat attacagaaa ctctgtagag gctgaactgt tgatgttcag    4860
gtggactaca tgaagataac atgcttaaaa atggaaagca gaaagtaact gcagtgatga    4920
acattttggt ccaaattctt gttttaaatc ttacacctga aagtaaaata ttgggatcac    4980
ttttccctgt ctaaactcca ggatacagta tccaatttat ccaaacagaa ctgtggtgtc    5040
aatgtgtaat taattgtgta aaatagcctt cccagtttc ttttttccctg gaaaataaaa    5100 aaggtaatag aacttgtagt ttatttaaac cccatgtcat gaggaggtac tagttccaag    5160
caacaaactc cttaatttgc tctaatagat aggtatggtt taatctttcc attgtgtctt    5220
ttcatttaat tttcctgaag cttgcaggat agattgaaat gttataggtt tgtttggagt    5280
aaccaaacag tatgcaaatt aagaaaaagc cagagaacct agaaaacatc cagtggatta    5340
cagaatttct tccccatatt cactcctcac ttttacaatt ttcccacaat cctctacttc    5400
agtgggatgc tgtgtctagt gattaaacaa aaatatagag ctgtgcaatt tgattttggc    5460
ttccacaacg aatatctgaa tccattccaa atgaaatttt agatataaca aagacttgtc    5520
ctaatcatac tgaaatattg gtgcacacct ctctgcatta gatttcactt ttttaaaaaa    5580
cccagtggac attgctataa ataagattta tttggctaca aataacctgg gatgttgctt    5640
attatgattg atgcctgctg gtttgttccc aagctgagtg aaattgaacc tcgtcctccc    5700
tactcatttt gatgactgag gctggtttat aagaaaagga agtttggaga agaaaaccga    5760
gattagaaaa tatcatgttt tggttggaga taagaaccag ggatggcaag taccagtgtg    5820
tacaaatgta tttcacggag tttgaaggaa cgcataatca agagggaaaa caatttgtcc    5880
ttcattggac gtattatttg gatttgggtg agcaacaaaa tggaatgtgg tctgttagga    5940
gcattctgtt tgttctttg tccctgatgt gatgaatcat tgccacatgc tagatggact    6000
cttcatatcc aggttttgtc cctcagggct gagcactgta ttaaagagtt tttgttgagt    6060
catttaacct tagtgtccac atccagatca gctgtaaaat ggggaagacg tgtgctgatt    6120
tggaatgaat gcaaaatatc actatcattt tcctaattac agaggagcaa aggttatctt    6180
```

```
cagcccttte agttctatgc tcacatattc aaatatcaaa tgtaatttag ctgaagttat    6240
ttaataatca agtctttcaa tatctgttca aagaaaaaga acacacttg aaaattctgc     6300 aaagctgtct cccagtcttt aaaatgtctg gaagcactct ccttctttac aataccaaca    6360
tcactggccc agaatcttcc ctgtgctagt ttgtaaatat aaataaatta cttgtttttgt   6420 aaacttttgt aaagaatatt ttggtagaaa tacttcaaac atattctttg ggttatattt    6480
atacatatgt gaaataaaata tactatcaaa aggttatatt ttatacaaaa agtaaattgc   6540
taccttttgt atgctaatat gcaaagtttt gtataatatg atggtttatt tttagctcta    6600
cacttaaacc ataggtggtt gagtgggaac ttttgaaaac tatcaagagg cttgttagac    6660
aaatttatat tctgaaacct caataagaaa gcattccagg tttcaatcct tgttttttgt    6720
cctgctccca aattctttt taaacccata gttcttgtgt cttatttgat tcttctgctg     6780
tgcacattgt attggtcctt gttgcatgta gtctactgtg tgttttccga ttttataagg    6840
cagcatttct ccatacaaaa agaaaaaaaa tgatgtacat ataaacgctt ttgttgtatg    6900
gctcctccat gttactgtat atatctgcca gcacttccca gttacactcc tgtgagtcag    6960
cttattttta ccctaacata aatagtatgt tttgtagtag ttatcaaatt taagagataa    7020
agcaatcaga atgtttggat tttcttctat cttaatgtga atttcataat taatgtctat    7080
ttattcagct attcattaaa atacaggatt ctttgggaaa a                       7121
```

<210> SEQ ID NO 3
<211> LENGTH: 3969
<212> TYPE: PRT
<213> ORGANISM: Homo sapiens

<400> SEQUENCE: 3

```
Met Ala His Ser Cys Arg Trp Arg Phe Pro Ala Arg Pro Gly Thr Thr
1               5                   10                  15

Gly Gly Gly Gly Gly Gly Gly Arg Arg Gly Leu Gly Gly Ala Pro Arg
                20                  25                  30

Gln Arg Val Pro Ala Leu Leu Leu Pro Pro Gly Pro Pro Val Gly Gly
            35                  40                  45

Gly Gly Pro Gly Ala Pro Pro Ser Pro Pro Ala Val Ala Ala Ala Ala
        50                  55                  60

Ala Ala Ala Gly Ser Ser Gly Ala Gly Val Pro Gly Gly Ala Ala Ala
65                  70                  75                  80

Ala Ser Ala Ala Ser Ser Ser Ser Ala Ser Ser Ser Ser Ser Ser Ser
                85                  90                  95

Ser Ser Ala Ser Ser Gly Pro Ala Leu Leu Arg Val Gly Pro Gly Phe
            100                 105                 110

Asp Ala Ala Leu Gln Val Ser Ala Ala Ile Gly Thr Asn Leu Arg Arg
            115                 120                 125

Phe Arg Ala Val Phe Gly Glu Ser Gly Gly Gly Gly Ser Gly Glu
        130                 135                 140

Asp Glu Gln Phe Leu Gly Phe Gly Ser Asp Glu Glu Val Arg Val Arg
145                 150                 155                 160

Ser Pro Thr Arg Ser Pro Ser Val Lys Thr Ser Pro Arg Lys Pro Arg
                165                 170                 175

Gly Arg Pro Arg Ser Gly Ser Asp Arg Asn Ser Ala Ile Leu Ser Asp
            180                 185                 190

Pro Ser Val Phe Ser Pro Leu Asn Lys Ser Glu Thr Lys Ser Gly Asp
            195                 200                 205
```

-continued

```
Lys Ile Lys Lys Lys Asp Ser Lys Ser Ile Glu Lys Lys Arg Gly Arg
    210                 215                 220

Pro Pro Thr Phe Pro Gly Val Lys Ile Lys Ile Thr His Gly Lys Asp
225                 230                 235                 240

Ile Ser Glu Leu Pro Lys Gly Asn Lys Glu Asp Ser Leu Lys Lys Ile
                245                 250                 255

Lys Arg Thr Pro Ser Ala Thr Phe Gln Gln Ala Thr Lys Ile Lys Lys
                260                 265                 270

Leu Arg Ala Gly Lys Leu Ser Pro Leu Lys Ser Lys Phe Lys Thr Gly
                275                 280                 285

Lys Leu Gln Ile Gly Arg Lys Gly Val Gln Ile Val Arg Arg Arg Gly
    290                 295                 300

Arg Pro Pro Ser Thr Glu Arg Ile Lys Thr Pro Ser Gly Leu Leu Ile
305                 310                 315                 320

Asn Ser Glu Leu Glu Lys Pro Gln Lys Val Arg Lys Asp Lys Glu Gly
                325                 330                 335

Thr Pro Pro Leu Thr Lys Glu Asp Lys Thr Val Val Arg Gln Ser Pro
                340                 345                 350

Arg Arg Ile Lys Pro Val Arg Ile Ile Pro Ser Ser Lys Arg Thr Asp
                355                 360                 365

Ala Thr Ile Ala Lys Gln Leu Leu Gln Arg Ala Lys Lys Gly Ala Gln
    370                 375                 380

Lys Lys Ile Glu Lys Glu Ala Ala Gln Leu Gln Gly Arg Lys Val Lys
385                 390                 395                 400

Thr Gln Val Lys Asn Ile Arg Gln Phe Ile Met Pro Val Val Ser Ala
                405                 410                 415

Ile Ser Ser Arg Ile Ile Lys Thr Pro Arg Arg Phe Ile Glu Asp Glu
                420                 425                 430

Asp Tyr Asp Pro Pro Ile Lys Ile Ala Arg Leu Glu Ser Thr Pro Asn
                435                 440                 445

Ser Arg Phe Ser Ala Pro Ser Cys Gly Ser Ser Glu Lys Ser Ser Ala
    450                 455                 460

Ala Ser Gln His Ser Ser Gln Met Ser Ser Asp Ser Ser Arg Ser Ser
465                 470                 475                 480

Ser Pro Ser Val Asp Thr Ser Thr Asp Ser Gln Ala Ser Glu Glu Ile
                485                 490                 495

Gln Val Leu Pro Glu Glu Arg Ser Asp Thr Pro Glu Val His Pro Pro
                500                 505                 510

Leu Pro Ile Ser Gln Ser Pro Glu Asn Glu Ser Asn Asp Arg Arg Ser
                515                 520                 525

Arg Arg Tyr Ser Val Ser Glu Arg Ser Phe Gly Ser Arg Thr Thr Lys
    530                 535                 540

Lys Leu Ser Thr Leu Gln Ser Ala Pro Gln Gln Gln Thr Ser Ser Ser
545                 550                 555                 560

Pro Pro Pro Pro Leu Leu Thr Pro Pro Pro Leu Gln Pro Ala Ser
                565                 570                 575

Ser Ile Ser Asp His Thr Pro Trp Leu Met Pro Pro Thr Ile Pro Leu
                580                 585                 590

Ala Ser Pro Phe Leu Pro Ala Ser Thr Ala Pro Met Gln Gly Lys Arg
                595                 600                 605

Lys Ser Ile Leu Arg Glu Pro Thr Phe Arg Trp Thr Ser Leu Lys His
    610                 615                 620
```

```
Ser Arg Ser Glu Pro Gln Tyr Phe Ser Ser Ala Lys Tyr Ala Lys Glu
625                 630                 635                 640

Gly Leu Ile Arg Lys Pro Ile Phe Asp Asn Phe Arg Pro Pro Pro Leu
                645                 650                 655

Thr Pro Glu Asp Val Gly Phe Ala Ser Gly Phe Ser Ala Ser Gly Thr
                660                 665                 670

Ala Ala Ser Ala Arg Leu Phe Ser Pro Leu His Ser Gly Thr Arg Phe
                675                 680                 685

Asp Met His Lys Arg Ser Pro Leu Leu Arg Ala Pro Arg Phe Thr Pro
        690                 695                 700

Ser Glu Ala His Ser Arg Ile Phe Glu Ser Val Thr Leu Pro Ser Asn
705                 710                 715                 720

Arg Thr Ser Ala Gly Thr Ser Ser Ser Gly Val Ser Asn Arg Lys Arg
                725                 730                 735

Lys Arg Lys Val Phe Ser Pro Ile Arg Ser Glu Pro Arg Ser Pro Ser
                740                 745                 750

His Ser Met Arg Thr Arg Ser Gly Arg Leu Ser Ser Ser Glu Leu Ser
                755                 760                 765

Pro Leu Thr Pro Pro Ser Ser Val Ser Ser Ser Leu Ser Ile Ser Val
        770                 775                 780

Ser Pro Leu Ala Thr Ser Ala Leu Asn Pro Thr Phe Thr Phe Pro Ser
785                 790                 795                 800

His Ser Leu Thr Gln Ser Gly Glu Ser Ala Glu Lys Asn Gln Arg Pro
                805                 810                 815

Arg Lys Gln Thr Ser Ala Pro Ala Glu Pro Phe Ser Ser Ser Ser Pro
                820                 825                 830

Thr Pro Leu Phe Pro Trp Phe Thr Pro Gly Ser Gln Thr Glu Arg Gly
                835                 840                 845

Arg Asn Lys Asp Lys Ala Pro Glu Glu Leu Ser Lys Asp Arg Asp Ala
        850                 855                 860

Asp Lys Ser Val Glu Lys Asp Lys Ser Arg Glu Arg Asp Arg Glu Arg
865                 870                 875                 880

Glu Lys Glu Asn Lys Arg Glu Ser Arg Lys Glu Lys Arg Lys Lys Gly
                885                 890                 895

Ser Glu Ile Gln Ser Ser Ser Ala Leu Tyr Pro Val Gly Arg Val Ser
                900                 905                 910

Lys Glu Lys Val Val Gly Glu Asp Val Ala Thr Ser Ser Ser Ala Lys
        915                 920                 925

Lys Ala Thr Gly Arg Lys Lys Ser Ser Ser His Asp Ser Gly Thr Asp
        930                 935                 940

Ile Thr Ser Val Thr Leu Gly Asp Thr Thr Ala Val Lys Thr Lys Ile
945                 950                 955                 960

Leu Ile Lys Lys Gly Arg Gly Asn Leu Glu Lys Thr Asn Leu Asp Leu
                965                 970                 975

Gly Pro Thr Ala Pro Ser Leu Glu Lys Glu Lys Thr Leu Cys Leu Ser
                980                 985                 990

Thr Pro Ser Ser Ser Thr Val Lys His Ser Thr Ser Ser Ile Gly Ser
                995                 1000                1005

Met Leu Ala Gln Ala Asp Lys Leu Pro Met Thr Asp Lys Arg Val Ala
        1010                1015                1020

Ser Leu Leu Lys Lys Ala Lys Ala Gln Leu Cys Lys Ile Glu Lys Ser
1025                1030                1035                1040

Lys Ser Leu Lys Gln Thr Asp Gln Pro Lys Ala Gln Gly Gln Glu Ser
```

-continued

```
              1045              1050              1055

Asp Ser Ser Glu Thr Ser Val Arg Gly Pro Arg Ile Lys His Val Cys
         1060              1065              1070

Arg Arg Ala Ala Val Ala Leu Gly Arg Lys Arg Ala Val Phe Pro Asp
         1075              1080              1085

Asp Met Pro Thr Leu Ser Ala Leu Pro Trp Glu Glu Arg Glu Lys Ile
         1090              1095              1100

Leu Ser Ser Met Gly Asn Asp Asp Lys Ser Ser Ile Ala Gly Ser Glu
    1105              1110              1115              1120

Asp Ala Glu Pro Leu Ala Pro Pro Ile Lys Pro Ile Lys Pro Val Thr
         1125              1130              1135

Arg Asn Lys Ala Pro Gln Glu Pro Pro Val Lys Lys Gly Arg Arg Ser
         1140              1145              1150

Arg Arg Cys Gly Gln Cys Pro Gly Cys Gln Val Pro Glu Asp Cys Gly
         1155              1160              1165

Val Cys Thr Asn Cys Leu Asp Lys Pro Lys Phe Gly Gly Arg Asn Ile
         1170              1175              1180

Lys Lys Gln Cys Cys Lys Met Arg Lys Cys Gln Asn Leu Gln Trp Met
    1185              1190              1195              1200

Pro Ser Lys Ala Tyr Leu Gln Lys Gln Ala Lys Ala Val Lys Lys Lys
         1205              1210              1215

Glu Lys Lys Ser Lys Thr Ser Glu Lys Lys Asp Ser Lys Glu Ser Ser
         1220              1225              1230

Val Val Lys Asn Val Val Asp Ser Ser Gln Lys Pro Thr Pro Ser Ala
         1235              1240              1245

Arg Glu Asp Pro Ala Pro Lys Lys Ser Ser Ser Glu Pro Pro Pro Arg
         1250              1255              1260

Lys Pro Val Glu Glu Lys Ser Glu Glu Gly Asn Val Ser Ala Pro Gly
    1265              1270              1275              1280

Pro Glu Ser Lys Gln Ala Thr Thr Pro Ala Ser Arg Lys Ser Ser Lys
         1285              1290              1295

Gln Val Ser Gln Pro Ala Leu Val Ile Pro Pro Gln Pro Pro Thr Thr
         1300              1305              1310

Gly Pro Pro Arg Lys Glu Val Pro Lys Thr Thr Pro Ser Glu Pro Lys
         1315              1320              1325

Lys Lys Gln Pro Pro Pro Pro Glu Ser Gly Pro Glu Gln Ser Lys Gln
         1330              1335              1340

Lys Lys Val Ala Pro Arg Pro Ser Ile Pro Val Lys Gln Lys Pro Lys
    1345              1350              1355              1360

Glu Lys Glu Lys Pro Pro Pro Val Asn Lys Gln Glu Asn Ala Gly Thr
         1365              1370              1375

Leu Asn Ile Leu Ser Thr Leu Ser Asn Gly Asn Ser Ser Lys Gln Lys
         1380              1385              1390

Ile Pro Ala Asp Gly Val His Arg Ile Arg Val Asp Phe Lys Glu Asp
         1395              1400              1405

Cys Glu Ala Glu Asn Val Trp Glu Met Gly Gly Leu Gly Ile Leu Thr
    1410              1415              1420

Ser Val Pro Ile Thr Pro Arg Val Val Cys Phe Leu Cys Ala Ser Ser
    1425              1430              1435              1440

Gly His Val Glu Phe Val Tyr Cys Gln Val Cys Cys Glu Pro Phe His
         1445              1450              1455

Lys Phe Cys Leu Glu Glu Asn Glu Arg Pro Leu Glu Asp Gln Leu Glu
         1460              1465              1470
```

-continued

```
Asn Trp Cys Cys Arg Arg Cys Lys Phe Cys His Val Cys Gly Arg Gln
        1475                1480                1485

His Gln Ala Thr Lys Gln Leu Leu Glu Cys Asn Lys Cys Arg Asn Ser
        1490                1495                1500

Tyr His Pro Glu Cys Leu Gly Pro Asn Tyr Pro Thr Lys Pro Thr Lys
1505                1510                1515                1520

Lys Lys Lys Val Trp Ile Cys Thr Lys Cys Val Arg Cys Lys Ser Cys
        1525                1530                1535

Gly Ser Thr Thr Pro Gly Lys Gly Trp Asp Ala Gln Trp Ser His Asp
        1540                1545                1550

Phe Ser Leu Cys His Asp Cys Ala Lys Leu Phe Ala Lys Gly Asn Phe
        1555                1560                1565

Cys Pro Leu Cys Asp Lys Cys Tyr Asp Asp Asp Tyr Glu Ser Lys
        1570                1575                1580

Met Met Gln Cys Gly Lys Cys Asp Arg Trp Val His Ser Lys Cys Glu
1585                1590                1595                1600

Asn Leu Ser Asp Glu Met Tyr Glu Ile Leu Ser Asn Leu Pro Glu Ser
        1605                1610                1615

Val Ala Tyr Thr Cys Val Asn Cys Thr Glu Arg His Pro Ala Glu Trp
        1620                1625                1630

Arg Leu Ala Leu Glu Lys Glu Leu Gln Ile Ser Leu Lys Gln Val Leu
        1635                1640                1645

Thr Ala Leu Leu Asn Ser Arg Thr Thr Ser His Leu Leu Arg Tyr Arg
        1650                1655                1660

Gln Ala Ala Lys Pro Pro Asp Leu Asn Pro Glu Thr Glu Glu Ser Ile
1665                1670                1675                1680

Pro Ser Arg Ser Ser Pro Glu Gly Pro Asp Pro Pro Val Leu Thr Glu
        1685                1690                1695

Val Ser Lys Gln Asp Asp Gln Gln Pro Leu Asp Leu Glu Gly Val Lys
        1700                1705                1710

Arg Lys Met Asp Gln Gly Asn Tyr Thr Ser Val Leu Glu Phe Ser Asp
        1715                1720                1725

Asp Ile Val Lys Ile Ile Gln Ala Ala Ile Asn Ser Asp Gly Gly Gln
        1730                1735                1740

Pro Glu Ile Lys Lys Ala Asn Ser Met Val Lys Ser Phe Phe Ile Arg
1745                1750                1755                1760

Gln Met Glu Arg Val Phe Pro Trp Phe Ser Val Lys Lys Ser Arg Phe
        1765                1770                1775

Trp Glu Pro Asn Lys Val Ser Ser Asn Ser Gly Met Leu Pro Asn Ala
        1780                1785                1790

Val Leu Pro Pro Ser Leu Asp His Asn Tyr Ala Gln Trp Gln Glu Arg
        1795                1800                1805

Glu Glu Asn Ser His Thr Glu Gln Pro Pro Leu Met Lys Lys Ile Ile
        1810                1815                1820

Pro Ala Pro Lys Pro Lys Gly Pro Gly Glu Pro Asp Ser Pro Thr Pro
1825                1830                1835                1840

Leu His Pro Pro Thr Pro Pro Ile Leu Ser Thr Asp Arg Ser Arg Glu
        1845                1850                1855

Asp Ser Pro Glu Leu Asn Pro Pro Gly Ile Glu Asp Asn Arg Gln
        1860                1865                1870

Cys Ala Leu Cys Leu Thr Tyr Gly Asp Asp Ser Ala Asn Asp Ala Gly
        1875                1880                1885
```

-continued

```
Arg Leu Leu Tyr Ile Gly Gln Asn Glu Trp Thr His Val Asn Cys Ala
    1890                1895                1900

Leu Trp Ser Ala Glu Val Phe Glu Asp Asp Gly Ser Leu Lys Asn
1905                1910                1915                1920

Val His Met Ala Val Ile Arg Gly Lys Gln Leu Arg Cys Glu Phe Cys
                1925                1930                1935

Gln Lys Pro Gly Ala Thr Val Gly Cys Cys Leu Thr Ser Cys Thr Ser
            1940                1945                1950

Asn Tyr His Phe Met Cys Ser Arg Ala Lys Asn Cys Val Phe Leu Asp
            1955                1960                1965

Asp Lys Lys Val Tyr Cys Gln Arg His Arg Asp Leu Ile Lys Gly Glu
    1970                1975                1980

Val Val Pro Glu Asn Gly Phe Glu Val Phe Arg Arg Val Phe Val Asp
1985                1990                1995                2000

Phe Glu Gly Ile Ser Leu Arg Arg Lys Phe Leu Asn Gly Leu Glu Pro
                2005                2010                2015

Glu Asn Ile His Met Met Ile Gly Ser Met Thr Ile Asp Cys Leu Gly
            2020                2025                2030

Ile Leu Asn Asp Leu Ser Asp Cys Glu Asp Lys Leu Phe Pro Ile Gly
            2035                2040                2045

Tyr Gln Cys Ser Arg Val Tyr Trp Ser Thr Thr Asp Ala Arg Lys Arg
    2050                2055                2060

Cys Val Tyr Thr Cys Lys Ile Val Glu Cys Arg Pro Pro Val Val Glu
2065                2070                2075                2080

Pro Asp Ile Asn Ser Thr Val Glu His Asp Glu Asn Arg Thr Ile Ala
            2085                2090                2095

His Ser Pro Thr Ser Phe Thr Glu Ser Ser Ser Lys Glu Ser Gln Asn
            2100                2105                2110

Thr Ala Glu Ile Ile Ser Pro Pro Ser Pro Asp Arg Pro Pro His Ser
            2115                2120                2125

Gln Thr Ser Gly Ser Cys Tyr Tyr His Val Ile Ser Lys Val Pro Arg
    2130                2135                2140

Ile Arg Thr Pro Ser Tyr Ser Pro Thr Gln Arg Ser Pro Gly Cys Arg
2145                2150                2155                2160

Pro Leu Pro Ser Ala Gly Ser Pro Thr Pro Thr Thr His Glu Ile Val
            2165                2170                2175

Thr Val Gly Asp Pro Leu Leu Ser Ser Gly Leu Arg Ser Ile Gly Ser
            2180                2185                2190

Arg Arg His Ser Thr Ser Ser Leu Ser Pro Gln Arg Ser Lys Leu Arg
            2195                2200                2205

Ile Met Ser Pro Met Arg Thr Gly Asn Thr Tyr Ser Arg Asn Asn Val
    2210                2215                2220

Ser Ser Val Ser Thr Thr Gly Thr Ala Thr Asp Leu Glu Ser Ser Ala
2225                2230                2235                2240

Lys Val Val Asp His Val Leu Gly Pro Leu Asn Ser Ser Thr Ser Leu
                2245                2250                2255

Gly Gln Asn Thr Ser Thr Ser Ser Asn Leu Gln Arg Thr Val Val Thr
            2260                2265                2270

Val Gly Asn Lys Asn Ser His Leu Asp Gly Ser Ser Ser Ser Glu Met
            2275                2280                2285

Lys Gln Ser Ser Ala Ser Asp Leu Val Ser Lys Ser Ser Ser Leu Lys
    2290                2295                2300

Gly Glu Lys Thr Lys Val Leu Ser Ser Lys Ser Ser Glu Gly Ser Ala
```

-continued

```
2305                2310                2315                2320

His Asn Val Ala Tyr Pro Gly Ile Pro Lys Leu Ala Pro Gln Val His
                    2325                2330                2335

Asn Thr Thr Ser Arg Glu Leu Asn Val Ser Lys Ile Gly Ser Phe Ala
                2340                2345                2350

Glu Pro Ser Ser Val Ser Phe Ser Ser Lys Glu Ala Leu Ser Phe Pro
            2355                2360                2365

His Leu His Leu Arg Gly Gln Arg Asn Asp Arg Asp Gln His Thr Asp
        2370                2375                2380

Ser Thr Gln Ser Ala Asn Ser Ser Pro Asp Glu Asp Thr Glu Val Lys
2385                2390                2395                2400

Thr Leu Lys Leu Ser Gly Met Ser Asn Arg Ser Ser Ile Ile Asn Glu
                2405                2410                2415

His Met Gly Ser Ser Ser Arg Asp Arg Arg Gln Lys Gly Lys Lys Ser
                2420                2425                2430

Cys Lys Glu Thr Phe Lys Glu Lys His Ser Ser Lys Ser Phe Leu Glu
            2435                2440                2445

Pro Gly Gln Val Thr Thr Gly Glu Glu Gly Asn Leu Lys Pro Glu Phe
        2450                2455                2460

Met Asp Glu Val Leu Thr Pro Glu Tyr Met Gly Gln Arg Pro Cys Asn
2465                2470                2475                2480

Asn Val Ser Ser Asp Lys Ile Gly Asp Lys Gly Leu Ser Met Pro Gly
                2485                2490                2495

Val Pro Lys Ala Pro Pro Met Gln Val Glu Gly Ser Ala Lys Glu Leu
                2500                2505                2510

Gln Ala Pro Arg Lys Arg Thr Val Lys Val Thr Leu Thr Pro Leu Lys
            2515                2520                2525

Met Glu Asn Glu Ser Gln Ser Lys Asn Ala Leu Lys Glu Ser Ser Pro
        2530                2535                2540

Ala Ser Pro Leu Gln Ile Glu Ser Thr Ser Pro Thr Glu Pro Ile Ser
2545                2550                2555                2560

Ala Ser Glu Asn Pro Gly Asp Gly Pro Val Ala Gln Pro Ser Pro Asn
                2565                2570                2575

Asn Thr Ser Cys Gln Asp Ser Gln Ser Asn Asn Tyr Gln Asn Leu Pro
                2580                2585                2590

Val Gln Asp Arg Asn Leu Met Leu Pro Asp Gly Pro Lys Pro Gln Glu
            2595                2600                2605

Asp Gly Ser Phe Lys Arg Arg Tyr Pro Arg Arg Ser Ala Arg Ala Arg
        2610                2615                2620

Ser Asn Met Phe Phe Gly Leu Thr Pro Leu Tyr Gly Val Arg Ser Tyr
2625                2630                2635                2640

Gly Glu Glu Asp Ile Pro Phe Tyr Ser Ser Ser Thr Gly Lys Lys Arg
                2645                2650                2655

Gly Lys Arg Ser Ala Glu Gly Gln Val Asp Gly Ala Asp Asp Leu Ser
            2660                2665                2670

Thr Ser Asp Glu Asp Asp Leu Tyr Tyr Tyr Asn Phe Thr Arg Thr Val
        2675                2680                2685

Ile Ser Ser Gly Gly Glu Glu Arg Leu Ala Ser His Asn Leu Phe Arg
        2690                2695                2700

Glu Glu Glu Gln Cys Asp Leu Pro Lys Ile Ser Gln Leu Asp Gly Val
2705                2710                2715                2720

Asp Asp Gly Thr Glu Ser Asp Thr Ser Val Thr Ala Thr Thr Arg Lys
                2725                2730                2735
```

-continued

```
Ser Ser Gln Ile Pro Lys Arg Asn Gly Lys Glu Asn Gly Thr Glu Asn
        2740                2745                2750

Leu Lys Ile Asp Arg Pro Glu Asp Ala Gly Glu Lys Glu His Val Thr
        2755                2760                2765

Lys Ser Ser Val Gly His Lys Asn Glu Pro Lys Met Asp Asn Cys His
        2770                2775                2780

Ser Val Ser Arg Val Lys Thr Gln Gly Gln Asp Ser Leu Glu Ala Gln
2785                2790                2795                2800

Leu Ser Ser Leu Glu Ser Ser Arg Arg Val His Thr Ser Thr Pro Ser
                2805                2810                2815

Asp Lys Asn Leu Leu Asp Thr Tyr Asn Thr Glu Leu Leu Lys Ser Asp
                2820                2825                2830

Ser Asp Asn Asn Asn Ser Asp Asp Cys Gly Asn Ile Leu Pro Ser Asp
                2835                2840                2845

Ile Met Asp Phe Val Leu Lys Asn Thr Pro Ser Met Gln Ala Leu Gly
        2850                2855                2860

Glu Ser Pro Glu Ser Ser Ser Ser Glu Leu Leu Asn Leu Gly Glu Gly
2865                2870                2875                2880

Leu Gly Leu Asp Ser Asn Arg Glu Lys Asp Met Gly Leu Phe Glu Val
                2885                2890                2895

Phe Ser Gln Gln Leu Pro Thr Thr Glu Pro Val Asp Ser Ser Val Ser
                2900                2905                2910

Ser Ser Ile Ser Ala Glu Glu Gln Phe Glu Leu Pro Leu Glu Leu Pro
                2915                2920                2925

Ser Asp Leu Ser Val Leu Thr Thr Arg Ser Pro Thr Val Pro Ser Gln
        2930                2935                2940

Asn Pro Ser Arg Leu Ala Val Ile Ser Asp Ser Gly Glu Lys Arg Val
2945                2950                2955                2960

Thr Ile Thr Glu Lys Ser Val Ala Ser Ser Glu Ser Asp Pro Ala Leu
                2965                2970                2975

Leu Ser Pro Gly Val Asp Pro Thr Pro Glu Gly His Met Thr Pro Asp
        2980                2985                2990

His Phe Ile Gln Gly His Met Asp Ala Asp His Ile Ser Ser Pro Pro
        2995                3000                3005

Cys Gly Ser Val Glu Gln Gly His Gly Asn Asn Gln Asp Leu Thr Arg
        3010                3015                3020

Asn Ser Ser Thr Pro Gly Leu Gln Val Pro Val Ser Pro Thr Val Pro
3025                3030                3035                3040

Ile Gln Asn Gln Lys Tyr Val Pro Asn Ser Thr Asp Ser Pro Gly Pro
                3045                3050                3055

Ser Gln Ile Ser Asn Ala Ala Val Gln Thr Thr Pro Pro His Leu Lys
        3060                3065                3070

Pro Ala Thr Glu Lys Leu Ile Val Val Asn Gln Asn Met Gln Pro Leu
        3075                3080                3085

Tyr Val Leu Gln Thr Leu Pro Asn Gly Val Thr Gln Lys Ile Gln Leu
        3090                3095                3100

Thr Ser Ser Val Ser Ser Thr Pro Ser Val Met Glu Thr Asn Thr Ser
3105                3110                3115                3120

Val Leu Gly Pro Met Gly Gly Gly Leu Thr Leu Thr Thr Gly Leu Asn
                3125                3130                3135

Pro Ser Leu Pro Thr Ser Gln Ser Leu Phe Pro Ser Ala Ser Lys Gly
        3140                3145                3150
```

-continued

```
Leu Leu Pro Met Ser His His Gln His Leu His Ser Phe Pro Ala Ala
        3155                3160                3165

Thr Gln Ser Ser Phe Pro Pro Asn Ile Ser Asn Pro Pro Ser Gly Leu
        3170                3175                3180

Leu Ile Gly Val Gln Pro Pro Asp Pro Gln Leu Leu Val Ser Glu
3185                3190                3195                3200

Ser Ser Gln Arg Thr Asp Leu Ser Thr Thr Val Ala Thr Pro Ser Ser
        3205                3210                3215

Gly Leu Lys Lys Arg Pro Ile Ser Arg Leu Gln Thr Arg Lys Asn Lys
        3220                3225                3230

Lys Leu Ala Pro Ser Ser Thr Pro Ser Asn Ile Ala Pro Ser Asp Val
        3235                3240                3245

Val Ser Asn Met Thr Leu Ile Asn Phe Thr Pro Ser Gln Leu Pro Asn
        3250                3255                3260

His Pro Ser Leu Leu Asp Leu Gly Ser Leu Asn Thr Ser Ser His Arg
3265                3270                3275                3280

Thr Val Pro Asn Ile Ile Lys Arg Ser Lys Ser Ser Ile Met Tyr Phe
        3285                3290                3295

Glu Pro Ala Pro Leu Leu Pro Gln Ser Val Gly Gly Thr Ala Ala Thr
        3300                3305                3310

Ala Ala Gly Thr Ser Thr Ile Ser Gln Asp Thr Ser His Leu Thr Ser
        3315                3320                3325

Gly Ser Val Ser Gly Leu Ala Ser Ser Ser Ser Val Leu Asn Val Val
        3330                3335                3340

Ser Met Gln Thr Thr Thr Thr Pro Thr Ser Ser Ala Ser Val Pro Gly
3345                3350                3355                3360

His Val Thr Leu Thr Asn Pro Arg Leu Leu Gly Thr Pro Asp Ile Gly
        3365                3370                3375

Ser Ile Ser Asn Leu Leu Ile Lys Ala Ser Gln Gln Ser Leu Gly Ile
        3380                3385                3390

Gln Asp Gln Pro Val Ala Leu Pro Pro Ser Ser Gly Met Phe Pro Gln
        3395                3400                3405

Leu Gly Thr Ser Gln Thr Pro Ser Thr Ala Ala Ile Thr Ala Ala Ser
        3410                3415                3420

Ser Ile Cys Val Leu Pro Ser Thr Gln Thr Thr Gly Ile Thr Ala Ala
3425                3430                3435                3440

Ser Pro Ser Gly Glu Ala Asp Glu His Tyr Gln Leu Gln His Val Asn
        3445                3450                3455

Gln Leu Leu Ala Ser Lys Thr Gly Ile His Ser Ser Gln Arg Asp Leu
        3460                3465                3470

Asp Ser Ala Ser Gly Pro Gln Val Ser Asn Phe Thr Gln Thr Val Asp
        3475                3480                3485

Ala Pro Asn Ser Met Gly Leu Glu Gln Asn Lys Ala Leu Ser Ser Ala
        3490                3495                3500

Val Gln Ala Ser Pro Thr Ser Pro Gly Gly Ser Pro Ser Ser Pro Ser
3505                3510                3515                3520

Ser Gly Gln Arg Ser Ala Ser Pro Ser Val Pro Gly Pro Thr Lys Pro
        3525                3530                3535

Lys Pro Lys Thr Lys Arg Phe Gln Leu Pro Leu Asp Lys Gly Asn Gly
        3540                3545                3550

Lys Lys His Lys Val Ser His Leu Arg Thr Ser Ser Ser Glu Ala His
        3555                3560                3565

Ile Pro Asp Gln Glu Thr Thr Ser Leu Thr Ser Gly Thr Gly Thr Pro
```

-continued

```
              3570                3575                3580

Gly Ala Glu Ala Glu Gln Gln Asp Thr Ala Ser Val Glu Gln Ser Ser
3585                3590                3595                3600

Gln Lys Glu Cys Gly Gln Pro Ala Gly Gln Val Ala Val Leu Pro Glu
                3605                3610                3615

Val Gln Val Thr Gln Asn Pro Ala Asn Glu Gln Glu Ser Ala Glu Pro
                3620                3625                3630

Lys Thr Val Glu Glu Glu Glu Ser Asn Phe Ser Ser Pro Leu Met Leu
                3635                3640                3645

Trp Leu Gln Gln Glu Gln Lys Arg Lys Glu Ser Ile Thr Glu Lys Lys
                3650                3655                3660

Pro Lys Lys Gly Leu Val Phe Glu Ile Ser Ser Asp Asp Gly Phe Gln
3665                3670                3675                3680

Ile Cys Ala Glu Ser Ile Glu Asp Ala Trp Lys Ser Leu Thr Asp Lys
                3685                3690                3695

Val Gln Glu Ala Arg Ser Asn Ala Arg Leu Lys Gln Leu Ser Phe Ala
                3700                3705                3710

Gly Val Asn Gly Leu Arg Met Leu Gly Ile Leu His Asp Ala Val Val
                3715                3720                3725

Phe Leu Ile Glu Gln Leu Ser Gly Ala Lys His Cys Arg Asn Tyr Lys
                3730                3735                3740

Phe Arg Phe His Lys Pro Glu Glu Ala Asn Glu Pro Pro Leu Asn Pro
3745                3750                3755                3760

His Gly Ser Ala Arg Ala Glu Val His Leu Arg Lys Ser Ala Phe Asp
                3765                3770                3775

Met Phe Asn Phe Leu Ala Ser Lys His Arg Gln Pro Pro Glu Tyr Asn
                3780                3785                3790

Pro Asn Asp Glu Glu Glu Glu Val Gln Leu Lys Ser Ala Arg Arg
                3795                3800                3805

Ala Thr Ser Met Asp Leu Pro Met Pro Met Arg Phe Arg His Leu Lys
3810                3815                3820

Lys Thr Ser Lys Glu Ala Val Gly Val Tyr Arg Ser Pro Ile His Gly
3825                3830                3835                3840

Arg Gly Leu Phe Cys Lys Arg Asn Ile Asp Ala Gly Glu Met Val Ile
                3845                3850                3855

Glu Tyr Ala Gly Asn Val Ile Arg Ser Ile Gln Thr Asp Lys Arg Glu
                3860                3865                3870

Lys Tyr Tyr Asp Ser Lys Gly Ile Gly Cys Tyr Met Phe Arg Ile Asp
                3875                3880                3885

Asp Ser Glu Val Val Asp Ala Thr Met His Gly Asn Ala Ala Arg Phe
                3890                3895                3900

Ile Asn His Ser Cys Glu Pro Asn Cys Tyr Ser Arg Val Ile Asn Ile
3905                3910                3915                3920

Asp Gly Gln Lys His Ile Val Ile Phe Ala Met Arg Lys Ile Tyr Arg
                3925                3930                3935

Gly Glu Glu Leu Thr Tyr Asp Tyr Lys Phe Pro Ile Glu Asp Ala Ser
                3940                3945                3950

Asn Lys Leu Pro Cys Asn Cys Gly Ala Lys Lys Cys Arg Lys Phe Leu
                3955                3960                3965

Asn
```

<210> SEQ ID NO 4
<211> LENGTH: 1156

<212> TYPE: PRT
<213> ORGANISM: Homo sapiens

<400> SEQUENCE: 4

```
Met Gly Asp Thr Ala Pro Pro Gln Ala Pro Ala Gly Gly Leu Gly Gly
1               5                  10                  15

Ala Ser Gly Ala Gly Leu Leu Gly Gly Gly Ser Val Thr Pro Arg Val
            20                  25                  30

His Ser Ala Ile Val Glu Arg Leu Arg Ala Arg Ile Ala Val Cys Arg
            35                  40                  45

Gln His His Leu Ser Cys Glu Gly Arg Tyr Glu Arg Gly Arg Ala Glu
        50                  55                  60

Ser Ser Asp Arg Glu Arg Glu Ser Thr Leu Gln Leu Leu Ser Leu Val
65                  70                  75                  80

Gln His Gly Gln Gly Ala Arg Lys Ala Gly Lys His Thr Lys Ala Thr
                85                  90                  95

Ala Thr Ala Ala Thr Thr Thr Ala Pro Pro Pro Pro Ala Ala Pro
            100                 105                 110

Pro Ala Ala Ser Gln Ala Ala Ala Thr Ala Ala Pro Pro Pro Pro Pro
            115                 120                 125

Asp Tyr His His His His Gln Gln His Leu Leu Asn Ser Ser Asn Asn
            130                 135                 140

Gly Gly Ser Gly Gly Ile Asn Gly Glu Gln Gln Pro Pro Ala Ser Thr
145                 150                 155                 160

Pro Gly Asp Gln Arg Asn Ser Ala Leu Ile Ala Leu Gln Gly Ser Leu
                165                 170                 175

Lys Arg Lys Gln Val Val Asn Leu Ser Pro Ala Asn Ser Lys Arg Pro
                180                 185                 190

Asn Gly Phe Val Asp Asn Ser Phe Leu Asp Ile Lys Arg Ile Arg Val
                195                 200                 205

Gly Glu Asn Leu Ser Ala Gly Gln Gly Gly Leu Gln Ile Asn Asn Gly
        210                 215                 220

Gln Ser Gln Ile Met Ser Gly Thr Leu Pro Met Ser Gln Ala Pro Leu
225                 230                 235                 240

Arg Lys Thr Asn Thr Leu Pro Ser His Thr His Ser Pro Gly Asn Gly
                245                 250                 255

Leu Phe Asn Met Gly Leu Lys Glu Val Lys Lys Glu Pro Gly Glu Thr
            260                 265                 270

Leu Ser Cys Ser Lys His Met Asp Gly Gln Met Thr Gln Glu Asn Ile
            275                 280                 285

Phe Pro Asn Arg Tyr Gly Asp Asp Pro Gly Glu Gln Leu Met Asp Pro
        290                 295                 300

Glu Leu Gln Glu Leu Phe Asn Glu Leu Thr Asn Ile Ser Val Pro Pro
305                 310                 315                 320

Met Ser Asp Leu Glu Leu Glu Asn Met Ile Asn Ala Thr Ile Lys Gln
            325                 330                 335

Asp Asp Pro Phe Asn Ile Asp Leu Gly Gln Gln Ser Gln Arg Ser Thr
            340                 345                 350

Pro Arg Pro Ser Leu Pro Met Glu Lys Ile Val Ile Lys Ser Glu Tyr
            355                 360                 365

Ser Pro Gly Leu Thr Gln Gly Pro Ser Gly Ser Pro Gln Leu Arg Pro
        370                 375                 380

Pro Ser Ala Gly Pro Ala Phe Ser Met Ala Asn Ser Ala Leu Ser Thr
385                 390                 395                 400
```

-continued

Ser Ser Pro Ile Pro Ser Val Pro Gln Ser Gln Ala Gln Pro Gln Thr
            405                 410                 415

Gly Ser Gly Ala Ser Arg Ala Leu Pro Ser Trp Gln Glu Val Ser His
            420                 425                 430

Ala Gln Gln Leu Lys Gln Ile Ala Ala Asn Arg Gln Gln His Ala Arg
            435                 440                 445

Met Gln Gln His Gln Gln Gln His Gln Pro Thr Asn Trp Ser Ala Leu
    450                 455                 460

Pro Ser Ser Ala Gly Pro Ser Pro Gly Pro Phe Gly Gln Glu Lys Ile
465                 470                 475                 480

Pro Ser Pro Ser Phe Gly Gln Gln Thr Phe Ser Pro Gln Ser Ser Pro
            485                 490                 495

Met Pro Gly Val Ala Gly Gly Ser Gly Gln Ser Lys Val Met Ala Asn
            500                 505                 510

Tyr Met Tyr Lys Ala Gly Pro Ser Ala Gln Gly Gly His Leu Asp Val
            515                 520                 525

Leu Met Gln Gln Lys Pro Gln Asp Leu Ser Arg Ser Phe Ile Asn Asn
    530                 535                 540

Pro His Pro Ala Met Glu Pro Arg Gln Gly Asn Thr Lys Pro Leu Phe
545                 550                 555                 560

His Phe Asn Ser Asp Gln Ala Asn Gln Gln Met Pro Ser Val Leu Pro
            565                 570                 575

Ser Gln Asn Lys Pro Ser Leu Leu His Tyr Thr Gln Gln Gln Gln
            580                 585                 590

Gln Gln Gln Gln Gln Gln Gln Gln Gln Gln Gln Gln Gln Gln Gln
            595                 600                 605

Gln Gln Gln Gln Gln Gln Gln Gln Gln Gln Gln Gln Gln Ser Ser Ile
    610                 615                 620

Ser Ala Gln Gln Gln Gln Gln Gln Gln Ser Ser Ile Ser Ala Gln Gln
625                 630                 635                 640

Gln Gln Gln Gln Gln Gln Gln Gln Gln Gln Gln Gln Gln Gln Gln Gln
            645                 650                 655

Gln Gln Gln Gln Gln Gln Gln Gln Gln Pro Ser Ser Gln Pro Ala Gln
            660                 665                 670

Ser Leu Pro Ser Gln Pro Leu Leu Arg Ser Pro Leu Pro Leu Gln Gln
            675                 680                 685

Lys Leu Leu Leu Gln Gln Met Gln Asn Gln Pro Ile Ala Gly Met Gly
    690                 695                 700

Tyr Gln Val Ser Gln Gln Gln Arg Gln Asp Gln His Ser Val Val Gly
705                 710                 715                 720

Gln Asn Thr Gly Pro Ser Pro Ser Pro Asn Pro Cys Ser Asn Pro Asn
            725                 730                 735

Thr Gly Ser Gly Tyr Met Asn Ser Gln Gln Ser Leu Leu Asn Gln Gln
            740                 745                 750

Leu Met Gly Lys Lys Gln Thr Leu Gln Arg Gln Ile Met Glu Gln Lys
            755                 760                 765

Gln Gln Leu Leu Leu Gln Gln Gln Met Leu Ala Asp Ala Glu Lys Ile
    770                 775                 780

Ala Pro Gln Asp Gln Ile Asn Arg His Leu Ser Arg Pro Pro Pro Asp
785                 790                 795                 800

Tyr Lys Asp Gln Arg Arg Asn Val Gly Asn Met Gln Pro Thr Ala Gln
            805                 810                 815

-continued

```
Tyr Ser Gly Gly Ser Ser Thr Ile Ser Leu Asn Ser Asn Gln Ala Leu
            820                 825                 830

Ala Asn Pro Val Ser Thr His Thr Ile Leu Thr Pro Asn Ser Ser Leu
            835                 840                 845

Leu Ser Thr Ser His Gly Thr Arg Met Pro Ser Leu Ser Thr Ala Val
            850                 855                 860

Gln Asn Met Gly Met Tyr Gly Asn Leu Pro Cys Asn Gln Pro Asn Thr
865                 870                 875                 880

Tyr Ser Val Thr Ser Gly Met Asn Gln Leu Thr Gln Gln Arg Asn Pro
                    885                 890                 895

Lys Gln Leu Leu Ala Asn Gln Asn Asn Pro Met Met Pro Arg Pro Pro
                900                 905                 910

Thr Leu Gly Pro Ser Asn Asn Asn Asn Val Ala Thr Phe Gly Ala Gly
            915                 920                 925

Ser Val Gly Asn Ser Gln Gln Leu Arg Pro Asn Leu Thr His Ser Met
            930                 935                 940

Ala Ser Met Pro Pro Gln Arg Thr Ser Asn Val Met Ile Thr Ser Asn
945                 950                 955                 960

Thr Thr Ala Pro Asn Trp Ala Ser Gln Glu Gly Thr Ser Lys Gln Gln
                965                 970                 975

Glu Ala Leu Thr Ser Ala Gly Val Arg Phe Pro Thr Gly Thr Pro Ala
                980                 985                 990

Ala Tyr Thr Pro Asn Gln Ser Leu Gln Gln Ala Val Gly Ser Gln Gln
            995                 1000                1005

Phe Ser Gln Arg Ala Val Ala Pro Pro Asn Gln Leu Thr Pro Ala Val
    1010                1015                1020

Gln Met Arg Pro Met Asn Gln Met Ser Gln Thr Leu Asn Gly Gln Thr
1025                1030                1035                1040

Met Gly Pro Leu Arg Gly Leu Asn Leu Arg Pro Asn Gln Leu Ser Thr
                1045                1050                1055

Gln Ile Leu Pro Asn Leu Asn Gln Ser Gly Thr Gly Leu Asn Gln Ser
            1060                1065                1070

Arg Thr Gly Ile Asn Gln Pro Pro Ser Leu Thr Pro Ser Asn Phe Pro
            1075                1080                1085

Ser Pro Asn Gln Ser Ser Arg Ala Phe Gln Gly Thr Asp His Ser Ser
    1090                1095                1100

Asp Leu Ala Phe Asp Phe Leu Ser Gln Gln Asn Asp Asn Met Gly Pro
1105                1110                1115                1120

Ala Leu Asn Ser Asp Ala Asp Phe Ile Asp Ser Leu Leu Lys Thr Glu
                1125                1130                1135

Pro Gly Asn Asp Asp Trp Met Lys Asp Ile Asn Leu Asp Glu Ile Leu
            1140                1145                1150

Gly Asn Asn Ser
            1155
```

<210> SEQ ID NO 5
<211> LENGTH: 16600
<212> TYPE: DNA
<213> ORGANISM: Homo sapiens

<400> SEQUENCE: 5

```
gcttcacttc acggggcgaa catggcgcac agctgtcggt ggcgcttccc cgcccgaccc      60
gggaccaccg ggggcggcgg cggcggggggg cgcggggggcc tagggggcgc cccgcggcaa     120
cgcgtcccgg ccctgctgct tcccccccggg ccccccggtcg gcggtggcgg ccccgggggcg    180
```

```
cccccctccc ccccggctgt ggcggccgcg gcggcggcgg cgggaagcag cggggctggg      240
gttccagggg gagcggccgc cgcctcagca gcctcctcgt cgtccgcctc gtcttcgtct      300
tcgtcatcgt cctcagcctc ttcagggccg gccctgctcc gggtgggccc gggcttcgac      360
gcggcgctgc aggtctcggc cgccatcggc accaacctgc gccggttccg ggccgtgttt      420
ggggagagcg gcgggggagg cggcagcgga gaggatgagc aattcttagg ttttggctca      480
gatgaagaag tcagagtgcg aagtcccaca aggtctcctt cagttaaaac tagtcctcga      540
aaacctcgtg ggagacctag aagtggctct gaccgaaatt cagctatcct ctcagatcca      600
tctgtgtttt cccctctaaa taaatcagag accaaatctg gagataagat caagaagaaa      660
gattctaaaa gtatagaaaa gaagagagga agacctccca ccttccctgg agtaaaaatc      720
aaaataacac atggaaagga catttcagag ttaccaaagg gaaacaaaga agatagcctg      780
aaaaaaatta aaaggacacc ttctgctacg tttcagcaag ccacaaagat taaaaaatta      840
agagcaggta aactctctcc tctcaagtct aagtttaaga cagggaagct tcaaatagga      900
aggaaggggg tacaaattgt acgacggaga ggaaggcctc catcaacaga aaggataaag      960
accccttcgg gtctcctcat taattctgaa ctggaaaagc cccagaaagt ccggaaagac     1020
aaggaaggaa cacctccact tacaaaagaa gataagacag ttgtcagaca aagccctcga     1080
aggattaagc cagttaggat tattccttct tcaaaaagga cagatgcaac cattgctaag     1140
caactcttac agagggcaaa aaaggggct caaaagaaaa ttgaaaaaga agcagctcag     1200
ctgcagggaa gaaaggtgaa gacacaggtc aaaaatattc gacagttcat catgcctgtt     1260
gtcagtgcta tctcctcgcg gatcattaag accectcggc ggtttataga ggatgaggat     1320
tatgaccctc caattaaaat tgcccgatta gagtctacac cgaatagtag attcagtgcc     1380
ccgtcctgtg gatcttctga aaaatcaagt gcagcttctc agcactcctc tcaaatgtct     1440
tcagactcct ctcgatctag tagccccagt gttgatacct ccacagactc tcaggcttct     1500
gaggagattc aggtacttcc tgaggagcgg agcgataccc ctgaagttca tcctccactg     1560
cccatttccc agtcccaga aaatgagagt aatgatagga gaagcagaag gtattcagtg     1620
tcggagagaa gttttggatc tagaacgacg aaaaaattat caactctaca aagtgccccc     1680
cagcagcaga cctcctcgtc tccacctcca cctctgctga ctccaccgcc accactgcag     1740
ccagcctcca gtatctctga ccacacacct tggcttatgc ctccaacaat ccccttagca     1800
tcaccatttt tgcctgcttc cactgctcct atgcaaggga agcgaaaatc tattttgcga     1860
gaaccgacat ttaggtggac ttctttaaag cattctaggt cagagccaca atactttcc      1920 tcagcaaagt atgccaaaga aggtcttatt cgcaaaccaa tatttgataa tttccgaccc     1980
cctccactaa ctcccgagga cgttggcttt gcatctggtt tttctgcatc tggtaccgct     2040
gcttcagccc gattgttttc gccactccat tctggaacaa ggtttgatat gcacaaaagg     2100
agccctcttc tgagagctcc aagatttact ccaagtgagg ctcactctag aatatttgag     2160
tctgtaacct tgcctagtaa tcgaacttct gctggaacat cttcttcagg agtatccaat     2220
agaaaaagga aagaaaagt gtttagtcct attcgatctg aaccaagatc tccttctcac     2280
tccatgagga caagaagtgg aaggcttagt agttctgagc tctcacctct caccccccccg     2340 tcttctgtct cttcctcgtt aagcatttct gttagtcctc ttgccactag tgccttaaac     2400
ccaactttta cttttccttc tcattccctg actcagtctg gggaatctgc agagaaaaat     2460
cagagaccaa ggaagcagac tagtgctccg gcagagccat tttcatcaag tagtcctact     2520
```

-continued

```
cctctcttcc cttggtttac cccaggctct cagactgaaa gagggagaaa taaagacaag    2580
gcccccgagg agctgtccaa agatcgagat gctgacaaga gcgtggagaa ggacaagagt    2640
agagagagag accgggagag agaaaaggag aataagcggg agtcaaggaa agagaaaagg    2700
aaaaagggat cagaaattca gagtagttct gctttgtatc ctgtgggtag ggtttccaaa    2760
gagaaggttg ttggtgaaga tgttgccact tcatcttctg ccaaaaaagc aacagggcgg    2820
aagaagtctt catcacatga ttctgggact gatattactt ctgtgactct tggggataca    2880
acagctgtca aaaccaaaat acttataaag aaagggagag gaaatctgga aaaaaccaac    2940
ttggacctcg gcccaactgc cccatccctg gagaaggaga aaaccctctg cctttccact    3000
ccttcatcta gcactgttaa acattccact tcctccatag gctccatgtt ggctcaggca    3060
gacaagcttc caatgactga caagagggtt gccagcctcc taaaaaaggc caaagctcag    3120
ctctgcaaga ttgagaagag taagagtctt aaacaaaccg accagcccaa agcacagggt    3180
caagaaagtg actcatcaga gacctctgtg cgaggacccc ggattaaaca tgtctgcaga    3240
agagcagctg ttgcccttgg ccgaaaacga gctgtgtttc ctgatgacat gcccaccctg    3300
agtgccttac catgggaaga acgagaaaag attttgtctt ccatgggaa tgatgacaag    3360 tcatcaattg ctggctcaga agatgctgaa cctcttgctc cacccatcaa accaattaaa    3420
cctgtcacta gaaacaaggc accccaggaa cctccagtaa agaaaggacg tcgatcgagg    3480
cggtgtgggc agtgtcccgg ctgccaggtg cctgaggact gtggtgtttg tactaattgc    3540
ttagataagc ccaagtttgg tggtcgcaat ataaagaagc agtgctgcaa gatgagaaaa    3600
tgtcagaatc tacaatggat gccttccaaa gcctacctgc agaagcaagc taaagctgtg    3660
aaaaagaaag agaaaaagtc taagaccagt gaaaagaaag acagcaaaga gagcagtgtt    3720
gtgaagaacg tggtggactc tagtcagaaa cctaccccat cagcaagaga ggatcctgcc    3780
ccaaagaaaa gcagtagtga gcctcctcca cgaaagcccg tcgaggaaaa gagtgaagaa    3840
gggaatgtct cggcccctgg gcctgaatcc aaacaggcca ccactccagc ttccaggaag    3900
tcaagcaagc aggtctccca gccagcactg gtcatcccgc ctcagccacc tactacagga    3960
ccgccaagaa aagaagttcc caaaaccact cctagtgagc ccaagaaaaa gcagcctcca    4020
ccaccagaat caggtccaga gcagagcaaa cagaaaaaag tggctccccg cccaagtatc    4080
cctgtaaaac aaaaaccaaa agaaaaggaa aaaccacctc cggtcaataa gcaggagaat    4140
gcaggcactt tgaacatcct cagcactctc tccaatggca atagttctaa gcaaaaaatt    4200
ccagcagatg gagtccacag gatcagagtg gactttaagg aggattgtga agcagaaaat    4260
gtgtgggaga tgggaggctt aggaatcttg acttctgttc ctataacacc cagggtggtt    4320
tgctttctct gtgccagtag tgggcatgta gagtttgtgt attgccaagt ctgttgtgag    4380
cccttccaca agttttgttt agaggagaac gagcgccctc tggaggacca gctggaaaat    4440
tggtgttgtc gtcgttgcaa attctgtcac gtttgtggaa ggcaacatca ggctacaaag    4500
cagctgctgg agtgtaataa gtgccgaaac agctatcacc ctgagtgcct gggaccaaac    4560 tacccacca aacccacaaa gaagaagaaa gtctggatct gtaccaagtg tgttcgctgt    4620
aagagctgtg atccacaac tccaggcaaa gggtgggatg cacagtggtc tcatgatttc    4680
tcactgtgtc atgattgcgc caagctcttt gctaaaggaa acttctgccc tctctgtgac    4740
aaatgttatg atgatgatga ctatgagagt aagatgatgc aatgtggaaa gtgtgatcgc    4800
tgggtccatt ccaaatgtga gaatctttca ggtacagaag atgagatgta tgagattcta    4860
tctaatctgc cagaaagtgt ggcctacact tgtgtgaact gtactgagcg gcaccctgca    4920
```

-continued

```
gagtggcgac tggcccttga aaaagagctg cagatttctc tgaagcaagt tctgacagct    4980
ttgttgaatt ctcggactac cagccatttg ctacgctacc ggcaggctgc caagcctcca    5040
gacttaaatc ccgagacaga ggagagtata ccttcccgca gctcccccga aggacctgat    5100
ccaccagttc ttactgaggt cagcaaacag gatgatcagc agcctttaga tctagaagga    5160
gtcaagagga agatggacca agggaattac acatctgtgt tggagttcag tgatgatatt    5220
gtgaagatca ttcaagcagc cattaattca gatggaggac agccagaaat taaaaaagcc    5280
aacagcatgg tcaagtcctt cttcattcgg caaatggaac gtgttttcc atggttcagt    5340 gtcaaaaagt ccaggttttg ggagccaaat aaagtatcaa gcaacagtgg gatgttacca    5400
aacgcagtgc ttccaccttc acttgaccat aattatgctc agtggcagga gcgagaggaa    5460
aacagccaca ctgagcagcc tcctttaatg aagaaaatca ttccagctcc caaacccaaa    5520
ggtcctggag aaccagactc accaactcct ctgcatcctc ctacaccacc aattttgagt    5580
actgatagga gtcgagaaga cagtccagag ctgaacccac ccccaggcat agaagacaat    5640
agacagtgtg cgttatgttt gacttatggt gatgacagtg ctaatgatgc tggtcgttta    5700
ctatatattg gccaaaatga gtggacacat gtaaattgtg ctttgtggtc agcggaagtg    5760
tttgaagatg atgacggatc actaaagaat gtgcatatgg ctgtgatcag gggcaagcag    5820
ctgagatgtg aattctgcca aaagccagga gccaccgtgg gttgctgtct cacatcctgc    5880
accagcaact atcacttcat gtgttcccga gccaagaact gtgtctttct ggatgataaa    5940
aaagtatatt gccaacgaca tcgggatttg atcaaaggcg aagtggttcc tgagaatgga    6000
tttgaagttt tcagaagagt gtttgtggac tttgaaggaa tcagcttgag aaggaagttt    6060
ctcaatggct tggaaccaga aaatatccac atgatgattg ggtctatgac aatcgactgc    6120
ttaggaattc taaatgatct ctccgactgt gaagataagc tctttcctat tggatatcag    6180
tgttccaggg tatactggag caccacagat gctcgcaagc gctgtgtata tacatgcaag    6240
atagtggagt gccgtcctcc agtcgtagag ccggatatca acagcactgt tgaacatgat    6300
gaaaacagga ccattgccca tagtccaaca tcttttacag aaagttcatc aaaagagagt    6360
caaaacacag ctgaaattat aagtcctcca tcaccagacc gacctcctca ttcacaaacc    6420
tctggctcct gttattatca tgtcatctca aaggtcccca ggattcgaac acccagttat    6480
tctccaacac agagatcccc tggctgtcga ccgttgcctt ctgcaggaag tcctacccca    6540
accactcatg aaatagtcac agtaggtgat cctttactct cctctggact tcgaagcatt    6600
ggctccaggc gtcacagtac ctcttcctta tcaccccagc ggtccaaact ccggataatg    6660
tctccaatga gaactgggaa tacttactct aggaataatg tttcctcagt ctccaccacc    6720
gggaccgcta ctgatcttga atcaagtgcc aaagtagttg atcatgtctt agggccactg    6780
aattcaagta ctagtttagg gcaaaacact ccacctctt caaatttgca aaggacagtg    6840
gttactgtag gcaataaaaa cagtcacttg gatggatctt catcttcaga aatgaagcag    6900
tccagtgctt cagacttggt gtccaagagc tcctctttaa agggagagaa gaccaaagtg    6960
ctgagttcca agagctcaga gggatctgca cataatgtgg cttaccctgg aattcctaaa    7020
ctggccccac aggttcataa cacaaacatct agagaactga atgttagtaa aatcggctcc    7080
tttgctgaac cctcttcagt gtcgtttct tctaaagagg ccctctcctt cccacacctc    7140
catttgagag ggcaaaggaa tgatcgagac caacacacag attctaccca atcagcaaac    7200
tcctctccag atgaagatac tgaagtcaaa accttgaagc tatctggaat gagcaacaga    7260
```

-continued

```
tcatccatta tcaacgaaca tatgggatct agttccagag ataggagaca gaaagggaaa    7320
aaatcctgta aagaaacttt caaagaaaag cattccagta aatctttttt ggaacctggt    7380
caggtgacaa ctggtgagga aggaaacttg aagccagagt ttatggatga ggttttgact    7440
cctgagtata tgggccaacg accatgtaac aatgtttctt ctgataagat tggtgataaa    7500
ggcctttcta tgccaggagt ccccaaagct ccacccatgc aagtagaagg atctgccaag    7560
gaattacagg caccacggaa acgcacagtc aaagtgacac tgacacctct aaaaatggaa    7620
aatgagagtc aatccaaaaa tgccctgaaa gaaagtagtc ctgcttcccc tttgcaaata    7680
gagtcaacat ctcccacaga accaatttca gcctctgaaa atccaggaga tggtccagtg    7740
gcccaaccaa gccccaataa tacctcatgc caggattctc aaagtaacaa ctatcagaat    7800
cttccagtac aggacagaaa cctaatgctt ccagatggcc ccaaacctca ggaggatggc    7860
tcttttaaaa ggaggtatcc ccgtcgcagt gcccgtgcac gttctaacat gttttttggg    7920
cttaccccac tctatggagt aagatcctat ggtgaagaag acattccatt ctacagcagc    7980
tcaactggga agaagcgagg caagagatca gctgaaggac aggtggatgg ggccgatgac    8040
ttaagcactt cagatgaaga cgacttatac tattacaact tcactagaac agtgatttct    8100
tcaggtggag aggaacgact ggcatcccat aatttatttc gggaggagga acagtgtgat    8160
cttccaaaaa tctcacagtt ggatggtgtt gatgatggga cagagagtga tactagtgtc    8220
acagccacaa caaggaaaag cagccagatt ccaaaaagaa atggtaaaga aaatggaaca    8280
gagaacttaa agattgatag acctgaagat gctggggaga aagaacatgt cactaagagt    8340
tctgttggcc acaaaaatga gccaaagatg gataactgcc attctgtaag cagagttaaa    8400
acacagggac aagattcctt ggaagctcag ctcagctcat tggagtcaag ccgcagagtc    8460
cacacaagta cccctccga caaaaattta ctggacacct ataatactga gctcctgaaa    8520
tcagattcag acaataacaa cagtgatgac tgtgggaata tcctgccttc agacattatg    8580
gactttgtac taaagaatac tccatccatg caggctttgg gtgagagccc agagtcatct    8640
tcatcagaac tcctgaatct tggtgaagga ttgggtcttg acagtaatcg tgaaaaagac    8700
atgggtcttt ttgaagtatt ttctcagcag ctgcctacaa cagaacctgt ggatagtagt    8760
gtctcttcct ctatctcagc agaggaacag tttgagttgc ctctagagct accatctgat    8820
ctgtctgtct tgaccaccg gagtcccact gtccccagcc agaatcccag tagactagct    8880
gttatctcag actcaggga gaagagagta accatcacag aaaaatctgt agcctcctct    8940
gaaagtgacc cagcactgct gagcccagga gtagatccaa ctcctgaagg ccacatgact    9000
cctgatcatt ttatccaagg acacatggat gcagaccaca tctctagccc tccttgtggt    9060
tcagtagagc aaggtcatgg caacaatcag gatttaacta ggaacagtag cacccctggc    9120
cttcaggtac ctgtttcccc aactgttccc atccagaacc agaagtatgt gcccaattct    9180
actgatagtc ctggcccgtc tcagatttcc aatgcagctg tccagaccac tccacccac    9240 ctgaagccag ccactgagaa actcatagtt gttaaccaga acatgcagcc actttatgtt    9300
ctccaaactc ttccaaatgg agtgacccaa aaaatccaat tgacctcttc tgttagttct    9360
acacccagtg tgatggagac aaatacttca gtattgggac ccatgggagg tggtctcacc    9420
cttaccacag gactaaatcc aagcttgcca acttctcaat ctttgttccc ttctgctagc    9480
aaaggattgc tacccatgtc tcatcaccag cacttacatt ccttccctgc agctactcaa    9540
agtagtttcc caccaaacat cagcaatcct ccttcaggcc tgcttattgg ggttcagcct    9600
cctccggatc cccaactttt ggtttcagaa tccagccaga ggacagacct cagtaccaca    9660
```

-continued

```
gtagccactc catcctctgg actcaagaaa agacccatat ctcgtctaca gacccgaaag    9720
aataaaaaac ttgctccctc tagtacccct tcaaacattg ccccttctga tgtggtttct    9780
aatatgacat tgattaactt cacaccctcc cagcttccta atcatccaag tctgttagat    9840
ttggggtcac ttaatacttc atctcaccga actgtcccca acatcataaa aagatctaaa    9900
tctagcatca tgtattttga accggcaccc ctgttaccac agagtgtggg aggaactgct    9960
gccacagcgg caggcacatc aacaataagc caggatacta gccacctcac atcagggtct   10020
gtgtctggct tggcatccag ttcctctgtc ttgaatgttg tatccatgca aactaccaca   10080
acccctacaa gtagtgcgtc agttccagga cacgtcacct taaccaaccc aaggttgctt   10140
ggtaccccag atattggctc aataagcaat cttttaatca aagctagcca gcagagcctg   10200
gggattcagg accagcctgt ggctttaccg ccaagttcag gaatgtttcc acaactgggg   10260
acatcacaga ccccctctac tgctgcaata acagcggcat ctagcatctg tgtgctcccc   10320
tccactcaga ctacgggcat aacagccgct tcaccttctg gggaagcaga cgaacactat   10380
cagcttcagc atgtgaacca gctccttgcc agcaaaactg ggattcattc ttcccagcgt   10440
gatcttgatt ctgcttcagg gccccaggta tccaacttta cccagacggt agacgctcct   10500
aatagcatgg gactggagca gaacaaggct ttatcctcag ctgtgcaagc cagccccacc   10560
tctcctgggg gttctccatc ctctccatct tctggacagc ggtcagcaag cccttcagtg   10620
ccgggtccca ctaaacccaa accaaaaacc aaacggtttc agctgcctct agacaaaggg   10680
aatggcaaga agcacaaagt ttcccatttg cggaccagtt cttctgaagc acacattcca   10740
gaccaagaaa cgacatccct gacctcaggc acagggactc caggagcaga ggctgagcag   10800
caggatacag ctagcgtgga gcagtcctcc cagaaggagt gtgggcaacc tgcagggcaa   10860
gtcgctgttc ttccggaagt tcaggtgacc caaaatccag caaatgaaca agaaagtgca   10920
gaacctaaaa cagtggaaga agaggaaagt aatttcagct ccccactgat gctttggctt   10980
cagcaagaac aaaagcggaa ggaaagcatt actgagaaaa aacccaagaa aggacttgtt   11040
tttgaaattt ccagtgatga tggctttcag atctgtgcag aaagtattga agatgcctgg   11100
aagtcattga cagataaagt ccaggaagct cgatcaaatg cccgcctaaa gcagctctca   11160
tttgcaggtg ttaacggttt gaggatgctg gggattctcc atgatgcagt tgtgttcctc   11220
attgagcagc tgtctggtgc caagcactgt cgaaattaca aattccgttt ccacaagcca   11280
gaggaggcca atgaacccc cttgaaccct cacggctcag ccagggctga agtccacctc   11340
aggaagtcag catttgacat gtttaacttc ctggcttcta aacatcgtca gcctcctgaa   11400
tacaacccca atgatgaaga agaggaggag gtacagctga agtcagctcg gagggcaact   11460
agcatggatc tgccaatgcc catgcgcttc cggcacttaa aaaagacttc taaggaggca   11520
gttggtgtct acaggtctcc catccatggc cggggtcttt tctgtaagag aaacattgat   11580
gcaggtgaga tggtgattga gtatgccggc aacgtcatcc gctccatcca gactgacaag   11640
cgggaaaagt attacgacag caagggcatt ggttgctata tgttccgaat tgatgactca   11700
gaggtagtgg atgccaccat gcatggaaat gctgcacgct tcatcaatca ctcgtgtgag   11760
cctaactgct attctcgggt catcaatatt gatgggcaga agcacattgt catctttgcc   11820
atgcgtaaga tctaccgagg agaggaactc acttacgact ataagttccc cattgaggat   11880
gccagcaaca agctgcccctg caactgtggc gccaagaaat gccggaagtt cctaaactaa   11940
agctgctctt ctcccccagt gttggagtgc aaggaggcgg ggccatccaa agcaacgctg   12000
```

-continued

```
aaggcctttt ccagcagctg ggagctcccg gattgcgtgg cacagctgag gggcctctgt   12060
gatggctgag ctctcttatg tcctatactc acatcagaca tgtgatcata gtcccagaga   12120
cagagttgag gtctcgaaga aaagatccat gatcggcttt ctcctggggc ccctccaatt   12180
gtttactgtt agaaagtggg aatggggtcc ctagcagact tgcctggaag gagcctatta   12240
tagagggttg gttatgttgg gagattgggc ctgaatttct ccacagaaat aagttgccat   12300
cctcaggttg gccctttccc aagcactgta agtgagtggg tcaggcaaag ccccaaatgg   12360
agggttggtt agattcctga cagtttgcca gccaggcccc acctacagcg tctgtcgaac   12420
aaacagaggt ctggtggttt tccctactat cctcccactc gagagttcac ttctggttgg   12480
gagacaggat tcctagcacc tccggtgtca aaaggctgtc atggggttgt gccaattaat   12540
taccaaacat tgagcctgca ggctttgagt gggagtgttg cccccaggag ccttatctca   12600
gccaattacc tttcttgaca gtaggagcgg cttccctctc ccattccctc ttcactccct   12660
tttcttcctt tcccctgtct tcatgccact gctttcccat gcttctttcg ggttgtaggg   12720
gagactgact gcctgctcaa ggacactccc tgctgggcat aggatgtgcc tgcaaaaagt   12780
tccctgagcc tgtaagcact ccaggtgggg aagtggacag gagccattgg tcataaccag   12840
acagaatttg gaaacatttt cataaagctc catggagagt tttaaagaaa catatgtagc   12900
atgattttgt aggagaggaa aaagattatt taaataggat ttaaatcatg caacaacgag   12960
agtatcacag ccaggatgac ccttgggtcc cattcctaag acatggttac tttattttcc   13020
ccttgttaag acataggaag acttaatttt taaacggtca gtgtccagtt gaaggcagaa   13080
cactaatcag atttcaaggc ccacaacttg gggactagac caccttatgt tgagggaact   13140
ctgccacctg cgtgcaaccc acagctaaag taaattcaat gacactactg ccctgattac   13200 tcctaggat gtggtcaaaa cagcatcaaa tgtttcttct cttcctttcc ccaagacaga   13260
gtcctgaacc tgttaaatta agtcattgga ttttactctg ttctgtttac agtttactat   13320
ttaaggtttt ataaatgtaa atatattttg tatatttttc tatgagaagc acttcatagg   13380
gagaagcact tatgacaagg ctattttta aaccgcggta ttatcctaat ttaaaagaag   13440
atcggttttt aataattttt tattttcata ggatgaagtt agagaaaata ttcagctgta   13500
cacacaaagt ctggtttttc ctgcccaact tcccctgga aggtgtactt tttgttgttt   13560
aatgtgtagc ttgtttgtgc cctgttgaca taaatgtttc ctgggtttgc tctttgacaa   13620
taaatggaga aggaaggtca cccaactcca ttgggccact cccctcctc ccctattgaa   13680 gctcctcaaa aggctacagt aatatcttga tacaacagat tctcttcttt cccgcctctc   13740
tcctttccgg cgcaacttcc agagtggtgg gagacggcaa tctttacatt tccctcatct   13800
ttcttacttc agagttagca aacaacaagt tgaatggcaa cttgacattt ttgcatcacc   13860
atctgcctca taggccactc tttcctttcc ctctgcccac caagtcctca tatctgcaga   13920
gaacccattg atcaccttgt gccctctttt ggggcagcct gttgaaactg aagcacagtc   13980
tgaccactca cgataaagca gatttttctc tgcctctgcc acaaggtttc agagtagtgt   14040
agtccaagta gagggtgggg cacccttttc tcgccgcaag aagcccattc ctatggaagt   14100
ctagcaaagc aatacgactc agcccagcac tctctgcccc aggactcatg gctctgctgt   14160
gccttccatc ctgggctccc ttctctcctg tgaccttaag aactttgtct ggtggctttg   14220
ctggaacatt gtcactgttt tcactgtcat gcagggagcc cagcactgtg gccaggatgg   14280
cagagacttc cttgtcatca tggagaagtg ccagcagggg actgggaaaa gcactctacc   14340
cagacctcac ctcccttcct ccttttgccc atgaacaaga tgcagtggcc ctagggttc   14400
```

-continued

```
cactagtgtc tgctttcctt tattattgca ctgtgtgagg tttttttgta aatccttgta   14460
ttcctatttt ttttaaagaa aaaaaaaaaa ccttaagctg catttgttac tgaaatgatt   14520
aatgcactga tgggtcctga attcaccttg agaaagaccc aaaggccagt caggggtgg    14580 ggggaactca gctaaataga cctagttact gccctgctag gccatgctgt actgtgagcc   14640
cctcctcact ctctaccaac cctaaaccct gaggacaggg gaggaaccca cagcttcctt   14700
ctcctgccag ctgcagatgg tttgccttgc ctttccaccc cctaattgtc aaccacaaaa   14760
atgagaaatt cctcttctag ctcagccttg agtccattgc caaattttca gcacacctgc   14820
cagcaacttg ggggaataag cgaaggtttc cctacaagag ggaaagaagg caaaaacggc   14880
acagctatct ccaaacacat ctgagttcat ttcaaaagtg accaagggaa tctccgcaca   14940
aaagtgcaga ttgaggaatt gtgatgggtc attcccaaga atcccccaag gggcatccca   15000
aatccctgag gagtaacagc tgcaaacctg gtcagttctc agtgagagcc agctcactta   15060
tagctttgct gctagaacct gttgtggctg catttcctgg tggccagtga caactgtgta   15120
accagaatag ctgcatggcg ctgacccttt ggccggaact tggtctcttg gctccctcct   15180
tggccaccca ccacctctcg cacagcccct ctgtttttac accaataaca agaattaagg   15240
gggaagccct ggcagctata cgttttcaac cagactcctt tgccgggacc cagcccgcca   15300
ccctgctcgc ctccgtcaaa cccccggcca atgcagtgag caccatgtag ctcccttgat   15360
ttaaaaaaaa taaaaaataa aaaaaaaagg aaaaaaaaat acaacacaca cacaaaaata   15420
aaaaaaatat tctaatgaat gtatctttct aaaggactga cgttcaatca aatatctgaa   15480
aatactaaag gtcaaaacct tgtcagatgt taacttctaa gttcggtttg ggattttttt   15540
tttttaatag aaatcaagtt gttttgtttt ttaggaaaa gcgggtcatt gcaaagggct    15600
gggtgtaatt ttatgtttca tttccttcat tttaaagcaa tacaaggtta tggagcagat   15660
ggttttgtgc cgaatcatga atactagtca agtcacacac tctggaaact tgcaactttt   15720
tgtttgtttt ggttttcaaa taaatataaa tatgatatat ataggaacta atatagtaat   15780
gcaccatgta acaaagccta gttcagtcca tggcttttaa ttctcttaac actatagata   15840
aggattgtgt tacagttgct agtagcggca ggaagatgtc aggctcactt tcctctgatt   15900
cccgaaatgg ggggaacctc taaccataaa ggaatggtag aacagtccat tcctcggatc   15960
agagaaaaat gcagacatgg tgtcacctgg attttttttct gcccatgaat gttgccagtc   16020
agtacctgtc ctccttgttt ctctattttt ggttatgaat gttggggtta ccacctgcat   16080
ttaggggaaa attgtgttct gtgctttcct ggtatcttgt tccgaggtac tctagttctg   16140
tctttcaacc aagaaaatag aattgtggtg tttctttat tgaacttta acagtctctt     16200 tagtaaatac aggtagttga ataattgttt caagagctca acagatgaca agcttctttt   16260
ctagaaataa gacatttttt gacaacttta tcatgtataa cagatctgtt ttttttcctt   16320
gtgttcttcc aagcttctgg ttagagaaaa agagaaaaaa aaaaaggaa aatgtgtcta    16380 aagtccatca gtgttaactc cctgtgacag ggatgaagga aaatacttta atagttcaaa   16440
aaataataat gctgaaagct ctctacgaaa gactgaatgt aaaagtaaaa agtgtacata   16500
gttgtaaaaa aaaggagttt ttaaacatgt ttattttcta tgcacttttt tttatttaag   16560
tgatagttta attaataaac atgtcaagtt tattgctgca             16600
```

<210> SEQ ID NO 6
<211> LENGTH: 3972
<212> TYPE: PRT

-continued

```
<213> ORGANISM: Homo sapiens

<400> SEQUENCE: 6

Met Ala His Ser Cys Arg Trp Arg Phe Pro Ala Arg Pro Gly Thr Thr
1               5                   10                  15

Gly Gly Gly Gly Gly Gly Gly Arg Arg Gly Leu Gly Gly Ala Pro Arg
            20                  25                  30

Gln Arg Val Pro Ala Leu Leu Leu Pro Pro Gly Pro Pro Val Gly Gly
        35                  40                  45

Gly Gly Pro Gly Ala Pro Pro Ser Pro Pro Ala Val Ala Ala Ala Ala
    50                  55                  60

Ala Ala Ala Gly Ser Ser Gly Ala Gly Val Pro Gly Gly Ala Ala Ala
65                  70                  75                  80

Ala Ser Ala Ala Ser Ser Ser Ser Ala Ser Ser Ser Ser Ser Ser Ser
                85                  90                  95

Ser Ser Ala Ser Ser Gly Pro Ala Leu Leu Arg Val Gly Pro Gly Phe
            100                 105                 110

Asp Ala Ala Leu Gln Val Ser Ala Ala Ile Gly Thr Asn Leu Arg Arg
        115                 120                 125

Phe Arg Ala Val Phe Gly Glu Ser Gly Gly Gly Gly Ser Gly Glu
        130                 135                 140

Asp Glu Gln Phe Leu Gly Phe Gly Ser Asp Glu Glu Val Arg Val Arg
145                 150                 155                 160

Ser Pro Thr Arg Ser Pro Ser Val Lys Thr Ser Pro Arg Lys Pro Arg
                165                 170                 175

Gly Arg Pro Arg Ser Gly Ser Asp Arg Asn Ser Ala Ile Leu Ser Asp
            180                 185                 190

Pro Ser Val Phe Ser Pro Leu Asn Lys Ser Glu Thr Lys Ser Gly Asp
            195                 200                 205

Lys Ile Lys Lys Lys Asp Ser Lys Ser Ile Glu Lys Lys Arg Gly Arg
    210                 215                 220

Pro Pro Thr Phe Pro Gly Val Lys Ile Lys Ile Thr His Gly Lys Asp
225                 230                 235                 240

Ile Ser Glu Leu Pro Lys Gly Asn Lys Glu Asp Ser Leu Lys Lys Ile
                245                 250                 255

Lys Arg Thr Pro Ser Ala Thr Phe Gln Gln Ala Thr Lys Ile Lys Lys
            260                 265                 270

Leu Arg Ala Gly Lys Leu Ser Pro Leu Lys Ser Lys Phe Lys Thr Gly
    275                 280                 285

Lys Leu Gln Ile Gly Arg Lys Gly Val Gln Ile Val Arg Arg Arg Gly
    290                 295                 300

Arg Pro Pro Ser Thr Glu Arg Ile Lys Thr Pro Ser Gly Leu Leu Ile
305                 310                 315                 320

Asn Ser Glu Leu Glu Lys Pro Gln Lys Val Arg Lys Asp Lys Glu Gly
            325                 330                 335

Thr Pro Pro Leu Thr Lys Glu Asp Lys Thr Val Val Arg Gln Ser Pro
            340                 345                 350

Arg Arg Ile Lys Pro Val Arg Ile Ile Pro Ser Ser Lys Arg Thr Asp
        355                 360                 365

Ala Thr Ile Ala Lys Gln Leu Leu Gln Arg Ala Lys Lys Gly Ala Gln
    370                 375                 380

Lys Lys Ile Glu Lys Glu Ala Ala Gln Leu Gln Gly Arg Lys Val Lys
385                 390                 395                 400
```

```
Thr Gln Val Lys Asn Ile Arg Gln Phe Ile Met Pro Val Val Ser Ala
            405             410             415

Ile Ser Ser Arg Ile Ile Lys Thr Pro Arg Arg Phe Ile Glu Asp Glu
            420             425             430

Asp Tyr Asp Pro Pro Ile Lys Ile Ala Arg Leu Glu Ser Thr Pro Asn
            435             440             445

Ser Arg Phe Ser Ala Pro Ser Cys Gly Ser Ser Glu Lys Ser Ser Ala
    450             455             460

Ala Ser Gln His Ser Ser Gln Met Ser Ser Asp Ser Ser Arg Ser Ser
465             470             475             480

Ser Pro Ser Val Asp Thr Ser Thr Asp Ser Gln Ala Ser Glu Glu Ile
            485             490             495

Gln Val Leu Pro Glu Glu Arg Ser Asp Thr Pro Glu Val His Pro Pro
            500             505             510

Leu Pro Ile Ser Gln Ser Pro Glu Asn Glu Ser Asn Asp Arg Arg Ser
            515             520             525

Arg Arg Tyr Ser Val Ser Glu Arg Ser Phe Gly Ser Arg Thr Thr Lys
    530             535             540

Lys Leu Ser Thr Leu Gln Ser Ala Pro Gln Gln Gln Thr Ser Ser Ser
545             550             555             560

Pro Pro Pro Pro Leu Leu Thr Pro Pro Pro Leu Gln Pro Ala Ser
            565             570             575

Ser Ile Ser Asp His Thr Pro Trp Leu Met Pro Pro Thr Ile Pro Leu
            580             585             590

Ala Ser Pro Phe Leu Pro Ala Ser Thr Ala Pro Met Gln Gly Lys Arg
            595             600             605

Lys Ser Ile Leu Arg Glu Pro Thr Phe Arg Trp Thr Ser Leu Lys His
    610             615             620

Ser Arg Ser Glu Pro Gln Tyr Phe Ser Ser Ala Lys Tyr Ala Lys Glu
625             630             635             640

Gly Leu Ile Arg Lys Pro Ile Phe Asp Asn Phe Arg Pro Pro Pro Leu
            645             650             655

Thr Pro Glu Asp Val Gly Phe Ala Ser Gly Phe Ser Ala Ser Gly Thr
            660             665             670

Ala Ala Ser Ala Arg Leu Phe Ser Pro Leu His Ser Gly Thr Arg Phe
    675             680             685

Asp Met His Lys Arg Ser Pro Leu Leu Arg Ala Pro Arg Phe Thr Pro
    690             695             700

Ser Glu Ala His Ser Arg Ile Phe Glu Ser Val Thr Leu Pro Ser Asn
705             710             715             720

Arg Thr Ser Ala Gly Thr Ser Ser Ser Gly Val Ser Asn Arg Lys Arg
            725             730             735

Lys Arg Lys Val Phe Ser Pro Ile Arg Ser Glu Pro Arg Ser Pro Ser
            740             745             750

His Ser Met Arg Thr Arg Ser Gly Arg Leu Ser Ser Ser Glu Leu Ser
    755             760             765

Pro Leu Thr Pro Pro Ser Ser Val Ser Ser Ser Leu Ser Ile Ser Val
    770             775             780

Ser Pro Leu Ala Thr Ser Ala Leu Asn Pro Thr Phe Thr Phe Pro Ser
785             790             795             800

His Ser Leu Thr Gln Ser Gly Glu Ser Ala Glu Lys Asn Gln Arg Pro
            805             810             815

Arg Lys Gln Thr Ser Ala Pro Ala Glu Pro Phe Ser Ser Ser Ser Pro
```

-continued

```
                 820                 825                 830

Thr Pro Leu Phe Pro Trp Phe Thr Pro Gly Ser Gln Thr Glu Arg Gly
        835                 840                 845

Arg Asn Lys Asp Lys Ala Pro Glu Glu Leu Ser Lys Asp Arg Asp Ala
    850                 855                 860

Asp Lys Ser Val Glu Lys Asp Lys Ser Arg Glu Arg Asp Arg Glu Arg
865                 870                 875                 880

Glu Lys Glu Asn Lys Arg Glu Ser Arg Lys Glu Lys Arg Lys Lys Gly
                885                 890                 895

Ser Glu Ile Gln Ser Ser Ser Ala Leu Tyr Pro Val Gly Arg Val Ser
                900                 905                 910

Lys Glu Lys Val Val Gly Glu Asp Val Ala Thr Ser Ser Ser Ala Lys
        915                 920                 925

Lys Ala Thr Gly Arg Lys Lys Ser Ser Ser His Asp Ser Gly Thr Asp
    930                 935                 940

Ile Thr Ser Val Thr Leu Gly Asp Thr Thr Ala Val Lys Thr Lys Ile
945                 950                 955                 960

Leu Ile Lys Lys Gly Arg Gly Asn Leu Glu Lys Thr Asn Leu Asp Leu
                965                 970                 975

Gly Pro Thr Ala Pro Ser Leu Glu Lys Glu Lys Thr Leu Cys Leu Ser
            980                 985                 990

Thr Pro Ser Ser Ser Thr Val Lys His Ser Thr Ser Ser Ile Gly Ser
        995                 1000                1005

Met Leu Ala Gln Ala Asp Lys Leu Pro Met Thr Asp Lys Arg Val Ala
    1010                1015                1020

Ser Leu Leu Lys Lys Ala Lys Ala Gln Leu Cys Lys Ile Glu Lys Ser
1025                1030                1035                1040

Lys Ser Leu Lys Gln Thr Asp Gln Pro Lys Ala Gln Gly Gln Glu Ser
            1045                1050                1055

Asp Ser Ser Glu Thr Ser Val Arg Gly Pro Arg Ile Lys His Val Cys
            1060                1065                1070

Arg Arg Ala Ala Val Ala Leu Gly Arg Lys Arg Ala Val Phe Pro Asp
        1075                1080                1085

Asp Met Pro Thr Leu Ser Ala Leu Pro Trp Glu Glu Arg Glu Lys Ile
    1090                1095                1100

Leu Ser Ser Met Gly Asn Asp Asp Lys Ser Ser Ile Ala Gly Ser Glu
1105                1110                1115                1120

Asp Ala Glu Pro Leu Ala Pro Pro Ile Lys Pro Ile Lys Pro Val Thr
            1125                1130                1135

Arg Asn Lys Ala Pro Gln Glu Pro Pro Val Lys Lys Gly Arg Arg Ser
        1140                1145                1150

Arg Arg Cys Gly Gln Cys Pro Gly Cys Gln Val Pro Glu Asp Cys Gly
        1155                1160                1165

Val Cys Thr Asn Cys Leu Asp Lys Pro Lys Phe Gly Gly Arg Asn Ile
    1170                1175                1180

Lys Lys Gln Cys Cys Lys Met Arg Lys Cys Gln Asn Leu Gln Trp Met
1185                1190                1195                1200

Pro Ser Lys Ala Tyr Leu Gln Lys Gln Ala Lys Ala Val Lys Lys Lys
            1205                1210                1215

Glu Lys Lys Ser Lys Thr Ser Glu Lys Lys Asp Ser Lys Glu Ser Ser
            1220                1225                1230

Val Val Lys Asn Val Val Asp Ser Ser Gln Lys Pro Thr Pro Ser Ala
        1235                1240                1245
```

-continued

```
Arg Glu Asp Pro Ala Pro Lys Lys Ser Ser Ser Glu Pro Pro Pro Arg
    1250                1255                1260

Lys Pro Val Glu Glu Lys Ser Glu Glu Gly Asn Val Ser Ala Pro Gly
1265                1270                1275                1280

Pro Glu Ser Lys Gln Ala Thr Thr Pro Ala Ser Arg Lys Ser Ser Lys
                1285                1290                1295

Gln Val Ser Gln Pro Ala Leu Val Ile Pro Pro Gln Pro Pro Thr Thr
                1300                1305                1310

Gly Pro Pro Arg Lys Glu Val Pro Lys Thr Thr Pro Ser Glu Pro Lys
            1315                1320                1325

Lys Lys Gln Pro Pro Pro Pro Glu Ser Gly Pro Glu Gln Ser Lys Gln
            1330                1335                1340

Lys Lys Val Ala Pro Arg Pro Ser Ile Pro Val Lys Gln Lys Pro Lys
1345                1350                1355                1360

Glu Lys Glu Lys Pro Pro Pro Val Asn Lys Gln Glu Asn Ala Gly Thr
                1365                1370                1375

Leu Asn Ile Leu Ser Thr Leu Ser Asn Gly Asn Ser Ser Lys Gln Lys
                1380                1385                1390

Ile Pro Ala Asp Gly Val His Arg Ile Arg Val Asp Phe Lys Glu Asp
            1395                1400                1405

Cys Glu Ala Glu Asn Val Trp Glu Met Gly Gly Leu Gly Ile Leu Thr
    1410                1415                1420

Ser Val Pro Ile Thr Pro Arg Val Val Cys Phe Leu Cys Ala Ser Ser
1425                1430                1435                1440

Gly His Val Glu Phe Val Tyr Cys Gln Val Cys Cys Glu Pro Phe His
                1445                1450                1455

Lys Phe Cys Leu Glu Glu Asn Glu Arg Pro Leu Glu Asp Gln Leu Glu
            1460                1465                1470

Asn Trp Cys Cys Arg Arg Cys Lys Phe Cys His Val Cys Gly Arg Gln
            1475                1480                1485

His Gln Ala Thr Lys Gln Leu Leu Glu Cys Asn Lys Cys Arg Asn Ser
    1490                1495                1500

Tyr His Pro Glu Cys Leu Gly Pro Asn Tyr Pro Thr Lys Pro Thr Lys
1505                1510                1515                1520

Lys Lys Lys Val Trp Ile Cys Thr Lys Cys Val Arg Cys Lys Ser Cys
                1525                1530                1535

Gly Ser Thr Thr Pro Gly Lys Gly Trp Asp Ala Gln Trp Ser His Asp
            1540                1545                1550

Phe Ser Leu Cys His Asp Cys Ala Lys Leu Phe Ala Lys Gly Asn Phe
        1555                1560                1565

Cys Pro Leu Cys Asp Lys Cys Tyr Asp Asp Asp Tyr Glu Ser Lys
    1570                1575                1580

Met Met Gln Cys Gly Lys Cys Asp Arg Trp Val His Ser Lys Cys Glu
1585                1590                1595                1600

Asn Leu Ser Gly Thr Glu Asp Glu Met Tyr Glu Ile Leu Ser Asn Leu
                1605                1610                1615

Pro Glu Ser Val Ala Tyr Thr Cys Val Asn Cys Thr Glu Arg His Pro
            1620                1625                1630

Ala Glu Trp Arg Leu Ala Leu Glu Lys Glu Leu Gln Ile Ser Leu Lys
            1635                1640                1645

Gln Val Leu Thr Ala Leu Leu Asn Ser Arg Thr Thr Ser His Leu Leu
    1650                1655                1660
```

-continued

```
Arg Tyr Arg Gln Ala Ala Lys Pro Pro Asp Leu Asn Pro Glu Thr Glu
1665                1670                1675                1680

Glu Ser Ile Pro Ser Arg Ser Ser Pro Glu Gly Pro Asp Pro Pro Val
                1685                1690                1695

Leu Thr Glu Val Ser Lys Gln Asp Asp Gln Gln Pro Leu Asp Leu Glu
                1700                1705                1710

Gly Val Lys Arg Lys Met Asp Gln Gly Asn Tyr Thr Ser Val Leu Glu
            1715                1720                1725

Phe Ser Asp Asp Ile Val Lys Ile Ile Gln Ala Ala Ile Asn Ser Asp
        1730                1735                1740

Gly Gly Gln Pro Glu Ile Lys Lys Ala Asn Ser Met Val Lys Ser Phe
1745                1750                1755                1760

Phe Ile Arg Gln Met Glu Arg Val Phe Pro Trp Phe Ser Val Lys Lys
                1765                1770                1775

Ser Arg Phe Trp Glu Pro Asn Lys Val Ser Ser Asn Ser Gly Met Leu
                1780                1785                1790

Pro Asn Ala Val Leu Pro Pro Ser Leu Asp His Asn Tyr Ala Gln Trp
            1795                1800                1805

Gln Glu Arg Glu Glu Asn Ser His Thr Glu Gln Pro Pro Leu Met Lys
        1810                1815                1820

Lys Ile Ile Pro Ala Pro Lys Pro Lys Gly Pro Gly Glu Pro Asp Ser
1825                1830                1835                1840

Pro Thr Pro Leu His Pro Pro Thr Pro Pro Ile Leu Ser Thr Asp Arg
                1845                1850                1855

Ser Arg Glu Asp Ser Pro Glu Leu Asn Pro Pro Pro Gly Ile Glu Asp
            1860                1865                1870

Asn Arg Gln Cys Ala Leu Cys Leu Thr Tyr Gly Asp Asp Ser Ala Asn
        1875                1880                1885

Asp Ala Gly Arg Leu Leu Tyr Ile Gly Gln Asn Glu Trp Thr His Val
    1890                1895                1900

Asn Cys Ala Leu Trp Ser Ala Glu Val Phe Glu Asp Asp Asp Gly Ser
1905                1910                1915                1920

Leu Lys Asn Val His Met Ala Val Ile Arg Gly Lys Gln Leu Arg Cys
                1925                1930                1935

Glu Phe Cys Gln Lys Pro Gly Ala Thr Val Gly Cys Cys Leu Thr Ser
            1940                1945                1950

Cys Thr Ser Asn Tyr His Phe Met Cys Ser Arg Ala Lys Asn Cys Val
        1955                1960                1965

Phe Leu Asp Asp Lys Lys Val Tyr Cys Gln Arg His Arg Asp Leu Ile
    1970                1975                1980

Lys Gly Glu Val Val Pro Glu Asn Gly Phe Glu Val Phe Arg Arg Val
1985                1990                1995                2000

Phe Val Asp Phe Glu Gly Ile Ser Leu Arg Arg Lys Phe Leu Asn Gly
                2005                2010                2015

Leu Glu Pro Glu Asn Ile His Met Met Ile Gly Ser Met Thr Ile Asp
            2020                2025                2030

Cys Leu Gly Ile Leu Asn Asp Leu Ser Asp Cys Glu Asp Lys Leu Phe
        2035                2040                2045

Pro Ile Gly Tyr Gln Cys Ser Arg Val Tyr Trp Ser Thr Thr Asp Ala
    2050                2055                2060

Arg Lys Arg Cys Val Tyr Thr Cys Lys Ile Val Glu Cys Arg Pro Pro
2065                2070                2075                2080

Val Val Glu Pro Asp Ile Asn Ser Thr Val Glu His Asp Glu Asn Arg
```

-continued

```
              2085            2090            2095

Thr Ile Ala His Ser Pro Thr Ser Phe Thr Glu Ser Ser Ser Lys Glu
            2100            2105            2110

Ser Gln Asn Thr Ala Glu Ile Ile Ser Pro Pro Ser Pro Asp Arg Pro
        2115            2120            2125

Pro His Ser Gln Thr Ser Gly Ser Cys Tyr Tyr His Val Ile Ser Lys
    2130            2135            2140

Val Pro Arg Ile Arg Thr Pro Ser Tyr Ser Pro Thr Gln Arg Ser Pro
2145            2150            2155            2160

Gly Cys Arg Pro Leu Pro Ser Ala Gly Ser Pro Thr Pro Thr Thr His
            2165            2170            2175

Glu Ile Val Thr Val Gly Asp Pro Leu Leu Ser Ser Gly Leu Arg Ser
            2180            2185            2190

Ile Gly Ser Arg Arg His Ser Thr Ser Ser Leu Ser Pro Gln Arg Ser
        2195            2200            2205

Lys Leu Arg Ile Met Ser Pro Met Arg Thr Gly Asn Thr Tyr Ser Arg
    2210            2215            2220

Asn Asn Val Ser Ser Val Ser Thr Thr Gly Thr Ala Thr Asp Leu Glu
2225            2230            2235            2240

Ser Ser Ala Lys Val Val Asp His Val Leu Gly Pro Leu Asn Ser Ser
            2245            2250            2255

Thr Ser Leu Gly Gln Asn Thr Ser Thr Ser Ser Asn Leu Gln Arg Thr
            2260            2265            2270

Val Val Thr Val Gly Asn Lys Asn Ser His Leu Asp Gly Ser Ser Ser
        2275            2280            2285

Ser Glu Met Lys Gln Ser Ser Ala Ser Asp Leu Val Ser Lys Ser Ser
    2290            2295            2300

Ser Leu Lys Gly Glu Lys Thr Lys Val Leu Ser Ser Lys Ser Ser Glu
2305            2310            2315            2320

Gly Ser Ala His Asn Val Ala Tyr Pro Gly Ile Pro Lys Leu Ala Pro
            2325            2330            2335

Gln Val His Asn Thr Thr Ser Arg Glu Leu Asn Val Ser Lys Ile Gly
            2340            2345            2350

Ser Phe Ala Glu Pro Ser Ser Val Ser Phe Ser Ser Lys Glu Ala Leu
        2355            2360            2365

Ser Phe Pro His Leu His Leu Arg Gly Gln Arg Asn Asp Arg Asp Gln
    2370            2375            2380

His Thr Asp Ser Thr Gln Ser Ala Asn Ser Ser Pro Asp Glu Asp Thr
2385            2390            2395            2400

Glu Val Lys Thr Leu Lys Leu Ser Gly Met Ser Asn Arg Ser Ser Ile
            2405            2410            2415

Ile Asn Glu His Met Gly Ser Ser Ser Arg Asp Arg Arg Gln Lys Gly
            2420            2425            2430

Lys Lys Ser Cys Lys Glu Thr Phe Lys Glu Lys His Ser Ser Lys Ser
        2435            2440            2445

Phe Leu Glu Pro Gly Gln Val Thr Thr Gly Glu Glu Gly Asn Leu Lys
    2450            2455            2460

Pro Glu Phe Met Asp Glu Val Leu Thr Pro Glu Tyr Met Gly Gln Arg
2465            2470            2475            2480

Pro Cys Asn Asn Val Ser Ser Asp Lys Ile Gly Asp Lys Gly Leu Ser
            2485            2490            2495

Met Pro Gly Val Pro Lys Ala Pro Pro Met Gln Val Glu Gly Ser Ala
            2500            2505            2510
```

Lys Glu Leu Gln Ala Pro Arg Lys Arg Thr Val Lys Val Thr Leu Thr
        2515                2520                2525

Pro Leu Lys Met Glu Asn Glu Ser Gln Ser Lys Asn Ala Leu Lys Glu
        2530                2535                2540

Ser Ser Pro Ala Ser Pro Leu Gln Ile Glu Ser Thr Ser Pro Thr Glu
2545                2550                2555                2560

Pro Ile Ser Ala Ser Glu Asn Pro Gly Asp Gly Pro Val Ala Gln Pro
                2565                2570                2575

Ser Pro Asn Asn Thr Ser Cys Gln Asp Ser Gln Ser Asn Asn Tyr Gln
                2580                2585                2590

Asn Leu Pro Val Gln Asp Arg Asn Leu Met Leu Pro Asp Gly Pro Lys
        2595                2600                2605

Pro Gln Glu Asp Gly Ser Phe Lys Arg Arg Tyr Pro Arg Arg Ser Ala
        2610                2615                2620

Arg Ala Arg Ser Asn Met Phe Phe Gly Leu Thr Pro Leu Tyr Gly Val
2625                2630                2635                2640

Arg Ser Tyr Gly Glu Glu Asp Ile Pro Phe Tyr Ser Ser Ser Thr Gly
                2645                2650                2655

Lys Lys Arg Gly Lys Arg Ser Ala Glu Gly Gln Val Asp Gly Ala Asp
                2660                2665                2670

Asp Leu Ser Thr Ser Asp Glu Asp Asp Leu Tyr Tyr Tyr Asn Phe Thr
                2675                2680                2685

Arg Thr Val Ile Ser Ser Gly Gly Glu Glu Arg Leu Ala Ser His Asn
        2690                2695                2700

Leu Phe Arg Glu Glu Glu Gln Cys Asp Leu Pro Lys Ile Ser Gln Leu
2705                2710                2715                2720

Asp Gly Val Asp Asp Gly Thr Glu Ser Asp Thr Ser Val Thr Ala Thr
                2725                2730                2735

Thr Arg Lys Ser Ser Gln Ile Pro Lys Arg Asn Gly Lys Glu Asn Gly
                2740                2745                2750

Thr Glu Asn Leu Lys Ile Asp Arg Pro Glu Asp Ala Gly Glu Lys Glu
        2755                2760                2765

His Val Thr Lys Ser Ser Val Gly His Lys Asn Glu Pro Lys Met Asp
        2770                2775                2780

Asn Cys His Ser Val Ser Arg Val Lys Thr Gln Gly Gln Asp Ser Leu
2785                2790                2795                2800

Glu Ala Gln Leu Ser Ser Leu Glu Ser Ser Arg Arg Val His Thr Ser
                2805                2810                2815

Thr Pro Ser Asp Lys Asn Leu Leu Asp Thr Tyr Asn Thr Glu Leu Leu
                2820                2825                2830

Lys Ser Asp Ser Asp Asn Asn Asn Ser Asp Asp Cys Gly Asn Ile Leu
                2835                2840                2845

Pro Ser Asp Ile Met Asp Phe Val Leu Lys Asn Thr Pro Ser Met Gln
        2850                2855                2860

Ala Leu Gly Glu Ser Pro Glu Ser Ser Ser Ser Glu Leu Leu Asn Leu
2865                2870                2875                2880

Gly Glu Gly Leu Gly Leu Asp Ser Asn Arg Glu Lys Asp Met Gly Leu
                2885                2890                2895

Phe Glu Val Phe Ser Gln Gln Leu Pro Thr Thr Glu Pro Val Asp Ser
                2900                2905                2910

Ser Val Ser Ser Ser Ile Ser Ala Glu Glu Gln Phe Glu Leu Pro Leu
        2915                2920                2925

-continued

Glu Leu Pro Ser Asp Leu Ser Val Leu Thr Thr Arg Ser Pro Thr Val
    2930                2935                2940

Pro Ser Gln Asn Pro Ser Arg Leu Ala Val Ile Ser Asp Ser Gly Glu
2945                2950                2955                2960

Lys Arg Val Thr Ile Thr Glu Lys Ser Val Ala Ser Ser Glu Ser Asp
                2965                2970                2975

Pro Ala Leu Leu Ser Pro Gly Val Asp Pro Thr Pro Glu Gly His Met
            2980                2985                2990

Thr Pro Asp His Phe Ile Gln Gly His Met Asp Ala Asp His Ile Ser
        2995                3000                3005

Ser Pro Pro Cys Gly Ser Val Glu Gln Gly His Gly Asn Asn Gln Asp
    3010                3015                3020

Leu Thr Arg Asn Ser Ser Thr Pro Gly Leu Gln Val Pro Val Ser Pro
3025                3030                3035                3040

Thr Val Pro Ile Gln Asn Gln Lys Tyr Val Pro Asn Ser Thr Asp Ser
            3045                3050                3055

Pro Gly Pro Ser Gln Ile Ser Asn Ala Ala Val Gln Thr Thr Pro Pro
            3060                3065                3070

His Leu Lys Pro Ala Thr Glu Lys Leu Ile Val Val Asn Gln Asn Met
        3075                3080                3085

Gln Pro Leu Tyr Val Leu Gln Thr Leu Pro Asn Gly Val Thr Gln Lys
    3090                3095                3100

Ile Gln Leu Thr Ser Ser Val Ser Ser Thr Pro Ser Val Met Glu Thr
3105                3110                3115                3120

Asn Thr Ser Val Leu Gly Pro Met Gly Gly Gly Leu Thr Leu Thr Thr
            3125                3130                3135

Gly Leu Asn Pro Ser Leu Pro Thr Ser Gln Ser Leu Phe Pro Ser Ala
            3140                3145                3150

Ser Lys Gly Leu Leu Pro Met Ser His His Gln His Leu His Ser Phe
        3155                3160                3165

Pro Ala Ala Thr Gln Ser Ser Phe Pro Pro Asn Ile Ser Asn Pro Pro
    3170                3175                3180

Ser Gly Leu Leu Ile Gly Val Gln Pro Pro Pro Asp Pro Gln Leu Leu
3185                3190                3195                3200

Val Ser Glu Ser Ser Gln Arg Thr Asp Leu Ser Thr Thr Val Ala Thr
            3205                3210                3215

Pro Ser Ser Gly Leu Lys Lys Arg Pro Ile Ser Arg Leu Gln Thr Arg
            3220                3225                3230

Lys Asn Lys Lys Leu Ala Pro Ser Ser Thr Pro Ser Asn Ile Ala Pro
        3235                3240                3245

Ser Asp Val Val Ser Asn Met Thr Leu Ile Asn Phe Thr Pro Ser Gln
    3250                3255                3260

Leu Pro Asn His Pro Ser Leu Leu Asp Leu Gly Ser Leu Asn Thr Ser
3265                3270                3275                3280

Ser His Arg Thr Val Pro Asn Ile Ile Lys Arg Ser Lys Ser Ser Ile
            3285                3290                3295

Met Tyr Phe Glu Pro Ala Pro Leu Leu Pro Gln Ser Val Gly Gly Thr
            3300                3305                3310

Ala Ala Thr Ala Ala Gly Thr Ser Thr Ile Ser Gln Asp Thr Ser His
        3315                3320                3325

Leu Thr Ser Gly Ser Val Ser Gly Leu Ala Ser Ser Ser Ser Val Leu
    3330                3335                3340

Asn Val Val Ser Met Gln Thr Thr Thr Thr Pro Thr Ser Ser Ala Ser

-continued

```
3345             3350              3355              3360

Val Pro Gly His Val Thr Leu Thr Asn Pro Arg Leu Leu Gly Thr Pro
                3365              3370              3375

Asp Ile Gly Ser Ile Ser Asn Leu Leu Ile Lys Ala Ser Gln Gln Ser
                3380              3385              3390

Leu Gly Ile Gln Asp Gln Pro Val Ala Leu Pro Pro Ser Ser Gly Met
                3395              3400              3405

Phe Pro Gln Leu Gly Thr Ser Gln Thr Pro Ser Thr Ala Ala Ile Thr
                3410              3415              3420

Ala Ala Ser Ser Ile Cys Val Leu Pro Ser Thr Gln Thr Thr Gly Ile
3425              3430              3435              3440

Thr Ala Ala Ser Pro Ser Gly Glu Ala Asp Glu His Tyr Gln Leu Gln
                3445              3450              3455

His Val Asn Gln Leu Leu Ala Ser Lys Thr Gly Ile His Ser Ser Gln
                3460              3465              3470

Arg Asp Leu Asp Ser Ala Ser Gly Pro Gln Val Ser Asn Phe Thr Gln
                3475              3480              3485

Thr Val Asp Ala Pro Asn Ser Met Gly Leu Glu Gln Asn Lys Ala Leu
                3490              3495              3500

Ser Ser Ala Val Gln Ala Ser Pro Thr Ser Pro Gly Gly Ser Pro Ser
3505              3510              3515              3520

Ser Pro Ser Ser Gly Gln Arg Ser Ala Ser Pro Ser Val Pro Gly Pro
                3525              3530              3535

Thr Lys Pro Lys Pro Lys Thr Lys Arg Phe Gln Leu Pro Leu Asp Lys
                3540              3545              3550

Gly Asn Gly Lys Lys His Lys Val Ser His Leu Arg Thr Ser Ser Ser
                3555              3560              3565

Glu Ala His Ile Pro Asp Gln Glu Thr Thr Ser Leu Thr Ser Gly Thr
                3570              3575              3580

Gly Thr Pro Gly Ala Glu Ala Glu Gln Gln Asp Thr Ala Ser Val Glu
3585              3590              3595              3600

Gln Ser Ser Gln Lys Glu Cys Gly Gln Pro Ala Gly Gln Val Ala Val
                3605              3610              3615

Leu Pro Glu Val Gln Val Thr Gln Asn Pro Ala Asn Glu Gln Glu Ser
                3620              3625              3630

Ala Glu Pro Lys Thr Val Glu Glu Glu Ser Asn Phe Ser Ser Pro
                3635              3640              3645

Leu Met Leu Trp Leu Gln Gln Glu Gln Lys Arg Lys Glu Ser Ile Thr
                3650              3655              3660

Glu Lys Lys Pro Lys Lys Gly Leu Val Phe Glu Ile Ser Ser Asp Asp
3665              3670              3675              3680

Gly Phe Gln Ile Cys Ala Glu Ser Ile Glu Asp Ala Trp Lys Ser Leu
                3685              3690              3695

Thr Asp Lys Val Gln Glu Ala Arg Ser Asn Ala Arg Leu Lys Gln Leu
                3700              3705              3710

Ser Phe Ala Gly Val Asn Gly Leu Arg Met Leu Gly Ile Leu His Asp
                3715              3720              3725

Ala Val Val Phe Leu Ile Glu Gln Leu Ser Gly Ala Lys His Cys Arg
3730              3735              3740

Asn Tyr Lys Phe Arg Phe His Lys Pro Glu Glu Ala Asn Glu Pro Pro
3745              3750              3755              3760

Leu Asn Pro His Gly Ser Ala Arg Ala Glu Val His Leu Arg Lys Ser
                3765              3770              3775
```

-continued

```
Ala Phe Asp Met Phe Asn Phe Leu Ala Ser Lys His Arg Gln Pro Pro
        3780                3785                3790

Glu Tyr Asn Pro Asn Asp Glu Glu Glu Glu Val Gln Leu Lys Ser
        3795                3800                3805

Ala Arg Arg Ala Thr Ser Met Asp Leu Pro Met Pro Met Arg Phe Arg
        3810                3815                3820

His Leu Lys Lys Thr Ser Lys Glu Ala Val Gly Val Tyr Arg Ser Pro
3825                3830                3835                3840

Ile His Gly Arg Gly Leu Phe Cys Lys Arg Asn Ile Asp Ala Gly Glu
            3845                3850                3855

Met Val Ile Glu Tyr Ala Gly Asn Val Ile Arg Ser Ile Gln Thr Asp
            3860                3865                3870

Lys Arg Glu Lys Tyr Tyr Asp Ser Lys Gly Ile Gly Cys Tyr Met Phe
            3875                3880                3885

Arg Ile Asp Asp Ser Glu Val Val Asp Ala Thr Met His Gly Asn Ala
        3890                3895                3900

Ala Arg Phe Ile Asn His Ser Cys Glu Pro Asn Cys Tyr Ser Arg Val
3905                3910                3915                3920

Ile Asn Ile Asp Gly Gln Lys His Ile Val Ile Phe Ala Met Arg Lys
            3925                3930                3935

Ile Tyr Arg Gly Glu Glu Leu Thr Tyr Asp Tyr Lys Phe Pro Ile Glu
            3940                3945                3950

Asp Ala Ser Asn Lys Leu Pro Cys Asn Cys Gly Ala Lys Lys Cys Arg
            3955                3960                3965

Lys Phe Leu Asn
    3970
```

```
<210> SEQ ID NO 7
<211> LENGTH: 50
<212> TYPE: DNA
<213> ORGANISM: Homo sapiens

<400> SEQUENCE: 7
agaggaagta attccttcac atggaaagta tcaaaccatg atgattcctt                50

<210> SEQ ID NO 8
<211> LENGTH: 50
<212> TYPE: DNA
<213> ORGANISM: Homo sapiens

<400> SEQUENCE: 8
ttatacacac atacacacat atacatagaa aaatgtatat aatacatatt                50

<210> SEQ ID NO 9
<211> LENGTH: 50
<212> TYPE: DNA
<213> ORGANISM: Homo sapiens

<400> SEQUENCE: 9
tttgtttgct tggttatctt ctcttatata acccagcact cttagcaaat                50

<210> SEQ ID NO 10
<211> LENGTH: 50
<212> TYPE: DNA
<213> ORGANISM: Homo sapiens

<400> SEQUENCE: 10
tatcaaacca tgatgattcc ttgagtcagc aaaactgtaa gagaaattca                50
```

```
<210> SEQ ID NO 11
<211> LENGTH: 50
<212> TYPE: DNA
<213> ORGANISM: Homo sapiens

<400> SEQUENCE: 11
aaatactctg acattgtgat gtcacactaa ttttatgctt ttcatcctta              50

<210> SEQ ID NO 12
<211> LENGTH: 50
<212> TYPE: DNA
<213> ORGANISM: Homo sapiens

<400> SEQUENCE: 12
ctttggccag ccagctctga ttaggccccc aagccatttt tcagccccaa              50

<210> SEQ ID NO 13
<211> LENGTH: 50
<212> TYPE: DNA
<213> ORGANISM: Homo sapiens

<400> SEQUENCE: 13
agtccgtgtc tgagattaaa actttttaaa gcagcagtta tttttggact              50

<210> SEQ ID NO 14
<211> LENGTH: 50
<212> TYPE: DNA
<213> ORGANISM: Homo sapiens

<400> SEQUENCE: 14
tccatgttgg cttttaaagt ttcctcttaa caaattttca gtgtgaaatc              50

<210> SEQ ID NO 15
<211> LENGTH: 50
<212> TYPE: DNA
<213> ORGANISM: Homo sapiens

<400> SEQUENCE: 15
ttacatagtc attgcttaat gaatatgtat tgaattaaat atatgccagt              50

<210> SEQ ID NO 16
<211> LENGTH: 50
<212> TYPE: DNA
<213> ORGANISM: Homo sapiens

<400> SEQUENCE: 16
attgtatccc aggtagagga tcttatttaa acacacacac acacacacac              50

<210> SEQ ID NO 17
<211> LENGTH: 50
<212> TYPE: DNA
<213> ORGANISM: Homo sapiens

<400> SEQUENCE: 17
atgaattgtg atatttattt ttttttttaag ttaaagagta caaaattgta            50

<210> SEQ ID NO 18
<211> LENGTH: 50
<212> TYPE: DNA
<213> ORGANISM: Homo sapiens

<400> SEQUENCE: 18
```

-continued

```
gaagggtatg gttgattatg tttttctaca tattatttga catacttcta                50

<210> SEQ ID NO 19
<211> LENGTH: 50
<212> TYPE: DNA
<213> ORGANISM: Homo sapiens

<400> SEQUENCE: 19
ggaatcttga cttctgttcc tataacaccc agggtggttt gctttctctg                50

<210> SEQ ID NO 20
<211> LENGTH: 50
<212> TYPE: DNA
<213> ORGANISM: Homo sapiens

<400> SEQUENCE: 20
gaagcaactg ggatgaacta tttatcttcc tgatcactgc aaggaaacac                50

<210> SEQ ID NO 21
<211> LENGTH: 50
<212> TYPE: DNA
<213> ORGANISM: Homo sapiens

<400> SEQUENCE: 21
tgttcctata acacccaggg tggtttgctt tctctgtgcc agtagtgggc                50

<210> SEQ ID NO 22
<211> LENGTH: 50
<212> TYPE: DNA
<213> ORGANISM: Homo sapiens

<400> SEQUENCE: 22
tcaagttgct tttgtaattg ggaagctagg aggtgatgta ttttgctaag                50

<210> SEQ ID NO 23
<211> LENGTH: 50
<212> TYPE: DNA
<213> ORGANISM: Homo sapiens

<400> SEQUENCE: 23
tttcctaagt gacctttctc tctccacagg aggattgtga agcagaaaat                50

<210> SEQ ID NO 24
<211> LENGTH: 50
<212> TYPE: DNA
<213> ORGANISM: Homo sapiens

<400> SEQUENCE: 24
aatttcagtc tcttcttaca tatgtttatt gaggaagaat tgaaaggagc                50

<210> SEQ ID NO 25
<211> LENGTH: 50
<212> TYPE: DNA
<213> ORGANISM: Homo sapiens

<400> SEQUENCE: 25
gcgccctctg gaggaccagc tggaaaattg gtgttgtcgt cgttgcaaat                50

<210> SEQ ID NO 26
<211> LENGTH: 50
<212> TYPE: DNA
<213> ORGANISM: Homo sapiens

<400> SEQUENCE: 26
```

-continued

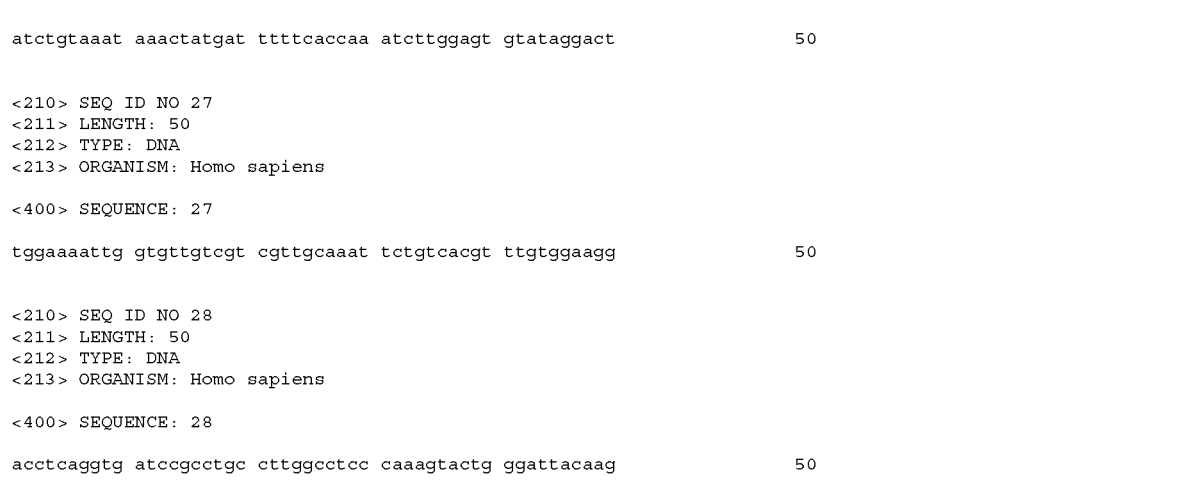

What is claimed is:

1. A method of treating a thymoma in an individual, comprising administering to the individual an effective amount of an anti-cancer therapy, wherein the thymoma comprises a KMT2A-MAML2 fusion nucleic acid molecule or a KMT2A-MAML2 fusion polypeptide;
    wherein the anti-cancer therapy is an agent that inhibits activity or expression of the KMT2A-MAML2 polypeptide, a NOTCH pathway inhibitor, or an agent that inhibits activity or expression of epidermal growth factor receptor (EGFR).

2. A method of treating a thymoma in an individual, comprising, responsive to knowledge of a KMT2A-MAML2 fusion nucleic acid molecule or of a KMT2A-MAML2 fusion polypeptide in a sample from the individual, administering to the individual an effective amount of an anti-cancer therapy;
    wherein the anti-cancer therapy is an agent that inhibits activity or expression of the KMT2A-MAML2 polypeptide, a NOTCH pathway inhibitor, or an agent that inhibits activity or expression of epidermal growth factor receptor (EGFR).

3. A method of treating a thymoma in an individual, comprising:
    (a) acquiring knowledge of a KMT2A-MAML2 fusion nucleic acid molecule or a KMT2A-MAML2 fusion polypeptide in a sample from the individual; and
    (b) administering to the individual an effective amount of an anti-cancer therapy, wherein the anti-cancer therapy is an agent that inhibits activity or expression of the KMT2A-MAML2 polypeptide, a NOTCH pathway inhibitor, or an agent that inhibits activity or expression of epidermal growth factor receptor (EGFR).

4. The method of claim 3, wherein acquiring knowledge comprises detecting the KMT2A-MAML2 fusion nucleic acid molecule or the KMT2A-MAML2 fusion polypeptide in a sample from the individual.

5. The method of claim 3, wherein the method comprises acquiring knowledge of the KMT2A-MAML2 fusion nucleic acid molecule in the sample from the individual, and wherein the KMT2A-MAML2 fusion nucleic acid molecule comprises:
    exon 7 or a portion thereof, intron 7 or a portion thereof, exon 8 or a portion thereof, intron 8 or a portion thereof, exon 9 or a portion thereof, intron 9 or a portion thereof, exon 10 or a portion thereof, intron 10 or a portion thereof, exon 11 or a portion thereof, or intron 11 or a portion thereof, of KMT2A and intron 1 or a portion thereof, exon 2 or a portion thereof, intron 2 or a portion thereof, exon 3 or a portion thereof, intron 3 or a portion thereof, or exon 4, of MAML2; and
    a KMT2A-MAML2 breakpoint that fuses exon 7 or the portion thereof, intron 7 or the portion thereof, exon 8 or the portion thereof, intron 8 or the portion thereof, exon 9 or the portion thereof, intron 9 or the portion thereof, exon 10 or the portion thereof, intron 10 or the portion thereof, exon 11 or the portion thereof, or intron 11 or the portion thereof, of KMT2A to intron 1 or the portion thereof, exon 2 or the portion thereof, intron 2 or the portion thereof, exon 3 or the portion thereof, intron 3 or the portion thereof, or exon 4, of MAML2.

6. The method of claim 5, wherein the KMT2A-MAML2 fusion nucleic acid molecule comprises 5 or more nucleotides from exon 7, intron 7, exon 8, intron 8, exon 9, intron 9, exon 10, intron 10, exon 11, or intron 11 of KMT2A on a 5' end of the KMT2A-MAML2 breakpoint, and 5 or more nucleotides from intron 1, exon 2, intron 2, exon 3, intron 3, or exon 4 of MAML2 on a 3' end of the KMT2A-MAML2 breakpoint.

7. The method of claim 3, wherein the method comprises acquiring knowledge of the KMT2A-MAML2 fusion nucleic acid molecule in the sample from the individual, and wherein the KMT2A-MAML2 fusion nucleic acid molecule comprises:
    (a) exon 7 or a portion thereof, exon 8 or a portion thereof, exon 9 or a portion thereof, exon 10 or a portion thereof, or exon 11 or a portion thereof, of KMT2A fused to exon 2 or a portion thereof, exon 3 or a portion thereof, or exon 4 or a portion thereof, of MAML2;
    (b) intron 7, 8, 9, 10, or 11, or a portion thereof, of KMT2A fused to intron 1, 2, or 3, or a portion thereof, of MAML2;
    (c) exon 7 or a portion thereof, exon 8 or a portion thereof, exon 9 or a portion thereof, exon 10 or a portion thereof, or exon 11 or a portion thereof, of KMT2A fused to intron 1, 2, or 3, or a portion thereof, of MAML2; or (d) intron 7, 8, 9, 10, or 11, or a portion thereof, of KMT2A fused to exon 2 or a portion thereof, exon 3 or a portion thereof, or exon 4 or a portion thereof, of MAML2.

8. The method of claim 3, wherein the method comprises acquiring knowledge of the KMT2A-MAML2 fusion nucleic acid molecule in the sample from the individual, and wherein the KMT2A-MAML2 fusion nucleic acid molecule comprises a nucleotide sequence comprising, in the 5' to 3' direction:

(a) exons 1-6 and exon 7, or a portion of exon 7, of KMT2A and exon 2 or a portion thereof and exons 3-5, exon 3 or a portion thereof and exons 4-5, or exons 4-5, of MAML2;

(b) exons 1-7 and exon 8, or a portion of exon 8, of KMT2A and exon 2 or a portion thereof and exons 3-5, exon 3 or a portion thereof and exons 4-5, or exons 4-5, of MAML2;

(c) exons 1-8 and exon 9, or a portion of exon 9, of KMT2A and exon 2 or a portion thereof and exons 3-5, exon 3 or a portion thereof and exons 4-5, or exons 4-5, of MAML2;

(d) exons 1-9 and exon 10, or a portion of exon 10, of KMT2A and exon 2 or a portion thereof and exons 3-5, exon 3 or a portion thereof and exons 4-5, or exons 4-5, MAML2; or (e) exons 1-10 and exon 11, or a portion of exon 11, of KMT2A and exon 2 or a portion thereof and exons 3-5, exon 3 or a portion thereof and exons 4-5, or exons 4-5, of MAML2.

9. The method of claim 3, wherein the method comprises acquiring knowledge of the KMT2A-MAML2 fusion polypeptide in the sample from the individual, and wherein the KMT2A-MAML2 fusion polypeptide comprises:

(a) an amino acid sequence encoded by a nucleic acid molecule comprising:

exon 7 or a portion thereof, exon 8 or a portion thereof, exon 9 or a portion thereof, exon 10 or a portion thereof, or exon 11 or a portion thereof, of KMT2A and exon 2 or a portion thereof, exon 3 or a portion thereof, or exon 4, of MAML2; and a KMT2A-MAML2 breakpoint that fuses exon 7 or the portion thereof, exon 8 or the portion thereof, exon 9 or the portion thereof, exon 10 or the portion thereof, or exon 11 or the portion thereof, of KMT2A to exon 2 or the portion thereof, exon 3 or the portion thereof, or exon 4, of MAML2; or (b) an amino acid sequence at least about 85% identical to the KMT2A-MAML2 fusion polypeptide of (a).

10. The method of claim 9, wherein the KMT2A-MAML2 fusion polypeptide comprises 5 or more amino acids encoded by a 3' end of exon 7 or the portion thereof, a 3' end of exon 8 or the portion thereof, a 3' end of exon 9 or the portion thereof, a 3' end of exon 10 or the portion thereof, or a 3' end of exon 11 or the portion thereof, of KMT2A fused to 5 or more amino acids encoded by a 5' end of exon 2 or the portion thereof, exon 3 or the portion thereof, or exon 4, of MAML2.

11. The method of claim 3, wherein the method comprises acquiring knowledge of the KMT2A-MAML2 fusion polypeptide in the sample from the individual, and wherein the KMT2A-MAML2 fusion polypeptide comprises:

(a) an amino acid sequence encoded by a KMT2A-MAML2 fusion nucleic acid molecule comprising, in the 5' to 3' direction:

(i) exons 1-6 and exon 7, or a portion of exon 7, of KMT2A and exon 2 or a portion thereof and exons 3-5, exon 3 or a portion thereof and exons 4-5, or exons 4-5, of MAML2, (ii) exons 1-7 and exon 8, or a portion of exon 8, of KMT2A and exon 2 or a portion thereof and exons 3-5, exon 3 or a portion thereof and exons 4-5, or exons 4-5, of MAML2, (iii) exons 1-8 and exon 9, or a portion of exon 9, of KMT2A and exon 2 or a portion thereof and exons 3-5, exon 3 or a portion thereof and exons 4-5, or exons 4-5, of MAML2, (iv) exons 1-9 and exon 10, or a portion of exon 10, of KMT2A and exon 2 or a portion thereof and exons 3-5, exon 3 or a portion thereof and exons 4-5, or exons 4-5, of MAML2, or (v) exons 1-10 and exon 11, or a portion of exon 11, of KMT2A and exon 2 or a portion thereof and exons 3-5, exon 3 or a portion thereof and exons 4-5, or exons 4-5, of MAML2; or (b) an amino acid sequence at least about 85% identical to the KMT2A-MAML2 fusion polypeptide of (a).

12. The method of claim 9, wherein in vivo expression of the KMT2A-MAML2 fusion polypeptide results in modulation in the expression of one or more genes in the NOTCH pathway.

13. The method of claim 9, wherein the KMT2A-MAML2 fusion polypeptide comprises a histone methyltransferase activity.

14. The method of claim 9, wherein the KMT2A-MAML2 fusion polypeptide comprises a constitutive histone methyltransferase activity.

15. The method of claim 9, wherein the thymoma is an adult thymoma.

16. The method of claim 9, wherein the thymoma has a B2 histology, a B3 histology, or a B2-B3 histology.

17. The method of claim 9, wherein the thymoma is a stage 2b, 4a, or 4b thymoma.

18. The method of claim 9, wherein the thymoma is recurrent.

19. The method of claim 9, wherein the thymoma is metastatic.

20. The method of claim 9, wherein the thymoma comprises a mutation in a gene selected from the group consisting of TP53, ARIDIA, TERT, and SF3B1.

21. The method of claim 3, wherein the individual has received a prior anti-cancer treatment.

22. The method of claim 9, wherein the individual has received a prior anti-cancer treatment comprising one or more of a chemotherapy, surgical resection, radiation, MGCD516, BBI608, paclitaxel, or sunitinib.

23. The method of claim 3, wherein the anti-cancer therapy is a small molecule, an antibody, or a nucleic acid.

24. The method of claim 3, wherein the anti-cancer therapy is an agent that inhibits activity or expression of the KMT2A-MAML2 polypeptide, or a NOTCH pathway inhibitor.

25. The method of claim 24, wherein the NOTCH pathway inhibitor inhibits Notch1.

26. The method of claim 3, wherein the anti-cancer therapy is an agent that inhibits activity or expression of epidermal growth factor receptor (EGFR).

27. The method of claim 26, wherein the agent is a small molecule, an antibody, or a nucleic acid.

28. The method of claim 26, wherein the agent is selected from the group consisting of lapatinib, gefitinib, erlotinib, cetuximab, canertinib, panitumumab, nimotuzumab, OSI- 632, vandetanib, afatinib, MP-412, AEE-788, neratinib, XL-647, dacomitinib, AZD-8931, CUDC-101, and CO-1686.

29. The method of claim 3, wherein the sample comprises fluid, cells, or tissue.

30. The method of claim 29, wherein the sample comprises a tumor biopsy, blood, or a circulating tumor cell.

31. The method of claim 3, wherein the sample is a nucleic acid sample.

32. The method of claim 31, wherein the nucleic acid sample comprises mRNA, genomic DNA, circulating tumor DNA, cell-free DNA, or cell-free RNA.

33. The method of claim 31, wherein the KMT2A-MAML2 fusion nucleic acid molecule is detected in the sample by a nucleic acid hybridization assay, an amplification-based assay, a PCR-RFLP assay, real-time PCR, sequencing, next-generation sequencing, a screening analysis, FISH, spectral karyotyping or MFISH, comparative genomic hybridization, in situ hybridization, sequence-specific priming (SSP) PCR, HPLC, or mass-spectrometric genotyping.

34. The method of claim 3, wherein the sample is a protein sample.

35. The method of claim 34, wherein the KMT2A-MAML2 fusion polypeptide is detected in the sample by immunoblotting, ELISA, immunohistochemistry, or mass spectrometry.

36. The method of claim 3, wherein the fusion nucleic acid molecule comprises a KMT2A-MAML2 breakpoint comprising:

(a) the nucleic acid sequence of SEQ ID NO: 7 or a nucleic acid sequence at least about 85% identical to SEQ ID NO: 7 fused to the nucleic acid sequence of SEQ ID NO: 8 or a nucleic acid sequence at least about 85% identical to SEQ ID NO: 8;

(b) the nucleic acid sequence of SEQ ID NO: 9 or a nucleic acid sequence at least about 85% identical to SEQ ID NO: 9 fused to the nucleic acid sequence of SEQ ID NO: 10 or a nucleic acid sequence at least about 85% identical to SEQ ID NO: 10;

(c) the nucleic acid sequence of SEQ ID NO: 11 or a nucleic acid sequence at least about 85% identical to SEQ ID NO: 11 fused to the nucleic acid sequence of SEQ ID NO: 12 or a nucleic acid sequence at least about 85% identical to SEQ ID NO: 12;

(d) the nucleic acid sequence of SEQ ID NO: 13 or a nucleic acid sequence at least about 85% identical to SEQ ID NO: 13 fused to the nucleic acid sequence of SEQ ID NO: 14 or a nucleic acid sequence at least about 85% identical to SEQ ID NO: 14;

(e) the nucleic acid sequence of SEQ ID NO: 15 or a nucleic acid sequence at least about 85% identical to SEQ ID NO: 15 fused to the nucleic acid sequence of SEQ ID NO: 16 or a nucleic acid sequence at least about 85% identical to SEQ ID NO: 16;

(f) the nucleic acid sequence of SEQ ID NO: 17 or a nucleic acid sequence at least about 85% identical to SEQ ID NO: 17 fused to the nucleic acid sequence of SEQ ID NO: 18 or a nucleic acid sequence at least about 85% identical to SEQ ID NO: 18;

(g) the nucleic acid sequence of SEQ ID NO: 19 or a nucleic acid sequence at least about 85% identical to SEQ ID NO: 19 fused to the nucleic acid sequence of SEQ ID NO: 20 or a nucleic acid sequence at least about 85% identical to SEQ ID NO: 20;

(h) the nucleic acid sequence of SEQ ID NO: 21 or a nucleic acid sequence at least about 85% identical to SEQ ID NO: 21 fused to the nucleic acid sequence of SEQ ID NO: 22 or a nucleic acid sequence at least about 85% identical to SEQ ID NO: 22;

(i) the nucleic acid sequence of SEQ ID NO: 23 or a nucleic acid sequence at least about 85% identical to SEQ ID NO: 23 fused to the nucleic acid sequence of SEQ ID NO: 24 or a nucleic acid sequence at least about 85% identical to SEQ ID NO: 24;

(j) the nucleic acid sequence of SEQ ID NO: 25 or a nucleic acid sequence at least about 85% identical to SEQ ID NO: 25 fused to the nucleic acid sequence of SEQ ID NO: 26 or a nucleic acid sequence at least about 85% identical to SEQ ID NO: 26; or (k) the nucleic acid sequence of SEQ ID NO: 27 or a nucleic acid sequence at least about 85% identical to SEQ ID NO: 27 fused to the nucleic acid sequence of SEQ ID NO: 28 or a nucleic acid sequence at least about 85% identical to SEQ ID NO: 28.

* * * * *